(12) United States Patent
Adams et al.

(10) Patent No.: US 12,054,559 B2
(45) Date of Patent: Aug. 6, 2024

(54) ANTI-IgE ANTIBODIES

(71) Applicant: UCB BIOPHARMA SRL, Brussels (BE)

(72) Inventors: Ralph Adams, Slough (GB); Thomas Allen Ceska, Slough (GB); Anna Marie Davies, London (GB); Alistair James Henry, Slough (GB); Xiaofeng Liu, Slough (GB); James Michael McDonnell, London (GB); Brian John Sutton, London (GB); Marta Katarzyna Westwood, Slough (GB)

(73) Assignee: UCB BIOPHARMA SRL, Brussels (BE)

(*) Notice: Subject to any disclaimer, the term of this patent is extended or adjusted under 35 U.S.C. 154(b) by 318 days.

(21) Appl. No.: 17/541,932

(22) Filed: Dec. 3, 2021

(65) Prior Publication Data

US 2022/0235146 A1   Jul. 28, 2022

Related U.S. Application Data

(62) Division of application No. 16/307,454, filed as application No. PCT/EP2017/063916 on Jun. 8, 2017, now Pat. No. 11,214,627.

(30) Foreign Application Priority Data

Jun. 10, 2016 (GB) .................... 1610198
Feb. 15, 2017 (GB) .................... 1702435

(51) Int. Cl.
  *C07K 16/42* (2006.01)
  *A61P 37/08* (2006.01)
  *C07K 14/735* (2006.01)
  *C07K 16/28* (2006.01)

(52) U.S. Cl.
  CPC .......... *C07K 16/4291* (2013.01); *A61P 37/08* (2018.01); *C07K 14/70535* (2013.01); *C07K 16/2851* (2013.01); *C07K 2317/565* (2013.01); *C07K 2317/92* (2013.01)

(58) Field of Classification Search
  None
  See application file for complete search history.

(56) References Cited

U.S. PATENT DOCUMENTS

| | | | |
|---|---|---|---|
| 5,994,511 A * | 11/1999 | Lowman | A61P 43/00 530/387.3 |
| 6,172,213 B1 | 1/2001 | Lowman et al. | |
| 6,267,958 B1 | 7/2001 | Andya et al. | |
| 7,157,085 B2 | 1/2007 | Lowman et al. | |
| 7,867,494 B2 * | 1/2011 | Liu | A61P 7/04 424/152.1 |
| 2008/0003218 A1 | 1/2008 | Lowman et al. | |
| 2008/0206237 A1 | 8/2008 | Owen et al. | |
| 2012/0034160 A1 | 2/2012 | Ghayur et al. | |
| 2013/0243750 A1 | 9/2013 | Scheerens et al. | |

FOREIGN PATENT DOCUMENTS

| | | | | |
|---|---|---|---|---|
| CN | 104987412 A | 10/2015 | | |
| JP | 2009-055902 A | 3/2009 | | |
| TW | I233946 B | 6/2005 | | |
| WO | WO93/04173 A1 | 3/1993 | | |
| WO | WO97/04801 A1 | 2/1997 | | |
| WO | WO97/04807 A1 | 2/1997 | | |
| WO | WO-9704807 A1 * | 2/1997 | ....... A61K 39/39591 |
| WO | WO-9733616 A1 * | 9/1997 | ......... C07K 16/4291 |
| WO | WO-9938531 A1 * | 8/1999 | .............. A61P 17/00 |
| WO | WO-0072879 A1 * | 12/2000 | ......... C07K 16/4291 |
| WO | WO2006/082052 A1 | 8/2006 | | |
| WO | WO2009/081201 A2 | 7/2009 | | |
| WO | WO2011/056606 A1 | 5/2011 | | |
| WO | WO2013/068571 A1 | 5/2013 | | |

(Continued)

OTHER PUBLICATIONS

Stryer, L., Biochemistry, 4th edition, W. H. Freeman and Company, 1995, pp. 18-23.*
Moro et al., Biomolecules. Oct. 10, 2020;10(10):1432. doi: 10.3390/biom10101432. PMID: 33050407 PMCID: PMC7600534.*
Cai et al., Lasers Med Sci. Oct. 2022;37(8):3085-3105. doi: 10.1007/s10103-022-03620-1. Epub Aug. 1, 2022. PMID: 35913536.*
Janeway et al, Immunobiology, 3rd edition, 1997, Garland Publishing Inc., pp. 11:12-11:17.*
Chen et al., "Enhancement and destruction of antibody function by somatic mutation: unequal occurrence is controlled by V gene combinatorial associations," The EMBO Journal 14(12): 2784-2794 (1995).

(Continued)

*Primary Examiner* — Michael Szperka
(74) *Attorney, Agent, or Firm* — MEDLER FERRO WOODHOUSE & MILLS PLLC

(57) ABSTRACT

The present invention relates to the area of improved anti-IgE antibodies and antigen binding agents, and compositions thereof, which target IgE, for instance: for use in treating disorders caused by IgE (such as allergic responses, or certain autoimmune responses); and, in particular, disorders caused by the interaction of IgE with the FcεRI receptor. In particular, this invention relates to improved anti-IgE antibodies and antigen binding agents related to novel mutants of omalizumab (Xolair®). The improved anti-IgE antibodies and antigen binding agents of the invention may have improved affinity for IgE and/or an improved interaction with the Cε2 domain of IgE and/or an improved modified epitope on IgE (for instance further involving the Cε2 domain of IgE) and/or the ability to disassociate IgE from the FcεRI receptor for instance at pharmaceutically-relevant concentrations. In one aspect, improved or novel treatments for IgE mediated disorders are disclosed in which IgE is targeted (for instance free IgE and/or IgE complexed with the FcεRI receptor).

12 Claims, 16 Drawing Sheets

Specification includes a Sequence Listing.

(56) References Cited

FOREIGN PATENT DOCUMENTS

| WO | WO2015/013668 A1 | 1/2015 |
|---|---|---|
| WO | WO2017/044664 A1 | 3/2017 |

OTHER PUBLICATIONS

Edwards et al., "The Remarkable Flexibility of the Human Antibody Repertoire; Isolation of Over One Thousand Different Antibodies to a Single Protein, BLyS", Journal of Molecular Biology 334(1):103-118 (2003).
Goel, et al., "Plasticity within the Antigen-Combining Site May Manifest as Molecular Mimicry in the Humoral Immune Response", Journal of Immunology 173(12):7358-67 (2004).
Jakubke et al.,"Aminokisloty, peptidy, belki (translated from German)," M: Mir, -456 p., ill.; 356-363 (1985).
Janeway et al., Immunolobiology, $3^{rd}$ edition, Garland Publishing, Inc., p. 3:1-3.11 (1997).
Kanyavuz et al., "Breaking the law: unconventional strategies for antibody diversification", Nature Reviews Immunology 19(6):355-368 (2019).
Kim, Beomkyu et al., Accelerated disassembly of IgE-receptor complexes by a disruptive macromolecular inhibitor, Nature, Oct. 28, 2012, 613-617 XP055395651, 491 (7425).
Lescar et al, "Crystal Structure of a Cross-reactive Complex between Fab F9.13.7 and Guinea Fowl Lysosome", Journal of Biological Chemistry 270(30):18067-18076 (1995).
Lloyd et al., "Modelling the human immune response: performance of a $10^{11}$ human antibody repertoire against a broad panel of therapeutically relevant antigens", Protein Engineering Design and Selection 22(3):159-168 (2009). Epub Oct. 29, 2008.
Pakula et al., "Genetic Analysis of Protein Stability and Function," Annu. Rev. Genet. 23:289-310, (1989).
Pennington, L.F. et al., Structural basis of omalizumab therapy and omalizumab-mediated IgE exchange, Nature Communications, Jan. 1, 2016, 11610 XP055371496, 7.
Presta, L.G., et al., Humanization of an Antibody Directed Against IgE, Journal of Immunology, Sep. 1, 1993, pp. 2623-2632, 151.
Roitt et al., "Immunologia," Moscow, "Mir", pp. 110-111 (2000).
Rudikoff et al., "Single amino acid substitution altering antigen-binding specificity," Proc. Natl. Acad. Sci. USA 79(6):1979-1983 (Mar. 1982).
Tarantul, "Tokovyj biotechnologicheskij slovar," Jazyki slavjanskih kul'tur, Moscow, p. 472 (2009).
Office Action issued Nov. 20, 2020, in Russian Application No. 2019100034/10 (000036).
Office Action issued Apr. 22, 2021 in Japanese Patent Application No. 2018-564417.
Search Report issued Jul. 19, 2021 in Taiwanese Patent Application No. 106119366.

\* cited by examiner

Figure 16.

SEQ ID NO: 108

```
224
 VASRDFTPPT VKILQSSCDG GGHFPPTIQL LCLVSGYTPG TINITWLEDG QVMDVDLSTA
                                                        * * * * * * *
 STTQEGELAS TQSELTLSQK HWLSDRTYTC QVTYQGHTFE DSTKKCADSN PRGVSAYLSR
                 *
 PSPFDLFIRK SPTITCLVVD LAPSKGTVNL TWSRASGKPV NHSTRKEEKQ RNGTLTVTST
                                  * * * * * * * * *
 LPVGTRDWIE GETYQCRVTH PHLPRALMRS TTKTSGPRAA PEVYAFATPE WPGSRDKRTL
                 * * *        * * *   *
 ACLIQNFMPE DISVQWLHNE VQLPDARHST TQPRKTKGSG FFVFSRLEVT RAEWEQKDEF

ICRAVHEAAS PSQTVQRAVS VNPGK
                              547
```

ANTI-IgE ANTIBODIES

REFERENCE TO AN ELECTRONIC SEQUENCE LISTING

The contents of the electronic sequence listing (0089-0022US1_SL.txt; Size: 123,000 bytes; and Date of Creation Nov. 13, 2018) is herein incorporated by reference in its entirety.

FIELD OF THE INVENTION

This invention is in the area of improved anti-IgE antibodies and antigen binding agents, and compositions thereof, which target IgE, for instance for use in treating disorders caused by IgE (such as allergic responses, or certain autoimmune responses), and in particular disorders caused by the interaction of IgE with the FcɛRI receptor. In particular, this invention relates to improved anti-IgE antibodies and antigen binding agents related to novel mutants of omalizumab (Xolair®). The improved anti-IgE antibodies and antigen binding agents of the invention may have improved affinity for IgE and/or an improved interaction with the Cɛ2 domain of IgE and/or an improved modified epitope on IgE (for instance further involving the Cɛ2 domain of IgE) and/or the ability to disassociate IgE from the FcɛRI receptor at pharmaceutically-relevant concentrations. In one aspect, improved or novel treatments for IgE mediated disorders are disclosed in which IgE is targeted (for instance free IgE and/or IgE complexed with the FcɛRI receptor).

BACKGROUND OF THE INVENTION

IgE is a member of the immunoglobulin family that mediates allergic responses such as asthma, food allergies, type 1 hypersensitivity and the familiar sinus inflammation suffered on a widespread basis. IgE is secreted by, and expressed on the surface of, B-cells. IgE synthesized by B-cells is anchored in the B-cell membrane by a transmembrane domain linked to the mature IgE sequence by a short membrane binding region. IgE also is bound to B-cells (and monocytes, eosinophils and platelets) through its Fc region to a low affinity IgE receptor (FcɛRII). Upon exposure of a mammal to an allergen, B-cells are clonally amplified which synthesize IgE that binds the allergen. This IgE in turn is released into the circulation by the B-cells where it is bound by B-cells (through FcɛRII) and by mast cells and basophils through the so-called high affinity receptor (FcɛRI) found on the surface of the mast cells ad basophils. Such mast cells and basophils are thereby sensitized for allergen. The next exposure to the allergen cross-links the FcɛRI on these cells and thus activate their release of histamine and other factors which are responsible for clinical hypersensitivity and anaphylaxis.

Omalizumab (Xolair®) is a recombinant DNA-derived humanized IgG1κ monoclonal antibody that selectively binds to human immunoglobulin E (IgE) [the Cɛ3 domain]. The antibody has a molecular weight of approximately 149 kD. Xolair® is produced by a Chinese hamster ovary cell suspension culture in a nutrient medium containing the antibiotic gentamicin. Xolair® is a sterile, white, preservative-free, lyophilized powder contained in a single-use vial that is reconstituted with Sterile Water for Injection (SWFI), USP, (or, alternatively, as a liquid formulation in a sterile syringe) and administered as a subcutaneous (SC) injection [see EP602126 (and SPC/GB06/005 based thereon); WO93/04173; U.S. Pat. No. 6,267,958 (and the Xolair® PTE based on this patent); WO97/04807; WO97/04801; Presta et al. (1993) J. Immunol. 151:2623-2632].

Omalizumab is presently indicated for the treatment of moderate to severe persistent asthma in patients with a positive skin test or in vitro reactivity to a perennial aeroallergen and symptoms that are inadequately controlled by inhaled corticosteroids (from Xolair® Prescribing Information).

Problems exist with omalizumab in that: 1) it targets free IgE but does not (or does not efficiently) target the pathogenic species of the IgE/FcɛRI complex at pharmaceutically-relevant doses; 2) possibly due to the pathogenic species of the IgE/FcɛRI complex not being targeted, it takes "at least 12-16 weeks for Xolair treatment to show effectiveness" (Xolair® 150 mg solution—Summary of Product Characteristics 2014)—or indeed to establish whether Xolair® will work for a particular patient or whether a different treatment is necessitated; 3) it should not be for patients with high levels of IgE (for instance because the pathogenic species of the IgE/FcɛRI complex is not targeted and does not dissipate with time given the high levels of free IgE in the patient); 4) "Type I local or systemic reactions, including anaphylaxis and anaphylactic shock, may occur when taking omalizumab" (Xolair® 150 mg solution—Summary of Product Characteristics 2014); 5) its affinity for IgE is not particular good (approximately 2 nM).

It is an object of the present invention to identify novel antibodies to ameliorate one or more of these problems.

A further object is to identify antibodies against novel epitopes (with an increased IgE Cɛ2 interaction compared with omalizumab), and/or antibodies based on novel mutants of omalizumab with improved affinity and/or improved ability to disassociate the IgE/FcɛRI complex.

A still further object of the invention to identify new compounds, methods, and compositions for the treatment of disorders associated with IgE, in particular disorders associated with the complex of IgE/FcɛRI, for instance allergic disorders.

SUMMARY OF THE INVENTION

In one aspect of the invention an anti-IgE antibody, or antigen binding agent, is provided which contacts an epitope comprising residues T373, W374, S375, R376, A377, S378, G379, P381, Q417, C418, R419, T421, P426, R427, A428 of a Cɛ3 domain and residues D278 and T281 of a Cɛ2 domain of human IgE. In further embodiments the epitope may further comprise one or more of residues K380 and/or M430 of the Cɛ3 domain of human IgE and/or one or more of residues D276, V277, L279, S280, A282 and/or T298 of the Cɛ2 domain of human IgE.

The invention is based on the observations of the crystal structure of Example 1 which, for the first time, shows the interaction of an improved antibody (based on omalizumab) with IgE-Fc where significant interactions were observed with the IgE Cɛ2 domain in the region of mutation. This may result in improved functional characteristics of the anti-IgE antibody, or antigen binding agent, relative to omalizumab and/or omalizumab Fab. For instance, the anti-IgE antibody, or antigen binding agent, may be capable of disassociating human IgE from FcɛRI at concentrations (or peak serum concentrations) of less than 7, 3, 1, 0.66, 0.5 or 0.3 µM (for instance as carried out by the method described in Example 2). For instance, the anti-IgE antibody, or antigen binding agent, may have an improved/stronger affinity (lower $K_D$) for human IgE (for instance using IgE-Fc) (for example as carried out by the method described in Example 6) relative to omalizumab and/or omalizumab Fab; and/or an improved ability to disassociate the IgE/FcεRI complex (for instance as determined by the method described in Example 2), relative to omalizumab and/or omalizumab Fab; and/or a capability of disassociating human IgE from FcεRI at concentrations (or peak serum concentrations) lower than for omalizumab and/or omalizumab Fab (for instance as determined by the method described in Example 2). By an improved $K_D$ it is meant at least 5, 10, 20, 30, 40, or 50% lower than that of omalizumab and/or omalizumab Fab. The $K_D$ of the anti-IgE antibody, or antigen binding agent, of the invention may be less than 2, 1.9, 1.8, 1.7, 1.6, 1.5, 1.4, 1.3, 1.2, 1.1, 1.0, 0.9, 0.8, 0.7, 0.6, 0.5, 0.4, or 0.3 nM. By an improved ability or capability of disassociating human IgE from FcεRI it is meant at least 5, 10, 20, 30, 40, 50, or 100% improved over omalizumab and/or omalizumab Fab (for instance when measuring the % disassociation and/or apparent disassociation rate of the IgE/FcεRI complex as described in Examples 2 and 7), and/or the achievement of disassociation at a concentration where omalizumab and/or omalizumab Fab does not achieve disassociation.

For the avoidance of doubt, the anti-IgE antibody, or antigen binding agent, of the invention is not omalizumab or omalizumab Fab.

In one embodiment, the epitope is determined crystallographically (for Example as described in Example 1) by determining IgE residues within 4 or 5 Å of the anti-IgE antibody, or antigen binding agent, in a crystal structure of complexed IgE-Fc/anti-IgE antibody, or antigen binding agent. The IgE-Fc used may be as that of Seq. ID No. 108 (with the additional N265Q & N371Q mutations).

In one embodiment, the anti-IgE antibody, or antigen binding agent, at a particular binding site, contacts the epitope wherein the Cε3 domain and the Cε2 domain parts of the epitope are on different chains of the human IgE. IgE has two chains in the Fc domain each with a Cε3 domain and a Cε2 domain.

In one embodiment, the anti-IgE antibody, or antigen binding agent, at a particular binding site, contacts the epitope wherein the Cε3 domain and the Cε2 domain parts of the epitope are on the same chain of the human IgE.

For the avoidance of doubt, two anti-IgE antibodies, or antigen binding agents, of the invention may bind to human IgE, but only one of these needs interact with the epitope of the invention comprising Cε3 and Cε2 domains (the other may only interact with the other Cε3 domain for instance).

In one embodiment (optionally further adopting the features of the first aspect of the invention) the anti-IgE antibody, or antigen binding agent, is specific for said epitope comprising residues T373, W374, S375, R376, A377, S378, G379, P381, Q417, C418, R419, T421, P426, R427, A428 of a Cε3 domain and residues D278 and T281 of a Cε2 domain of human IgE. Optionally, said the epitope may further comprise one or more of residues K380 and/or M430 of the Cε3 domain of human IgE and/or one or more of residues D276, V277, L279, S280, A282 and/or T298 of the Cε2 domain of human IgE. For the avoidance of doubt, the anti-IgE antibody, or antigen binding agent is specific for said epitope if it recognizes and binds to the specific human IgE structure comprising said epitope rather than to human IgE generally.

In a further aspect (optionally further adopting the features of the first aspect of the invention) there is provided an anti-IgE antibody, or antigen binding agent, comprising a heavy chain variable region comprising a complementarity determining region, CDR-H3, with an amino acid sequence which is Seq. ID No. 18, and a light chain variable region comprising a complementarity determining region, CDR-L1, with an amino acid sequence which is Seq. ID No. 29, wherein the light chain variable region further comprises a framework region, FR-L3, with an amino acid sequence selected from Seq. ID No. 32 which has one, two, three, four, five, six, seven or more amino acid substitutions to strengthen the interaction of the anti-IgE antibody, or antigen binding agent, with the Cε2 domain of human IgE.

In a further aspect (optionally further adopting the features of the previous aspects of the invention) there is provided an anti-IgE antibody, or antigen binding agent, comprising a heavy chain variable region comprising a complementarity determining region, CDR-H3, with an amino acid sequence which is Seq. ID No. 18, and a light chain variable region comprising a complementarity determining region, CDR-L1, with an amino acid sequence which is Seq. ID No. 29, wherein the light chain variable region further comprises a framework region, FR-L1, with an amino acid sequence which is Seq. ID No. 28 which has one, two, three, four, five, six, seven or more amino acid substitutions to strengthen the interaction of the anti-IgE antibody, or antigen binding agent, with the Cε2 domain of human IgE.

Where the CDR-H3 and CDR-L1 regions anchor and orientate the anti-IgE antibody, or antigen binding agent, on IgE Cε3 region (as per omalizumab), the change(s) to the FR-L3 and/or FR-L1 sequences allow a stronger interaction with the Cε2 domain of human IgE. The stronger interaction of the mutant relative to omalizumab or omalizumab Fab may be assessed through affinity measurements [lower $K_D$] (for instance as carried out by the method described in Example 6) and/or the characteristic of improved disassociation of the IgE/FcεRI complex (for instance as determined by the method described in Example 2).

The stronger interaction of the anti-IgE antibody, or antigen binding agent, with the Cε2 domain of human IgE may be characterised by improved functional characteristics of the anti-IgE antibody, or antigen binding agent, relative to omalizumab and/or omalizumab Fab. For instance, the anti-IgE antibody, or antigen binding agent, may be capable of disassociating human IgE from FcεRI at concentrations (or peak serum concentrations) of less than 7, 3, 1, 0.66, 0.5 or 0.3 μM (for instance as carried out by the method described in Example 2). For instance, the anti-IgE antibody, or antigen binding agent, may have an improved/stronger affinity (lower $K_D$) for human IgE (for instance using IgE-Fc) (for example as carried out by the method described in Example 6) relative to omalizumab and/or omalizumab Fab; and/or an improved ability to disassociate the IgE/FcεRI complex (for instance as determined by the method described in Example 2), relative to omalizumab and/or omalizumab Fab; and/or a capability of disassociating human IgE from FcεRI at concentrations (or peak serum concentrations) lower than for omalizumab and/or omalizumab Fab (for instance as determined by the method described in Example 2). By an improved $K_D$ it is meant at least 5, 10, 20, 30, 40, or 50% lower than that of omalizumab and/or omalizumab Fab. The $K_D$ of the anti-IgE antibody, or antigen binding agent, of the invention may be less than 2, 1.9, 1.8, 1.7, 1.6, 1.5, 1.4, 1.3, 1.2, 1.1, 1.0, 0.9, 0.8, 0.7, 0.6, 0.5, 0.4, or 0.3 nM. By an improved ability or capability of disassociating human IgE from FcεRI it is meant at least 5, 10, 20, 30, 40, 50, or 100% improved over omalizumab and/or omalizumab Fab (for instance when measuring the % disassociation and/or apparent disassociation rate of the IgE/FcεRI complex as described in Examples 2 and 7), and/or the achievement of disassociation at a concentration where omalizumab and/or omalizumab Fab does not achieve disassociation.

For the avoidance of doubt, the anti-IgE antibody, or antigen binding agent, of the invention is not omalizumab or omalizumab Fab.

In one embodiment, the FR-L3 region is mutated, with reference to SEQ ID NO; 129, at one or more of position S60, S63, S76, S77, and/or Q79 (Kabat) to one of the other natural amino acids.

For instance, the FR-L3 region may be mutated at position S60 (Kabat) to one of the other natural amino acids, for instance to M, R, K, N, Q or T, in particular M.

For instance, the FR-L3 region may be mutated at position S63 (Kabat) to one of the other natural amino acids, for instance W or Y, in particular Y.

For instance, the FR-L3 region may be mutated at position S76 (Kabat) to one of the other natural amino acids, in particular N.

For instance, the FR-L3 region may be mutated at position S77 (Kabat) to one of the other natural amino acids, for instance R or K, in particular R.

For instance, the FR-L3 region may be mutated at position Q79 (Kabat) to one of the other natural amino acids, for instance R or K, in particular R.

For instance, the FR-L1 region may be mutated, with reference to SEQ ID NO: 20, on G16 and/or R18 (Kabat) to one of the other natural amino acids.

In certain embodiments, the amino acid sequence of the mutated FR-L3 region of the anti-IgE antibody, or antigen binding agent, is selected from Seq. ID No. 43-49, 60-83, 131 or 138.

In a further embodiment, the FR-L3 region is further mutated, with reference to SEQ ID NO: 129, at position S67 (Kabat) to one of the other natural amino acids to improve its affinity (lower $K_D$) for human IgE. In this case the mutation may be strengthening the interaction of the anti-IgE antibody, or antigen binding agent, for the Cε3 domain of IgE. For instance, the FR-L3 region may be mutated at position S67 (Kabat) to M (in particular), E, or D. In certain embodiments, the amino acid sequence of the mutated FR-L3 region of the anti-IgE antibody, or antigen binding agent, is selected from Seq. ID No. 53-59, 84-107, 131 or 138.

The anti-IgE antibody, or antigen binding agent, of the invention may have the light chain variable region further comprising a complementarity determining region, CDR-L2, with an amino acid sequence which is Seq. ID No. 31.

In one embodiment, the CDR-L2 region is mutated at position S52 (Kabat) to one of the other natural amino acids to improve its affinity (lower $K_D$) for human IgE. In this case the mutation may be strengthening the interaction of the anti-IgE antibody, or antigen binding agent, for the Cε3 domain of IgE. For instance, the CDR-L2 region may be mutated, with reference to SEQ ID NO: 129, at position S52 (Kabat) to D (in particular), E, Q or R. In certain embodiments the amino acid sequence of the mutated CDR-L2 region is selected from Seq. ID No. 50 or Seq. ID No. 51.

The anti-IgE antibody, or antigen binding agent, of the invention may have the heavy chain variable region further comprising a complementarity determining region, CDR-H1, with an amino acid sequence which is Seq. ID No. 14.

The anti-IgE antibody, or antigen binding agent, of the invention may have the heavy chain variable region further comprising a complementarity determining region, CDR-H2, with an amino acid sequence which is Seq. ID No. 16.

The anti-IgE antibody, or antigen binding agent, of the invention may have the light chain variable region further comprising a complementarity determining region, CDR-L3, with an amino acid sequence which is Seq. ID No. 33.

The anti-IgE antibody, or antigen binding agent, of the invention may have the heavy chain variable region further comprising a framework region, FR-H1, with an amino acid sequence which is Seq. ID No. 13.

The anti-IgE antibody, or antigen binding agent, of the invention may have the heavy chain variable region further comprising a framework region, FR-H2, with an amino acid sequence which is Seq. ID No. 15.

The anti-IgE antibody, or antigen binding agent, of the invention may have the heavy chain variable region further comprising a framework region, FR-H3, with an amino acid sequence which is Seq. ID No. 17.

The anti-IgE antibody, or antigen binding agent, of the invention may have the heavy chain variable region further comprising a framework region, FR-H4, with an amino acid sequence which is Seq. ID No. 19.

The anti-IgE antibody, or antigen binding agent, of the invention may have the light chain variable region further comprising a framework region, FR-L2, with an amino acid sequence which is Seq. ID No. 30.

The anti-IgE antibody, or antigen binding agent, of the invention may have the light chain variable region further comprising a framework region, FR-L4, with an amino acid sequence which is Seq. ID No. 34.

The anti-IgE antibody, or antigen binding agent, of the invention may have the light chain variable region, VL, having an amino acid sequence selected from Seq. ID No. 35, Seq. ID No. 132 or Seq ID No. 134 or Seq. ID No. 141 or Seq ID No. 144, or Seq ID No. 145 or Seq ID No. 158 or Seq ID No. 159.

The anti-IgE antibody, or antigen binding agent, of the invention may have the heavy chain variable region, VH, having an amino acid sequence which is Seq. ID No. 1.

The anti-IgE antibody, or antigen binding agent, of the invention may further comprise a light chain constant region.

The anti-IgE antibody, or antigen binding agent, of the invention may have a light chain constant region which is a kappa constant region.

The anti-IgE antibody, or antigen binding agent, of the invention may have the light chain constant region having a mutation L154P (Kabat).

The anti-IgE antibody, or antigen binding agent, of the invention may have the light chain variable region and light chain constant region, VL-CL, having an amino acid sequence selected from Seq. ID No. 39, or Seq. ID No. 41, or Seq. ID No. 117, or Seq. ID No. 119, or Seq. ID No. 125, or Seq. ID No. 127, or Seq. ID No. 136 or Seq. ID No. 143, optionally comprising a signal sequence which has an amino acid sequence which is Seq ID No. 160.

The anti-IgE antibody, or antigen binding agent, of the invention may further comprise a heavy chain constant region, CH1.

The anti-IgE antibody, or antigen binding agent, of the invention may have the heavy chain variable region and heavy chain constant region, VH-CH1, having an amino acid sequence which is Seq. ID No. 5.

The anti-IgE antibody, or antigen binding agent, of the invention may further comprise a heavy chain Fc region, Fc.

The anti-IgE antibody, or antigen binding agent, of the invention may have an Fc which is from human IgG1 or human IgG4.

The anti-IgE antibody, or antigen binding agent, of the invention may have the heavy chain variable region, heavy chain constant region and heavy chain Fc region, VH-CH1-Fc, having an amino acid sequence which is Seq. ID No. 9.

In a further aspect of the invention there is provided an anti-IgE antibody, or antigen binding agent, comprising a heavy chain variable region comprising a complementarity determining region, CDR-H3, with an amino acid sequence which is Seq. ID No. 18, and a light chain variable region comprising a complementarity determining region, CDR-L1, with an amino acid sequence which is Seq. ID No. 29, wherein:
 a. the light chain variable region further comprises a framework region, FR-L3, with an amino acid sequence which is Seq. ID No. 32, wherein the FR-L3 region is mutated, with reference to SEQ ID NO: 129, at position S67 (Kabat) to one of the other natural amino acids to improve the affinity (lower $K_D$) of the anti-IgE antibody, or antigen binding agent, for human IgE; and/or
 b. the light chain variable region further comprises a complementarity determining region, CDR-L2, with an amino acid sequence which is Seq. ID No. 31, wherein the CDR-L2 region is mutated, with reference to SEQ ID NO: 129, at position S52 (Kabat) to one of the other natural amino acids to improve the affinity (lower $K_D$) of the anti-IgE antibody, or antigen binding agent, for human IgE.

The present inventors, have found herein that either or both of these mutations may surprisingly improve the affinity (improved or lower $K_D$) of an anti-IgE antibody, or antigen binding agent, based on omalizumab or omalizumab Fab, for human IgE (for instance using IgE-Fc) (for example as carried out by the method described in Example 6). In particular, the improvement in affinity is relative to omalizumab and/or omalizumab Fab. The mutations may improve the interaction with the Cε3 domain of IgE. By an improved or lower $K_D$ it is meant at least 5, 10, 20, 30, 40, or 50% lower than that of omalizumab and/or omalizumab Fab. The $K_D$ of the anti-IgE antibody, or antigen binding agent, of the invention may be less than 2, 1.9, 1.8, 1.7, 1.6, 1.5, 1.4, 1.3, 1.2, 1.1, 1.0, 0.9, 0.8, 0.7, 0.6, 0.5, 0.4, or 0.3 nM.

For instance, the FR-L3 region may be mutated, with reference to SEQ ID NO: 129, at position S67 (Kabat) to M (in particular), E, or D.

In certain embodiments, the amino acid sequence of the mutated FR-L3 region of the anti-IgE antibody, or antigen binding agent, is selected from Seq. ID No. 52-59, 84-107, 131 or 138.

For instance, the CDR-L2 region may be mutated, with reference to SEQ ID NO: 129, at position S52 (Kabat) to D (in particular), E, Q or R.

In certain embodiments, the amino acid sequence of the mutated CDR-L2 region of the anti-IgE antibody, or antigen binding agent, is selected from Seq. ID No. 50 (in particular) or Seq. ID No. 51.

The anti-IgE antibody, or antigen binding agent, may have the heavy chain variable region further comprising a complementarity determining region, CDR-H1, with an amino acid sequence which is Seq. ID No. 14.

The anti-IgE antibody, or antigen binding agent, may have the heavy chain variable region further comprising a complementarity determining region, CDR-H2, with an amino acid sequence which is Seq. ID No. 16.

The anti-IgE antibody, or antigen binding agent, may have the light chain variable region further comprising a complementarity determining region, CDR-L3, with an amino acid sequence which is Seq. ID No. 33.

The anti-IgE antibody, or antigen binding agent, may have the heavy chain variable region further comprising a framework region, FR-H1, with an amino acid sequence which is Seq. ID No. 13.

The anti-IgE antibody, or antigen binding agent, may have the heavy chain variable region further comprising a framework region, FR-H2, with an amino acid sequence which is Seq. ID No. 15.

The anti-IgE antibody, or antigen binding agent, may have the heavy chain variable region further comprising a framework region, FR-H3, with an amino acid sequence which is Seq. ID No. 17.

The anti-IgE antibody, or antigen binding agent, may have the heavy chain variable region further comprising a framework region, FR-H4, with an amino acid sequence which is Seq. ID No. 19.

The anti-IgE antibody, or antigen binding agent, may have the light chain variable region further comprising a framework region, FR-L2, with an amino acid sequence which is Seq. ID No. 30.

The anti-IgE antibody, or antigen binding agent, may have the light chain variable region further comprising a framework region, FR-L4, with an amino acid sequence which is Seq. ID No. 34.

The anti-IgE antibody, or antigen binding agent, may have the light chain variable region, VL, comprising consecutive FR-L1, CDR-L1, FR-L2, CDR-L2, FR-L3, CDR-L3, and FR-L4 regions, and having an amino acid sequence which is Seq. ID No. 20, except that the CDR-L2 region has an amino acid sequence selected from Seq. ID No. 50 (in particular) or Seq. ID No. 51.

The anti-IgE antibody, or antigen binding agent, may have the light chain variable region, VL, comprising consecutive FR-L1, CDR-L1, FR-L2, CDR-L2, FR-L3, CDR-L3, and FR-L4 regions, and having an amino acid sequence which is Seq. ID No. 20, except that the FR-L3 region has an amino acid sequence which is Seq. ID No. 52.

The anti-IgE antibody, or antigen binding agent, may have the light chain variable region, VL, comprising consecutive FR-L1, CDR-L1, FR-L2, CDR-L2, FR-L3, CDR-L3, and FR-L4 regions, and having an amino acid sequence which is Seq. ID No. 20, except that the CDR-L2 region has an amino acid sequence selected from Seq. ID No. 50 (in particular) or Seq. ID No. 51, and the FR-L3 region has an amino acid sequence which is selected from Seq. ID No. 52, 131 or 138.

The anti-IgE antibody, or antigen binding agent, of the invention may have the heavy chain variable region, VH, having an amino acid sequence which is Seq. ID No. 1.

The anti-IgE antibody, or antigen binding agent, may further comprise a light chain constant region.

The anti-IgE antibody, or antigen binding agent, may have a light chain constant region which is a kappa constant region.

The anti-IgE antibody, or antigen binding agent, may have the light chain variable region and light chain constant region, VL-CL, having an amino acid sequence which is Seq. ID No. 24, except that the CDR-L2 region has an amino acid sequence selected from Seq. ID No. 50 (in particular) or Seq. ID No. 51.

The anti-IgE antibody, or antigen binding agent, may have the light chain variable region and light chain constant region, VL-CL, having an amino acid sequence which is Seq. ID No. 24, except that the FR-L3 region has an amino acid sequence which is Seq. ID No. 52.

The anti-IgE antibody, or antigen binding agent, may have the light chain variable region and light chain constant region, VL-CL, having an amino acid sequence which is Seq. ID No. 24, except that the CDR-L2 region has an amino acid sequence selected from Seq. ID No. 50 (in particular) or Seq. ID No. 51, and the FR-L3 region has an amino acid sequence which is selected from Seq. ID No. 52, 131 or 138. In a further aspect, the invention provides for an anti-IgE antibody, or antigen binding agent, comprising a heavy chain variable region and a light chain variable region, wherein:
a. the heavy chain variable region comprises a CDR-H1 with an amino acid sequence which is Seq ID No. 14, a CDR-H2 with an amino acid sequence which is Seq ID No. 16 and a CDR-H3 with an amino acid sequence which is Seq ID No. 18 and the light chain variable region comprises CDR-L1 with an amino acid sequence which is Seq ID No. 29, a CDR-L2 with an amino acid sequence which is Seq ID No. 50, a CDR-L3 with an amino acid sequence which is Seq ID No. 33 and a framework region FW-L3 with an amino acid sequence which is Seq ID No. 131 or 138; or
b. the heavy chain variable region comprises an amino acid sequence which is Seq ID No. 1 and the light chain variable region comprises an amino acid sequence selected from Seq ID No. 132 or 139.

In one embodiment, the anti-IgE antibody, or antigen binding agent may further comprise a light chain constant region, wherein the light chain variable region and the light chain constant region VL-CL have an amino acid sequence selected from Seq ID No. 136 or 143, optionally comprising a signal sequence which has an amino acid sequence which is Seq ID No. 160.

The anti-IgE antibody, or antigen binding agent, in all embodiments as described herein may further comprise a heavy chain constant region, CH1.

The anti-IgE antibody, or antigen binding agent, may have the heavy chain variable region and heavy chain constant region, VH-CH1, having an amino acid sequence which is Seq. ID No. 5.

The anti-IgE antibody, or antigen binding agent, may further comprise a heavy chain Fc region, Fc.

The anti-IgE antibody, or antigen binding agent, may have the Fc from human IgG1 or human IgG4.

The anti-IgE antibody, or antigen binding agent, may have the heavy chain variable region, heavy chain constant region and heavy chain Fc region, VH-CH1-Fc, having an amino acid sequence which is Seq. ID No. 9.

The anti-IgE antibody, or antigen binding agent, of all aspects of the invention may be selected from the group consisting of: a complete antibody molecule having full length heavy and light chains, or a fragment thereof.

The anti-IgE antibody, or antigen binding agent, of the invention may be elected from the group consisting of: a Fab fragment, modified Fab' fragment, Fab' fragment, F(ab')$_2$ fragment, Fv, scFv, scab, a diabody, bispecific antibody, triabody, FabFv, Fab-Fv-Fv, tribody, or a (Fab-Fv)$^2$-Fc. Without being bound by theory, an anti-IgE antibody, or antigen binding agent, of the invention may have less anaphylaxis risk associated with it if it has only one rather than multiple anti-IgE antigen binding sites.

In one embodiment, the anti-IgE antibody is a Fab fragment linked directly or via a linker to a scFv that binds to a serum carrier protein, such as human serum albumin.

In one embodiment the scFv may comprise a heavy chain variable region and a light chain variable region, preferably linked via a linker having Seq. ID No. 151, wherein the heavy chain variable region comprises a CDR-H1 with an amino acid sequence which is Seq ID No. 152, a CDR-H2 with an amino acid sequence which is Seq ID No. 153 and a CDR-H3 with an amino acid sequence which is Seq ID No. 154 and the light chain variable region comprises CDR-L1 with an amino acid sequence which is Seq ID No. 155, a CDR-L2 with an amino acid sequence which is Seq ID No. 156, a CDR-L3 with an amino acid sequence which is Seq ID No. 157.

In one embodiment the scFv has an amino acid sequence which is Seq ID No. 150. In one preferred embodiment, the Fab fragment comprises a heavy chain variable region and a light chain variable region, wherein:
a. the heavy chain variable region comprises a CDR-H1 with an amino acid sequence which is Seq ID No. 14, a CDR-H2 with an amino acid sequence which is Seq ID No. 16 and a CDR-H3 with an amino acid sequence which is Seq ID No. 18 and the light chain variable region comprises CDR-L1 with an amino acid sequence which is Seq ID No. 29, a CDR-L2 with an amino acid sequence which is Seq ID No. 50, a CDR-L3 with an amino acid sequence which is Seq ID No. 33 and a framework region FW-L3 with an amino acid sequence which is Seq ID No. 131 or 138; or
b. the heavy chain variable region comprises an amino acid sequence which is Seq ID No. 1 and the light chain variable region comprises an amino acid sequence selected from Seq ID No. 132 or 139.

In another embodiment, the Fab fragment further comprises a heavy chain constant region and a light chain constant region, wherein the heavy chain variable region and the heavy chain constant region VL-CH1 has an amino acid sequence which is Seq ID No. 5 and wherein the light chain variable region and the light chain constant region VL-CL has an amino acid sequence selected from Seq ID No. 136 or 143, optionally comprising a signal sequence which has an amino acid sequence which is Seq ID No. 160.

In another embodiment scFv is linked to the CH1 of the Fab fragment via a linker having amino acid sequence which is Seq ID No. 149.

In one embodiment, the heavy chain variable region and the heavy chain constant region, the linker and the scFv has an amino acid sequence which is Seq ID No. 147, optionally comprising a signal sequence which has an amino acid sequence which is Seq ID No. 160.

In one other embodiment the heavy chain of the Fab fragment linked to the scFv with Seq. ID No. 147 is paired with a light chain variable and constant region which has Seq ID No. 136 or 143.

The anti-IgE antibody, or antigen binding agent, of the invention may have an effector or a reporter molecule attached to it.

The anti-IgE antibody, or antigen binding agent, of the invention may be glycosylated (for instance within the Fc domain) and/or may be conjugated to a polymer selected from starch, albumin, and polyethylene glycol (PEG). In one embodiment, conjugated PEG may have a molecular weight in the range 5 to 50 kDa.

The anti-IgE antibody, or antigen binding agent, of the invention may be humanized.

A further aspect of the invention relates to an isolated DNA sequence encoding the heavy and/or light chain(s) of the anti-IgE antibody, or antigen binding agent, of the invention. Further provided is a cloning or expression vector comprising one or more DNA sequences of the invention. For instance, a cloning or expression vector may comprise one or more DNA sequences selected from Seq. ID No. 36, Seq. ID No. 38, Seq. ID No. 40, or Seq. ID No. 42, or Seq. ID No. 133, or Seq ID No. 135, or Seq ID No. 137, or Seq ID No. 140, or Seq. ID No. 142, or Seq ID No. 144 and, optionally, may further comprise one or more DNA sequences selected from Seq. ID No. 2, Seq. ID No. 4, Seq. ID No. 6, Seq. ID No. 8, Seq. ID No. 10, or Seq. ID No. 12 or Seq. ID No. 148.

A further aspect of the invention is a host cell comprising one or more cloning or expression vectors of the invention. The host cell of the invention may optionally further comprise one or more cloning or expression vectors comprising one or more DNA sequences selected from Seq. ID No. 2, Seq. ID No. 4, Seq. ID No. 6, Seq. ID No. 8, Seq. ID No. 10, or Seq. ID No. 12 or Seq ID No. 148.

A process for the production of the anti-IgE antibody, or antigen binding agent, of the invention is also provided, comprising culturing the host cell of the invention and isolating the anti-IgE antibody, or antigen binding agent.

A further aspect relates to a pharmaceutical composition comprising the anti-IgE antibody, or antigen binding agent, of the invention, in combination with one or more of a pharmaceutically acceptable excipient, diluent or carrier. Suitably, the anti-IgE antibody, or antigen binding agent, of the invention is present at a dose of 50-200, preferably around or exactly 150 mg per mL diluent. In certain embodiments, the excipient comprises one or both of L-arginine, L-histidine. The excipient may separately or in combination comprise Polysorbate 20. The diluent may be water or an aqueous isotonic solution.

The pharmaceutical composition of the invention may be carried within a sterile vial as a powder for reconstitution prior to subcutaneous administration, or within a sterile syringe for its immediate subcutaneous administration.

The pharmaceutical composition of the invention may contain a total dose of anti-IgE antibody, or antigen binding agent, of 75-600 mg—for instance around or exactly 100 or 150 mg.

The pharmaceutical composition of the invention may additionally comprise other active ingredients either contained together with the anti-IgE antibody, or antigen binding agent, or for separate coadministration with the anti-IgE antibody, or antigen binding agent. For instance, the pharmaceutical composition of the invention may be used in the context of allergy-based specific immunotherapy, where the anti-IgE antibody, or antigen binding agent, of the invention is separately coadministered (but may be co-packaged) with an allergen. The pharmaceutical composition of the invention may thus be for use in allergy-based specific immunotherapy, where the patient receives the pharmaceutical composition of the invention 7, 6, 5, 4, 3, 2, or 1 days before (or on the same day) as the therapeutic allergen.

The anti-IgE antibody, or antigen binding agent, or composition, of the invention may be for use as a medicament.

The anti-IgE antibody, or antigen binding agent, or composition, of the invention may be for use in the treatment or prevention of disease.

The anti-IgE antibody, or antigen binding agent, or composition, of the invention may be for use in the treatment or prevention of disorders associated with the complex of human IgE and FcεRI.

The anti-IgE antibody, or antigen binding agent, or composition, of the invention may be for use in the treatment or prevention of disorders through the disassociation of the complex of human IgE and FcεRI and the binding of human IgE by the anti-IgE antibody, or antigen binding agent.

The anti-IgE antibody, or antigen binding agent, or composition, of the invention may be for use in the treatment or prevention of one or more of: allergy; allergic asthma; severe asthma; moderate asthma; chronic spontaneous urticaria; chronic idiopathic urticaria; perennial allergic rhinitis; seasonal allergic rhinitis; acute asthma exacerbations; acute bronchospasm; status asthmaticus; hyper IgE syndrome; allergic bronchopulmonary aspergillosis; prevention of anaphylactic reactions; food allergy; atopic dermatitis; allergic rhinitis; bee venom sensitivity; idiopathic anaphylaxis; peanut allergy; latex allergy; inflammatory skin diseases; urticaria (solar, cold-induced, local heat-induced, and/or delayed pressure-induced); cutaneous mastocytosis; systemic mastocytosis; eosinophil-associated gastrointestinal disorder; bullous pemphigoid; interstitial cystitis; nasal polyps; idiopathic angioedema; or non-allergic asthma.

Further provided is a method for the treatment or prevention of a disease in a human subject, the method comprising administering to the subject an effective amount of the anti-IgE antibody, or antigen binding agent, or a composition of the invention. The method may be for the treatment or prevention of disorders associated with the complex of human IgE and FcεRI. The method of the invention may treat or prevent disease through the disassociation of the complex of human IgE and FcεRI and the binding of human IgE by the anti-IgE antibody, or antigen binding agent of the invention.

The method of the invention may be for the treatment or prevention of one or more of: allergy; allergic asthma; severe asthma; moderate asthma; chronic spontaneous urticaria; chronic idiopathic urticaria; perennial allergic rhinitis; seasonal allergic rhinitis; acute asthma exacerbations; acute bronchospasm; status asthmaticus; hyper IgE syndrome; allergic bronchopulmonary aspergillosis; prevention of anaphylactic reactions; food allergy; atopic dermatitis; allergic rhinitis; bee venom sensitivity; idiopathic anaphylaxis; peanut allergy; latex allergy; inflammatory skin diseases; urticaria (solar, cold-induced, local heat-induced, and/or delayed pressure-induced); cutaneous mastocytosis; systemic mastocytosis; eosinophil-associated gastrointestinal disorder; bullous pemphigoid; interstitial cystitis; nasal polyps; idiopathic angioedema; or non-allergic asthma.

In the present invention, it has been elucidated that an antibody or an antigen binding agent against a first polypeptide, which polypeptide elicits its physiological response by virtue of binding to a second polypeptide (such as a receptor), is capable of binding to both the free and bound first polypeptide, stabilising a conformation of such first polypeptide. Such stabilised conformation has a binding affinity for the second polypeptide weaker than in the absence of the antibody or antigen binding agent hence, triggering faster dissociation of the first polypeptide from the second polypeptide.

In this respect, the invention provides a further aspect which relates to an antibody or an antigen binding agent, capable of binding free and FcεRI bound human IgE and stabilising a conformation of IgE. When the IgE is in such conformation, it has a binding affinity for FcεRI weaker than in the absence of the antibody or antigen binding agent and wherein the FcεRI bound human IgE dissociates from FcεRI. Optionally, when the IgE is in such conformation, the IgE has a lower binding affinity for omalizumab or a fragment thereof than the antibody or antigen binding agent of the invention. For example, the antibody or antigen binding agent is an antibody as described herein.

In a further aspect, the invention relates to a process for selecting such antibodies or antigen binding agents as described herein. The process comprises:

a. Contacting a test antibody or antigen binding agent with a sample comprising human IgE bound to human FcεRI;
b. Measuring the constant of dissociation of the test antibody or antigen binding agent for dissociation the human IgE from human FcεRI;
c. Comparing the constant of dissociation as measured in step b) with the constant of dissociation of omalizumab or a fragment thereof for dissociating the human IgE from to human FcεRI;
d. Selecting the antibody or antigen binding agent if said antibody or antigen binding agent dissociates the IgE from FcεRI faster than omalizumab or a fragment thereof.

Alternatively, the process for selecting antibodies or antigen binding agents according to the invention comprises:
a. Contacting a test antibody or antigen binding agent with a sample comprising human IgE bound to human FcεRI;
b. Measuring the binding affinity of the test antibody or antigen binding agent for human IgE from human FcεRI;
c. Comparing the binding affinity as measured in step b) with the binding affinity of human IgE for FcεRI;
d. Selecting the antibody or antigen binding agent if said antibody or antigen binding agent has a higher binding affinity for IgE than the IgE for FcεRI.

Optionally, the selected antibodies or antigen binding agents cause the IgE, whilst still bound to FcεRI, to adopt a conformation wherein the IgE in said stabilised conformation may dissociate from FcεRI faster than the IgE bound to FcεRI in the presence of omalizumab or a fragment thereof; and/or may have a binding affinity higher for the antibody or antigen binding agent than for the FcεRI.

In a final aspect, the present invention relates to specific antibodies or antigen binding agent comprising:
a. a heavy chain variable region comprising Seq. ID No.: 1 and a light chain variable region comprising:
   i. Seq. ID No.: 109; or
   ii. Seq. ID No.: 113; or
   iii. Seq. ID No.: 121; or
   iv. Seq. ID No.: 132; or
   v. Seq. ID No.: 139; or
b. Seq. ID No.: 5 and
   i. Seq. ID No.: 24, wherein S77 and S79 are replaced by Q;
   ii. Seq. ID No.: 117 or
   iii. Seq. ID No.: 125; or
   iv. Seq. ID No.: 136; or
   v. Seq. ID No.: 143.

In one embodiment of this last aspect of the invention, the anti-IgE antibody or antigen binding agent contacts or, contacts and is specific for, an epitope comprising, with reference to SEQ ID NO: 108, residues T373, W374, S375, R376, A377, S378, G379, P381, Q417, C418, R419, T421, P426, R427, A428 of a Cε3 domain and residues D278 and T281 of a Cε2 domain of human IgE.

BRIEF DESCRIPTION OF THE DRAWINGS

References and SEQ IDs are found in the Examples referring to the Figures.

FIG. 16. Residues 224 to 547 of wild-type human IgE-Fc sequence (as shown in SEQ ID NO: 108) with residues 224 and 547 shown in bold. The numbering is according to Dorrington and Bennich (1978) Immunol. Rev. 41:3-25, whereby the L (Leu; leucine) after L253 is numbered as L235a (boxed) and the subsequent residue is C254. The remaining residues are numbered consecutively with no further additions. The epitope residues are shown with an asterisk (*).

DETAILED DESCRIPTION OF THE INVENTION

Figure 1:
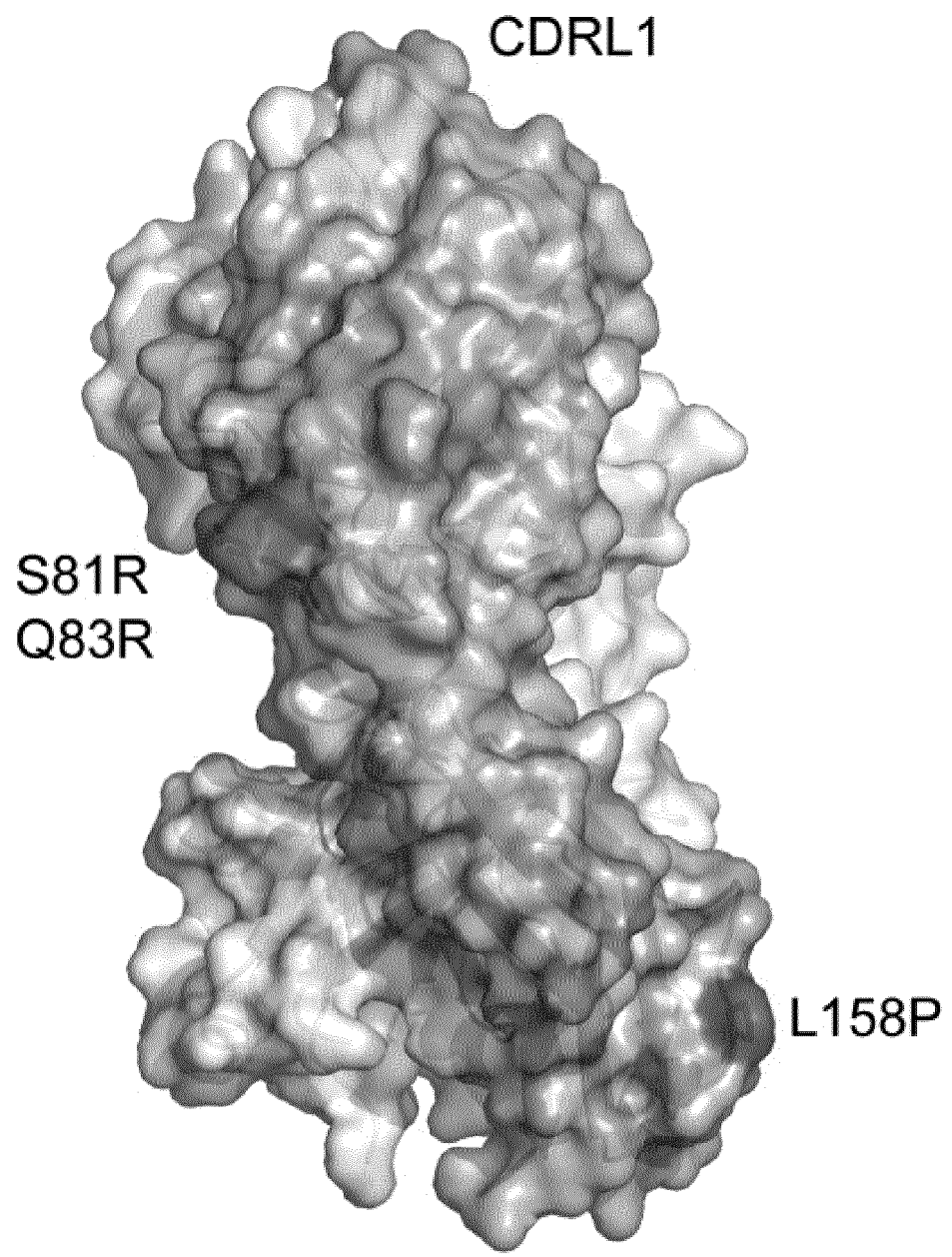
FIG. 1. omalizumab Fab3 contains three point mutations. omalizumab Fab3 is derived from omalizumab, and contains three point mutations distal to the antigen binding CDRs, two in the VL domain framework region (Ser81 Arg, Gln83Arg) and one in the Cκ domain (Leu158Pro). The heavy and light chains are colored white and blue, respectively. The mutated residues are colored red, and CRDL1 in green, to indicate the orientation of the Fab.

Antibody amino acid numbering herein will either be from the consecutive amino acid sequence of an antibody (for instance omalizumab comprising VII sequence of Seq. ID No. 1 and VL sequence of Seq. ID No. 20 or SEQ ID NO: 129)—the so called "pdb" numbering—or may utilize the common Kabat numbering scheme. Where the common immunoglobulin parts (CDRs—complementarity determining regions, or FRs—framework regions) of a VH or VL sequence are described, they are linked in the standard order (VH=FR-H1.CDR-H1.FR-H2.CDR-H2.FR-H3.CDR-H3.FR-H4; VL=FR-L1.CDR-L1.FR-L2.CDR-L2.FR-L3.CDR-L3.FR-L4). For omalizumab "pdb" numbering of VH (Seq. ID No. 1) parts is: FR-H1 (amino acids 1-25), CDR-H1 (26-36), FR-H2 (37-50), CDR-H2 (51-66), FR-H3 (67-98), CDR-H3 (99-110), FR-H4 (111-121); whereas Kabat numbering is: FR-H1 (amino acids 1-25), CDR-H1 (26-35), FR-H2 (36-49), CDR-H2 (50-65), FR-H3 (66-94), CDR-H3 (95-102), FR-H4 (103-113). For omalizumab "pdb" numbering of VL (Seq. ID No. 20) parts is: FR-L1 (amino acids 1-23), CDR-L1 (24-38), FR-L2 (39-53), CDR-L2 (54-60), FR-L3 (61-92), CDR-L3 (93-101), FR-L4 (102-111); whereas Kabat numbering is: FR-L1 (amino acids 1-23), CDR-L1 (24-34), FR-L2 (35-49), CDR-L2 (50-56), FR-L3 (57-88), CDR-L3 (89-97), FR-LA (98-107).

IgE antibody numbering is as reported by Dorrington & Bennich (1978) Immunol. Rev. 41:3-25. Thus, the IgE-Fc polypeptides used in this invention (see Seq. ID No. 108) are from V224-K547 (including a C225A mutation). As shown in FIG. 16, the numbering followed is according to Dorrington and Bennich (1978) Immunol. Rev. 41:3-25 where the L (Leu, leucine) following position 253 is numbered L253a and the remaining residues are numbered consecutively from L253a as C254 etc. In the crystallography experiments the following mutations were also inserted into the IgE-Fc to simplify the glycosylation pattern: N265Q & N371Q. The Cε2 region of IgE-Fc is generally accepted to occupy the sequence 5226-D330. Reference to IgE herein may be a reference to human IgE (and vice versa), and may also constitute a reference to IgE-Fc in the context of the assays and methods described herein. The sequence of the Fab arms of the full length human IgE antibody are not included in this description as they are not present in the crystal structures.

Herein reference to "omalizumab" is a reference to the commercially-sold Xolair® product; or to an IgG full-length antibody comprising a heavy chain comprising the VH amino acid sequence which is Seq. ID No. 1, and a light chain comprising the VL amino acid sequence which is Seq. ID No. 20; or to an IgG full-length antibody comprising a heavy chain comprising the VH-CH1 amino acid sequence which is Seq. ID No. 5, and a light chain comprising the VL-CL amino acid sequence which is Seq. ID No. 24; or to an IgG full-length antibody comprising a heavy chain comprising the VH-CH1-Fc amino acid sequence which is Seq. ID No. 9, and a light chain comprising the VL-CL amino acid sequence which is Seq. ID No. 24. Reference to "omalizumab Fab" is a reference to a Fab fragment comprising a heavy chain comprising the VH amino acid sequence which is Seq. ID No. 1, and a light chain comprising the VL amino acid sequence which is Seq. ID No. 20; or (in particular) to a Fab fragment comprising a heavy chain comprising the VH-CH1 amino acid sequence which is Seq. ID No. 5, and a light chain comprising the VL-CL amino acid sequence which is Seq. ID No. 24.

General Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics, and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques may be performed according to manufacturer's specifications, as commonly accomplished in the art or as described herein. The nomenclatures used in connection with, and the laboratory procedures and techniques of, analytical chemistry, synthetic organic chemistry, and medicinal, and pharmaceutical chemistry described herein are those well-known and commonly used in the art. Standard techniques are used for chemical syntheses, chemical analyses, pharmaceutical preparation, formulation, and delivery, and treatment of patients.

That the present invention may be more readily understood, selected terms are defined below.

The term "host" as used herein, typically refers to a human subject, and in particular where a human or humanized framework is used as an acceptor structure. Where another host is treated, it is understood by those of skill in the art that the antibody or antigen binding agent may need to be tailored to that host to avoid rejection or to make more compatible. It is known how to use the CDRs in the present invention and engineer them into the proper framework or peptide sequence for desired delivery and function for a range of hosts. Other hosts may include other mammals or vertebrate species. The term "host," therefore, can alternatively refer to animals such as mice, monkeys, dogs, pigs, rabbits, domesticated swine (pigs and hogs), ruminants, equine, poultry, felines, murines, bovines, canines, and the like, where the antibody or antigen binding agent, if necessary is suitably designed for compatibility with the host.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments, and polypeptide analogs of a protein sequence. A polypeptide may be monomeric or polymeric.

The term "recovering" as used herein, refers to the process of rendering a chemical species such as a polypeptide substantially free of naturally associated components by isolation, e.g., using protein purification techniques well known in the art.

The terms "specific binding" or "specifically binding", as used herein, in reference to the interaction of an antibody, a protein, or a peptide with a second chemical species, mean that the interaction is dependent upon the presence of a particular structure (e.g., an "antigenic determinant" or "epitope" as defined below) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. Where an epitope of the invention is mentioned herein, the anti-IgE antibody, or antigen binding agent, of the invention is specific for said epitope.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains at least some portion of the epitope binding features of an Ig molecule allowing it to specifically bind to IgE. Such mutant, variant, or derivative antibody formats are known in the art and described below. Non limiting embodiments of which are discussed below. An antibody is said to be "capable of binding" a molecule (or epitope) if it is capable of specifically reacting with the molecule (or epitope) to thereby bind the molecule (or epitope) to the antibody.

A "monoclonal antibody" as used herein is intended to refer to a preparation of antibody molecules, which share a common heavy chain and common light chain amino acid sequence, or any functional fragment, mutant, variant, or derivation thereof which retains at least the light chain epitope binding features of an Ig molecule, in contrast with "polyclonal" antibody preparations that contain a mixture of different antibodies. Monoclonal antibodies can be generated by several known technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) Nature 256:495-497).

In a full-length antibody, each heavy chain is comprised of a heavy chain variable region (abbreviated herein as HCVR or VH) and a heavy chain constant region (CH). The heavy chain constant region is comprised of four domains—either CH1, Hinge, CH2, and CH3 (heavy chains γ, α and δ), or CH1, CH2, CH3, and CH4 (heavy chains μ and ε). Each light chain is comprised of a light chain variable region (abbreviated herein as LCVR or VL) and a light chain constant region (CL). The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen binding agent" as used herein, refers to one or more fragments or portions of an antibody that retain the ability to specifically bind to an antigen (e.g., IgE), or synthetic modifications of antibody fragments that retain the desired binding ability to the antigen. It has been shown that the antigen-binding function of an antibody can be performed by fragments or certain portions of a full-length antibody, or modifications thereof. Embodiments include bispecific, dual specific and multi-specific formats which may specifically bind to two or more different antigens or to several epitopes or discontinuous epitope regions of an antigen. Non limiting examples of antigen binding agents include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; (vi) an isolated complementarity determining region (CDR), (vii) fusions of antibody fragments such as those that are immunoglobulin in character, for example, diabodies, scab, bispecific, triabody, Fab-Fv, Fab-Fv-Fv, tribody, (Fab-Fv)2-Fc, and (viii) antibody portions such as CDRs or antibody loops grafted onto non-immunoglobulin frameworks such as fibronectin or leucine zippers (see Binz et al. (2005) Nat. Biotech. 23:1257-1268, incorporated herein). Furthermore, although the two domains of the Fv fragment, VL and VH, are coded for by separate genes, they can be joined, using recombinant or other methods, by a synthetic or naturally occurring linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term antigen binding agent. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more of the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain, for example a human IgA, IgD, IgE, IgG or IgM constant domains. Heavy chain and light chain constant domain amino acid sequences are known in the art. Non-limiting examples of Ig heavy chain γ1 constant region and Ig light chain λ and κ chains are provided for in Tables 8 and 6, respectively.

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds IgE is substantially free of antibodies that specifically bind antigens other than IgE). An isolated antibody that specifically binds, for example, human IgE may, however, have cross-reactivity to other antigens, such as IgE molecules from other species. Moreover, an isolated antibody may be substantially free of other cellular material and/or chemicals.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having human heavy and light chain variable regions in which one or more of the human CDRs (e.g., CDR3) has been replaced with murine CDR sequences.

The terms "Kabat numbering", "Kabat definitions" and "Kabat labelling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31-35 (CDR-H1), residues 50-65 (CDR-H2) and residues 95-102 (CDR-H3) according to the Kabat numbering system. However, according to Chothia (Chothia et al., (1987) J. Mol. Biol., 196, 901-917 (1987)), the loop equivalent to CDR-H1 extends from residue 26 to residue 32. Thus, unless indicated otherwise "CDR-H1" as employed herein is intended to refer to residues 26 to 35, as described by a combination of the Kabat numbering system and Chothia's topological loop definition. For the light chain variable region, the hypervariable region ranges from amino acid positions 24 to 34 for CDRL1, amino acid positions 50 to 56 for CDRL2, and amino acid positions 89 to 97 for CDRL3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDRH1, CDRH2 and CDRH3 for the heavy chain CDRs, and CDRL1, CDRL2, and CDRL3 for the light chain CDRs. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia, or a mixture thereof, defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227:799 (1992), both are incorporated herein by reference). According to Chothia et al., critical portions of the CDRs of many antibodies have nearly identical peptide backbone conformations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. See, e.g., Shapiro et al., Crit. Rev. Immunol. 22(3): 183-200 (2002); Marchalonis et al., Adv Exp Med Biol. 484:13-30 (2001). One of the advantages provided by various embodiments of the present invention takes advantage of the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or 0-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

The term "humanized antibody" generally refers to antibodies which comprise heavy and light chain variable region sequences from a non-human species (e.g., a rabbit, mouse, etc.) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. Another type of humanized antibody is a CDR-grafted antibody, in which at least one non-human CDR is inserted into a human framework. The latter is typically the focus of the present invention.

In particular, the term "humanized antibody" as used herein, is an antibody or a variant, derivative, analog or fragment thereof which immuno-specifically binds to an antigen of interest and which comprises a framework (FR) region having substantially the amino acid sequence of a human antibody and a complementarity determining region (CDR) having substantially the amino acid sequence of a non-human antibody. As used herein, the term "substantially" in the context of a CDR refers to a CDR having an amino acid sequence at least 50, 55, 60, 65, 70, 75 or 80%, preferably at least 85%, at least 90%, at least 95%, at least 98% or at least 99% identical to the amino acid sequence of a non-human antibody CDR. In one embodiment, the humanized antibody has a CDR region having one or more (for example 1, 2, 3 or 4) amino acid substitutions, additions and/or deletions in comparison to the non-human antibody CDR. Further, the non-human CDR can be engineered to be more "human-like" or compatible with the human body, using known techniques. A humanized antibody comprises substantially all of at least one, and typically two, variable domains (Fab, Fab', F(ab')2, F(ab')c, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, and CH3, or CH1, CH2, CH3, and CH4 of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain. Though some of the mutations discussed herein may not be commonly "human", these are insufficient for the anti-IgE antibody, or antigen binding agent, of the invention not to be "humanized".

The humanized antibody can be selected from any class of immunoglobulins, including IgY, IgM, IgG, IgD, IgA and IgE, and any isotype, including without limitation IgA1, IgA2, IgG1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond exactly to either the donor antibody or the consensus framework. In a preferred embodiment, such mutations, however, will not be extensive. Usually, at least 50, 55, 60, 65, 70, 75 or 80%, preferably at least 85%, more preferably at least 90%, and most preferably at least 95%, 98% or 99% of the humanized antibody residues will correspond to those of the parental FR and CDR sequences. In one embodiment, one or more (for example 1, 2, 3, 4, 5, 6, 7, 8, 9 or 10) amino acid substitutions, additions and/or deletions may be present in the humanized antibody compared to the parental FR and CDR sequences (for instance compared to the omalizumab or omalizumab Fab sequences). As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

As used herein, the term "neutralizing" refers to neutralization of biological activity of IgE, when an anti-IgE antibody, or antigen binding agent, of the invention described herein specifically binds the IgE protein. Neutralizing may be the result of different ways of binding of said antibody to IgE. Preferably a neutralizing antibody is an antibody whose binding to IgE results in neutralization of a biological activity of IgE. Preferably the neutralizing binding protein binds IgE and decreases a biologically activity of IgE by at least about 5%, 10%, 15%, 20%, 25%, 30%, 35%, 40%, 50%, 60%, 80%, 85%, or more. Neutralization of a biological activity of IgE by a neutralizing antibody can be assessed by measuring one or more indicators of IgE biological activity described herein.

A "neutralizing monoclonal antibody" as used herein is intended to refer to a preparation of antibody molecules, which upon binding to IgE are able to inhibit or reduce the biological activity of IgE either partially or fully.

As used herein, the term "attenuation," "attenuate," and the like refers to the lessening or reduction in the severity of a symptom or condition caused by elevated serum IgE levels.

The term "epitope" or "antigenic determinant" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "$k_{on}$", as used herein, is intended to refer to the on rate constant for association of an antibody to the antigen to form the antibody/antigen complex as is known in the art.

The term "$k_{off}$", as used herein, is intended to refer to the off rate constant for dissociation of an antibody from the antibody/antigen complex as is known in the art.

The term "$k_d$" or "$k_D$", as used herein, is intended to refer to the dissociation constant of a particular antibody-antigen interaction as is known in the art.

The strength, or affinity of immunological binding interactions can be expressed in terms of the dissociation constant ($k_D$ or $k_d$) of the interaction, wherein a smaller $k_d$ represents a greater or higher affinity. Immunological binding properties of selected polypeptides can be quantified using methods well known in the art. One such method involves measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ("$k_{on}$") and the "off rate constant" ("$k_{off}$") can be determined by calculation of the concentrations and the actual rates of association and dissociation. (Nature 361:186-87 (1993)). The ratio of $k_{off}/k_{on}$ enables the cancellation of all parameters not related to affinity, and is equal to the dissociation constant $k_d$. Davies et al. (1990) Annual Rev Biochem 59:439-473.

The term "antibody conjugate" refers to a binding protein, such as an antibody or antibody fragment or binding portion thereof, chemically linked to a second chemical moiety, such as a therapeutic or cytotoxic agent. The term "agent" is used herein to denote a chemical compound, a mixture of chemical compounds, a biological macromolecule, or an extract made from biological materials.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein means a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences, which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation," as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g. prophylactic or therapeutic agent).

The specific region or epitope mapping of human IgE protein provided herein can be identified by any suitable epitope mapping method known in the art in combination with any one of the antibodies provided by the present invention. Examples of such methods include screening peptides of varying lengths derived from IgE for binding to the antibody of the present invention with the smallest fragment that can specifically bind to the antibody containing the sequence of the epitope recognized by the antibody. The IgE peptides may be produced synthetically or by proteolytic digestion of the IgE protein. Peptides that bind the antibody can be identified by, for example, mass spectrometric analysis. In another example, NMR spectroscopy or X-ray crystallography can be used to identify the epitope bound by an antibody of the present invention. Crystallization and X-ray crystallography techniques are preferred for determining the structure of IgE and the epitope on IgE that the anti-IgE antibody, or antigen binding agent, of the invention binds to.

Antibodies for use in the invention may be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and International Patent Application number WO2004/106377. Screening for antibodies can be performed using assays to measure binding to human IgE and/or assays to measure the ability to block IgE binding to its natural receptor. An example of a binding assay is an ELISA.

Humanized antibodies (which include CDR-grafted antibodies) are antibody molecules having one or more complementarity determining regions (CDRs) from a non-human species (e.g., a rabbit or mouse) and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanized antibodies may optionally further comprise one or more framework residues derived from the non-human species from which the CDRs were derived. The latter are often referred to as donor residues. The antibody molecules of the present invention suitably have a binding affinity ($K_D$) of less than 2 nM. Affinity may be measured using any suitable method known in the art, including BIAcore, as described in the Examples herein (see Example 6), using isolated natural or recombinant IgE or a suitable fusion protein/polypeptide.

The affinity of an antibody or antigen binding agent of the present invention, as well as the extent to which a binding agent (such as an antibody) inhibits binding, can be determined by one of ordinary skill in the art using conventional techniques, for example those described by Scatchard et al. (Ann. KY. Acad. Sci. 51:660-672 (1949)) or by surface plasmon resonance (SPR) using systems such as BIAcore. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analysed to yield apparent rate constants for the association and dissociation phases of the binding reaction. The ratio of these values gives the apparent equilibrium constant (affinity) (see, e.g., Wolff et al, Cancer Res. 53:2560-65 (1993)).

It will be appreciated that the affinity of antibodies provided by the present invention may be altered using any suitable method known in the art. The present invention therefore also relates to variants of the antibody molecules of the present invention, which have an improved affinity for IgE. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

Humanized Antibodies and Antigen Binding Agents

In one aspect of the present invention, provided herein are humanized anti-IgE monoclonal antibodies and antigen binding agents. Humanized antibodies are antibodies wherein the heavy and/or light chain contains one or more CDRs (including, if desired, one or more modified CDRs) from a donor antibody (e.g. a non-human antibody such as a murine or rabbit monoclonal antibody) grafted into a heavy and/or light chain variable region framework of an acceptor antibody (e.g. a human antibody). For a review, see Vaughan et al, Nature Biotechnology, 16, 535-539, 1998.

In one embodiment, rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein are transferred to the human antibody framework. In another embodiment only the specificity determining residues from each of the CDRs described herein are transferred to the human antibody framework.

When the CDRs or specificity determining residues are grafted, any appropriate acceptor variable region framework sequence may be used having regard to the class/type of the donor antibody from which the CDRs are derived, including mouse, rabbit, primate and human framework regions.

Suitably, the humanized antibody according to the present invention has a variable domain comprising human acceptor framework regions as well as one or more of the CDRs provided specifically herein. Thus, provided in one embodiment is a humanized monoclonal antibody which binds human IgE wherein the variable domain comprises human acceptor framework regions (with optional mutations as described herein) and non-human donor CDRs.

Construction of CDR-grafted antibodies is generally described in European Patent Application EP-A-0239400, which discloses a process in which the CDRs of a mouse monoclonal antibody are grafted onto the framework regions of the variable domains of a human immunoglobulin by site directed mutagenesis using long oligonucleotides, and is incorporated herein. The CDRs determine the antigen binding specificity of antibodies and are relatively short peptide sequences carried on the framework regions of the variable domains.

The earliest work on humanizing monoclonal antibodies by CDR-grafting was carried out on monoclonal antibodies recognizing synthetic antigens, such as NP. However, examples in which a mouse monoclonal antibody recognizing lysozyme and a rat monoclonal antibody recognizing an antigen on human T-cells were humanized by CDR-grafting have been described by Verhoeyen et al. (Science, 239, 1534-1536, 1988) and Riechmann et al (Nature, 332, 323-324, 1988), respectively. Antibody humanization is achieved by grafting CDRs of a non-human antibody, such as a mouse, rat, goat, or rabbit antibody, onto a "similar" human framework (acceptor) and selecting minimal number of key framework residues (back-mutations) that are manually selected from the donor monoclonal antibody and incorporated into human acceptor framework in order to maintain the original CDR conformation. Such methods are known in the art, and include those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5): 489-498 (1991); Studnicka et al., Protein Engineering 7(6): 805-814 (1994); Roguska. et al., PNAS 91:969-973 (1994); PCT publication WO 91/09967, PCT: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, which are incorporated herein.

The human variable heavy and light chain germline subfamily classification can be derived from the Kabat germline subgroup designations: VH1, VH2, VH3, VH4, VH5, VH6 or VH7 for a particular VH sequence and JH1, JH2, JH3, JH4, JH5, and JH6 for a for a particular variable heavy joining group for framework 4; VK1, VK2, VK3, VK4, VK5 or VK6 for a particular VL kappa sequence for framework 1, 2, and 3, and JK1, JK2, JK3, JK4, or JK5 for a particular kappa joining group for framework 4; or VL1, VL2, VL3, VL4, VL5, VL6, VL7, VL8, VL9, or VL10 for a particular VL lambda sequence for framework 1, 2, and 3, and JL1, JL2, JL3, or JL7 for a particular lambda joining group for framework 4.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular embodiments, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

CDR and Human Framework Modifications

Riechmann et al., found that the transfer of the CDRs alone (as defined by Kabat (Kabat et al. (supra) and Wu et al., J. Exp. Med., 132, 211-250, 1970)) was not sufficient to provide satisfactory antigen binding activity in the CDR-grafted product. It was found that a number of framework residues have to be altered so that they correspond to those of the donor framework region. Proposed criteria for selecting which framework residues need to be altered are described in International Patent Application WO 90/07861, which is incorporated herein.

The substitution of non-human CDRs into a human variable domain framework is most likely to result in retention of the CDR's correct spatial orientation if the human variable domain framework adopts the same or similar conformation to the non-human variable framework from which the CDRs originated. This is achieved by obtaining the human variable domains from human antibodies whose framework sequences exhibit a high degree of sequence identity with the non-human variable framework domains from which the CDRs were derived. As described above, the heavy and light chain variable framework regions can be derived from the same or different human antibody sequences. The human antibody sequences can be the sequences of naturally occurring human antibodies or can be consensus sequences of several human antibodies. See Kettleborough et al, Protein Engineering 4:773 (1991); Kolbinger et al., Protein Engineering 6:971 (1993) and Carter et al, WO 92/22653.

Having identified the complementarity determining regions of the non-human donor immunoglobulin and appropriate human acceptor immunoglobulins, the next step is to determine which, if any, residues from these components should be substituted to optimize the properties of the resulting humanized antibody. In general, substitution of human amino acid residues with non-human amino acid residues should be minimized, because introduction of non-human residues increases the risk of the antibody eliciting a human-anti-donor-antibody (HADA) response in humans. Art-recognized methods of determining immune response can be performed to monitor a HADA response in a particular host or during clinical trials. Hosts administered humanized antibodies can be given an immunogenicity assessment at the beginning and throughout the administration of said therapy. The HADA response is measured, for example, by detecting antibodies to the humanized therapeutic reagent, in serum samples from the host using a method known to one in the art, including surface plasmon resonance technology (BIACORE) and/or solid-phase ELISA analysis.

The selection of amino acid residues for substitution (also "mutation" herein) is determined, in part, by computer modelling. Computer hardware and software are described herein for producing three-dimensional images of immunoglobulin molecules. In general, molecular models are produced starting from solved structures for immunoglobulin chains or domains thereof. The chains to be modelled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modelling, and preferably those sharing at least 60%, 70%, 80%, 90%, sequence identity or more are selected for modelling. The solved starting structures are modified to allow for differences between the actual amino acids in the immunoglobulin chains or domains being modelled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a donor variable region framework residue and a selected human variable region framework residue, the human framework amino acid should usually be substituted by the equivalent framework amino acid from the donor antibody when it is reasonably expected that the amino acid:

(1) noncovalently binds antigen directly,
(2) is adjacent to a CDR region,
(3) otherwise interacts with a CDR region (e.g., is within about 3-6 Angstrom of a CDR region as determined by computer modelling), or
(4) participates in the VL-VH interface.

Residues which "noncovalently bind antigen directly" include amino acids in positions in framework regions which have a good probability of directly' interacting with amino acids on the antigen according to established chemical forces, for example, by hydrogen bonding, Van der Waals forces, hydrophobic interactions, and the like. CDR and framework regions are as defined by Kabat et al. or Chothia et al, supra. When framework residues, as defined by Kabat et al, supra, constitute structural loop residues as defined by Chothia et al, supra, the amino acids present in the donor antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk 1 MB 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al, Science, 233:747 (1986), which is incorporated herein by reference) and selecting these amino acids from the donor may be desirable to keep all the antigen contacts that provide affinity in the original antibody. As described herein, FR sequences may also be substituted/mutated to improve the affinity of the anti-IgE antibody, or antigen binding agent, of the invention for IgE (and/or to extend its interaction or epitope on Cε2 of IgE).

Residues that "otherwise interact with a CDR region" include those that are determined by secondary structural analysis to be in a spatial orientation sufficient to effect a CDR region. In one embodiment, residues that "otherwise interact with a CDR region" are identified by analysing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units (A) of some atom in the CDRs and must contain an atom that could interact with the CDR atoms according to established chemical forces, such as those listed above. In the case of atoms that may form a hydrogen bond, the 3 A° is measured between their nuclei, but for atoms that do not form a bond, the 3 A° is measured between their Van der Waals surfaces. Hence, in the latter case, the nuclei must be within about 6 A° (3 A plus the sum of the Van der Waals radii) for the atoms to be considered capable of interacting. In many cases the nuclei will be from 4 or 5 to 6 A° apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids that are capable of interacting with amino acids in the CDRs (or FRs), may be identified in yet another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art (e.g., Connolly, J. Appl. Cryst. 16:548 (1983) and Lee and Richards, J. Mol. Biol. 55:379 (1971), both of which are incorporated herein by reference). Framework amino acids may also occasionally interact with the CDRs indirectly, by affecting the conformation of another framework amino acid that in turn contacts the CDRs.

Particular amino acids at several positions in the framework are known to be capable of interacting with the CDRs in many antibodies (Chothia and Lesk, supra, Chothia et al, supra and Tramontano et al, J. Mol. Biol. 215:175 (1990), all of which are incorporated herein by reference). Notably, the amino acids at positions 2, 48, 64, and 71 of the light chain and 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain residues capable of interacting with the CDR region, such as the first 5 amino acids of the light chain, may sometimes be chosen from the acceptor immunoglobulin without loss of affinity in the humanized immunoglobulin.

Residues which "participate in the VL-VH interface" or "packing residues" include those residues at the interface between VL and VH as defined, for example, by Novotny and Haber, Proc. Natl. Acad. Sci. USA, 82:4592-66 (1985) or Chothia et al, supra. Generally, unusual packing residues should be retained in the humanized antibody if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. Although not usually desirable, it is sometimes possible to make one or more conservative amino acid substitutions of CDR residues without appreciably affecting the binding affinity of the resulting humanized immunoglobulin. By conservative or similar substitutions is intended combinations such as, for example, leucine being substituted for isoleucine or valine. Other amino acids which can often be substituted for one another include but are not limited to:

- phenylalanine, tyrosine and tryptophan (amino acids having aromatic side chains);
- lysine, arginine and histidine (amino acids having basic side chains);
- aspartate and glutamate (amino acids having acidic side chains);
- asparagine and glutamine (amino acids having amide side chains); and,
- cysteine and methionine (amino acids having sulphur-containing side chains).

Additional candidates for substitution are acceptor human framework amino acids that are unusual or "rare" for a human immunoglobulin at that position. These amino acids can be substituted with amino acids from the equivalent position of the donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criteria help ensure that an atypical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare", as used herein, indicates an amino acid occurring at that position in less than about 20% but usually less than about 10% of sequences in a representative sample of sequences, and the term "common," as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al, supra). When deciding whether an amino acid in a human acceptor sequence is "rare" or "common" among human sequences, it will often be preferable to consider only those human sequences in the same subgroup as the acceptor sequence.

Additional candidates for substitution are acceptor framework residues that correspond to a rare or unusual donor framework residue. Rare or unusual donor framework residues are those that are rare or unusual (as defined herein) for donor antibodies at that position. For donor antibodies, the subgroup can be determined according to Kabat and residue positions identified which differ from the consensus. These donor specific differences may point to somatic mutations in the donor sequence, which enhance activity. Unusual residues that are predicted to affect binding are retained, whereas residues predicted to be unimportant for binding could be substituted.

Additional candidates for substitution are non-germline residues occurring in an acceptor framework region. For example, when an acceptor antibody chain (i.e., a human antibody chain sharing significant sequence identity with the donor antibody chain) is aligned to a germline antibody chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized immunoglobulins are usually substantially identical, and more usually, identical to the framework regions of the human antibodies from which they were derived (except as described herein for the purposes of the present invention). Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Thus, in one embodiment the variable framework region of the humanized immunoglobulin shares at least 65, 75 or 85% sequence similarity or identity to a human variable framework region sequence or consensus of such sequences. In another embodiment, the variable framework region of the humanized immunoglobulin shares at least 90%, preferably 95%, more preferably 96%, 97%, 98%, or 99%, sequence similarity or identity to a human variable framework region sequence or consensus of such sequences. In general, however, such substitutions are undesirable (except those described herein).

As used herein, degrees of identity and similarity can be readily calculated, for example as described in Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656, which are incorporated by reference herein.

A number of reviews discussing CDR-grafted antibodies have been published, including Vaughan et al. (Nature Biotechnology, 16, 535-539, 1998), which is incorporated by reference herein.

The anti-IgE antibodies of the present invention may include further additional binding domains for example as per the molecule DVD-Ig as disclosed in WO 2007/024715, or the so-called (FabFv)2Fc described in WO2011/030107. Thus, antibody as employed herein includes bi, tri or tetra-valent full length antibodies.

Antigen Binding Agents

Antigen binding agents include single chain antibodies (i.e. a full length heavy chain and light chain); Fab, modified Fab, Fab', modified Fab', F(ab')2, Fv, Fab-Fv, Fab-dsFv, single domain antibodies (e.g. VH or VL or VHH) for example as described in WO 2001090190, scFv, bi, tri or tetra-valent antibodies, Bis-scFv, diabodies, tribodies, triabodies, tetrabodies and epitope-antigen binding agents of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). The Fab-Fv format was first disclosed in WO2009/040562 and the disulphide stabilised versions thereof, the Fab-dsFv was first disclosed in WO2010/035012. Other antibody fragments for use in the present invention include the Fab and Fab' fragments described in International patent applications WO2005/003169, WO2005/003170, and WO2005/003171. Multi-valent antibodies may comprise multiple specificities e.g. bispecific or may be monospecific (see for example WO 92/22583 and WO05/113605). One such example of the latter is a Tri-Fab (or TFM) as described in WO92/22583.

A typical Fab' molecule comprises a heavy and a light chain pair in which the heavy chain comprises a variable region VH, a constant domain CH1 and a natural or modified hinge region and the light chain comprises a variable region VL and a constant domain CL.

In one embodiment, there is provided a dimer of a Fab' according to the present disclosure to create a F(ab')2 for example dimerization may be through a natural hinge sequence described herein, or derivative thereof, or a synthetic hinge sequence.

An antibody binding domain will generally comprise 6 CDRs, three from a heavy chain and three from a light chain. In one embodiment, the CDRs are in a framework and together form a variable region. Thus in one embodiment, the antigen binding agent includes a binding domain specific for IgE comprising a light chain variable region and a heavy chain variable region.

It will be appreciated that one or more (for example 1, 2, 3 or 4) amino acid substitutions, additions and/or deletions may be made to the CDRs or other sequences (e.g variable domains) provided by the present invention, as described above or below, without significantly altering the ability of the antibody to bind to IgE. The effect of any amino acid substitutions, additions and/or deletions can be readily tested by one skilled in the art, for example by using the methods described herein, in particular in the Examples.

In one embodiment, one or more (for example 1, 2, 3 or 4) amino acid substitutions, additions and/or deletions may be made to the CDRs or framework region employed in the antibody or fragment provided by the present invention so that the binding affinity ($K_D$) of the anti-IgE antibody, or antigen binding agent, of the invention to IgE is less than 2, 1.9, 1.8, 1.7, 1.6, 1.5, 1.4, 1.3, 1.2, 1.1, 1.0, 0.9, 0.8, 0.7, 0.6, 0.5, 0.4, or 0.3 nM. In one embodiment, provided is a modified humanized antibody wherein modifications have been made to either the CDRs, framework regions, or both, in order to decrease the $K_D$ for example to less than 2, 1.9, 1.8, 1.7, 1.6, 1.5, 1.4, 1.3, 1.2, 1.1, 1.0, 0.9, 0.8, 0.7, 0.6, 0.5, 0.4, or 0.3 nM.

The antibody fragment of the present invention includes Fab, Fab', F(ab')2, scFv, diabody, scFAb, dFv, single domain light chain antibodies, dsFv, a peptide comprising CDR, and the like.

A Fab is an antibody fragment having a molecular weight of about 50,000 and antigen binding activity, in which about a half of the N-terminal side of H chain and the entire L chain, among fragments obtained by treating IgG with a protease, papain (cut at an amino acid residue at position 224 of the H chain), are bound together through a disulfide bond.

The Fab of the present invention can be obtained by treating a humanised CDR-grafted antibody of the present invention which specifically reacts with IgE, with a protease, papain. Also, the Fab can be produced by inserting DNA encoding Fab of the antibody into an expression vector for prokaryote or an expression vector for eukaryote, and introducing the vector into a prokaryote or eukaryote to express the Fab.

An F(ab')2 is an antibody fragment having a molecular weight of about 100,000 and antigen binding activity, which is slightly larger than the Fab bound via a disulfide bond of the hinge region, among fragments obtained by treating IgG with a protease, pepsin.

The F(ab')2 of the present invention can be obtained by treating a human CDR-grafted antibody which specifically reacts with IgE, with a protease, pepsin. Also, the F(ab')2 can be produced by binding Fab' described below via a thioether bond or a disulfide bond.

A Fab' is an antibody fragment having a molecular weight of about 50,000 and antigen binding activity, which is obtained by cutting a disulfide bond of the hinge region of the F(ab')2.

The Fab' of the present invention can be obtained by treating the F(ab')2 which specifically reacts with IgE, with a reducing agent, dithiothreitol. Also, the Fab' of the present invention can be produced by inserting DNA encoding a Fab' of a human CDR-grafted antibody of the present invention which specifically reacts with IgE into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (P) of 12 or more residues and which has an antigen-binding activity.

The scFv of the present invention can be produced by obtaining cDNAs encoding VH and VL of a human CDR-grafted antibody which specifically reacts with IgE of the present invention, constructing DNA encoding scFv, inserting the DNA into an expression vector for prokaryote or an expression vector for eukaryote, and then introducing the expression vector into a prokaryote or eukaryote to express the scFv.

The Fab fragment of the present invention may be linked, directly or via a linker to a scFv. "Single chain variable fragment" or "scFv" as employed herein refers to a single chain variable fragment which is stabilized by a peptide linker between the VH and VL variable domains, for example a peptide linker with amino acid sequence which is Seq ID No. 151. The linkage to the Fab fragment can be a chemical conjugation but is most preferably a translation fusion, i.e. a genetic fusion where the sequence of each is encoded in sequence by an expression vector. The linker is therefore typically an amino acid linker as described herein. The scFv of the present invention linked to the Fab fragment may bind to a serum carrier protein in order to extend the half-life of the antibody fusion protein in vivo. Extending half-life in such a way is independent of IgE binding and may be advantageous.

"Serum carrier protein" as employed herein refers to any suitable plasma carrier protein to which the scFv may bind, in one example the serum carrier protein is selected from thyroxine binding protein, transthyretin, α1-acid glycoprotein, transferrin, fibrinogen and albumin, or a fragment of any thereof. Typically, the scFv binds to albumin, preferably human serum albumin.

Any suitable albumin binding scFv may be incorporated into the antibody fusion proteins of the invention. Suitable albumin binding domains have previously been described in the art.

A diabody is an antibody fragment in which scFv's having the same or different antigen binding specificity forms a dimer, and has a divalent antigen binding activity to the same antigen or two specific antigen binding activities to different antigens.

The diabody of the present invention, for example, a divalent diabody which specifically reacts with IgE, can be produced by obtaining cDNAs encoding VII and VL of an antibody which specifically reacts with IgE, constructing DNA encoding scFv having a polypeptide linker of 3 to 10 residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VII and VL is substituted with a cysteine residue via a disulfide bond between the cysteine residues. The amino acid residue, which is substituted with a cysteine residue can be selected based on a three-dimensional structure estimation of the antibody in accordance with the method shown by Reiter et al. (Protein Engineering, 7, 697 (1994)).

The dsFv of the present invention can be produced by obtaining cDNAs encoding VH and VL of a human CDR-grafted antibody which specifically reacts with IgE of the present invention, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including at least one region of H chain and L chain CDRs. Plural CDRs can be bound directly or via an appropriate peptide linker.

The peptide comprising CDR of the present invention can be produced by obtaining cDNA encoding CDR of VH and VL of a human CDR-grafted antibody which specifically reacts with IgE, constructing DNA encoding CDR, inserting the DNA into an expression vector for prokaryote or an expression vector for eukaryote, and then by introducing the expression vector into a prokaryote or eukaryote to express the peptide. Also, the peptide comprising CDR can also be produced by a chemical synthesis method such as an Fmoc method (fluorenylmethoxycarbonyl method), a tBoc method (t-butyloxycarbonyl method), or the like.

The antibody of the present invention includes antibody derivatives in which a radioisotope, a protein, an agent or the like is chemically or genetically conjugated to the antibody of the present invention.

The antibody derivatives of the present invention can be produced by chemically conjugating a radioisotope, a protein or an agent to the N-terminal side or C-terminal side of an H chain or an L chain of an antibody or antibody fragment which specifically reacts with IgE, to an appropriate substituent group or side chain of the antibody or antibody fragment or to a sugar chain in the antibody or antibody fragment (Antibody Engineering Handbook, edited by Osamu Kanemitsu, published by Chijin Shokan (1994)).

Also, it can be genetically produced by linking a DNA encoding the antibody or the antibody fragment of the present invention which specifically reacts with IgE to other DNA encoding a protein to be bound, inserting the DNA into an expression vector, and introducing the expression vector into a host cell.

The radioisotope includes 131I, 125I and the like, and it can be conjugated to the antibody by, e.g., a chloramine T method.

The agent is preferably a low molecular weight compound. Examples include anticancer agents such as alkylating agents (e.g., nitrogen mustard, cyclophosphamide), metabolic antagonists (e.g., 5-fluorouracil, methotrexate), antibiotics (e.g., daunomycin, bleomycin, mitomycin C, daunorubicin, doxorubicin), plant alkaloids (e.g., vincristine, vinblastine, vindesine), hormone drugs (e.g., tamoxifen, dexamethasone), and the like (Clinical Oncology, edited by Japanese Society of Clinical Oncology, published by Cancer and Chemotherapy (1996)); anti-inflammatory agents such as steroid agents (e.g., hydrocortisone, prednisone), non-steroidal drugs (e.g., aspirin, indometacin), immunomodulators (e.g., aurothiomalate, penicillamine), immunosuppressing agents (e.g., cyclophosphamide, azathioprine) and antihistaminic agents (e.g., chlorpheniramine maleate, clemastine) (Inflammation and Anti-inflammatory Therapy, Ishiyaku Shuppan (1982)); and the like. The method for conjugating daunomycin to an antibody includes a method in which daunomycin and an amino group of an antibody are conjugated via glutaraldehyde, a method in which an amino group of daunomycin and a carboxyl group of an antibody are conjugated via a water-soluble carbodiimide, and the like.

Also, in order to inhibit cancer cells directly, a toxin such as ricin, diphtheria toxin and the like, can be used. For example, a fusion antibody with a protein can be produced by linking a cDNA encoding an antibody or antibody fragment to other cDNA encoding the protein, constructing DNA encoding the fusion antibody, inserting the DNA into an expression vector for prokaryote or an expression vector for eukaryote, and then introducing it into a prokaryote or eukaryote to express the fusion antibody.

Further contemplated herein are antibody fragments or antigen binding agents including fusions of binding agents, for example immunoglobulin like fragments and agents such as diabodies, scAbs, bispecific fragments, triabodies, Fab-Fv-Fv, Fab-Fv, tribody, (Fab-Fv)2-Fc, and antibody fragments or portions, such as CDRs or antibody loops including CDRs, which are grafted onto non-Ig frameworks such as fibronectin or leucine zippers, as descried in Binz et al., (2005) Nat. Biotech. 23:1257-1268, incorporated in its entirety herein.

Conjugated Anti-IgE Monoclonal Antibodies and Antigen Binding Agents

If desired, an antibody or antigen binding agent for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, antigen binding agents, synthetic (including PEG) or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM- CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

In one embodiment a half-life provided by an effector molecule which is independent of IgE or an anti-human IgE antibody is advantageous.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents, which may be present on the above-mentioned synthetic polymers, include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Specific naturally occurring polymers include lactose, amylose, dextran, glycogen or derivatives thereof.

In one embodiment the polymer is albumin or a fragment thereof, such as human serum albumin or a fragment thereof. In one embodiment the polymer is a PEG molecule.

"Derivatives" as used herein in regard to conjugates is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the natural or synthetic polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above.

The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, AL, USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington DC and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

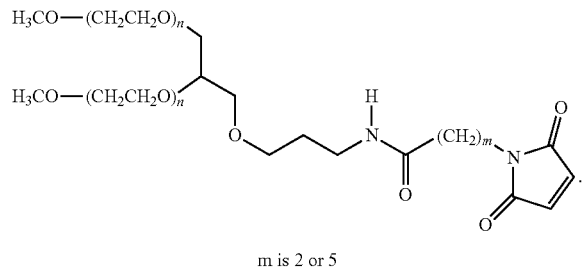

m is 2 or 5

That is to say each PEG is about 20,000 Da.

Thus in one embodiment the PEG is 2,3-Bis(methylpolyoxyethylene-oxy)-1-{[3-(6-maleimido-1-oxohexyl)amino]propyloxy}hexane (the 2 arm branched PEG, —CH2) 3NHCO(CH2)5-MAL, Mw 40,000 known as SUNBRIGHT GL2-400MA3.

Further alternative PEG effector molecules of the following type:

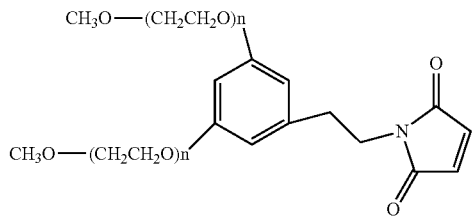

are available from Dr Reddy, NOF and Jenkem.

In one embodiment there is provided an antibody of the invention which is PEGylated (for example with a PEG described herein), attached through a cysteine amino acid residue at or about amino acid 226 in the chain, for example amino acid 226 of the heavy chain (by sequential numbering).

In one embodiment the present disclosure provides a Fab'PEG molecule comprising one or more PEG polymers, for example 1 or 2 polymers such as a 40 kDa polymer or polymers.

Fab'-PEG molecules according to the present disclosure may be particularly advantageous in that they have a half-life independent of the Fc fragment. In one example the present invention provides a method treating a disease ameliorated by modulating human IgE biological activity comprising administering a therapeutically effective amount of an anti-IgE antibody or antigen binding agent thereof wherein the antibody or antigen binding agent thereof has a half-life that is independent of Fc binding to IgE.

In one embodiment there is provided a Fab' conjugated to a polymer, such as a PEG molecule, a starch molecule or an albumin molecule.

In one embodiment there is provided a scFv conjugated to a polymer, such as a PEG molecule, a starch molecule or an albumin molecule.

In one embodiment the antibody or fragment is conjugated to a starch molecule, for example to increase the half-life. Methods of conjugating starch to a protein as described in U.S. Pat. No. 8,017,739 incorporated herein by reference.

Polynucleotides

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised synthesized on the basis of their known amino acid sequences.

Standard techniques of molecular biology may be used to prepare DNA sequences coding for the antibody molecule of the present invention. Desired DNA sequences may be synthesized completely or in part using oligonucleotide synthesis techniques. Site-directed mutagenesis and polymerase chain reaction (PCR) techniques may be used as appropriate.

The present invention also relates to a cloning or expression vector comprising one or more DNA sequences of the present invention. Accordingly, provided is a cloning or expression vector comprising one or more DNA sequences encoding an antibody of the present invention. Suitably, the cloning or expression vector comprises two DNA sequences, encoding the light chain and the heavy chain of the antibody molecule of the present invention, respectively and suitable signal sequences. In one example the vector comprises an intergenic sequence between the heavy and the light chains (see WO03/048208).

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbour Publishing.

Host Cells Expressing Anti-IgE Antibodies or Fragments Thereof

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

Suitable types of Chinese Hamster Ovary (CHO cells) for use in the present invention may include CHO and CHO-K1 cells including dhfr− CHO cells, such as CHO-DG44 cells and CHO-DXB11 cells and which may be used with a DHFR selectable marker or CHOK1-SV cells which may be used with a glutamine synthetase selectable marker. Other cell types of use in expressing antibodies include lymphocytic cell lines, e.g., NSO myeloma cells and SP2 cells, COS cells. Other suitable cells may include human embryonic kidney (hek) fibroblasts, for example hek293F and ExpiHek cells, which are known in the art.

CHO is preferred for full-length Ab of the invention, given this is standard host for the production of omalizumab (in one embodiment giving the antibodies of the invention the standard glycosylation pattern of omalizumab) [see also WO 2013/181577].

Production of Anti-IgE Antibodies or Fragments Thereof

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

There is a provided a process for culturing a host cell and expressing an antibody or fragment thereof, isolating the latter and optionally purifying the same to provide an isolated antibody or fragment. In one embodiment the process further comprises the step of conjugating an effector molecule to the isolated antibody or fragment, for example conjugating to a PEG polymer in particular as described herein.

In one embodiment there is provided a process for purifying an antibody (in particular an antibody or fragment according to the invention) comprising the steps: performing anion exchange chromatography in non-binding mode such that the impurities are retained on the column and the antibody is eluted.

In one embodiment the purification employs affinity capture on a Protein A column, and then titration. On one embodiment, the purification employs affinity capture on a Protein G column, and then HPLC titration. On one embodiment, the purification employs affinity capture on an IgE column, and then titration.

In one embodiment the purification employs cibacron blue or similar for purification of albumin fusion or conjugate molecules.

Suitable ion exchange resins for use in the process include Q.FF resin (supplied by GE-Healthcare). The step may, for example be performed at a pH about 8.

The process may further comprise an initial capture step employing cation exchange chromatography, performed for example at a pH of about 4 to 5, such as 4.5. The cation exchange chromatography may, for example employ a resin such as CaptoS resin or SP sepharose FF (supplied by GE-Healthcare). The antibody or fragment can then be eluted from the resin employing an ionic salt solution such as sodium chloride, for example at a concentration of 200 mM.

Thus the chromatograph step or steps may include one or more washing steps, as appropriate.

The purification process may also comprise one or more filtration steps, such as a diafiltration step or HPLC filtration step.

Thus in one embodiment there is provided a purified anti-IgE antibody or fragment, for example a humanised antibody or fragment, in particular an antibody or fragment according to the invention, in substantially purified from, in particular free or substantially free of endotoxin and/or host cell protein or DNA.

Purified from as used supra is intended to refer to at least 90% purity, such as 91, 92, 93, 94, 95, 96, 97, 98, 99% w/w or purer.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 μg per mg of antibody product or less such as 100 μg per mg or less, in particular 20 μg per mg, as appropriate.

Pharmaceutical Compositions

As the antibodies of the present invention are useful in the treatment and/or prophylaxis of a pathological condition, the present invention also provides a pharmaceutical or diagnostic composition comprising an antibody or antigen binding agent of the present invention in combination with one or more of a pharmaceutically acceptable excipient, diluent, or carrier. Accordingly, provided is the use of an antibody or antigen binding agent of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable excipient.

The present invention also provides a process for preparation of a pharmaceutical or diagnostic composition comprising adding and mixing the antibody or antigen binding agent of the present invention together with one or more of a pharmaceutically acceptable excipient, diluent, or carrier.

The antibody or antigen binding agent may be the sole active ingredient in the pharmaceutical or diagnostic composition or may be accompanied by other active ingredients including other antibody ingredients or non-antibody ingredients such as steroids or other drug molecules, in particular drug molecules whose half-life is independent of IgE binding.

The pharmaceutical compositions suitably comprise a therapeutically effective amount of the antibody or antigen binding agent of the invention. The term "therapeutically effective amount" as used herein refers to an amount of a therapeutic agent needed to treat, ameliorate, or prevent a targeted disease or condition, or to exhibit a detectable therapeutic or preventative effect. For any disclosed antibody or antigen binding agent, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/Kg, such as 100 mg/Kg. Pharmaceutical compositions may be conveniently presented in unit dose forms containing a predetermined amount of an active agent of the invention per dose.

Therapeutic doses of the antibodies or antigen binding agents according to the present disclosure show no apparent toxicology effects in vivo.

Advantageously, the levels of IgE activity in vivo may be maintained at an appropriately reduced level by administration of sequential doses of the antibody or binding agent according to the disclosure.

Compositions may be administered individually to a patient or may be administered in combination (e.g. simultaneously, sequentially, or separately) with other agents, drugs or hormones.

A pharmaceutical composition may also contain a pharmaceutically acceptable carrier for administration of the antibody or antigen binding agent. The carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously (in particular), intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

Structural-Functional Properties

In one aspect of the present invention, the antibody or antigen binding agent binds to free and FcεRI bound human IgE. When the antibody (or antigen binding agent) of the invention binds to the FcεRI bound human IgE, it stabilizes a conformation of IgE. In such stabilized conformation, the IgE has a binding affinity for FcεRI or omalizumab (or fragments thereof) weaker than in the absence of the antibody or antigen binding agent of the present invention and wherein the FcεRI bound human IgE dissociates from FcεRI. Preferably, the IgE, upon dissociation from the FcεRI, remains bound to the antibody or antigen binding agent as described herein. As it will be shown hereinafter (for instance in Example 1 and FIG. 2), the antibody or antigen binding agent of the invention binds to the IgE in a conformation which is different from the conformation IgE has when bound to omalizumab.

Without wishing to be bound by theory, the antibody of the present invention causes the IgE to adopt a partially bent conformation (FIGS. 2C and 5C&D), hence, unbending from the free or FcεRI bound IgE structures. Such unbending compromises the ability of the IgE to bind or keep binding the FcεRI. As it will be shown in the example section, because the antibody of the present invention competes with the binding site on IgE for binding to the FcεRI, it is believed that the antibody may be capable of forming a complex with the IgE bound to the FcεRI altering the structure of the IgE when bound to the FcεRI and dissociating it from the FcεRI. Antibodies according to the present invention which possess these properties are those described herein such as antibodies or antigen binding agent comprising:

a. a heavy chain variable region comprising Seq ID No.: 1 and a light chain variable region comprising:
  i. Seq ID No.: 109; or
  ii. Seq ID No.: 113; or
  iii. Seq ID No.: 121; or
  iv. Seq ID No.: 132; or
  v. Seq ID NO. 139; or
b. Seq ID No.: 5 and
  i. Seq ID No., wherein S77 and S79 are replaced by Q;
  ii. Seq ID No.: 117 or
  iii. Seq ID No.: 125; or
  iv. Seq ID No.: 136; or
  v. Seq ID No.: 143.

Anti-IgE antibodies or antigen binding agents possessing such properties contact or contact and are specific for an epitope comprising, with reference to SEQ ID NO: 108, residues T373, W374, S375, R376, A377, S378, G379, P381, Q417, C418, R419, P426, R427, A428 of a Cε3 domain and residues D278 and T281 of a Cε2 domain of human IgE.

The antibodies of the present invention possess at several positions methionine residues. Oxidation of methionine residues is among the most common protein degradation pathway. The antibodies of the present invention where methionine residues have been introduced at position S64 and S71, with reference to Seq ID No. 20, may undergo complete oxidation without affecting the ability of the antibodies to accelerate dissociation of the IgE-Fc:sFcRIα complex.

Therefore, the present invention also provides for an anti-IgE antibody, or antigen-binding agent, which comprises a heavy chain variable region which has an amino acid sequence which is Seq ID No. 1 and a light chain variable region which comprises a CDR-L2 and a FW-L3, wherein the light chain variable region has an amino acid sequence which is Seq ID No. 20, except that the CDR-L2 has an amino acid sequence which is Seq ID No. 50 and that the FW-L3 has an amino acid sequence which is Seq ID No. 131 or 138, wherein methionine residues at positions 64 and/or 71, with reference to Seq ID No. 20, are oxidised.

The present invention also provides for an anti-IgE antibody, or antigen-binding agent, which comprises a heavy chain variable region which has an amino acid sequence which is Seq ID No. 1 and a light chain variable region which has an amino acid sequence which is Seq ID No. 132 or 139, wherein methionine residues at positions 64 and/or 71, with reference to Seq ID No. 132 or 139, are oxidised.

Further methionine residues in the antibodies of the present invention may be oxidised without affecting the ability of the antibodies to accelerate dissociation of the IgE-Fc:sFcRIα complex. The invention will now be further described by way of examples with references to embodiments illustrated in the accompanying drawings.

EXAMPLES

Example 1: Structure of a Mutant of the Therapeutic Anti-IgE Antibody Omalizumab Bound to IgE-Fc Reveals its Mechanism of Action Abstract Immunoglobulin E and its interactions with receptors FcεRI and CD23 play a central role in allergic disease. Omalizumab, a clinically-approved therapeutic antibody, inhibits the interaction between IgE and FcεRI, preventing mast cell and basophil activation, and blocks IgE binding to CD23. We solved the crystal structure of the 2:1 complex between an omalizumab-derived Fab and IgE-Fc, with one Fab bound to each Cε3 domain (but only one of the Fabs bound to a Cε2 domain). Although free IgE-Fc is predominantly acutely bent in solution, in the complex it is only partially bent, precluding interaction with FcεRI; CD23 binding is inhibited sterically due to overlapping binding sites on each Cε3 domain. Solution state interaction analyses demonstrate the orthosteric and allosteric basis for the inhibition of both receptor interactions and, together with the structure, reveal how omalizumab (and particularly the described omalizumab mutants) may accelerate dissociation of receptor-bound IgE from FcεRI, exploiting the intrinsic dynamics and allosteric potential of IgE.

Introduction

Immunoglobulin E (IgE) antibodies play a crucial role in allergic disease, binding to allergens through their Fab arms and expressing their effector functions by binding to receptors for the Fc region[1]. The two principal IgE receptors are FcεRI and CD23/FcεRII, commonly referred to as the high- and low-affinity receptors respectively. On mast cells and basophils, IgE binds to FcεRI so tightly ($K_D \approx 10^{-10}$ M$^{-1}$) that such cells are sensitized with pre-bound IgE, requiring only the presence of an allergen to cross-link IgE/FcεRI complexes and elicit an immediate reaction. CD23 is a homo-trimer and thus the intrinsically lower affinity of each IgE-binding, C-type lectin-like "head" domain ($K_D \approx 10^{-7}$ M$^{-1}$) can be enhanced by an avidity effect when binding to aggregated IgE in immune complexes, nearly matching that of FcεRI for IgE[2]. CD23 expressed on B cells is involved in IgE regulation, and expression on airway and gut epithelial cells mediates transcytosis of IgE/allergen complexes[1,2]. FcεRI and CD23 are also both expressed on a range of antigen-presenting cells. Thus, IgE-receptor interactions are involved in multiple aspects of the allergic response and IgE is a long-standing target for therapeutic intervention[3].

The Fc region of IgE comprises a disulphide-linked dimer of three domains: Cε2, Cε3 and Cε4. Early FRET studies of a chimeric IgE[4,5], and X-ray solution scattering studies of IgE-Fc[6], indicated a compact, bent structure, and the crystal structure of IgE-Fc later revealed an acutely and asymmetrically bent conformation, with the (Cε2)₂ domain pair folded back onto the Cε3 and Cε4 domains[7]. The bend, defined as the angle between the local two-fold axis of the (Cε2)₂ domain pair and that of Fcε3-4 (the region comprising only the Cε3 and Cε4 domains) was found to become even more acute (62° to 54°) in the crystal structure of IgE-Fc bound to sFcεRIα, the soluble extracellular domains of the IgE-binding α-chain of the receptor[8]. Recent FRET studies with N- and C-terminally labelled IgE-Fc confirmed this enhanced bend upon sFcεRIα binding[9].

The FcεRI binding site spans both Cε3 domains in the Cε2-proximal region[8,10], although the Cε2 domain is not directly involved; the engagement of both chains accounts for the 1:1 binding stoichiometry. In contrast, two CD23 molecules bind to IgE-Fc, one in each chain, and at the other, Cε4-proximal end of the Cε3 domain[11,12,13]. CD23 binding also causes a conformational change in IgE-Fc[14], but not one that significantly affects the bend[9]. However, the relatively "closed" disposition of the Cε3 domains in the complex with the soluble head domain of CD23 (sCD23), compared with free IgE-Fc, is incompatible with the more "open" arrangement of these domains that is required for FcεRI binding. This partly explains the mutual exclusion of FcεRI and CD23 binding[11,12], although other factors such as local conformational changes and modifications of conformational dynamics[15] also likely contribute to the allosteric communication between the two receptor-binding sites[2].

A more extreme degree of flexibility in IgE-Fc was recently discovered through studies of a complex with an anti-IgE-Fc Fab, termed aεFab[16]. Two aεFab molecules bound to IgE-Fc in a symmetrical manner, one on each Cε3 domain, trapping a fully extended conformation in which the local two-fold axes of the (Cε2)$_2$ domains and Fcε3-4 region were virtually coincident.

Analysis of the complex formation in solution, together with molecular dynamics simulations of free IgE-Fc, suggested that the (Cε2)$_2$ domain pair could "flip" over from one side of the Fcε3-4 region to the other[16]. The IgE-Fc conformation stabilized by this anti-IgE antibody is incompatible with FcεRI binding, explaining its inhibitory activity.

Omalizumab is an anti-IgE monoclonal IgG1 antibody that is approved for therapeutic use (Xolair®, Novartis)[17]. It binds to free IgE and inhibits both FcεRI and CD23 binding; the site of binding has been mapped to the Cε3 domain by peptide inhibition and molecular modelling[18,19] but its mechanism of action is unknown. However, binding to FRET-labelled IgE-Fc indicated a slight degree of unbending[9] and thus the potential for allosteric rather than direct inhibition.

Recently a type of inhibitor was discovered that actively disrupted preformed IgE/FcεRI complexes: a Designed Ankyrin Repeat Protein (DARPin) was found to bind to the Cε3 domain of receptor-bound IgE and accelerate its dissociation from FcεRI[20]. The crystal structure of the 2:1 complex of DARPin E2_79 with an Fcε3-4 molecule constrained by an engineered disulphide bond revealed the nature and location of the binding site, but left its mechanism of action unclear. It was subsequently reported that omalizumab could similarly facilitate dissociation of FcεRI-bound IgE, although only at very high concentrations that were substantially greater than those achieved in therapeutic use[21,22].

We report here the crystal structure of the complex between IgE-Fc and a new antibody fragment, a Fab derived from omalizumab (omalizumab Fab3) that contains three point mutations distal to the antigen (IgE-Fc) binding complementarity determining regions (CDRs). The mutations are S81R, Q83R and L158P with reference to Seq ID No. 125 (or S77R, Q79R and L154P with reference to Seq ID No. 129). The structure of the complex reveals the mechanism of action of omalizumab, and solution studies demonstrate that this mechanism exploits the intrinsic dynamics of IgE.

Results

Despite extensive efforts, crystallization trials for IgE-Fc in complex with the omalizumab Fab resulted in selective crystallization of the Fab fragment only. Others have reported similar failure to crystallize this complex[23]. We therefore designed a new antibody, a Fab derived from omalizumab, with three point mutations, two in the V$_L$ domain framework region (Ser81 Arg, Gln83Arg) and one in the Cκ domain (Leu158Pro) (Seq. ID No 125, PDB numbering) (FIG. 1), with the purpose of disrupting favorable crystal contacts observed in the omalizumab Fab crystal structure (results to be reported elsewhere). We term this omalizumab-derived Fab "omalizumab Fab3".

Overall Structure of the IgE-Fc/Omalizumab Fab3 Complex

We determined the crystal structure of the complex between IgE-Fc and omalizumab Fab3 to 3.7 Å resolution (FIG. 2A). Two omalizumab Fab3 molecules (Fab[1] and Fab[2]) bind to an asymmetric, partially bent IgE-Fc molecule, each Fab engaging one Cε3 domain (FIGS. 2B&C). Fab[1] engages the Cε3 domain of IgE-Fc chain B, while Fab[2] engages the Cε3 domain of IgE-Fc chain A. Due to the partially bent conformation of IgE-Fc in the complex, the light chain of Fab[2] also forms a minor interaction with the Cε2 domain from IgE-Fc chain B (see later in this example for details of this interaction).

The Interface Between IgE-Fc and Omalizumab Fab3

Figure 2:
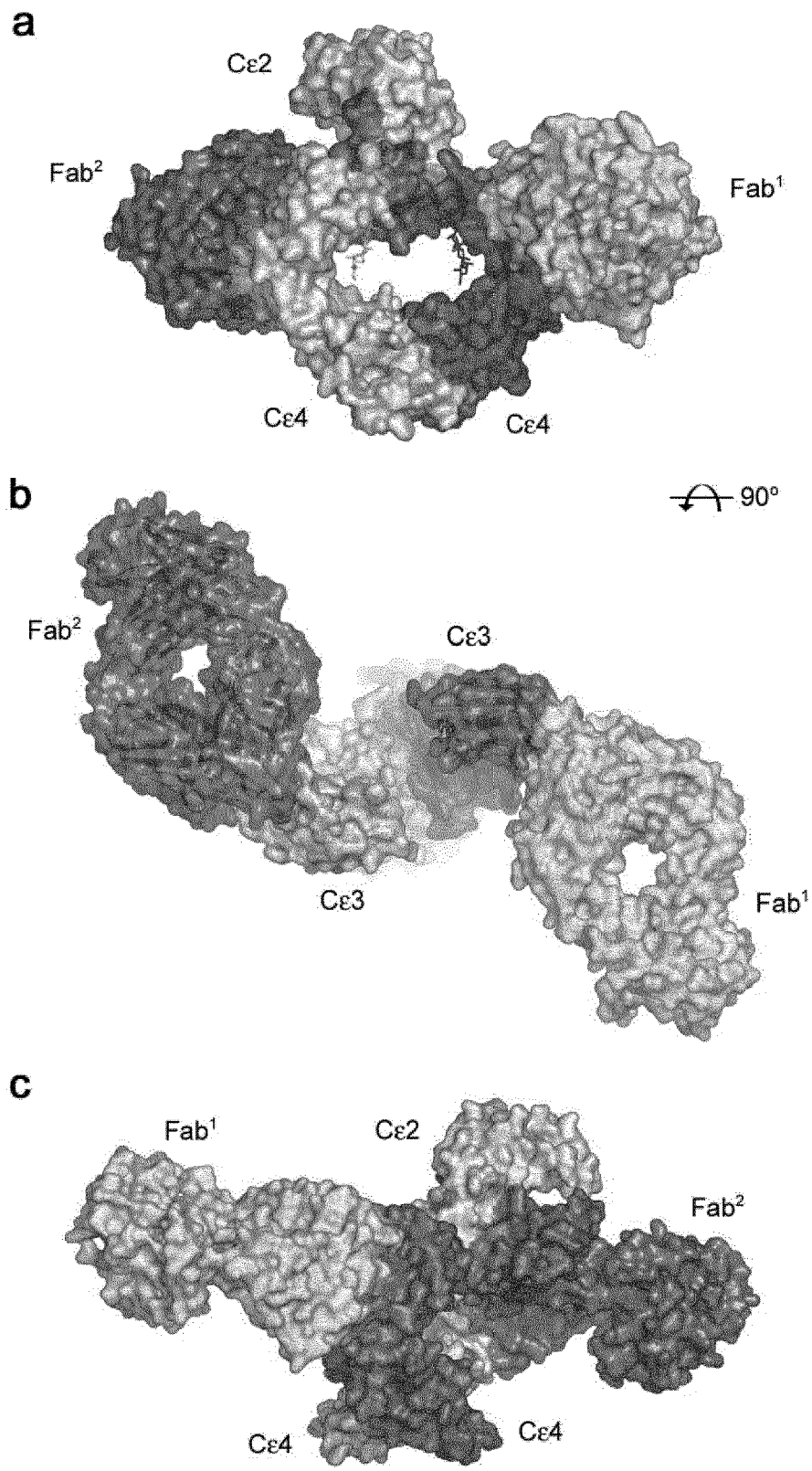
FIG. 2. Overall structure of IgE-Fc in complex with omalizumab Fab3. (A) omalizumab Fab3 binds to IgE-Fc with 2:1 stoichiometry. Fab[1] (green) engages IgE-Fc chain B (pink) exclusively through the Cε3 domain. Fab[2] (blue) interacts with IgE-Fc chain A (yellow) through the Cε3 domain and forms a minor interaction with the Cε2 domain from IgE-Fc chain B (pink). (B) The two Fabs form a pseudo-symmetric complex about the two-fold axis of the Fcε3-4 region. For clarity, the Cε2 domains are not shown. (C) IgE-Fc is asymmetrically bent in the omalizumab Fab3 complex. The Cε2 domain from chain B (pink) contacts Fab[2] (blue).
Figure 3:
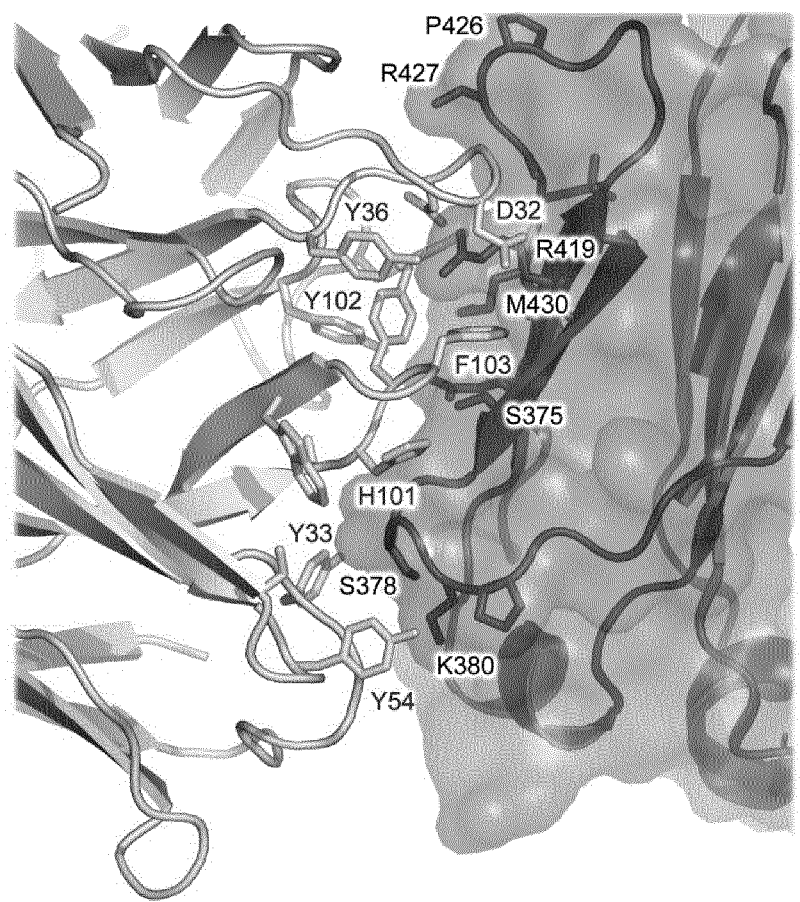
FIG. 3. Interface between omalizumab Fab3 and IgE-Fc. The interface between omalizumab Fab3 Fab[2] (heavy and light chains colored in green and yellow, respectively) and the Cε3 domain from IgE-Fc (pink) is shown. omalizumab Fab3 and Cε3 domain residue labels are colored blue and black, respectively. The interface comprises hydrogen bonds and van der Waals interactions. A notable feature of the interface is a cation-π interaction between Arg419 (Cε3 domain) and Phe103 (omalizumab Fab3 CDRH3). The Phe103 side chain is mostly buried in a pocket created by Thr373, Trp374, Ser375, Gln417 and Arg419 (Cε3 domain).

Each omalizumab Fab3 molecule engages one edge of the exposed face of the Cε3 domain (C, C', F and G strands, and base of the FcεRI receptor-binding FG loop). Both the heavy and light chain of omalizumab Fab3 are involved, the former contributing ~60% to an interface area of ~715 Å$^2$ (FIGS. 2&3).

The omalizumab Fab3 heavy chain (Seq. ID No. 5) contacts, which differ slightly between the two interfaces, may be summarised as follows: Gly32 and Tyr33 (CDRH1) form van der Waals interactions with Ala377 and Ser378 (Cε3) (IgE-Fc sequence as shown in Seq. ID No 108 and FIG. 16), while Tyr54 (CDRH2) contacts Gly379-Pro381 (Cε3). The CDRH3 residues contribute the largest contact area, and undergo a significant conformational change upon complex formation, when compared with unbound Fab structures (unpublished results,[19,23]). CDRH3 residues Ser100, His101, Tyr102 and Trp 106 all form van der Waals interactions with Cε3 domain residues that include Ser375-Gly379, Gln417 and Arg419 (Cε3). However, the most striking feature of this part of the interface is the interaction with Phe103 (CDRH3). Phe103 is mostly buried in a pocket created by Thr373, the Trp374 main chain, Ser375, Gln417 and Arg419 (Cε3), and forms a cation/π stacking interaction with Arg419 (FIG. 3).

Arg419 (Cε3) also plays a key role in the interaction with the omalizumab Fab3 light chain (Seq. ID No. 125) (FIG. 3). Arg419 (Cε3) is within hydrogen bonding distance of the Tyr31 (CDRL1) and Asp32 (CDRL1) main chain carbonyl oxygen atoms, in addition to contacting the Asp32, Asp34 and Tyr36 side chains (forming a hydrogen bond with the Tyr36 hydroxyl group). Asp32 also forms van der Waals interactions with Thr373 and Thr421 (Cε3). By contrast, only two CDRL2 residues contribute to the interface: Tyr53 (CDRL2) contacts Gln417 (Cε3), and both Tyr53 and Tyr57 form van der Waals interactions with Met430 (Cε3); Tyr57 also forms a hydrogen bond with the Met430 backbone. As for the heavy chain interaction, there are slight differences in the light chain contacts for Fab[1] and Fab[2].

CDR Contact Residues on Omalizumab Fab3 Numbering—in Format (Pdb/Kabat/Chothia).

Heavy Chain Sequence: Seq. ID No 5; Light Chain Sequence: Seq. ID No 125

CDRH1: Ser (31/31/31), Gly (32/32/31a), Tyr (33/33/32)
CDRH2: Tyr (54/53/53)
CDRH3: Ser (100/96/96), His (101/97/97), Tyr (102/98/98), Phe (103/99/99), Trp (106/101B/101B)
CDRL1: Asp (30/27C/30), Tyr (31/27D/30A), Asp (32/28/30B), Gly (33/29/30C), Asp (34/30/30D), Tyr (36/32/32)
CDRL2: Tyr (53/49/49), Ser (56/52/52), Tyr (57/53/53), Ser (60/56/56)

CDRL1 and CDRH3 have the most residues involved in the interaction, and therefore characterise how omalizumab binds and orients itself relative to IgE-Fc. CDRL3 is not involved in binding to IgE-Fc.

A Comparison of the Omalizumab Fab3 Interface with Other Anti-IgE Complexes

Figure 4:
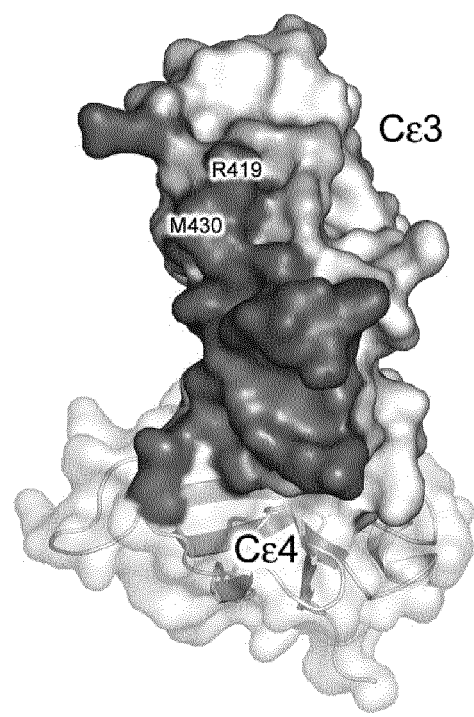
FIG. 4. omalizumab Fab3 and DARPin E2_79 bind to an overlapping interface. omalizumab Fab3 and DARPin E2_79[20] both bind to the Cε3 domain. IgE-Fc residues which only form part of the omalizumab Fab3 interface are colored orange, while those which only form part of the DARPin E2_79 interface, which includes part of the Cε3-Cε4 linker, are colored in blue. IgE-Fc residues colored in pink, which include Arg419 and Met430, are common to both omalizumab Fab3 and DARPin E2_79 interfaces.

The binding sites on the Cε3 domain for omalizumab Fab3 and the recently described DARPin E2_79[20] overlap (FIG. 4), and are of similar size at ~715 Å$^2$ and ~7531$^2$ respectively. The Cε3 domain residues shared between the two interfaces include Ser375-Gly379, Gln417, Arg419, Arg427 and Met430, but while omalizumab Fab3 forms more intimate contacts with the receptor-binding Cε3 FG loop, the DARPin E2_79 interface extends in the opposite direction to include the Cε3-4 domain linker.

Figure 5:
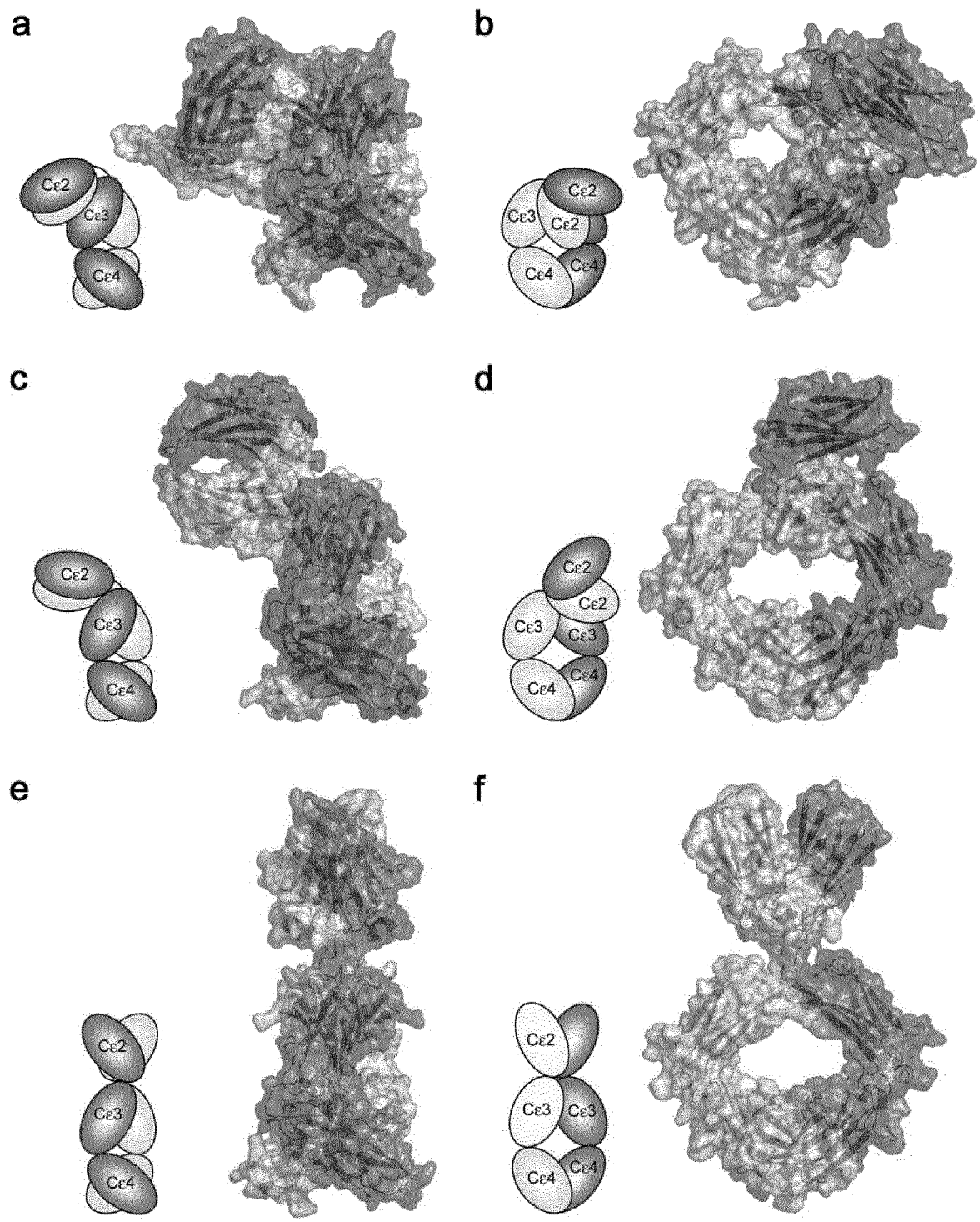
FIG. 5. Conformational flexibility in IgE-Fc. (A) Side view of free IgE-Fc[8] showing its acute, asymmetric bend. (B) Front view of free IgE-Fc (90° anti-clockwise rotation from the view shown in (A). (C) Side view of IgE-Fc from the omalizumab Fab3 complex, revealing a partially bent conformation. (D) Front view of IgE-Fc in the omalizumab Fab3 complex (90° anti-clockwise rotation from the view shown in (C). (E) Side view of fully extended IgE-Fc captured by an anti-IgE-Fc Fab (omalizumab Fab3)[16]. (F) Front view of extended IgE-Fc (90° anti-clockwise rotation from the view shown in (E).

The overlapping binding sites of omalizumab Fab3 and DARPin E2_79 differ markedly from the interface recently described for the omalizumab Fab3, which captured IgE-Fc in a fully extended conformation[16] (FIG. 5). Not only is the omalizumab Fab3 interface area approximately double that of omalizumab Fab3 and DARPin E2_79, at ~1400 Å$^2$, but omalizumab Fab3 engages IgE-Fc at a site centred on Arg393 in Cε3, and also contacts residues in the Cε2 domain and the Cε2-Cε3 linker[16]. The crystal structure of another anti-IgE antibody Fab, MEDI4212, in a 2:1 complex with Fcε3-4 reveals yet another site for antibody engagement within the Cε3 domain, this one involving the N-linked oligosaccharide moiety at Asn394[24].

IgE-Fc Adopts a Partially Bent Conformation when Bound to Omalizumab Fab3

IgE-Fc is predominantly bent in solution[5,6,9,25,26,27,28], and the crystal structure for free IgE-Fc revealed an acutely bent (62°), asymmetric conformation, in which the (Cε2)$_2$ domain pair folded back onto the Cε3 and Cε4 domains (FIGS. 5A&B), the Cε2 domain of one chain (chain B) contacting the Cε4 domain of the other (chain A)[7,8]. IgE-Fc becomes even more acutely bent (54°) upon FcεRIα engagement[8,9], and the associated conformational changes involve rotation of the Cε3 domain of chain A together with the (Cε2)$_2$ domain pair, as a rigid unit, away from the Cε3 domain of chain B[8].

In contrast to the omalizumab Fab3 complex, in which IgE-Fc adopts a fully extended, linear conformation[16], IgE-Fc adopts a partially bent conformation in the omalizumab Fab3 complex (FIGS. 2C and 5C&D), consistent with earlier FRET studies which revealed that omalizumab caused IgE-Fc to unbend[9]. The site to which Fab[1] binds is exposed in free, acutely bent IgE-Fc, but further unbending of IgE-Fc, to just over 90°, is required to render the site occupied by Fab[2] accessible. This unbending of IgE-Fc in the omalizumab Fab3 complex is associated with opening of both Cε3 domains, to create an almost symmetrical Fcε3-4 region (FIG. 2B). The (Cε2)$_2$ domain pair is located between the Cε3 and Cε4 domains from each chain and is no longer so closely associated with the Cε3 domain from chain A.

Figure 6:
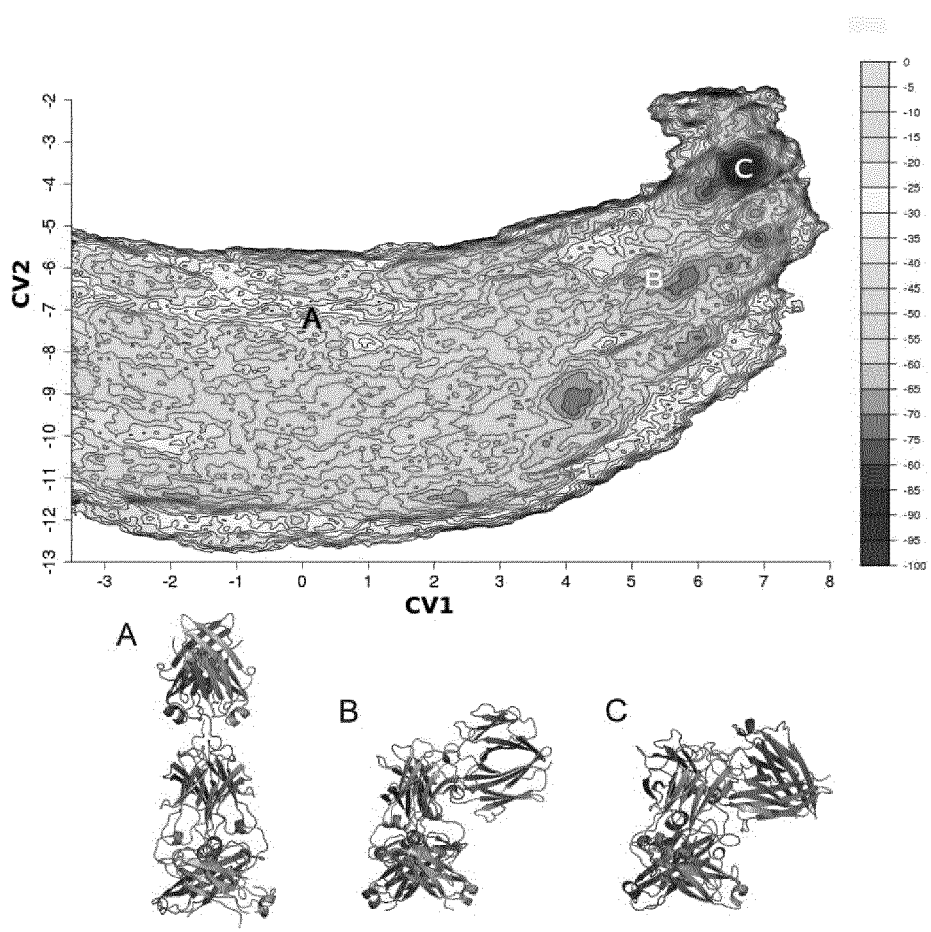
FIG. 6. Conformational flexibility in IgE-Fc. Flexibility of IgE-Fc, and unbending from the bent to a fully extended conformation, was previously explored by molecular dynamics[16]. IgE-Fc unbending is represented as a free energy surface, as previously described[16]. (A) Extended conformation of IgE-Fc captured in the crystal structure of the omalizumab Fab3/IgE-Fc complex[16]. (B) Partially bent IgE-Fc conformation observed in the crystal structure of the omalizumab Fab3/IgE-Fc complex. (C) Bent conformation of free IgE-Fc[7,8]. The bent conformation of IgE-Fc occupies the lowest energy basin, while the partially bent conformation observed in the omalizumab Fab3/IgE-Fc complex occupies a clearly distinct energy basin (B).

In a recent molecular dynamics simulation exploring unbending of IgE-Fc to an extended structure, it was found that while the acutely bent conformation observed in the crystal structure of free IgE-Fc occupied the lowest energy basin, another distinct and well defined energy basin, corresponding to partially bent IgE-Fc conformations, was observed[16]. The partially bent conformation adopted by IgE-Fc in the omalizumab Fab3/IgE-Fc complex occupies this particular energy basin (FIG. 6).

Figure 7:
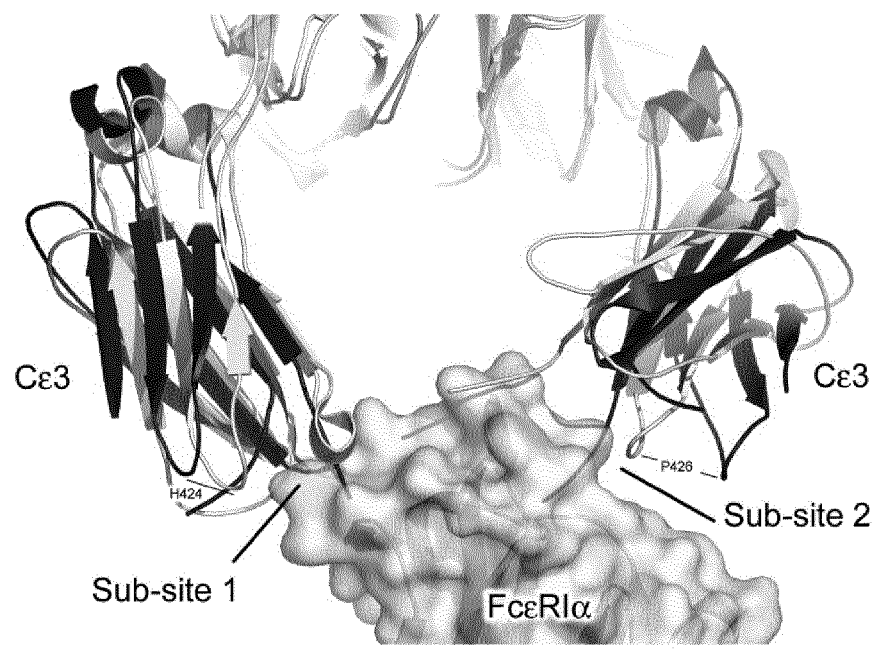
FIG. 7. Disruption of the interaction between IgE-Fc and FcεRI. In the omalizumab Fab3 complex, the Cε3 domains adopt the most open conformation reported thus far for IgE-Fc, which precludes engagement with FcεRIα. The structure of IgE-Fc in complex with FcεRIα[8] is colored yellow, and the two sub-sites of receptor engagement are indicated. The structure of omalizumab Fab3 in complex with IgE-Fc was superposed on the Cε4 domains, and the Cε3 domains are colored blue. Positions of His424 and Pro426 in the two structures are indicated, to highlight the different positions adopted by the Cε3 domains.

The Cε3 Domains Adopt a Markedly Open Conformation in the Omalizumab Fab3/IgE-Fc Complex In crystal structures of IgE-Fc and the Fcε3-4 sub-fragment, the Cε3 domains adopt a range of different orientations[7,8,10,11,13,14,16,24,29], a property associated with allosteric regulation of IgE binding to its two principal receptors, FcεRI and CD23[8,11,12,14]. Both the distance between the Cε3 domains, and their positions with respect to the Cε4 domains, has been used to describe the variety of conformations observed for the Fcε3-4 region[29] (a full description for these measurements is provided later in this example). In the omalizumab Fab3/IgE-Fc complex, the Cε3 domains are positioned further away from one another, and from the Cε4 domains, than in any other crystal structure containing IgE-Fc or Fcε3-4, and thus adopt the most open conformation observed thus far (FIG. 5); this conformation is significantly more open than the conformation for FcεRI-bound IgE-Fc (FIG. 7).

Effect of Omalizumab Fab3 on FcεRI and CD23 Receptor Binding

Omalizumab inhibits not only the interaction between IgE-Fc and FcεRI, but also the interaction between IgE-Fc and CD23[30]. Consistent with the latter, comparison of the omalizumab Fab3/IgE-Fc and CD23/Fcε3-4 complexes[11] reveals clashes between omalizumab Fab3 and CD23 at both sites of CD23 engagement on Fcε3-4. Furthermore, Cε3 domain residues Arg376, Ser378 and Lys380 are involved in both omalizumab Fab3 and CD23 binding[11,31].

Figure 8:
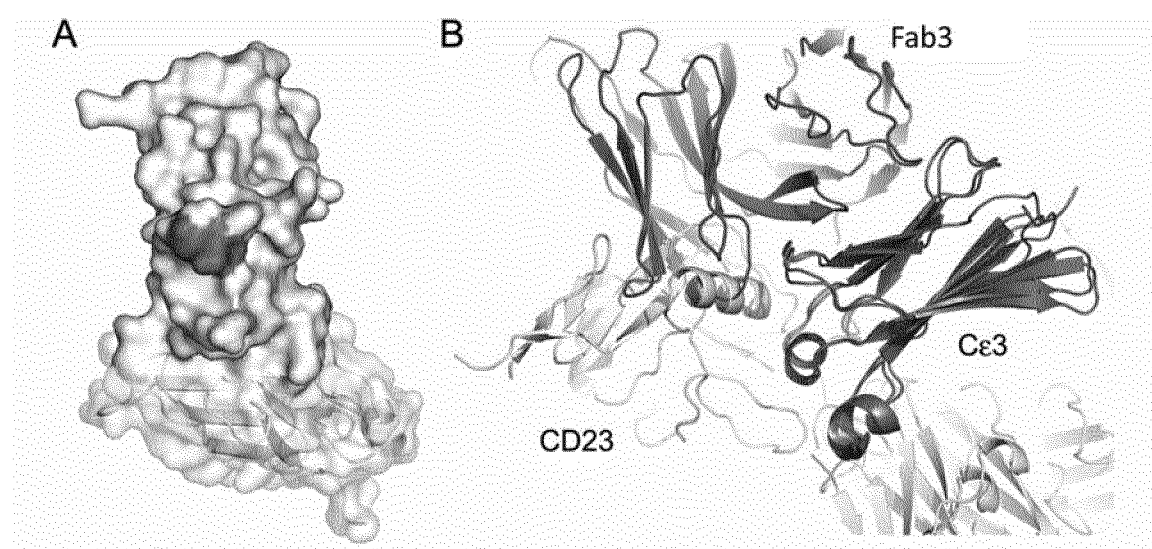
FIG. 8. Disruption of the interaction between IgE-Fc and CD23. (A) Cε3 domain residues which are common to both omalizumab Fab3 and CD23 interfaces are colored pink. (B) Superposition of the Cε3 domains (dark gray) from the omalizumab Fab3/IgE-Fc complex and CD23/Fcε3-4 complex[11] reveal clashes between CD23 (yellow) and omalizumab Fab3 (pink).

In contrast to CD23 binding to IgE, FcεRIα binds across both Cε3 domains. However, in the omalizumab Fab3/IgE-Fc complex, the Cε3 domains adopt a conformation that is too open to allow simultaneous engagement of both chains (FIG. 8). Furthermore, if the omalizumab Fab3/IgE-Fc and sFcεRIα/IgE-Fc complexes are superimposed on each of the Cε3 domains in turn, potential steric clashes occur in each case. If superimposed on the Cε3 domain of chain A, omalizumab Fab3 Fab[2] would clash with the (Cε2)$_2$ domain pair in the FcεRIα complex, and the Cε2-Cε3 linker from the omalizumab Fab3 complex would potentially clash with FcεRIα. If superimposed on the Cε3 domain of chain B, there would be a potential clash between both omalizumab Fab3 Fab[1] and the Cε2-Cε3 linker (of the omalizumab Fab3 complex) with FcεRIα—although the binding sites for Fab[1] and FcεRIα do not actually overlap.

However, omalizumab Fab3 CDRL1 residues are positioned immediately adjacent to the FcεRIα-binding Cε3 domain FG loop. This loop, in chain B, contributes to a hydrophobic "proline sandwich" interaction, in which Pro426 in Cε3 packs between two tryptophan residues of FcεRIα. Asp32 (CDRL1) contacts Thr421, Gly33 (CDRL1) contacts Pro426, Arg427 and Ala428, and Asp34 (CDRL1) contacts Arg427 and Ala428. These interactions alter the position of the Cε3 domain FG loop and would further compromise the binding of IgE to FcεRI.

Recently, binding of omalizumab to FcεRIα-bound IgE has been reported[21,32], although it is difficult to see how omalizumab might be able to engage FcεRI-bound IgE based on the static crystal structures of IgE-Fc in complex with sFcεRIα[8] and omalizumab Fab3. We therefore studied the binding of omalizumab Fab3 to IgE-Fc, and characterized the interaction between omalizumab Fab3 and the IgE-Fc/FcεRI complex. Our results provide insights into the mechanism of action of omalizumab.

Interaction of Omalizumab Fab3 with IgE-Fc in Solution

Figure 9:
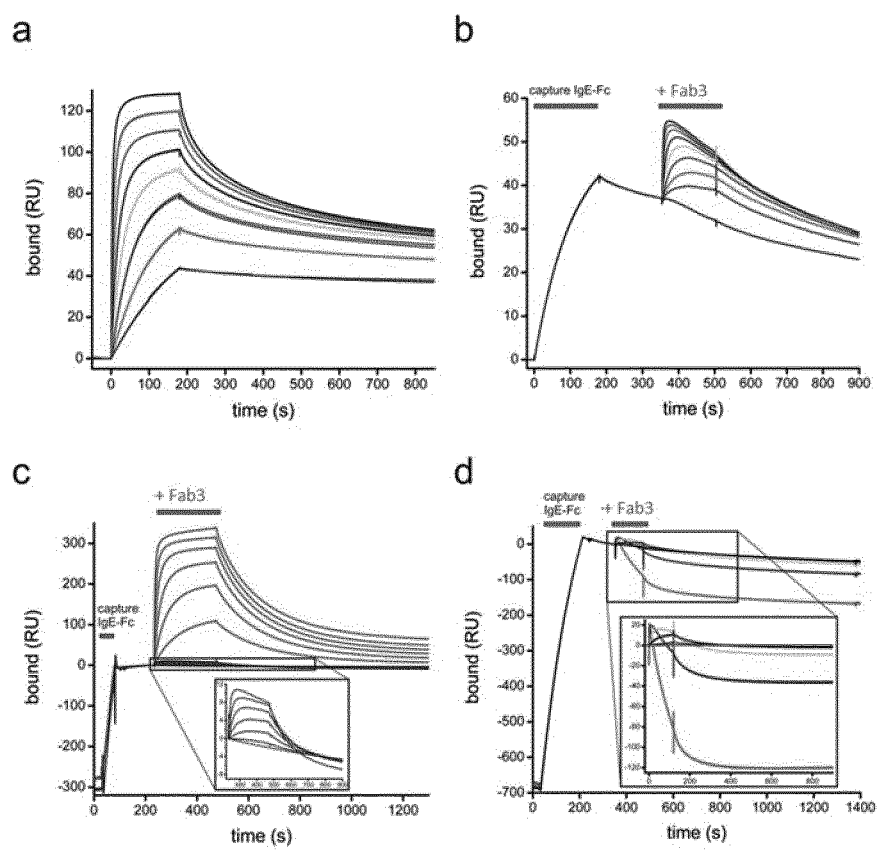
FIG. 9. Interaction studies of omalizumab Fab3 with IgE-Fc. (A) Binding of omalizumab Fab3 to IgE-Fc captured via a C-terminal His-tag; omalizumab Fab3 was flowed over IgE-Fc at the following concentrations 100 nM (black), 50 nM (red), 25 nM (green), 12.5 nM (blue), 6.2 nM (cyan), 3.1 nM (purple), 1.6 nM (magenta) and 0.8 nM (dark red). Standard double referencing methods were employed[36]; each concentration was run in duplicate. (B) Binding of the second omalizumab Fab3 binding site was characterized using an SPR sandwich binding experiment. IgE-Fc was captured on an omalizumab Fab3 surface, and then a second omalizumab Fab3 molecule was added to the IgE-Fc/omalizumab Fab3 complex at concentrations of 1000 nM (black), 500 nM (red), 250 nM (green), 125 nM (blue), 62.5 nM (cyan), 31.2 nM (purple), 15.6 nM (magenta), 7.8 nM (dark red) and 0 nM (navy). (C) A comparison of the ability of omalizumab Fab3 to bind to IgE-Fc captured by a C-terminal His-tag (red) and IgE-Fc captured by binding to FcεRIα (blue); a two-fold dilution series was tested for each, with a highest concentration of 1000 nM. The inset shows that omalizumab Fab3 can still bind to the IgE-Fc/FcεRIα complex, but with a low $B_{max}$ value. (D) Accelerated dissociation of the IgE-Fc/FcεRIα complex mediated by increasing concentrations of omalizumab Fab3. The 1:1 IgE-Fc/FcεRIα complex was first established by capturing IgE-Fc on immobilized FcεRIα and then binding omalizumab Fab3 at the following concentrations: 5000 nM (magenta), 1000 nM (purple), 200 nM (cyan), 40 nM (blue), 8 nM (green), 1.6 nM (red) and 0 nM (black). The inset shows a magnification of the accelerated dissociation process. All concentrations were run in duplicate. All binding experiments were performed at 25° C., except those characterizing the second omalizumab Fab3 binding site (FIG. 4B), which were done at 5° C. to minimize allosteric communication between the two sites.

We characterized the IgE-Fc/omalizumab Fab3 interaction in two different ways, either by directly immobilizing omalizumab Fab3 on a surface and binding IgE-Fc, or binding omalizumab Fab3 to a His-tagged captured IgE-Fc on an SPR sensor surface. A C-terminally His-tagged IgE-Fc construct was captured using an anti-His-tag antibody (GE Healthcare), and the binding characteristics of omalizumab Fab3, intact omalizumab and omalizumab Fab were compared. Not surprisingly, in competition binding experiments, all three molecules competed for the same binding sites and showed broadly similar binding affinities (data not shown). The omalizumab Fab3 construct demonstrates slightly higher affinity compared with omalizumab Fab3 and intact omalizumab (FIG. 8A-C). Consistent with the crystal structure, two omalizumab Fab3 molecules bind to IgE-Fc: the binding is clearly biphasic with a high-affinity (~1 nM) interaction observed at low ligand concentrations, and a second (weaker) binding site (~30 nM) observed at higher concentrations (FIG. 9A).

A sandwich SPR experiment allowed the two IgE-Fc/omalizumab Fab3 binding sites to be characterized separately. Using this approach, omalizumab Fab3 was covalently immobilized on a sensor surface, and IgE-Fc was flowed over this surface. At low concentrations, under these conditions, the high-affinity site dominates the interaction and the binding curves can be described by monophasic interaction kinetics ($K_D$~1 nM, $k_{on}$~1.2×10$^6$ M$^{-1}$ s$^{-1}$, $k_{off}$~8×10$^{-4}$ s$^{-1}$). This 1:1 IgE-Fc/omalizumab Fab3 complex, captured on the SPR biosensor surface, could then be used to measure the binding of the second omalizumab Fab3 molecule, the binding of which is significantly weaker ($K_D$~30 nM, $k_{on}$~2×10$^5$ M$^{-1}$ s$^{-1}$, $k_{off}$~6×10$^{-3}$ s$^{-1}$) than the first (FIG. 9B).

Competition Between the Omalizumab Fab3 and FcεRIα Binding Sites and the Formation of an Omalizumab Fab3/IgE-Fc/FcεRIα Complex We next investigated the capacity of omalizumab Fab3 to affect the interaction between IgE-Fc and FcεRIα. In solution competition binding experiments, increasing concentrations of omalizumab Fab3 inhibited binding of IgE-Fc to FcεRIα (FIG. 8D). Mechanistically, omalizumab Fab3 affects both the number of available binding sites ($B_{max}$) and the apparent $K_D$ of the IgE-Fc/FcεRIα interaction; this is characteristic of a mixed inhibition mechanism[33]. Reduction in $B_{max}$ values is indicative of an allosteric inhibitory process, and a decrease in the apparent affinity of the interaction is most commonly associated with direct competition for a shared binding site (i.e., orthosteric inhibition) but can also be seen for some allosteric inhibitors. Considering the binding sites observed in the crystal structure, it is likely that omalizumab Fab3 inhibits IgE-Fc binding to FcεRI using both orthosteric and allosteric mechanisms.

Competition between the omalizumab and FcεRIα binding sites has been described in many publications but has always been interpreted as direct competition for an identical (or overlapping) binding site. This interpretation has often been used to explain why omalizumab cannot bind to IgE-FcεRI complexes on cells. However, we observed that omalizumab Fab3 could bind with high affinity to IgE-Fc that was pre-bound to FcεRIα (FIG. 9C, inset). The existence of an omalizumab/IgE-Fc/FcεRI complex has been implied by other studies[21,32], but this complex has not before been experimentally characterized. The data indicate that while the binding of IgE-Fc to FcεRIα did not significantly change the affinity of omalizumab Fab3 for IgE-Fc, it did markedly change the number of available binding sites for omalizumab Fab3 in the population of FcεRIα-bound IgE-Fc molecules. We compared the $K_D$ and $B_{max}$ binding values for an IgE-Fc molecule captured via an anti-His-tag antibody with one captured by sFcεRIα, and found that FcεRIα-bound IgE-Fc had less than 10% of the omalizumab Fab3 binding sites compared to the His-tag captured IgE-Fc, which, as expected, showed binding levels consistent with 2:1 stoichiometry (FIG. 9C). So it is not, as has generally been assumed, that omalizumab does not bind to mast cell-bound IgE because the FcεRIα and omalizumab binding sites overlap. Instead, FcεRIα acts on IgE-Fc allosterically, changing a dynamic equilibrium of different IgE-Fc confonnations[16], resulting in a substantially reduced number of omalizumab binding sites in a population of FcεRIα-bound IgE-Fc molecules.

Figure 10:
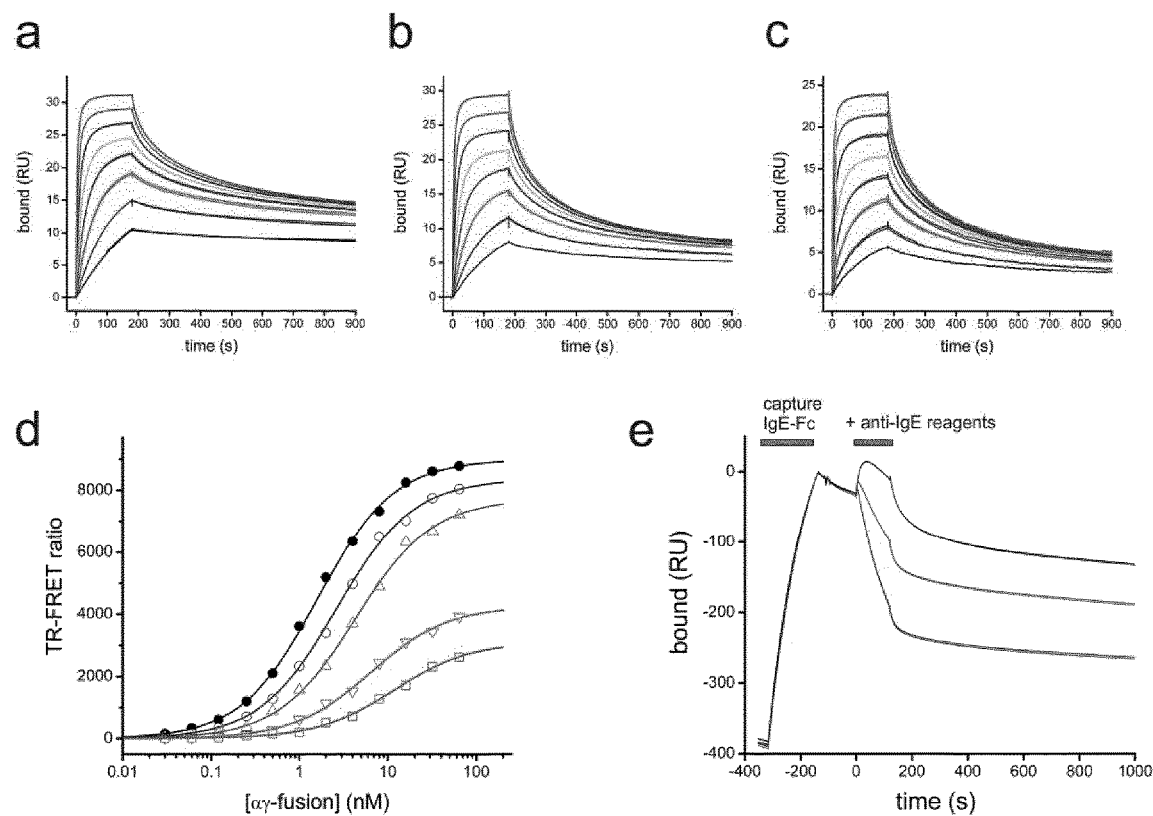
FIG. 10. Analysis of direct binding, competition experiments and accelerated dissociation. Direct binding was measured for IgE-Fc to immobilized omalizumab Fab3 (A), omalizumab Fab (B), and intact omalizumab (C). Fabs or intact antibody were covalently immobilized at low density using an amine coupling kit (GE Healthcare); IgE-Fc was flowed over these surfaces at a variety of concentrations, using a two-fold dilution series with a highest concentration of 100 nM. All concentrations were run in duplicate. (D) TR-FRET competition binding experiments between omalizumab Fab3 and ay-fusion protein for IgE-Fc. Binding between terbium-labeled ay-fusion protein and Alexa Fluor 647-labeled IgE-Fc was measured with increasing concentrations of unlabeled omalizumab Fab3 as inhibitor: 0 μM (black), 2.5 nM (blue), 5 nM (green), 10 nM (magenta), 20 nM (red). As an inhibitor, omalizumab Fab affects both the apparent $K_D$ and $B_{max}$ of the interaction between IgE-Fc and ay-fusion protein, indicating some allosteric inhibition properties. (E) Comparison of the accelerated dissociation of the IgE-Fc/sFcεRIα complex mediated by intact omalizumab (black), omalizumab Fab (red) or omalizumab Fab3 (blue), each at a concentration of 5 μM.

Mechanism of Omalizumab Fab3-Mediated Accelerated Dissociation of the IgE-Fc/FcεRIα Complex Kim et al.[20] reported that DARPin E2_79 could accelerate the disassembly of preformed complexes of IgE-FcεRI. Following up on this observation, Eggel et al.[21] later showed that omalizumab could also promote dissociation of IgE from FcεRI. Similar to these observations, we found that when omalizumab Fab3 bound to the IgE-Fc/FcεRIα complex, it could accelerate the dissociation of IgE-Fc from FcεRIα (FIG. 9D), and that omalizumab Fab3 did this more efficiently than omalizumab Fab3, and much more efficiently than intact omalizumab (FIG. 10E). One Fab engages the IgE-Fc/FcεRIα complex, but does not accelerate the dissociation of IgE-Fc from FcεRIα. Strikingly, it appears that accelerated dissociation occurs only after occupancy of the second binding site (i.e. the low-affinity site). The (omalizumab Fab3)$_2$/IgE-Fc/FcεRIα tetramolecular complex must alter the energy landscape of IgE-Fc in such a way to markedly reduce the energy barrier for IgE-Fc/FcεRIα dissociation, resulting in a rapid dissociation of this otherwise very stable complex.

Details of the Interaction Between the Omalizumab Fab3 Light Chain and the Cε2 Domain In the omalizumab Fab3/IgE-Fc complex, one Cε2 domain forms a minor interaction of approximately 260 Å$^2$ (compared with an average interaction area of ~715 Å$^2$ between omalizumab Fab3 and the Cε3 domain) with two of the mutated residues (Ser81Arg and Gln83Arg). There is no contact between Pro158 and IgE-Fc.

The Arg81 side chain, from the Fab$^2$ light chain (one of the mutated residues in omalizumab Fab3; (Seq. ID No 125, PDB numbering)), packs against Val277 and Asp278 from the Cε2 domain from chain B (Seq. ID No. 108). Ser80 (omalizumab Fab3) packs against Asp278, Leu279 and Thr281 (Cε2 domain), while Ser64 (omalizumab Fab3) packs against Asp276 and Asp278. Ser64 and Ser80 are identical in omalizumab and omalizumab Fab3.

In the omalizumab Fab3/IgE-Fc complex, Arg83 (one of the mutated residues in omalizumab Fab3) does not apparently contact the Cε2 domain, due to disorder in the Asp278 (Cε2 domain) side chain. However, if the Asp278 side chain were ordered, a hydrogen bond or salt bridge could potentially form between Arg83 and Asp278.

Crystallographically-Determined Contacts Between Omalizumab Fab3/IgE-Fc Complex

Contacts between antibody and antigen within 4 Å in a crystal structure are typically indicative of the epitope/paratope interface.

The IgE-Fc residues within 4 Å of the omalizumab Fab3 heavy and light chain CDRs define the following epitope: T 373, W 374, S 375, R 376, A 377, 3 S 78, G 379, P 381, Q 417, C418, R 419, P 426, R 427, A 428 (on chain A).

Furthermore, the IgE-Fc residues within 4 Å of the omalizumab Fab3 light chain FR1 and FR3 residues extend the epitope to:

D 278, T 281 (on chain B—Cε2 domain) [with contacts to R18, S64, S80 and R81 of the antibody—and further R83 as revealed during the molecular dynamics simulation described in Example 5].

Contacts between antibody and antigen within 5 Å in a crystal structure also are informative in defining the antibody/antigen interface.

The additional IgE-Fc residues within 5 Å of the omalizumab Fab3 heavy and light chain CDRs are: K380, M430 (on chain A).

Furthermore, the additional IgE-Fc residues within 5 Å of the omalizumab Fab3 light chain FR1 and FR3 residues are:

D276, V277, L279, S280, A282 (on chain B—Cε2 domain) [with further contacts to G16 of FR1 and R65 of FR3].

Analysis of Cε3 Domain Orientation in the Omalizumab Fab3/IgE-Fc Complex

In one method to analyses the position of the Cε3 domains with respect to the Cε4 domains, the interatomic distance between the Asn394 Cα atom from the Cε3 domain from one chain, and the Lys497 Cα atom from the Cε4 domain of the other chain has been used to describe the "openness" of the Cε3 domains[29]. The interatomic distance between the Val336 Cα has been used to describe the "swing", or how close the Cε3 domains are to one another[29].

For FcεRI-bound IgE-Fc, and FcεRI-bound Fcε3-4, in which the Cε3 domains adopt an open conformation, "openness" values range from 23.5-28.4 Å, while the "swing" values are an average of 23.3 Å[8,10]. Corresponding values for the omalizumab Fab3/IgE-Fc complex are an average of 29.5 for the "openness" and 29.4 Å for the "swing". In the omalizumab Fab3 complex, the Cε3 domains adopt the most open conformation (furthest apart from one another), described thus far.

Discussion

We report the structure, at 3.7 Å resolution, of the complex between IgE-Fc and a Fab fragment derived from the therapeutic anti-IgE antibody omalizumab; we call this Fab fragment, which contains three point mutations in framework regions distal to the antigen-binding site, omalizumab Fab3. The structure reveals two omalizumab Fab3 molecules in complex with IgE-Fc, one bound to each of the two Cε3 domains (but only one of the Fabs bound to a Cε2 domain), and provides an explanation for the ability of omalizumab to inhibit the binding of IgE to both FcεRI and CD23. IgE-Fc is also found to adopt a partially bent conformation in the omalizumab Fab3 complex, consistent with our earlier study using a FRET-labelled IgE-Fc, which indicated a slight unbending relative to free IgE-Fc[9].

IgE-Fc is predominantly bent in solution[5,6,9,25,26,27,28], and in the crystal structure of free IgE-Fc, the (Cε2)$_2$ domain pair is folded back against the Cε3 and Cε4 domains[7,8]. Recently, our understanding of the conformational flexibility of IgE-Fc was profoundly enhanced when we solved the structure of a fully extended conformation, captured in a complex with an anti-IgE-Fc Fab (aεFab)[16]. A molecular dynamics simulation, exploring IgE-Fc unbending from the acutely bent to the extended conformation, revealed energy basins corresponding to partially bent conformations (FIG. 6). The omalizumab Fab3/IgE-Fc complex reported here, in which the bend between the (Cε2)$_2$ domain pair and the Fcε3-4 domains is ~90°, corresponds to a distinct energy basin in this simulation[16]. Intriguingly, the location of the omalizumab Fab3 binding site would not preclude further unbending to the fully extended conformation and it is therefore possible that IgE-Fc can undergo substantial changes in conformation even when in complex with omalizumab.

In addition to the bending of the (Cε2)$_2$ domain pair relative to the Cε3 and Cε4 domains, the various IgE-Fc, Fcε3-4 and receptor complex structures have demonstrated that the Cε3 domains can adopt a range of relative orientations, from closed to open[7,8,10,11,13,14,16,24,29]. Opening and closing of the Cε3 domains contributes to the allosteric regulation of receptor binding in IgE-Fc[11,12]: in the CD23 complex they are relatively closed[11,13,14], whereas in the FcεRI complex they are more open[8,10]. Comparison of the structures of the CD23/Fcε3-4 and omalizumab Fab3/IgE-Fc complexes shows that the CD23 and omalizumab sites overlap, and competition binding experiments indicate that inhibition of IgE binding to CD23 by omalizumab is straightforwardly orthosteric.

However, inhibition of FcεRI binding is more complicated. In the omalizumab Fab3 complex, the Cε3 domains adopt a more open conformation than seen in any previous structure, so much so that the two sub-sites of interaction between IgE-Fc and FcεRI, one involving each Cε3 domain, cannot engage simultaneously. Another contribution to this inhibition may result from the proximal location of the omalizumab Fab3 (Fab) molecule to the receptor-binding FG loop in Cε3, which may directly affect the conformation of contact residues for FcεRIα. Finally, even though the omalizumab Fab3 and FcεRIα binding epitopes on IgE-Fc do not strictly overlap, there is the possibility of steric clashes if the two were bound simultaneously. Thus, the crystal structure suggests that omalizumab's mechanism of inhibition is principally allosteric but with a potential orthosteric component.

SPR studies enabled us to assess the kinetics and affinities for the two omalizumab Fab3 binding sites. The two affinities differ markedly, with $K_D$ values of ~1 nM and ~30 nM, the former associated with a faster association rate constant ($k_{on}$~2×10$^6$ M$^{-1}$ s$^{-1}$ compared with ~2×10$^5$ M$^{-1}$ s$^{-1}$) and a slightly slower dissociation rate constant ($k_{off}$~2×10$^{-3}$ s$^{-1}$ compared with ~6×10$^{-3}$ s$^{-1}$). It might be speculated that the higher affinity interaction corresponds to the binding of Fab$^1$, which would have unimpeded access to a bent IgE-Fc molecule, while the lower affinity and slower on-rate corresponds to Fab$^2$, but we cannot be definitive about this.

Further SPR experiments to investigate the mechanism of the inhibition of IgE-Fc binding to FcεRIα by omalizumab Fab3 revealed a reduction in the number of available sites for omalizumab Fab3 on IgE-Fc (reduced $B_{max}$) when in complex with FcεRIα. The inhibition of IgE binding to FcεRI by omalizumab has frequently been interpreted in terms of direct competition for overlapping sites, but there have been reports that indicate that omalizumab can bind to receptor-bound IgE[21,32]. We have here demonstrated directly the ability of omalizumab Fab3 to bind to IgE-Fc when it is already bound to FcεRIα to form a trimolecular complex. The effect of the pre-binding of IgE-Fc to FcεRIα is to reduce the number of omalizumab Fab3 binding sites on IgE-Fc to less than 10% of those available in free IgE-Fc; this effect can only be due to allosteric modulation.

The nature of the interaction of omalizumab Fab3 with the IgE-Fc/FcεRI complex provides insights into the mechanism of accelerated dissociation. This phenomenon was first reported for a DARPin and subsequently for omalizumab[20,21], the latter at substantially greater concentrations than those used therapeutically[22], and is now shown here for omalizumab Fab fragments. We further demonstrate that the dissociation occurs only after first binding of the second (lower affinity) omalizumab Fab3 molecule. Stated another way, a tetramolecular complex—(omalizumab Fab3)$_2$/IgE-Fc/FcεRIα—must be formed for significant accelerated dissociation to occur.

Based on our observations with omalizumab Fab3, IgE-Fc and sFcεRIα, we envisage the following mechanism occurring for omalizumab, IgE and FcεRI: IgE binds to FcεRI and, under these conditions, a small population of these bound IgE molecules adopt a conformation to which omalizumab molecules can bind; when a second omalizumab molecule binds to form the tetrameric complex, the energy landscape of IgE is changed such that the interaction with FcεRI is destabilized, and a rapid dissociation of IgE from FcεRI occurs. Key to understanding this mechanism is an appreciation of the complexity of the energy landscape for IgE, and the different conformational states that exist in dynamic equilibrium.

The inhibitory activities of omalizumab appear to take advantage of the intrinsic flexibility of IgE and, at least for the process of accelerated dissociation, the dynamics of the IgE/FcεRI complex. IgE has a number of unusual structural characteristics compared to other antibody isotypes, including the presence of the Cε2 domains and the uniquely conformationally dynamic, molten globule-like character of the Cε3 domains[34]. Together, these properties create an allosteric communication pathway that prevents simultaneous engagement of CD23 and FcεRI; this is essential to avoid allergen-independent mast cell activation by cross-linking of FcεRI-bound IgE by the trimeric CD23 molecule[12]. Other functional advantages associated with the dynamics of IgE have been proposed for the membrane-bound IgE B cell receptor[16]. The observation that omalizumab does not utilize the expected orthosteric mechanism for inhibition of the IgE/FcεRI interaction indicates that it also exploits the unusual dynamic properties of IgE, both in its capacity as a blocking antibody and its ability to avoid crosslinking of mast cell-bound IgE. Finally, omalizumab can actively dissociate IgE from FcεRI, albeit at concentrations higher than used therapeutically[21], by employing allostery and the intrinsic flexibility of IgE, present even when in complex with its receptors.

Methods

Cloning, protein expression and purification. Omalizumab human IgG$_1$ Fab and omalizumab Fab3 were cloned, expressed and purified as described in[16]. IgE-Fc was produced as described previously[35]. IgE-Fc was according to Seq. ID No. 108 (V224-K547 according to Dorrington & Bennich (1978) Immunol. Rev. 41:3-25, but with the following mutations inserted into the IgE-Fc to simplify the glycosylation pattern: N265Q & N371Q). Omalizumab was purchased from Novartis Europharm Limited. The 2:1 omalizumab Fab3/IgE-Fc complex was purified by size exclusion chromatography, eluted into 25 mM Tris-HCl pH7.5, 20 mM NaCl and 0.05% (w/v) NaN$_3$, and concentrated to 23 mg/mL.

Surface Plasmon Resonance. SPR experiments were carried out on a Biacore T200 instrument (GE Healthcare). Specific surfaces were prepared either by covalently coupling proteins using the amine coupling protocol (GE Healthcare), with coupling densities <300 resonance units, or capturing His-tagged proteins using an anti-His sensor surface. For capturing His-tagged ligands, an anti-His-tag monoclonal antibody was employed and immobilized according to manufacturer's instructions (Biacore His Capture Kit, GE Healthcare). In binding experiments, association times of 180-240 s were typically used, and dissociation components were monitored for at least 500 s. Injections were performed at a flow rate of 25 μL min$^{-1}$, in a running buffer of 20 mM HEPES pH 7.4, 150 mM NaCl, and 0.005% (v/v) surfactant P-20 (GE Healthcare). Most experimental measurements were performed at 25° C.; some of the sandwich binding experiments were done at 5° C. in order to minimize the accelerated dissociation phenomenon. Standard double referencing data subtraction methods were used[36] and kinetic fits were performed using Origin software (OriginLab).

TR-FRET. IgE-Fc was labeled with donor fluorophore by reacting 4 mg/mL protein in 100 mM sodium bicarbonate, 50 mM NaCl, pH 9.3, with a 5-fold molar excess of terbium chelate isothiocyanate (Invitrogen). After 3 hr incubation at room temperature with agitation, excess unreacted fluorophore was removed by dialyzing into PBS (20 mM phosphate buffer saline, 150 mM NaCl, pH 7.4). sFcεRIα-IgG4-Fc fusion protein (α-γ)[37] was labeled with acceptor fluorophore by reacting 3 mg/ml protein with a 2.5-fold molar excess of Alexa Fluor 647 succinimidyl ester (Invitrogen) for 1 hr at room temperature. Excess fluorophore was removed by dialyzing into PBS.

TR-FRET inhibition assays were performed by competing 1 nM terbium labeled IgE-Fc and 0-20 nM of Alexa Fluor 647 labeled sFcεRIα-IgG$_4$-Fc with a range of concentrations of omalizumab Fab3. Assays were conducted in 384 well hi-base, white plates (Greiner BioOne) using Lanthascreen buffer (Invitrogen) as a diluent. The plate was left to incubate overnight at room temperature and read by an Artemis plate reader (Berthold Technologies). TR-FRET ratios were then calculated for each well as the emission of acceptor at 665 nm divided by the emission of donor at 620 nm multiplied by 10,000.

Crystallization. Crystals with a rectangular morphology, up to 400 μm in length, were grown at 18° C. using the sitting drop vapour diffusion method. The reservoir contained 50 μL 4% (w/v) PEG 8000 and 0.03M sodium fluoride, and the drop contained 100 nL protein and 300 nL reservoir. Despite extensive efforts at optimisation, the diffraction quality of the crystals could not be further improved beyond that used for this study. Crystals typically started to grow after a few days, and often dissolved in their drops, but could be stabilized in 4M TMAO (trimethylamine N-oxide), which was successfully used as a cryoprotectant.

Data collection and processing. Data were collected at beamlines 102 and 103 at the Diamond Light Source (Harwell, UK). Integration was performed using XDS[38] as implemented in the xia2 package[39]. The crystals diffracted anisotropically, and data from multiple crystals were merged. The data were scaled to 3.7 Å resolution with AIMLESS from the CCP4 suite[40,41] and then truncated to resolution limits of 3.7 Å (a*), 3.9 Å (b*) and 4.2 Å (c*) using the UCLA Diffraction Anisotropy Server[42]. Calculation of the Matthews coefficient indicated a solvent content of ~62%, for a single 2:1 omalizumab Fab3/IgE-Fc complex (molecular mass of ~170 kDa) in the asymmetric unit.

Figure 11:
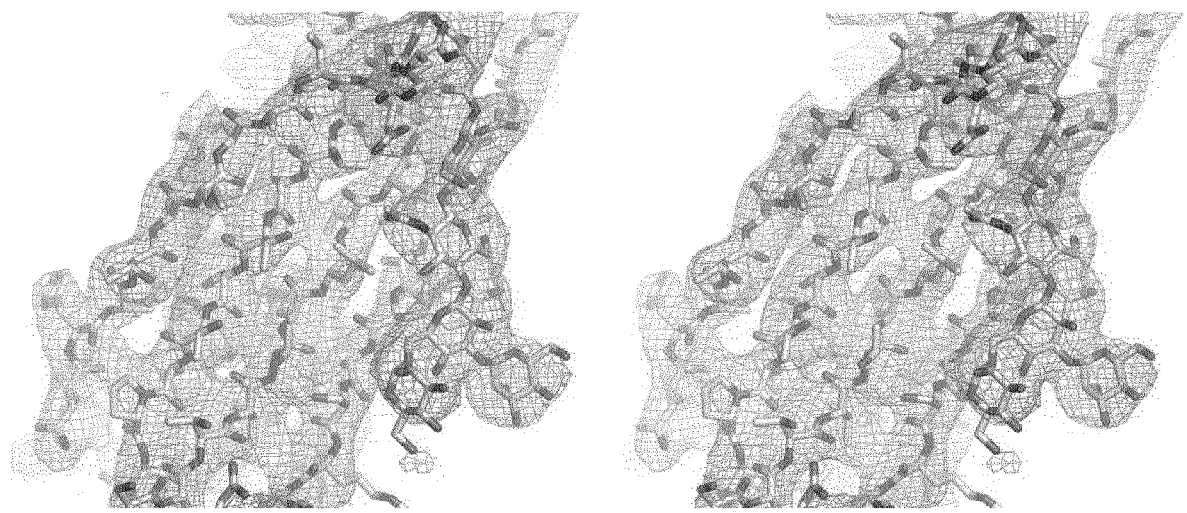
FIG. 11. Representative electron density map. A stereoview of the $2F_o-F_c$ electron density map, contoured at 1.1σ, is shown for a portion of the chain A Cε3 domain, and covalently N-linked oligosaccharide moiety at Asn394.
Figure 12:
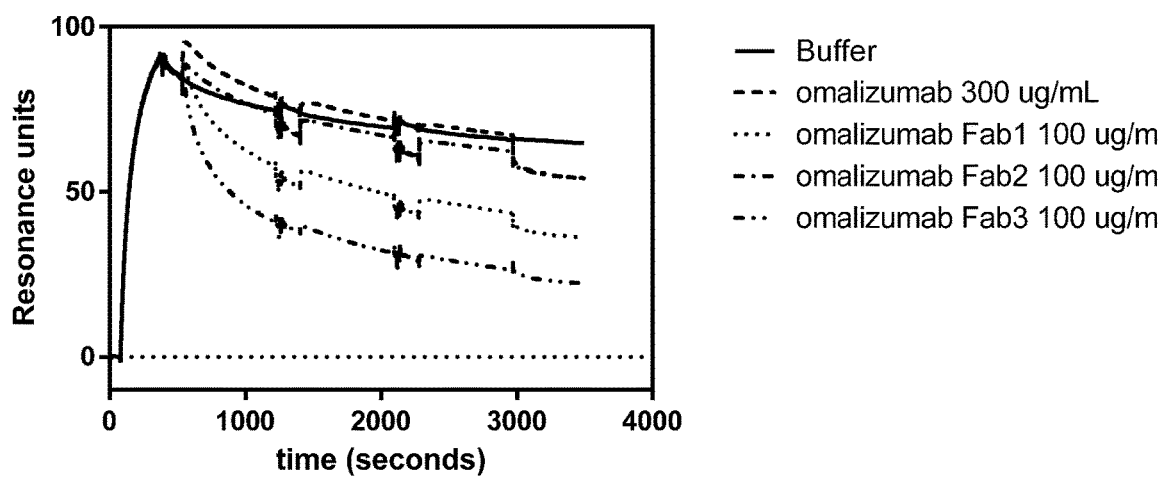
FIG. 12. Biacore sensorgram of the dissociation of IgE-Fc from immobilized sFcεRIα. Dissociation was monitored in the presence of running buffer (solid line) or IgE binding partners (all other sensorgrams). Assay performed as described in Assay Method (1) Example 2.
Figure 13:
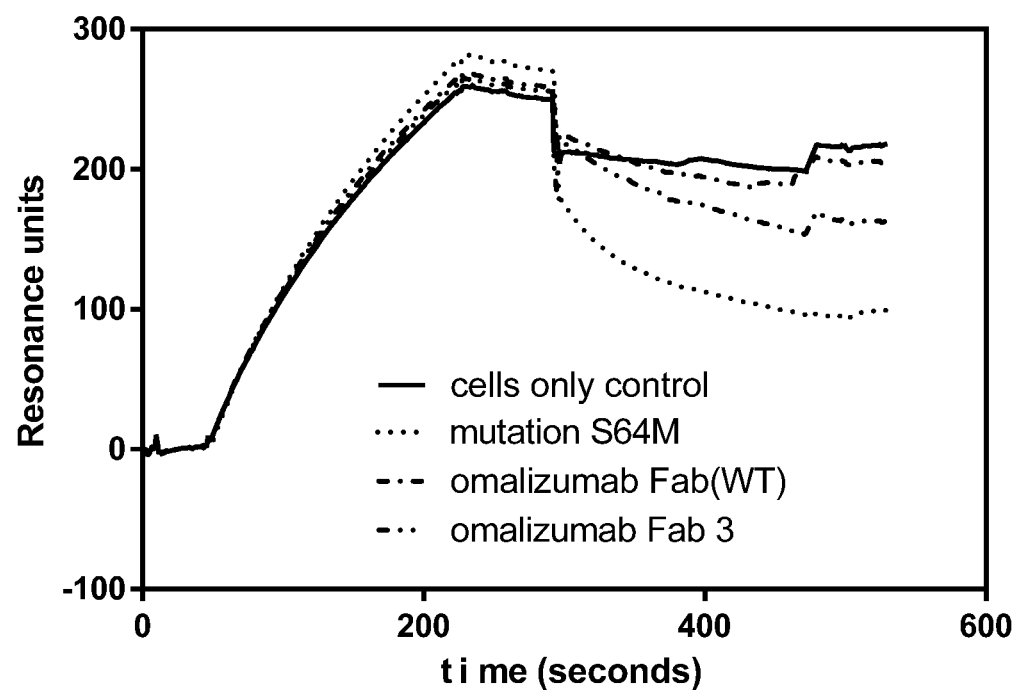
FIG. 13. Biacore sensorgram of the dissociation of IgE-Fc from immobilized sFcεRIα. Dissociation was monitored in the presence of control supernatant (solid line) or IgE binding partners (all other sensorgrams). Assay performed as described in Assay Method (2) Example 2.
Figure 14:
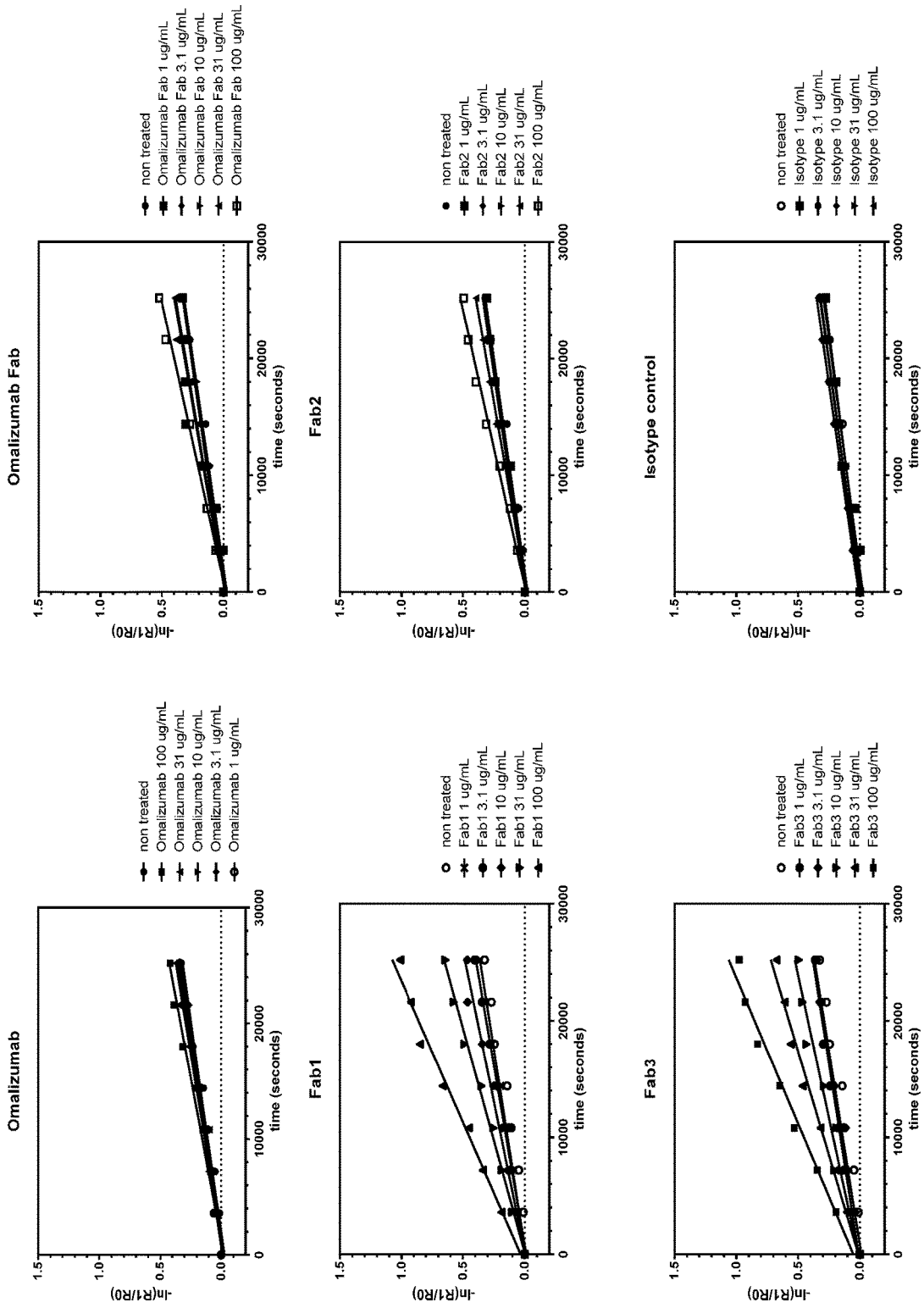
FIG. 14. Analysis of dissociation of Alexa488 labelled IgE-Fc from the surface of RBL-SX38 cells. Measured binding data normalized to 100% at t=0 and dissociation data plotted as the change in proportion of IgE-Fc remaining bound as a function of time.
Figure 15:
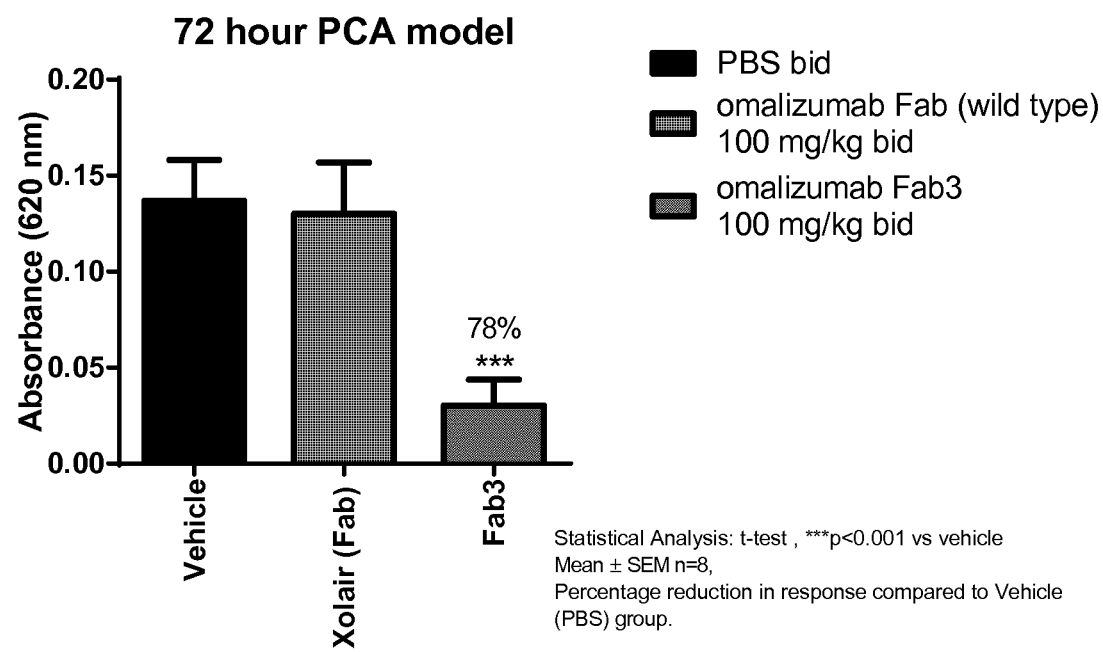
FIG. 15. Analysis of the effect of therapeutic dosing of wild type omalizumab Fab and omalizumab Fab3 on the 72 hour PCA model.

Structure determination, model building and refinement. The structure was solved by molecular replacement with PHASER[43] and MOLREP[44] from the CCP4 suite[40] using protein atoms from PDB entry 2wqr[8] and a 1.91 resolution omalizumab Fab structure (unpublished results) as search models. Refinement was initially performed with REFMAC[45] and later with PHENIX[46], and alternated with manual model building in Coot[47]. The quality of the model was assessed with MolProbity[48], POLYGON[49], and other validation tools within the PHENIX graphical interface[50]. Data processing and refinement statistics are presented in Table 1. A region of the electron density map is shown in FIG. 11. Interfaces were analysed with PISA[51], and figures were prepared with PyMOL[52].

TABLE 1

Data processing and refinement statistics

Data processing

| | |
|---|---|
| Space group | I 2$_1$ 2$_1$ 2$_1$ |
| Unit cell dimensions (Å) | a = 76.64, b = 231.19, c = 247.12 |

TABLE 1-continued

Data processing and refinement statistics

| | |
|---|---|
| Resolution (Å): overall (outer shell) | 115.59-3.70 (4.10-3.70) |
| Completeness (%)[a] | 99.9 (99.9) |
| Multiplicity[a] | 38.0 (38.4) |
| Mean $(\langle I \rangle/\sigma(I))$[a] | 17.9 (1.9) |
| $R_{pim}$ (%)[a] | 2.6 (56.3) |
| Refinement[b] | |
| $R_{work}/R_{free}$ (%)[c] | 25.88/30.92 |
| No. of reflections | 20 087 |
| RMSD | |
| Bond lengths (Å) | 0.002 |
| Bond angles (°) | 0.451 |
| Coordinate error (Å) | 0.60 |
| Ave. B-factor (Å$^2$) | 171.2 |
| Ramachandran plot | |
| Favoured (%) | 95.81 |
| Allowed (%) | 100.00 |

[a]Values in parentheses are for the highest resolution shell
[b]Refinement was performed with data truncated to resolution limits of 3.7 Å (a*), 3.9 Å (b*) and 4.2 Å (c*)
[c]$R_{free}$ set comprises 5% of reflections

REFERENCES

1. Gould, H. J., Sutton, B. J. IgE in allergy and asthma today. Nat. Rev. Immunol. 8, 205-217 (2008).
2. Sutton, B. J., Davies, A. M. Structure and dynamics of IgE-receptor interactions: FcεRI and CD23/FcεRII. Immunol. Rev. 268, 222-235 (2015).
3. Holgate, S. T. New strategies with anti-IgE in allergic diseases. World Allergy Organ. J. 7,17 (2014).
4. Holowka, D., Baird, B. Structural studies on the membrane-bound immunoglobulin E (IgE)-receptor complex. 2. Mapping of distances between sites on IgE and the membrane surface. Biochemistry 22, 3475-3484 (1983).
5. Zheng, Y., Shopes, B., Holowka, D., Baird, B. Conformations of IgE bound to its receptor Fc epsilon RI and in solution. Biochemistry 30, 9125-9132 (1991).
6. Beavil, A. J., Young, R. J., Sutton, B. J., Perkins, S. J. Bent domain structure of recombinant human IgE-Fc in solution by X-ray and neutron scattering in conjunction with an automated curve fitting procedure. Biochemistry 34, 1449-1461 (1995).
7. Wan, T. et al. The crystal structure of IgE Fc reveals an asymmetrically bent conformation. Nat. Immunol. 3, 681-686 (2002).
8. Holdom, M. D. et al., Conformational changes in IgE contribute to its uniquely slow dissociation rate from receptor FcεRI. Nat. Struct. Mol. Biol. 18, 571-576 (2011).
9. Hunt, J. et al. A fluorescent biosensor reveals conformational changes in human immunoglobulin E Fc: implications for mechanisms of receptor binding, inhibition, and allergen recognition. J. Biol. Chem. 287, 17459-17470 (2012).
10. Garman, S. C., Wurzburg, B. A., Tarchevskaya, S. S., Kinet, J. P., Jardetzky, T. S. Structure of the Fc fragment of human IgE bound to its high-affinity receptor FcεRIα. Nature 406, 259-266 (2000).
11. Dhaliwal, B. et al. Crystal structure of IgE bound to its B-cell receptor CD23 reveals a mechanism of reciprocal allosteric inhibition with high affinity receptor FcεRI. Proc. Natl. Acad. Sci USA 109, 12686-12691 (2012).
12. Borthakur, S. et al. Mapping of the CD23 binding site on immunoglobulin E (IgE) and allosteric control of the IgE-FcεRI interaction. J. Biol. Chem. 287, 31457-31461 (2012).
13. Yuan, D. et al. Ca$^{2+}$-dependent structural changes in the B-cell receptor CD23 increase its affinity for human immunoglobulin E. J. Biol. Chem. 288, 21667-21677 (2013).
14. Dhaliwal, B., Pang, M. O., Yuan, D., Beavil, A. J., Sutton, B. J. A range of Cε3-Cε4 interdomain angles in IgE Fc accommodate binding to its receptor CD23. Acta Crystallogr. F70, 305-309 (2014).
15. Cooper, A., Dryden, D. T. Allostery without conformational change. A plausible model. Eur. Biophys. J. 11, 103-109 (1984).
16. Drinkwater, N. et al. Human immunoglobulin E flexes between acutely bent and extended conformations. Nat. Struct. Mol. Biol. 21, 397-404 (2014).
17. Holgate, S., Casale, T., Wenzel, S., Bousquet, J., Deniz, Y., Reisner, C. The anti-inflammatory effects of omalizumab confirm the central role of IgE in allergic inflammation. J. Allergy Clin. Immunol. 115, 459-465 (2005).
18. Zheng, L. et al. Fine epitope mapping of humanized anti-IgE monoclonal antibody omalizumab. Biochem. Biophys. Res. Comm. 375, 619-622 (2008).
19. Wright, J. D. et al. Structural and Physical Basis for Anti-IgE Therapy. Sci. Rep. 5,11581 (2015).
20. Kim, B. et al. Accelerated disassembly of IgE-receptor complexes by a disruptive macromolecular inhibitor. Nature 491, 613-617 (2012).
21. Eggel, A. et al. Accelerated dissociation of IgE-FcεRI complexes by disruptive inhibitors actively desensitizes allergic effector cells. J. Allergy Clin. Immunol. 133, 1709-1719 (2014).
22. Lowe, P. J., Tannenbaum, S., Gautier, A., Jimenez, P. Relationship between omalizumab pharmacokinetics, IgE pharmacodynamics and symptoms in patients with severe persistent allergic (IgE-mediated) asthma. Br. J. Clin. Pharmacol. 68, 61-76 (2009).
23. Jensen, R. K. et al. Structure of the omalizumab Fab. Acta Crystallogr. F71, 419-426 (2015).
24. Cohen, E. S. et al. A novel IgE-neutralizing antibody for the treatment of severe uncontrolled asthma. mAbs 6, 755-763 (2014).
25. Zheng, Y., Shopes, B., Holowka, D., Baird, B. Dynamic conformations compared for IgE and IgG1 in solution and bound to receptors. Biochemistry 31, 7446-7456 (1992).
26. Holowka, D., Baird, B. Structural studies on the membrane-bound immunoglobulin E-receptor complex. 2. Mapping of distances between sites on IgE and the membrane-surface. Biochemistry 22, 3475-3484 (1983).
27. Holowka, D., Conrad, D. H., Baird, B. Structural mapping of membrane-bound immunoglobulin-E receptor complexes: use of monoclonal anti-IgE antibodies to probe the conformation of receptor-bound IgE. Biochemistry 24, 6260-6267 (1985).
28. Davis, K. G., Glennie, M., Harding, S. E. & Burton, D. R. A model for the solution conformation of rat IgE. Biochem. Soc. Trans. 18, 935-936 (1990).
29. Wurzburg, B. A., Jardetsky, T. S. Conformational Flexibility in Immunoglobulin E-Fc$_{3-4}$ Revealed in Multiple Crystal Forms. J. Mol. Biol. 393, 176-190 (2009).
30. Shiung, L. L. et al. An anti-IgE monoclonal antibody that binds to IgE on CD23 but not on high-affinity IgE.Fc receptors. Immunobiology 217, 676-683 (2012).
31. Borthakur, S., Andrejeva, G., McDonnell, J. M. Basis of the intrinsic flexibility of the Cε3 domain of IgE. Biochemistry 50, 4608-4614 (2011).
32. Serrano-Candelas, E. et al. Comparable actions of omalizumab on mast cells and basophils. Clin. Exp. Allergy. 46, 92-102(2016).

33. Fersht, A. *In Structure and Mechanism in Protein Science*. W. H. Freeman, New York, pp. 103-131 (1999).
34. Price, N. E., Price, N. C., Kelly, S. M., McDonnell, J. M. The key role of protein flexibility in modulating IgE interactions. *J. Biol. Chem.* 280, 2324-2330 (2005).
35. Young, R. J. et al. Secretion of recombinant human IgE-Fc by mammalian cells and biological activity of glycosylation site mutants. *Protein Eng.* 8, 193-199 (1995).
36. Myszyka, D. G. Improving biosensor analysis. *Journal of Molecular Recognition* 12, 279-284 (1999).
37. Shi, J. et al. Interaction of the Low-Affinity Receptor CD23/FcεRII Lectin Domain with the Fcε3-4 Fragment of Human Immunoglobulin E. *Biochemistry* 36, 2112-2122 (1997).
38. Kabsch, W. XDS. *Acta Crystallogr. D* 66, 125-132 (2010).
39. Winter, G. xia2: an expert system for macromolecular crystallography data reduction. *J. Appl. Cryst.* 43, 186-190 (2010).
40. Winn, M. D. et al. Overview of the CCP4 suite and current developments. *Acta Crystallogr.* D67, 235-242 (2011).
41. Evans, P. R., Murshudov, G. N. How good are my data and what is the resolution? *Acta Crystallogr.* D69, 1204-1214 (2013).
42. Strong, M., Sawaya, M. R., Wang, S., Phillips, M., Cascio, D., Eisenberg, D. Toward the structural genomics of complexes: Crystal structure of a PE/PPE protein complex from *Mycobacterium tuberculosis*. *Proc. Natl. Acad. Sci. USA*. 103, 8060-8065 (2006).
43. McCoy, A. J. et al., Phaser crystallographic software. *J. Appl. Cryst.* 40, 658-674 (2007).
44. Vagin, A., Teplyakov, A. Molecular replacement with MOLREP. *Acta. Cryst. D* 66, 22-25 (2010).
45. Murshudov, G. N. et al. REFMACS for the refinement of macromolecular crystal structures. *Acta Crystallogr. D* 67, 355-367 (2011).
46. P. V. Afonine et al., Towards automated crystallographic structure refinement with phenix.refine. *Acta Crystallogr. D* 68, 352-367 (2012).
47. Emsley, P., Lohkamp, B., Scott, W. G., Cowtan, K. Features and Development of *Coot*. *Acta Crystallogr. D* 66, 486-501 (2010).
48. Chen, V. B. et al. MolProbity: all-atom structure validation for macromolecular crystallography. *Acta Crystallogr. D* 66, 12-21 (2010).
49. Urhumsteva, L., Afonine, P. V., Adams, P. D., Urhumstev, A. Crystallographic model quality at a glance. *Acta Crystallogr. D* 65, 297-300 (2009).
50. Echols, N. et al. Graphical tools for macromolecular crystallography in PHENIX. *J. Appl. Cryst.* 45, 581-586 (2012).
51. Krissinel, E., Henrick, K. Inference of macromolecular assemblies from crystalline state. *J. Mol. Biol.* 372, 774-797 (2007).
52. The PyMOL Molecular Graphics System, Version 1.1r1 Schrödinger, LLC.

Example 2: Measuring of Accelerated Dissociation of IgE-Fc from Immobilised sFcεRIα by Biacore The Biacore technology measures the interaction between biomolecules without the requirement for labelling. One of the interactants, termed the ligand, is either immobilised directly on or captured to the sensor surface while the other, termed the analyte, flows in solution over the captured surface. The sensor detects the change in mass at the sensor surface as the analyte binds to the ligand and when the analyte dissociates from the ligand. These correspond to both the association and dissociation processes. In the accelerated dissociation assay sFcεRIα is the ligand and is immobilised to the sensor surface. IgE-Fc is the analyte and is captured by the sFcεRIα. The dissociation of IgE-Fc from sFcεRIα is monitored either with buffer flowing over the sensor surface or with a solution of IgE binding partner flowing over the sensor surface. Details of the method are as follows:

Instrument: Biacore 3000, GE Healthcare AB, Uppsala, Sweden

Sensor chip: CM5. Catalogue number BR100399

BIAnormalising solution: 70% (w/w) glycerol. Part of the BIAmaintenance Kit. Catalogue number BR100651. The BIAmaintenance kit was stored at 4° C.

Amine Coupling Kit: Catalogue number BR100633. Ethyl-3-(3-dimethylaminopropyl) carbodiimide hydrochloride (EDC) made up to 75 mg/mL in distilled water and stored in 200 uL aliquots at −70° C. N-Hydroxysuccinimide (NHS) made up to 11.5 mg/mL in distilled water and stored in 200 uL aliquots at −70° C. Ethanolamine hydrochloride-NaOH pH 8.5 stored at 4° C.

Reagent for the oxidisation of sFcεRIα. Carbohydrazide (SigmaAldrich, catalogue number C11006) made up to 5 mM in distilled water. Sodium cyanoborohydride (SigmaAldrich, catalogue number 156159) made up to 100 mM in sodium acetate, (BDH, cat. S1104-500GM) 100 mM pH=4. Sodium m-periodate (SigmaAldrich, catalogue number S-1878) made up to 50 mM in sodium acetate (BDH, cat. S1104-500GM) 100 mM, pH=5.5.

sFcεRIα was diluted to 1 mg/ml in pH 5.5, 0.1M sodium acetate. Then 4 ul of Sodium periodate (50 mM), dilution 1/50) was added to 200 ul of 1 mg/ml of sFcεRIα solution. The mixture was left on ice for 20 min. Prior the immobilisation the solution of sFcεRIα was diluted to 1 ug/ml with 10 mM sodium acetate (GE Healthcare, Catalogue number BR100669), pH=4.0.

Buffers: Running buffer is HBS-EP (being 10 mM HEPES pH 7.4, 150 mM NaCl 3 mM EDTA, 0.05% Surfactant P20, reconstituted from 10× stock solution): Catalogue number BR100669. Immobilisation buffer is Acetate 4.0 (being 10 mM sodium acetate pH 4.0). Catalogue number BR100349. Buffer stored at 4° C.

Ligand: sFcεRIα, being the extracellular portion of the alpha chain of the human high affinity IgE receptor. Expressed as a recombinant protein in CHO cells and purified.

Analyte: IgE-Fc, being the Fc portion of human IgE, expressed as a recombinant protein in CHO cells and purified. Wild-type human IgE-Fc (Cε2-Cε4 domains with numbering V224-K547 according to Dorrington & Bennich (1978) Immunol. Rev. 41:3-25) carrying a C225A mutation was used (Seq. ID No. 108).

Nomenclature of Mutants:
Omalizumab Fab 1: S81R, Q83R [S77R, Q79R according to Kabat numbering] (variable region light chain+Kappa constant region as Seq. ID No. 24 wherein S77 and S79 are replaced by Q; variable region heavy chain+CH1 constant region as SEQ ID NO: 5)
Omalizumab Fab 2: L158P [L154P according to Kabat numbering] (variable region light chain+Kappa constant region as Seq. ID No 113; variable region heavy chain+CH1 constant region as SEQ ID NO: 5)
Omalizumab Fab 3: S81R, Q83R, L158P [S77R, Q79R, L154P according to Kabat numbering] (variable region light chain Seq. ID No 121; variable region heavy chain+CH1 constant region as SEQ ID NO: 5)

IgE binding partners (1): full length Omalizumab (Novartis); recombinant Fab fragment of omalizumab expressed in CHO cells and purified.

IgE binding partners (2): recombinant Fab fragment of omalizumab, and mutations thereof, expressed in HEK-293 cells and assayed as culture supernatant. Culture supernatant was concentrated ten-fold prior to analysis.

Assay method (1): sFcεRIα was coupled to the sensor surface by aldehyde coupling to a level of ~500 response units (RU). HBS-EP buffer was uses as the running buffer at a flow rate of 30 uL/min. IgE-Fc was diluted to 10 nM in HBS-EP and injected over the immobilised sFcεRIα for 290 seconds followed by 3 injections, each of 690 seconds duration, of running buffer or of IgE binding partner diluted in running buffer. Capture level of IgE-Fc was ~90 RU. The surface was regenerated with two 60 second injections of 10 mM glycine-HCl, pH 2.5. The amount of dissociation of IgE-Fc from the immobilised sFcεRIα was calculated as a function of the initial binding amount and the rate of dissociation was calculated as the amount of loss of IgE-Fc from the immobilised sFcεRIα, normalised for the initial binding amount as a function of elapsed time.

Assay method (2): sFcεRIα was coupled to the sensor surface by aldehyde coupling to a level of ~2000 response units (RU). HBS-EP buffer was uses as the running buffer at a flow rate of 30 uL/min. IgE-Fc was diluted to 10 nM in HBS-EP and injected over the immobilised sFcεRIα for 180 seconds followed by 1 injection of 180 seconds duration, of running buffer or of IgE binding partner diluted in running buffer. Capture level of IgE-Fc was ~275 RU. The surface was regenerated with two 60 second injections of 10 mM glycine-HCl, pH 2.5. The amount of dissociation of IgE-Fc from the immobilised sFcεRIα was calculated as a function of the initial binding amount and the rate of dissociation was calculated as the amount of loss of IgE-Fc from the immobilised sFcεRIα, normalised for the initial binding amount as a function of elapsed time.

TABLE 2 calculation of the amount of dissociation of IgE-Fc from immobilised sFcεRIα. Initial binding of IgE to sFcεRIα is normalised to 100% and dissociation calculated relative to that. The apparent dissociation rate is based on an assumed single rate process.

| IgE binding partner | Capture level of IgE-Fc (%) | Amount of IgE-Fc remaining bound to sFcERIa after 1st injection (%) | Amount of IgE-Fc remaining bound to sFcERIa after 2nd injection (%) | Amount of IgE-Fc remaining bound to sFcERIa after 3rd injection (%) | Apparent dissociation rate based on 3$^{rd}$ Injection of IgE binding partner (1/s) |
|---|---|---|---|---|---|
| Omalizumab 300 ug/mL | 100.0 | 79.3 | 71.5 | 69.9 | 1.46E−04 |
| buffer | 100.0 | 87.6 | 81.9 | 77.9 | 1.02E−04 |
| Omalizumab Fab1 100 ug/mL | 100.0 | 61.3 | 51.0 | 47.3 | 3.06E−04 |
| Omalizumab Fab2 100 ug/mL | 100.0 | 79.4 | 71.5 | 69.5 | 1.48E−04 |
| Omalizumab Fab3 100 ug/mL | 100.0 | 45.3 | 34.6 | 30.8 | 4.80E−04 |

Additional mutagenesis was performed to determine if further mutations that accelerated the dissociation of IgE-Fc from sFcεRIα, outside of those described in Fab3, could be identified. This led to the m Conclusion Taken together, these data demonstrate that a mutated form of omalizumab Fab can accelerate the dissociation of IgE from an immobilised form of the high affinity IgE receptor, FcɛRI. The mutations in the light chain that enable this include, but are not necessarily limited to, S64M, S81R, Q83R and L158P with reference to SEQ ID NO: 24 and resulting in SEQ ID NO: 39.

Example 3: Measuring the Accelerated Dissociation of IgE-Fc from FcɛRI by Flow Cytometry Instrument: FACSCanto II flow cytometer (Becton Dickinson)

Cell line: RBL-SX38 cells expressing human FcɛRI were cultured in Minimal Essential Medium supplemented with 10% foetal bovine serum, 2 mM GlutaMAX and 500 µg/mL Geneticin (Life Technologies). At the time of assay, cells were washed in PBS and incubated in Accutase until detached, then resuspended at $1 \times 10^6$ cells/mL in culture media. All subsequence incubation steps were performed in culture media.

Assay method: RBL-SX38 cells at $1 \times 10^6$ cells/mL were incubated with 5 nM Alexa-488 labelled IgE-Fc for 1 hour at 37° C. Cells were washed twice in culture media to remove unbound IgE-488 then suspended at $1 \times 10^6$ cells/mL in culture media or 100 µg/mL IgE-binding agents diluted in culture media. Cells were then incubated at 37° C. with constant rotation. At each time point, $0.5 \times 10^5$ cells were removed, washed in ice-cold PBS and then fixed by resuspending in 1% paraformaldehyde in PBS for 16 hours at 4° C. The amount of cell-bound Alexa-488 fluorescence was determined using a FACSCanto II flow cytometer.

Flow cytometry: fixed cells were washed twice in FACS buffer (0.1% w/v BSA, 0.01% w/v $NaN_3$ in PBS, pH 7.4) and resuspended in 200 µL FACS buffer. Flow cytometry was performed on a FACSCanto II cytometer using standard methods and the geometric mean fluorescence intensity of Alexa-488 bound to intact cells was calculated using FlowJo software. The dissociation rate of Alexa-488 labelled IgE-Fc was calculated as the change in geometric mean fluorescence intensity as a function of time as a result of either incubating the cells in culture media, excess unlabelled IgE-Fc or in the presence of IgE binding agents.

Nomenclature of Mutants:

Omalizumab Fab 1: S81R, Q83R [S77R, Q79R according to Kabat numbering] (variable region light chain+Kappa constant region as Seq. ID No. 24 wherein S77 and S79 are replaced by Q; variable region heavy chain+CH1 constant region as SEQ ID NO: 5)

Omalizumab Fab 2: L158P [L154P according to Kabat numbering] (variable region light chain+Kappa constant region as Seq. ID No 113; variable region heavy chain+CH1 constant region as SEQ ID NO: 5)

Omalizumab Fab 3: S81R, Q83R, L158P [S77R, Q79R, L154P according to Kabat numbering] (variable region light chain+Kappa constant region as Seq. ID No 121; variable region heavy chain+CH1 constant region as SEQ ID NO: 5).

TABLE 4 calculated dissociation rate of Alexa488 labelled IgE-Fc from the surface of RBL-SX38 cells. Apparent dissociation rate determined from a linear regression fit of the plot of −ln(R1/R0) as a function of time for all available time points.

| IgE binding partner | Concentration (ug/mL) | Dissociation rate (×10−5) 1/s |
|---|---|---|
| UT | | 1.38 |
| Omalizumab | 100 | 1.77 |
| Omalizumab | 31 | 1.56 |
| Omalizumab | 10 | 1.32 |
| Omalizumab | 3.1 | 1.45 |
| Omalizumab | 1 | 1.36 |
| Omalizumab Fab | 100 | 2.09 |
| Omalizumab Fab | 31 | 1.63 |
| Omalizumab Fab | 10 | 1.35 |
| Omalizumab Fab | 3.1 | 1.38 |
| Omalizumab Fab | 1 | 1.59 |
| Omalizumab Fab1 | 100 | 4.14 |
| Omalizumab Fab1 | 31 | 2.6 |
| Omalizumab Fab1 | 10 | 1.93 |
| Omalizumab Fab1 | 3.1 | 1.61 |
| Omalizumab Fab1 | 1 | 1.46 |
| Omalizumab Fab2 | 100 | 2.11 |
| Omalizumab Fab2 | 31 | 1.65 |
| Omalizumab Fab2 | 10 | 1.39 |
| Omalizumab Fab2 | 3.1 | 1.36 |
| Omalizumab Fab2 | 1 | 1.29 |
| Omalizumab Fab3 | 100 | 3.99 |
| Omalizumab Fab3 | 31 | 2.81 |
| Omalizumab Fab3 | 10 | 2.03 |
| Omalizumab Fab3 | 3.1 | 1.5 |
| Omalizumab Fab3 | 1 | 1.47 |
| Isotype control | 100 | 1.3 |
| Isotype control | 31 | 1.28 |
| Isotype control | 10 | 1.35 |
| Isotype control | 3.1 | 1.19 |
| Isotype control | 1 | 1.25 |
| IgE Quench | | 1.24 |

Conclusion

Taken together, these data demonstrate that a mutated form of omalizumab Fab can accelerate the dissociation of IgE from the high affinity IgE receptor, FcɛRI, expressed on the cell surface. The mutations in the light chain that enable this include, but are not necessarily limited to, S81R, Q83R and L158P.

Example 4: Demonstrating that Omalizumab Fab3 has Superior Efficacy to Wild Type Omalizumab Fab when Dosed Therapeutically in the 72 Hour PCA Model A solution of 25 ug/mL of human anti DNP-IgE was prepared by adding 7.5 uL of 6.68 mg/mL stock to 1992.5 uL PBS. A 20 uL injection of this solution would give a 500 ng dose of IgE. Animals (hIgER Tg mice) were shaved on the flanks and then injected i.d on each flank at 2 pm on day 0.20 uL of PBS was injected into the left flank of each animal as a negative control. Anti DNP-IgE (20 uL) was injected into the right flank. A total of 40 mice were injected in total. Treatment with either wild type omalizumab Fab or omalizumab Fab3 (with S81R, Q83R, L158P mutations [S77R, Q79R, L154P according to Kabat numbering]) commenced 18 hours post IgE (8 am). Two groups of mice (n=8/gp) received 100 mg/kg s.c of either wild type omalizumab Fab or omalizumab Fab3. A further group of 8 mice received PBS s.c. Mice were dosed again as above 10 hrs later (6 pm). At this time point, 28 hrs post IgE, a further two groups (n=8/gp) were also dosed with either wild type omalizumab Fab or omalizumab Fab3 at 100 mg/kg sc. All groups were re-dosed at 8 am, 6 pm and again at 8 am on the final day of the experiment. 72 hours post i.d dosing (2 pm) all animals were injected i.v with 100 uL of 1 mg/mL DNP-HSA, 2.5% w/v Evans blue made up in 100 IU/ml of heparin. 1 hour later animals were killed by a schedule 1 method. The skin from the flanks around the i.d injection site was removed and a punch biopsy taken. Skin samples were placed into 700 uL formamide and digested overnight at 55° C. Following digestion 100 uL×2 fluid was removed from each sample and placed into a 96 well ELISA plate. Absorbance was then measured at 620 nm.

Conclusion

These data demonstrate that a mutated form of omalizumab Fab that can accelerate the dissociation of IgE from the high affinity IgE receptor, FcεRI, is also able to reduce passive cutaneous anaphylaxis (as shown by inhibition of leakage of Evans blue dye from the reaction site) in a statistically significant manner when compared with wild type omalizumab Fab. The mutations in the light chain that enable this include, but are not necessarily limited to, S81R, Q83R and L158P with reference to SEQ ID NO: 24 and resulting in SEQ ID NO: 39.

Example 5: Molecular Dynamics Simulation of OmalizumabFab3 in Complex with IgE Fc

Method

The crystal structure of Omalizumab Fab3 in complex with IgE Fc region (see Example 1) was prepared in Molecular Operating Environment (MOE) 2014.0901 (1) by completing the missing side chains in some residues and missing loops between Cε2 and Cε3 domains prior to molecular dynamics (MD) simulation using Amber 14 (2). The complex structure was hydrogen-added and solvated using TIP3P explicit water model with 0.15M NaCl salt solute in a truncated octahedron box that extended 10 Å from any edge of the box to the protein atoms. The system was setup using Amber ff12SB and oligosaccharides GLYCAM_06 j-1 (3) forcefields and minimized by conjugate gradient algorithm for 50,000 steps with a 10.0 Å cutoff set for Coulombic and Van der Waals interactions and a grid-based neighbour list. Afterwards the system was gradually heated from 0 to 300 K in 125 ps at constant volume followed by 2.25 ns equilibration in the NPT ensemble with restraints on all solute heavy atoms (harmonic force constraint is 5.0). For electrostatics, we used fourth order PME with a cutoff of 8.0 Å for Coulombic interactions with default Fourier spacing and tolerance settings. The temperature was controlled with weak-coupling algorithm applied to the protein and solvent respectively with a time constant of 1.0 ps, and the pressure was controlled with an isotropic Berenson barostat applied to the entire system with a time constant of 1.0 ps and a compressibility of $4.46\times10^{-5}$ $bar^{-1}$. Finally, a 1000 ns production simulation without any restriction was conducted used the same parameters as for equilibration. To enable a 4 fs time step on GPU infrastructure, the hydrogen mass of the protein and sugars were repartitioned to 3.024 daltons using ParmEd (4) while the mass of the atoms to which they are bonded were adjusted by the amount required to leave the total mass unchanged. The structure of wild type Omalizumab Fab in complex with IgE Fc region was modelled from the crystal complex structure of Omalizumab-mutant3 with IgE Fc by virtually mutating R81 and R83 in the antibody light chain to wildtype serine and asparagine, respectively. The MD simulation was conducted using the same setup protocol as for mutant3.

AmberTools cpptraj module (7) in was used for clustering analysis of the MD trajectories for both omalizumab Fab3 and omalizumab Fab in complex with IgE Fc. Hierarchical agglomerative algorithm was adopted with average-linkage distance between each cluster is below 2.0 Å. The distance between frames was calculated via best-fit coordinate RMSD between the Cα-atoms in antibody light chain V-region residues. The clustering was conducted only for every 10 frame and all other frames were added to clusters based on how close they are to cluster centroids after clustering.

REFERENCES

1. Molecular Operating Environment (MOE), 2014.09; Chemical Computing Group Inc., 1010 Sherbooke St. West, Suite #910, Montreal, QC, Canada, H3A 2R7, 2015.
2. Case, D. A., et al. AMBER 2014, 2014, University of California, San Francisco.
3. Kirschner, K. et al. GLYCAM06: A generalizable biomolecular force field. Carbohydrates. *J. Comput. Chem.*, 2008, 29, 622-655.
4. http://parmed.githubio/ParmEd/html/index html

Results

To study how S81R and Q83R mutations in light chain of omalizumab Fab3 affect the interaction with IgE, a one-microsecond molecular dynamic simulation was performed for omalizumab Fab and omalizumab Fab3 in complex with IgE Fc structures, respectively. The trajectory snapshopts were clustered and the top 2 populated cluster center structures were analyzed, which clearly demonstrates that in both clusters, the two arginine mutations in mutant3 form intense hydrogen-bond networks with residue D278 and S280 in the adjacent IgE Cε2 domain, respectively. The visual inspection of the trajectory confirms that the R81-S280 and R83-D278 pairwise interactions are much conserved and stable during simulation therefore the unbent Cε2 conformations relative to the closer Cε3 domain as disclosed in the crystal structure is frozen via the antibody bridging. Interestingly, although the double arginine mutations are spatially adjacent to Cε2 D278 and S280 in the crystal structure of omalizumab Fab3, there are not directly hydrogen-bonded as suggested in MD simulation. For omalizumab Fab, as expected the hydrogen bond networks as seen in mutant3 are missing in the top 2 cluster center structures. Visual trajectory inspection shows that Cε2 domains become less tethered to the antibody light chain framework and thus their relative positions to the closer Cε3 domain are more variable than that of omalizumab Fab3. In addition to this, the interface between omalizumab Fab3 and IgE-Fc in the complex of the same was subjected to an IOTA analysis (IOTA is a statistical potential tool for determining the probability of a given contact atom type at a protein interface or binding site) which predicted that light chain position S56, S64 and S71 in omalizumab Fab3 (with reference to SEQ ID NO: 113) could be mutated to increase the affinity of omaliuzumab for IgE-Fc and would thus enhance the effect predicted to be seen for the S81R and Q38R mutations detailed above.

Conclusion

In summary MD simulation proposes the hypothesis that S81R and Q38R mutations facilitates localization of IgE Cε2 domains to the antibody by direct electrostatic and hydrogen-bond interactions with adjacent D278 and S280 in Cε2, and affect IgE plasticity Fc by locking up the Cε2 unbent conformation. This is coupled with the statistical methodology that predicts the S64M mutation and S56 (changed to D, E, Q or R) and S71 (changed to D, E or M) would have a similar effect.

Example 6: Measuring Affinity of Anti-IgE Fabs for IgE-Fc by Biacore

The Biacore technology measures the interaction between biomolecules without the requirement for labelling. One of the interactants, termed the ligand, is either immobilized directly on or captured to the sensor surface while the other, termed the analyte, flows in solution over the captured surface. The sensor detects the change in mass at the sensor surface as the analyte binds to the ligand and when the analyte dissociates from the ligand. These correspond to both the association and dissociation processes. In the kinetic assay the anti-IgE Fab is the ligand and is captured to the sensor surface. IgE-Fc is the analyte and is captured by the anti-IgE Fab. The association and dissociation of IgE-Fc from the captured anti-IgE Fab is monitored either with IgE-Fc flowing over the sensor surface (association phase) or buffer flowing over the sensor surface (dissociation phase). Details of the method are as follows:

Instrument: Biacore 3000, GE Healthcare AB, Uppsala, Sweden

Sensor chip: CMS. Catalogue number BR100399

BIAnormalising solution: 70% (w/w) glycerol. Part of the BIAmaintenance Kit. Catalogue number BR100651. The BIAmaintenance kit was stored at 4° C.

Amine Coupling Kit: Catalogue number BR100633. Ethyl-3-(3-dimethylaminopropyl) carbodiimide hydrochloride (EDC) made up to 75 mg/mL in distilled water and stored in 200 uL aliquots at −70° C. N-Hydroxysuccinimide (NHS) made up to 11.5 mg/mL in distilled water and stored in 200 uL aliquots at −70° C. Ethanolamine hydrochloride-NaOH pH 8.5 stored at 4° C.

Buffers: Running buffer is HBS-EP (being 10 mM HEPES pH 7.4, 150 mM NaCl 3 mM EDTA, 0.05% Surfactant P20, reconstituted from 10× stock solution): Catalogue number BR100669. Immobilization buffer is Acetate 4.0 (being 10 mM sodium acetate pH 4.0). Catalogue number BR100349. Buffer stored at 4° C.

Ligand: anti-IgE Fabs were the ligand. These were transiently expressed as a recombinant protein in HEK-293 cells and used without further purification.

Analyte: IgE-Fc, being the Fc portion of human IgE, expressed as a recombinant protein in CHO cells and purified. Wild-type human IgE-Fc (Cε2-Cε4 domains with numbering V224-K547 according to Dorrington & Bennich (1978) Immunol. Rev. 41:3-25) carrying a C225A mutation was used (Seq. ID No. 108).

$Fab_2$ fragment of a goat anti-human IgG1 (Fab2 fragment specific) (Jackson Immunolabs, catalogue number 109-006-097) was immobilized to sensor surface by amine coupling using standard methods. Anti-IgE Fab was diluted in running buffer (HBS-EP) and approximately 200 resonance units were captured to the surface. IgE-Fc was diluted in running buffer and a serial dilution series from 2 nM to 125 pM was passed over the captured anti-IgE Fab. The association phase was for 180 seconds and the dissociation phase was for 300 seconds. The sensor surface was regenerated with a 60 second exposure to 40 mM HCl, followed by a 60 second exposure to 10 mM NaOH and then a further 60 second exposure to 40 mM HCl. All binding data was processed with double referencing using the BiaEvaluation software following standard procedures.

TABLE 5

Affinity of omalizumab Fab and mutants for IgE-Fc as measured in a Biacore kinetic assay. The dissociation constant (KD) calculated as kd/ka.

| Sample | ka (1/Ms) ×10^6 | kd (1/s) ×10^−3 | KD (nM) |
|---|---|---|---|
| omalizumab Fab (wildtype) | 1.97 ± 0.021 | 2.10 ± 0.005 | 1.07 |
| omalizumab Fab 1 | 2.17 ± 0.021 | 1.95 ± 0.005 | 0.902 |
| omalizumab Fab 2 | 2.21 ± 0.029 | 2.91 ± 0.007 | 1.32 |
| omalizumab Fab 3 | 2.36 ± 0.021 | 1.78 ± 0.005 | 0.754 |

TABLE 6

Affinity of omalizumab Fab (WT) and mutants for IgE-Fc as measured in a Biacore kinetic assay. The dissociation constant (KD) calculated as kd/ka. The four mutants are in the wild type sequence background (light chain Seq. ID No 20).

| Sample | ka (×10^6) 1/Ms | kd (×10^−3) 1/s | KD (pM) |
|---|---|---|---|
| WT | 2.86 | 1.42 | 496 |
| S56D | 3.26 | 0.713 | 219 |
| S56E | 2.86 | 0.717 | 251 |
| S71E | 2.57 | 0.583 | 226 |
| S71D | 2.51 | 0.696 | 278 |

TABLE 7a

Affinity of omalizumab Fab (WT) and mutants for IgE-Fc as measured in a Biacore kinetic assay. The dissociation constant (KD) calculated as kd/ka. The mutations are with reference to the light chain Seq. ID No 20).

| Sample | ka (×10^6) 1/Ms | kd (×10^−3) 1/s | KD (pM) |
|---|---|---|---|
| WT | 2.25 | 16.2 | 721 |
| S71E | 1.7 | 6.25 | 368 |
| S56D | 2.17 | 7.09 | 327 |
| S71D, S56D | 2.13 | 8.11 | 380 |
| S71E, S56D | 1.85 | 8.17 | 443 |
| S71M, S56D | 2.32 | 5.45 | 238 |
| S71D, S56E | 1.96 | 8.33 | 426 |
| S71E, S56E | 1.94 | 6.66 | 343 |
| S71M, S56E | 1.76 | 4.54 | 258 |
| S71D, S56Q | 1.85 | 6.12 | 331 |
| S71E, S56Q | 1.87 | 5.03 | 268 |
| S71M, S56Q | 1.44 | 4.11 | 286 |
| S71D, S56R | 1.5 | 4.86 | 325 |
| S71E, S56R | 1.65 | 4.63 | 281 |
| S71M, S56R | 1.05 | 5.58 | 534 |

TABLE 7b

Affinity of omalizmab Fab for IgE-Fc as measured in a Biacore kinetic assay. The dissociation constant (KD) is calculated as kd/ka. The mutations are in the light chain (with reference to Seq. ID No 20). The light chain variable region sequences of the Fab mutants are indicated in the left hand column (VL Seq. ID No.).

| VL Seq ID No. | Sample | ka (1/Ms) | kd (1/s) | KD (M) | KD (pM) |
|---|---|---|---|---|---|
| 20 | Omalizumab Fab wt | 2.52E+06 | 2.38E−03 | 9.42E−10 | 942 |
| 132 | S64M_S81R_Q83R_S56D_S71M | 3.23E+06 | 9.79E−04 | 3.04E−10 | 304 |
| 139 | S64K_S81R_Q83R_S56D_S71M | 2.85E+06 | 1.02E−03 | 3.58E−10 | 358 |
| 145 | S64Q_S81R_Q83R_S56D_S71M | 2.99E+06 | 9.12E−04 | 3.05E−10 | 305 |
| 146 | S64R_S81R_Q83R_S56D_D71M | 2.67E+06 | 6.27E−04 | 2.35E−10 | 235 |
| 158 | S64M_S81R_Q83R_D56D_D71M_S67W_S80N | 3.19E+06 | 5.40E−04 | 1.69E−10 | 169 |
| 159 | S64M_S81R_Q83R_D56D_D71M_S67Y_S80N | 3.07E+06 | 4.69E−04 | 1.53E−10 | 153 |

TABLE 7c

Affinity of omalizmab Fab mutant for IgE-Fc as measured in a Biacore kinetic assay. The dissociation constant (KD) is calculated as kd/ka. The mutations are in the light chain (with reference to Seq. ID No 20). The samples have been subjected to a forced oxidation study and the levels of methionine oxidation at each time point determine by mass spectrometry.

| Sample | % H2O2 | Time Course | ka (1/Ms) | kd (1/s) | KD (M) | KD (pM) |
|---|---|---|---|---|---|---|
| S64M__S81R__Q83R__S56D__S71M (Seq ID No. 132) | baseline | | 3.70E+06 | 1.18E−03 | 3.2E−10 | 320 |
| | 0.00% | 4 hours | 3.43E+06 | 1.38E−03 | 4.03E−10 | 403 |
| | | 1 Day | 3.40E+06 | 1.46E−03 | 4.3E−10 | 430 |
| | | 3 Days | 3.37E+06 | 1.38E−03 | 4.09E−10 | 409 |
| | | 7 Days | 3.25E+06 | 1.36E−03 | 4.18E−10 | 418 |
| | | 14 Days | 3.08E+06 | 1.22E−03 | 3.97E−10 | 397 |
| | 0.1 | 4 hours | 3.46E+06 | 1.44E−03 | 4.18E−10 | 418 |
| | | 1 Day | 3.41E+06 | 1.26E−03 | 3.71E−10 | 371 |
| | | 3 Days | 3.49E+06 | 1.23E−03 | 3.53E−10 | 353 |
| | | 7 Days | 5.64E+06 | 1.36E−03 | 2.41E−10 | 241 |
| | | 14 Days | 3.64E+06 | 1.20E−03 | 3.31E−10 | 331 |

Conclusion

These data demonstrate that mutated forms of omalizumab Fab can increase the affinity of omalizumab Fab for IgE-Fc. The best combination of mutations in terms of improved affinity is S71M combined with S56D. This increase in affinity is principally caused by a decrease in the dissociation rate of the Fab from IgE-Fc. The affinity of omalizumab Fab1 (with S81R, Q83R mutations [S77R, Q79R according to Kabat numbering]) and Fab3 (with S81R, Q83R, L158P mutations [S77R, Q79R, L154P according to Kabat numbering] with reference to SEQ ID NO; 125) is also improved given the improved interaction of the antibody with IgE-Fc Cε2 compared with the unmutated omalizumab Fab.

Example 7: Measuring of Accelerated Dissociation of IgE-Fc from Immobilized sFcεRIα by Biacore The effect of anti-IgE Fabs upon the dissociation of IgE-Fc from sFcεRIα was measured using the methods outlined in Example 2 (assay method 2). All anti-IgE Fabs had been expressed in HEK-29s Fabs, purified by standard methods and quantified by absorbance at 280 nm using the calculated molar extinction coefficients. In this assay the concentration of IgE-Fc was 2 nM and the dissociation time 200 seconds. The amount of dissociation of IgE-Fc from the immobilized sFcεRIα was calculated as a function of the initial binding amount and the rate of dissociation was calculated as the amount of loss of IgE-Fc from the immobilized sFcεRIα, normalized for the initial binding amount as a function of elapsed time.

S80N (pdb numbering) is thought to interact with D278 of Cε2 IgE, and S67W/Y (pdb numbering) is thought to interact with T298 of Cε2 IgE.

TABLE 8 calculation of the amount of dissociation of IgE-Fc from immobilized sFcεRIα. Initial binding of IgE to sFcεRIα is normalized to 100% and dissociation calculated relative to that. The apparent dissociation rate is based on an assumed single rate process.

| Sample | mutations | RU of IgE-Fc captured | RU of IgE-Fc after dissociation | % dissociation | apparent dissociation rate (1/s) |
|---|---|---|---|---|---|
| omalizumab Fab 3 | S81R_Q83R_L158P | 152.1 | 125.9 | 17.0 | 6.25E−04 |
| sample 1 | S64M_S81R_Q83R_L158P_56D_71M | 135.3 | 71.0 | 47.5 | 2.15E−03 |
| sample 2 | S64M_S81R_Q83R_L158P_56E_71M | 120.5 | 71.6 | 40.6 | 1.74E−03 |
| sample 3 | S64M_S81R_Q83R_L158P_56Q_71M | 97.5 | 65.4 | 33.0 | 1.33E−03 |
| sample 4 | S64M_S81R_Q83R_L158P_56Q_71E | 87.6 | 62.1 | 29.1 | 1.15E−03 |
| sample 5 | S64M_S81R_Q83R_L158P_56R_71E | 80.0 | 64.4 | 19.5 | 7.24E−04 |
| sample 6 | S64M_S81R_Q83R_56D_71M | 85.9 | 50.9 | 40.7 | 1.74E−03 |
| sample 7 | S64M_S81R_Q83R_56E_71M | 101.8 | 66.6 | 34.6 | 1.42E−03 |
| sample 8 | S64M_S81R_Q83R_56Q_71M | 109.1 | 77.6 | 28.9 | 1.14E−03 |
| sample 9 | S64M_S81R_Q83R_56Q_71E | 107.8 | 78.0 | 27.6 | 1.08E−03 |
| sample 10 | S64M_S81R_Q83R_56R_71E | 102.8 | 84.3 | 18.1 | 6.64E−04 |
| sample 11 | S56D_S64M_S71E_S81R_Q83R | 156.7 | 110.5 | 29.5 | 1.17E−03 |
| sample 12 | S56D_S64M_S71E_S81R_Q83R_S67W_S80N | 155.1 | 92.0 | 40.7 | 1.74E−03 |
| sample 13 | S56D_S64M_S71E_S81R_Q83R_S67Y_S80N | 137.6 | 71.5 | 48.0 | 2.18E−03 |
| buffer control | | 126.3 | 116.6 | 7.8 | 2.70E−04 |

Conclusion

These data demonstrate that a mutated form of omalizumab Fab can accelerate the dissociation of IgE from an immobilized form of the high affinity IgE receptor, FcεRI. The mutations in the light chain (Seq. ID No 20) that enable this include, but not necessarily limited to, mutations at positions S56, S64, S67, S71, S80, S81, Q83 & L158 (S52, S60, S63, S67, S76, S77, Q79 & L154, respectively, according to Kabat numbering).

Example 8: Forced Oxidation of Mutated Omalizumab Fab

Anti-IgE Fab samples were subjected to a forced oxidation regime to ascertain the effect of oxidising methionines in the light chain variable region on the affinity of the Fab for IgE-Fc and the ability to accelerate the dissociation of the IgE-Fc:sFcεRIα complex. Mutated omalizumab Fab was incubated with 0.1% and 1% (v/v) hydrogen peroxide for up to 14 days at room temperature. After incubation the samples were buffer exchanged back into PBS pH 7.4 and the concentration determined by absorbance at 280 nm using a calculated extinction coefficient. Mass spectral analysis to determine the amount of oxidation of the light chain variable regions methionines was performed by reduction and alkylation of the material under denaturing conditions followed by trypsin digestion (50 ug/mL Trypsin for 180 minutes at 37° C. followed by TFA quench) and then analysis by LC-MS using a Thermo Orbitrap Q Exactive Plus mass spectrometer. The percentage of oxidised methionine is calculated relative to the assumption that there is no methionine oxidation at the time of synthesis and compared with reference material that has been held at 4° C.

TABLE 9 the percentage of oxidised methionine in the light chain variable region of the mutated omalizumab Fab. This omalizumab Fab mutant contains the following mutations: S64M_S81R_Q83R_S56D_S71M (with respect to Seq ID No. 20).

| | % oxidized methionine present at each time point | | | | | | |
|---|---|---|---|---|---|---|---|
| | IgE Control | 4 hours | 1 Day | 3 Days | 7 Days | 14 Days | IgE Control |
| M37 (LC) | 0.30% | 0.40% | 0.30% | 0.40% | 0.60% | 0.90% | 0.30% |
| M64 (LC) | 18.10% | 81.70% | 99.70% | 99.90% | 99.90% | 99.90% | 20.00% |
| M71 (LC) | 6.70% | 90.00% | 99.70% | 99.80% | 99.80% | 99.90% | 6.90% |

Conclusion

These data indicate that it is possible to generate a mutated omalizumab Fab that has essentially complete oxidation of the critical light chain methionines (M64 and M71). Based on these data, material from the Day1, Day3 and Day 7 samples were pooled and used to determine the impact of the methionine oxidation on the affinity of the mutated omalizumab Fab for IgE-Fc and the ability to accelerate the dissociation of the IgE-Fc:sFcεRIα complex.

Example 9: Measuring Accelerated Dissociation of IgE-Fc from sFcεRIα by FRET

The effect of anti-IgE Fabs upon the dissociation of IgE-Fc from sFcεRIα was measured in a homogeneous FRET assay. All anti-IgE Fabs had been expressed in HEK-293 cells and purified by standard methods and quantified by absorbance at 280 nm using the calculated molar extinction methods. The FRET assay used Tb labelled IgE-Fc as the donor and Alexa488 labelled sFcεRIα as the acceptor. Both reagents were mixed and equilibrated at room temperature for 60 minutes at a final assay concentration of 1 nM. Anti-IgE Fabs were added to the mix at a final assay concentration of 500 nM and the fluorescence read (excitation at 330 nm, emission at 495 and 520 nm) every 20 minutes for 800 minutes. Fluorescence emission was plotted as a function of time and the dissociation rate of IgE-Fc from sFcεRIα calculated as the half-life of the complex. These data are reported in Tables 10 and 11.

TABLE 10

The effect of anti-IgE Fabs (WT and mutants) on the dissociation of IgE-Fc from sFcεRIα in a homogeneous FRET assay. The dissociation of the IgE-Fc:sFcεRIα complex is a two phase decay. The fast, initial phase is the phase in which the majority of the IgE-Fc:sFcεRIα complex dissociates and from which the half-life of the complex is determined.. The mutations are in the light chain (with reference to Seq. ID No 20). The light chain variable region sequences of the Fab mutants are indicated in the left hand column (VL Seq. ID No.).

| VL-Seq ID No. | Sample | half-life of complex (min) |
|---|---|---|
| 20 | Omalizumab Fab wt | 95.34 |
| 132 | S64M_S81R_Q83R_S56D_S71M | 22.94 |
| 145 | S64K_S81R_Q83R_S56D_S71M | 29.54 |
| 146 | S64Q_S81R_Q83R_S56D_S71M | 28.1 |
| 139 | S64R_S81R_Q83R_S56D_S71M | 19.26 |
| 158 | S64M_S81R_Q83R_S56D_S71M_S67W_S80N | 17.02 |
| 159 | S64M_S81R_Q83R_S56D_S71M_S67Y_S80N | 17 |

TABLE 11

The effect of methionine oxidation upon the ability of anti-IgE Fabs to dissociate IgE-Fc from sFcεRIα in a homogeneous FRET assay. The dissociation of the IgE-Fc:sFcεRIα complex is a two phase decay. The fast, initial phase is the phase in which the majority of the IgE-Fc:sFcεRIα complex dissociates and from which the half-life of the complex is determined.

| Sample | Half-life of complex (min) |
|---|---|
| buffer | 1240 |
| S64M_S81R_Q83R_S56D_S71M | 10.8 |

TABLE 11-continued

The effect of methionine oxidation upon the ability of anti-IgE Fabs to dissociate IgE-Fc from sFcεRIα in a homogeneous FRET assay. The dissociation of the IgE-Fc:sFcεRIα complex is a two phase decay. The fast, initial phase is the phase in which the majority of the IgE-Fc:sFcεRIα complex dissociates and from which the half-life of the complex is determined.

| Sample | Half-life of complex (min) |
|---|---|
| S64M_S81R_Q83R_S56D_Q71M forced oxidation | 17.3 |

Conclusions

These data demonstrate that the mutated forms of omalizumab are able to dissociate IgE-Fc from sFcεRIα at a faster rate than the wild type sequence. In particular, mutations in the light chain (with reference to Seq. ID No 20) that enable this include, but not necessarily limited to, mutations at positions S64 and S67. Furthermore, oxidation of the methionine (M64 and M71, Seq. ID No 20) has no significant effect on the ability of the Fab to accelerate the dissociation of the IgE-Fc: sFcεRIα complex.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Sequences

HEAVY CHAIN
v-region

Seq. ID No. 1

EVQLVESGGG LVQPGGSLRL SCAVSGYSIT SGYSWNWIRQ APGKGLEWVA

SITYDGSTNY NPSVKGRITI SRDDSKNTFY LQMNSLRAED TAVYYCARGS

HYFGHWHFAV WGQGTLVTVS S v-region

Seq. ID No. 2

GAAGTGCAGT TGGTGGAGTC GGGTGGAGGG CTGGTGCAGC CTGGCGGTAG

CCTGAGGCTG TCCTGTGCCG TGTCCGGATA CTCCATTACC TCCGGCTACT

CGTGGAACTG GATCAGACAG GCTCCCGGAA AGGGACTTGA GTGGGTGGCG

TCCATCACCT ACGACGGCTC AACCAACTAT AACCCGTCCG TGAAGGGCCG

CATCACCATT TCGCGCGACG ACAGCAAGAA TACTTTTTAC CTCCAAATGA

ACAGCCTGCG GGCCGAAGAT ACTGCCGTGT ACTACTGCGC GCGGGGATCA

CATTACTTCG GGCACTGGCA CTTCGCCGTC TGGGGACAGG GCACCCTCGT

CACTGTCTCG AGC v-region with signal sequence underlined and italicised

Seq. ID No. 3

*MKWVTFISLL* *FLFSSAYS*EV QLVESGGGLV QPGGSLRLSC AVSGYSITSG

YSWNWIRQAP GKGLEWVASI TYDGSTNYNP SVKGRITISR DDSKNTFYLQ

MNSLRAEDTA VYYCARGSHY FGHWHFAVWG QGTLVTVSS v-region with signal sequence underlined and italicised
Seq. ID No. 4

*ATGAAGTGGG* *TCACCTTCAT* *CTCCCTGCTG* *TTTCTGTTCT* *CCAGCGCCTA*

*CTCC*GAAGTG CAGTTGGTGG AGTCGGGTGG AGGGCTGGTG CAGCCTGGCG

GTAGCCTGAG GCTGTCCTGT GCCGTGTCCG GATACTCCAT TACCTCCGGC

TACTCGTGGA ACTGGATCAG ACAGGCTCCC GGAAAGGGAC TTGAGTGGGT

GGCGTCCATC ACCTACGACG GCTCAACCAA CTATAACCCG TCCGTGAAGG

GCCGCATCAC CATTTCGCGC GACGACAGCA AGAATACTTT TTACCTCCAA

ATGAACAGCC TGCGGGCCGA AGATACTGCC GTGTACTACT GCGCGCGGGG

ATCACATTAC TTCGGGCACT GGCACTTCGC CGTCTGGGGA CAGGGCACCC

TCGTCACTGT CTCGAGC v-region + gamma 1 CH1 constant region
Seq. ID No. 5

EVQLVESGGG LVQPGGSLRL SCAVSGYSIT SGYSWNWIRQ APGKGLEWVA

SITYDGSTNY NPSVKGRITI SRDDSKNTFY LQMNSLRAED TAVYYCARGS

HYFGHWHFAV WGQGTLVTVS SASTKGPSVF PLAPSSKSTS GGTAALGCLV

KDYFPEPVTV SWNSGALTSG VHTFPAVLQS SGLYSLSSVV TVPSSSLGTQ

TYICNVNHKP SNTKVDKKVE PKSC v-region + gamma 1 CH1 constant region
Seq. ID No. 6

GAAGTGCAGT TGGTGGAGTC GGGTGGAGGG CTGGTGCAGC CTGGCGGTAG

CCTGAGGCTG TCCTGTGCCG TGTCCGGATA CTCCATTACC TCCGGCTACT

CGTGGAACTG GATCAGACAG GCTCCCGGAA AGGGACTTGA GTGGGTGGCG

TCCATCACCT ACGACGGCTC AACCAACTAT AACCCGTCCG TGAAGGGCCG

CATCACCATT TCGCGCGACG ACAGCAAGAA TACTTTTTAC CTCCAAATGA

ACAGCCTGCG GGCCGAAGAT ACTGCCGTGT ACTACTGCGC GCGGGGATCA

CATTACTTCG GCACTGGCA CTTCGCCGTC TGGGGACAGG GCACCCTCGT

CACTGTCTCG AGCGCTTCTA CAAAGGGCCC ATCGGTCTTC CCCCTGGCAC

CCTCCTCCAA GAGCACCTCT GGGGGCACAG CGGCCCTGGG CTGCCTGGTC

AAGGACTACT TCCCCGAACC GGTGACGGTG TCGTGGAACT CAGGCGCCCT

GACCAGCGGC GTGCACACCT TCCCGGCTGT CCTACAGTCC TCAGGACTCT

ACTCCCTCAG CAGCGTGGTG ACCGTGCCCT CCAGCAGCTT GGGCACCCAG

ACCTACATCT GCAACGTGAA TCACAAGCCC AGCAACACCA AGGTGGACAA

GAAAGTTGAG CCCAAATCTT GT v-region + gamma 1 CH1 constant region with signal sequence
underlined and italicised
Seq. ID No. 7

*MKWVTFISLL* *FLFSSAYS*EV QLVESGGGLV QPGGSLRLSC AVSGYSITSG

YSWNWIRQAP GKGLEWVASI TYDGSTNYNP SVKGRITISR DDSKNTFYLQ

MNSLRAEDTA VYYCARGSHY FGHWHFAVWG QGTLVTVSSA STKGPSVFPL

APSSKSTSGG TAALGCLVKD YFPEPVTVSW NSGALTSGVH TFPAVLQSSG

LYSLSSVVTV PSSSLGTQTY ICNVNHKPSN TKVDKKVEPK Sc v-region + gamma 1 CH1 constant region with signal sequence
underlined and italicised
Seq. ID No. 8

*ATGAAGTGGG* *TCACCTTCAT* *CTCCCTGCTG* *TTTCTGTTCT* *CCAGCGCCTA*

-continued

<u>CTCC</u>GAAGTG CAGTTGGTGG AGTCGGGTGG AGGGCTGGTG CAGCCTGGCG

GTAGCCTGAG GCTGTCCTGT GCCGTGTCCG GATACTCCAT TACCTCCGGC

TACTCGTGGA ACTGGATCAG ACAGGCTCCC GGAAAGGGAC TTGAGTGGGT

GGCGTCCATC ACCTACGACG GCTCAACCAA CTATAACCCG TCCGTGAAGG

GCCGCATCAC CATTTCGCGC GACGACAGCA AGAATACTTT TTACCTCCAA

ATGAACAGCC TGCGGGCCGA AGATACTGCC GTGTACTACT GCGCGCGGGG

ATCACATTAC TTCGGGCACT GGCACTTCGC CGTCTGGGGA CAGGGCACCC

TCGTCACTGT CTCGAGCGCT TCTACAAAGG GCCCATCGGT CTTCCCCCTG

GCACCCTCCT CCAAGAGCAC CTCTGGGGGC ACAGCGGCCC TGGGCTGCCT

GGTCAAGGAC TACTTCCCCG AACCGGTGAC GGTGTCGTGG AACTCAGGCG

CCCTGACCAG CGGCGTGCAC ACCTTCCCGG CTGTCCTACA GTCCTCAGGA

CTCTACTCCC TCAGCAGCGT GGTGACCGTG CCCTCCAGCA GCTTGGGCAC

CCAGACCTAC ATCTGCAACG TGAATCACAA GCCCAGCAAC ACCAAGGTGG

ACAAGAAAGT TGAGCCCAAA TCTTGT v-region + gamma 1 full length constant region
Seq. ID No. 9
EVQLVESGGG LVQPGGSLRL SCAVSGYSIT SGYSWNWIRQ APGKGLEWVA

SITYDGSTNY NPSVKGRITI SRDDSKNTFY LQMNSLRAED TAVYYCARGS

HYFGHWHFAV WGQGTLVTVS SASTKGPSVF PLAPSSKSTS GGTAALGCLV

KDYFPEPVTV SWNSGALTSG VHTFPAVLQS SGLYSLSSVV TVPSSSLGTQ

TYICNVNHKP SNTKVDKKVE PKSCDKTHTC PPCPAPELLG GPSVFLFPPK

PKDTLMISRT PEVTCVVVDV SHEDPEVKFN WYVDGVEVHN AKTKPREEQY

NSTYRVVSVL TVLHQDWLNG KEYKCKVSNK ALPAPIEKTI SKAKGQPREP

QVYTLPPSRE EMTKNQVSLT CLVKGFYPSD IAVEWESNGQ PENNYKTTPP

VLDSDGSFFL YSKLTVDKSR WQQGNVFSCS VMHEALHNHY TQKSLSLSPG

K v-region + gamma 1 full length constant region
Seq. ID No. 10
GAAGTGCAGT TGGTGGAGTC GGGTGGAGGG CTGGTGCAGC CTGGCGGTAG

CCTGAGGCTG TCCTGTGCCG TGTCCGGATA CTCCATTACC TCCGGCTACT

CGTGGAACTG GATCAGACAG GCTCCCGGAA AGGGACTTGA GTGGGTGGCG

TCCATCACCT ACGACGGCTC AACCAACTAT AACCCGTCCG TGAAGGGCCG

CATCACCATT TCGCGCGACG ACAGCAAGAA TACTTTTTAC CTCCAAATGA

ACAGCCTGCG GGCCGAAGAT ACTGCCGTGT ACTACTGCGC GCGGGATCA

CATTACTTCG GGCACTGGCA CTTCGCCGTC TGGGGACAGG GCACCCTCGT

CACTGTCTCG AGCGCTTCTA CAAAGGGCCC CTCCGTGTTC CCGCTCGCTC

CATCATCGAA GTCTACCAGC GGAGGCACTG CGGCTCTCGG TTGCCTCGTG

AAGGACTACT TCCCGGAGCC GGTGACCGTG TCGTGGAACA GCGGAGCCCT

GACCAGCGGG GTGCACACCT TTCCGGCCGT CTTGCAGTCA AGCGGCCTTT

ACTCCCTGTC ATCAGTGGTG ACTGTCCCGT CCAGCTCATT GGGAACCCAA

ACCTACATCT GCAATGTGAA TCACAAACCT AGCAACACCA AGGTTGACAA

GAAAGTCGAG CCCAAATCGT GTGACAAGAC TCACACTTGT CCGCCGTGCC

-continued

```
CGGCACCCGA ACTGCTGGGA GGTCCCAGCG TCTTTCTGTT CCCTCCAAAG

CCGAAAGACA CGCTGATGAT CTCCCGCACC CCGGAGGTCA CTTGCGTGGT

CGTGGACGTG TCACATGAGG ACCCAGAGGT GAAGTTCAAT TGGTACGTGG

ATGGCGTCGA AGTCCACAAT GCCAAAACTA AGCCCAGAGA AGAACAGTAC

AATTCGACCT ACCGCGTCGT GTCCGTGCTC ACGGTGTTGC ATCAGGATTG

GCTGAACGGG AAGGAATACA AGTGCAAAGT GTCCAACAAG GCGCTGCCGG

CACCGATCGA GAAAACTATC TCCAAAGCGA AGGGACAGCC TAGGGAACCT

CAAGTCTACA CGCTGCCACC ATCACGGGAA GAAATGACTA AGAATCAAGT

CTCACTGACT TGTCTGGTGA AGGGGTTTTA CCCTAGCGAC ATTGCCGTGG

AGTGGGAATC CAACGGCCAG CCAGAGAACA ACTACAAGAC TACCCCTCCA

GTGCTCGACT CGGATGGATC GTTCTTCCTT TACTCGAAGC TCACCGTGGA

TAAGTCCCGG TGGCAGCAGG GAAACGTGTT CTCCTGCTCG GTGATGCATG

AAGCCCTCCA TAACCACTAT ACCCAAAAGT CGCTGTCCCT GTCGCCGGGA

AAG
``` v-region + gamma 1 full length constant region with signal
sequence underlined and italicised
Seq. ID No. 11

```
MKWVTFISLL FLFSSAYSEV QLVESGGGLV QPGGSLRLSC AVSGYSITSG

YSWNWIRQAP GKGLEWVASI TYDGSTNYNP SVKGRITISR DDSKNTFYLQ

MNSLRAEDTA VYYCARGSHY FGHWHFAVWG QGTLVTVSSA STKGPSVFPL

APSSKSTSGG TAALGCLVKD YFPEPVTVSW NSGALTSGVH TFPAVLQSSG

LYSLSSVVTV PSSSLGTQTY ICNVNHKPSN TKVDKKVEPK SCDKTHTCPP

CPAPELLGGP SVFLFPPKPK DTLMISRTPE VTCVVVDVSH EDPEVKFNWY

VDGVEVHNAK TKPREEQYNS TYRVVSVLTV LHQDWLNGKE YKCKVSNKAL

PAPIEKTISK AKGQPREPQV YTLPPSREEM TKNQVSLTCL VKGFYPSDIA

VEWESNGQPE NNYKTTPPVL DSDGSFFLYS KLTVDKSRWQ QGNVFSCSVM

HEALHNHYTQ KSLSLSPGK
``` v-region + gamma 1 full length constant region with signal
sequence underlined and italicised
Seq. ID No. 12

```
ATGAAGTGGG TCACCTTCAT CTCCCTGCTG TTTCTGTTCT CCAGCGCCTA

CTCCGAAGTG CAGTTGGTGG AGTCGGGTGG AGGGCTGGTG CAGCCTGGCG

GTAGCCTGAG GCTGTCCTGT GCCGTGTCCG GATACTCCAT TACCTCCGGC

TACTCGTGGA ACTGGATCAG ACAGGCTCCC GGAAAGGGAC TTGAGTGGGT

GGCGTCCATC ACCTACGACG GCTCAACCAA CTATAACCCG TCCGTGAAGG

GCCGCATCAC CATTTCGCGC GACGACAGCA AGAATACTTT TTACCTCCAA

ATGAACAGCC TGCGGGCCGA AGATACTGCC GTGTACTACT GCGCGCGGGG

ATCACATTAC TTCGGGCACT GGCACTTCGC CGTCTGGGGA CAGGGCACCC

TCGTCACTGT CTCGAGCGCT TCTACAAAGG GCCCCTCCGT GTTCCCGCTC

GCTCCATCAT CGAAGTCTAC AGCGGAGGC ACTGCGGCTC TCGGTTGCCT

CGTGAAGGAC TACTTCCCGG AGCCGGTGAC CGTGTCGTGG AACAGCGGAG

CCCTGACCAG CGGGGTGCAC ACCTTTCCGG CCGTCTTGCA GTCAAGCGGC

CTTTACTCCC TGTCATCAGT GGTGACTGTC CCGTCCAGCT CATTGGGAAC

CCAAACCTAC ATCTGCAATG TGAATCACAA ACCTAGCAAC ACCAAGGTTG
```

```
-continued
ACAAGAAAGT CGAGCCCAAA TCGTGTGACA AGACTCACAC TTGTCCGCCG

TGCCCGGCAC CCGAACTGCT GGGAGGTCCC AGCGTCTTTC TGTTCCCTCC

AAAGCCGAAA GACACGCTGA TGATCTCCCG CACCCCGGAG GTCACTTGCG

TGGTCGTGGA CGTGTCACAT GAGGACCCAG AGGTGAAGTT CAATTGGTAC

GTGGATGGCG TCGAAGTCCA CAATGCCAAA ACTAAGCCCA GAGAAGAACA

GTACAATTCG ACCTACCGCG TCGTGTCCGT GCTCACGGTG TTGCATCAGG

ATTGGCTGAA CGGGAAGGAA TACAAGTGCA AAGTGTCCAA CAAGGCGCTG

CCGGCACCGA TCGAGAAAAC TATCTCCAAA GCGAAGGGAC AGCCTAGGGA

ACCTCAAGTC TACACGCTGC CACCATCACG GGAAGAAATG ACTAAGAATC

AAGTCTCACT GACTTGTCTG GTGAAGGGGT TTTACCCTAG CGACATTGCC

GTGGAGTGGG AATCCAACGG CCAGCCAGAG AACAACTACA AGACTACCCC

TCCAGTGCTC GACTCGGATG GATCGTTCTT CCTTTACTCG AAGCTCACCG

TGGATAAGTC CCGGTGGCAG CAGGGAAACG TGTTCTCCTG CTCGGTGATG

CATGAAGCCC TCCATAACCA CTATACCCAA AAGTCGCTGT CCCTGTCGCC

GGGAAAG

FR H1                                              Seq. ID No. 13
EVQLVESGGG LVQPGGSLRL SCAVS

CDRH1                                              Seq. ID No. 14
GYSITSGYSW N

FR H2                                              Seq. ID No. 15
WIRQAPGKGL EWVA

CDRH2                                              Seq. ID No. 16
SITYDGSTNY NPSVKG

FR H3                                              Seq. ID No. 17
RITISRDDSK NTFYLQMNSL RAEDTAVYYC AR

CDRH3                                              Seq. ID No. 18
GSHYFGHWHF AV

FR H4                                              Seq. ID No. 19
WGQGTLVTVS S

LIGHT CHAIN
Omalizumab_v-region                                Seq. ID No. 20
DIQLTQSPSS LSASVGDRVT ITCRASQSVD YDGDSYMNWY QQKPGKAPKL

LIYAASYLES GVPSRFSGSG SGTDFTLTIS SLQPEDFATY YCQQSHEDPY

TFGQGTKVEI K

Omalizumab_v-region                                Seq. ID No. 21
GATATTCAGC TGACTCAGAG CCCGAGCTCA CTCTCCGCTT CCGTGGGGGA

TAGAGTGACC ATCACTTGCC GGGCATCCCA GTCGGTGGAC TACGACGGAG

ACTCCTACAT GAACTGGTAT CAGCAGAAGC CCGGAAAAGC CCCAAAGTTG

CTGATCTACG CCGCCTCATA CCTTGAAAGC GGCGTGCCTT CGCGCTTCTC

GGGAAGCGGG TCGGGCACCG ATTTCACCCT GACCATTTCG TCGCTGCAGC

CGGAGGACTT CGCGACTTAC TACTGCCAAC AGTCCCACGA GGACCCCTAT
```

ACGTTTGGCC AGGGAACCAA GGTCGAAATC AAG

Omalizumab_v-region with signal sequence underlined and italicised
Seq. ID No. 22

*MKWVTFISLL FLFSSAYS*DI QLTQSPSSLS ASVGDRVTIT CRASQSVDYD

GDSYMNWYQQ KPGKAPKLLI YAASYLESGV PSRFSGSGSG TDFTLTISSL

QPEDFATYYC QQSHEDPYTF GQGTKVEIK

Omalizumab_v-region with signal sequence underlined and italicised
Seq. ID No. 23

*ATGAAGTGGG TCACCTTCAT CTCCCTGCTG TTTCTGTTCT CCTCCGCCTA*

*CTCC*GATATT CAGCTGACTC AGAGCCCGAG CTCACTCTCC GCTTCCGTGG

GGGATAGAGT GACCATCACT TGCCGGGCAT CCCAGTCGGT GGACTACGAC

GGAGACTCCT ACATGAACTG GTATCAGCAG AAGCCCGGAA AAGCCCCAAA

GTTGCTGATC TACGCCGCCT CATACCTTGA AAGCGGCGTG CCTTCGCGCT

TCTCGGGAAG CGGGTCGGGC ACCGATTTCA CCCTGACCAT TTCGTCGCTG

CAGCCGGAGG ACTTCGCGAC TTACTACTGC AACAGTCCC ACGAGGACCC

CTATACGTTT GGCCAGGGAA CCAAGGTCGA AATCAAG

Omalizumab_v-region + kappa constant region
Seq. ID No. 24

DIQLTQSPSS LSASVGDRVT ITCRASQSVD YDGDSYMNWY QQKPGKAPKL

LIYAASYLES GVPSRFSGSG SGTDFTLTIS SLQPEDFATY YCQQSHEDPY

TFGQGTKVEI KRTVAAPSVF IFPPSDEQLK SGTASVVCLL NNFYPREAKV

QWKVDNALQS GNSQESVTEQ DSKDSTYSLS STLTLSKADY EKHKVYACEV

THQGLSSPVT KSFNRGEC

Omalizumab_v-region + kappa constant region
Seq. ID No. 25

GATATTCAGC TGACTCAGAG CCCGAGCTCA CTCTCCGCTT CCGTGGGGGA

TAGAGTGACC ATCACTTGCC GGGCATCCCA GTCGGTGGAC TACGACGGAG

ACTCCTACAT GAACTGGTAT CAGCAGAAGC CCGGAAAAGC CCCAAAGTTG

CTGATCTACG CCGCCTCATA CCTTGAAAGC GGCGTGCCTT CGCGCTTCTC

GGGAAGCGGG TCGGGCACCG ATTTCACCCT GACCATTTCG TCGCTGCAGC

CGGAGGACTT CGCGACTTAC TACTGCCAAC AGTCCCACGA GGACCCCTAT

ACGTTTGGCC AGGGAACCAA GGTCGAAATC AAGCGTACGG TAGCGGCCCC

ATCTGTCTTC ATCTTCCCGC CATCTGATGA GCAGTTGAAA TCTGGAACTG

CCTCTGTTGT GTGCCTGCTG AATAACTTCT ATCCCAGAGA GGCCAAAGTA

CAGTGGAAGG TGGATAACGC CCTCCAATCG GGTAACTCCC AGGAGAGTGT

CACAGAGCAG GACAGCAAGG ACAGCACCTA CAGCCTCAGC AGCACCCTGA

CGCTGAGCAA AGCAGACTAC GAGAAACACA AAGTCTACGC CTGCGAAGTC

ACCCATCAGG GCCTGAGCTC GCCCGTCACA AAGAGCTTCA ACAGGGGAGA GTGT

Omalizumab_v-region + kappa constant region with signal sequence underlined and italicised
Seq. ID No. 26

*MKWVTFISLL FLFSSAYS*DI QLTQSPSSLS ASVGDRVTIT CRASQSVDYD

GDSYMNWYQQ KPGKAPKLLI YAASYLESGV PSRFSGSGSG TDFTLTISSL

QPEDFATYYC QQSHEDPYTF GQGTKVEIKR TVAAPSVFIF PPSDEQLKSG

TASVVCLLNN FYPREAKVQW KVDNALQSGN SQESVTEQDS KDSTYSLSST

-continued

LTLSKADYEK HKVYACEVTH QGLSSPVTKS FNRGEC

Omalizumab_v-region + kappa constant region with signal sequence underlined and italicised Seq. ID No. 27

*<u>ATGAAGTGGG TCACCTTCAT CTCCCTGCTG TTTCTGTTCT CCTCCGCCTA</u>*

*<u>CTCC</u>*GATATT CAGCTGACTC AGAGCCCGAG CTCACTCTCC GCTTCCGTGG

GGGATAGAGT GACCATCACT TGCCGGGCAT CCCAGTCGGT GGACTACGAC

GGAGACTCCT ACATGAACTG GTATCAGCAG AAGCCCGGAA AAGCCCCAAA

GTTGCTGATC TACGCCGCCT CATACCTTGA AAGCGGCGTG CCTTCGCGCT

TCTCGGAAG CGGGTCGGGC ACCGATTTCA CCCTGACCAT TTCGTCGCTG

CAGCCGGAGG ACTTCGCGAC TTACTACTGC AACAGTCCC ACGAGGACCC

CTATACGTTT GGCCAGGGAA CCAAGGTCGA AATCAAGCGT ACGGTAGCGG

CCCCATCTGT CTTCATCTTC CCGCCATCTG ATGAGCAGTT GAAATCTGGA

ACTGCCTCTG TTGTGTGCCT GCTGAATAAC TTCTATCCCA GAGAGGCCAA

AGTACAGTGG AAGGTGGATA ACGCCCTCCA ATCGGGTAAC TCCCAGGAGA

GTGTCACAGA GCAGGACAGC AAGGACAGCA CCTACAGCCT CAGCAGCACC

CTGACGCTGA GCAAAGCAGA CTACGAGAAA CACAAAGTCT ACGCCTGCGA

AGTCACCCAT CAGGGCCTGA GCTCGCCCGT CACAAAGAGC TTCAACAGGG GAGAGTGT

FR L1

Seq. ID No. 28

DIQLTQSPSS LSASVGDRVT ITC

CDRL1

Seq. ID No. 29

RASQSVDYDG DSYMN

FR L2

Seq. ID No. 30

WYQQKPGKAP KLLIY

CDRL2

Seq. ID No. 31

AASYLES

FR L3

Seq. ID No. 32

GVPSRFSGSG SGTDFTLTIS SLQPEDFATY YC

CDRL3

Seq. ID No. 33

QQSHEDPYT

Seq. ID No. 34

FR L4
FGQGTKVEIK

MUTANT LIGHT CHAIN

Seq. ID No. 35

S60M_S77R_Q79R_v-region (Kabat)
DIQLTQSPSS LSASVGDRVT ITCRASQSVD YDGDSYMNWY QQKPGKAPKL

LIYAASYLES GVPMRFSGSG SGTDFTLTIS RLRPEDFATY YCQQSHEDPY

TFGQGTKVEI K

S60M_S77R_Q79R_v-region (Kabat)

Seq. ID No. 36

GATATTCAGC TGACTCAGAG CCCGAGCTCA CTCTCCGCTT CCGTGGGGGA

TAGAGTGACC ATCACTTGCC GGGCATCCCA GTCGGTGGAC TACGACGGAG

ACTCCTACAT GAACTGGTAT CAGCAGAAGC CCGGAAAAGC CCCAAAGTTG

CTGATCTACG CCGCCTCATA CCTTGAAAGC GGCGTGCCTA TGCGCTTCTC

```
GGGAAGCGGG TCGGGCACCG ATTTCACCCT GACCATTTCG AGACTGAGGC

CGGAGGACTT CGCGACTTAC TACTGCCAAC AGTCCCACGA GGACCCCTAT

ACGTTTGGCC AGGGAACCAA GGTCGAAATC AAG
```

S60M_S77R_Q79R_v-region with signal sequence underlined and
italicised (Kabat)
                                              Seq. ID No. 37
```
MKWVTFISLL FLFSSAYSDI QLTQSPSSLS ASVGDRVTIT CRASQSVDYD

GDSYMNWYQQ KPGKAPKLLI YAASYLESGV PMRFSGSGSG TDFTLTISRL

RPEDFATYYC QQSHEDPYTF GQGTKVEIK
```

S60M_S77R_Q79R_v-region with signal sequence underlined and
italicised (Kabat)
                                              Seq. ID No. 38
```
ATGAAGTGGG TCACCTTCAT CTCCCTGCTG TTTCTGTTCT CCTCCGCCTA

CTCCGATATT CAGCTGACTC AGAGCCCGAG CTCACTCTCC GCTTCCGTGG

GGGATAGAGT GACCATCACT TGCCGGGCAT CCCAGTCGGT GGACTACGAC

GGAGACTCCT ACATGAACTG GTATCAGCAG AAGCCCGGAA AAGCCCCAAA

GTTGCTGATC TACGCCGCCT CATACCTTGA AAGCGGCGTG CCTATGCGCT

TCTCGGGAAG CGGGTCGGGC ACCGATTTCA CCCTGACCAT TTCGAGACTG

AGGCCGGAGG ACTTCGCGAC TTACTACTGC AACAGTCCC ACGAGGACCC

CTATACGTTT GGCCAGGGAA CCAAGGTCGA AATCAAG
```

S60M_S77R_Q79R_v-region + kappa constant region including L154P
(Kabat)
                                              Seq. ID No. 39
```
DIQLTQSPSS LSASVGDRVT ITCRASQSVD YDGDSYMNWY QQKPGKAPKL

LIYAASYLES GVPMRFSGSG SGTDFTLTIS RLRPEDFATY YCQQSHEDPY

TFGQGTKVEI KRTVAAPSVF IFPPSDEQLK SGTASVVCLL NNFYPREAKV

QWKVDNAPQS GNSQESVTEQ DSKDSTYSLS STLTLSKADY EKHKVYACEV

THQGLSSPVT KSFNRGEC
```

S60M_S77R_Q79R_v-region + kappa constant region including L154P
(Kabat)
                                              Seq. ID No. 40
```
GATATTCAGC TGACTCAGAG CCCGAGCTCA CTCTCCGCTT CCGTGGGGGA

TAGAGTGACC ATCACTTGCC GGGCATCCCA GTCGGTGGAC TACGACGGAG

ACTCCTACAT GAACTGGTAT CAGCAGAAGC CCGGAAAAGC CCCAAAGTTG

CTGATCTACG CCGCCTCATA CCTTGAAAGC GGCGTGCCTA TGCGCTTCTC

GGGAAGCGGG TCGGGCACCG ATTTCACCCT GACCATTTCG AGACTGAGGC

CGGAGGACTT CGCGACTTAC TACTGCCAAC AGTCCCACGA GGACCCCTAT

ACGTTTGGCC AGGGAACCAA GGTCGAAATC AAGCGTACGG TAGCGGCCCC

ATCTGTCTTC ATCTTCCCGC CATCTGATGA GCAGTTGAAA TCTGGAACTG

CCTCTGTTGT GTGCCTGCTG AATAACTTCT ATCCCAGAGA GGCCAAAGTA

CAGTGGAAGG TGGATAACGC CCCGCAATCG GGTAACTCCC AGGAGAGTGT

CACAGAGCAG GACAGCAAGG ACAGCACCTA CAGCCTCAGC AGCACCCTGA

CGCTGAGCAA AGCAGACTAC GAGAAACACA AAGTCTACGC CTGCGAAGTC

ACCCATCAGG GCCTGAGCTC GCCCGTCACA AAGAGCTTCA ACAGGGGAGA GTGT
```

S60M_S77R_Q79R_v-region + kappa constant region including L154P
with signal sequence underlined and italicised (Kabat)
                                              Seq. ID No. 41
```
MKWVTFISLL FLFSSAYSDI QLTQSPSSLS ASVGDRVTIT CRASQSVDYD
```

-continued

```
GDSYMNWYQQ KPGKAPKLLI YAASYLESGV PMRFSGSGSG TDFTLTISRL

RPEDFATYYC QQSHEDPYTF GQGTKVEIKR TVAAPSVFIF PPSDEQLKSG

TASVVCLLNN FYPREAKVQW KVDNAPQSGN SQESVTEQDS KDSTYSLSST

LTLSKADYEK HKVYACEVTH QGLSSPVTKS FNRGEC
```

S60M S77R Q79R_v-region + kappa constant region including L154P
with signal sequence underlined and italicised (Kabat)

Seq. ID No. 42

```
ATGAAGTGGG TCACCTTCAT CTCCCTGCTG TTTCTGTTCT CCTCCGCCTA

CTCCGATATT CAGCTGACTC AGAGCCCGAG CTCACTCTCC GCTTCCGTGG

GGGATAGAGT GACCATCACT TGCCGGGCAT CCCAGTCGGT GGACTACGAC

GGAGACTCCT ACATGAACTG GTATCAGCAG AAGCCCGGAA AAGCCCCAAA

GTTGCTGATC TACGCCGCCT CATACCTTGA AAGCGGCGTG CCTATGCGCT

TCTCGGGAAG CGGGTCGGGC ACCGATTTCA CCCTGACCAT TTCGAGACTG

AGGCCGGAGG ACTTCGCGAC TTACTACTGC AACAGTCCC ACGAGGACCC

CTATACGTTT GGCCAGGGAA CCAAGGTCGA AATCAAGCGT ACGGTAGCGG

CCCCATCTGT CTTCATCTTC CCGCCATCTG ATGAGCAGTT GAAATCTGGA

ACTGCCTCTG TTGTGTGCCT GCTGAATAAC TTCTATCCCA GAGAGGCCAA

AGTACAGTGG AAGGTGGATA ACGCCCCGCA ATCGGGTAAC TCCCAGGAGA

GTGTCACAGA GCAGGACAGC AAGGACAGCA CCTACAGCCT CAGCAGCACC

CTGACGCTGA GCAAAGCAGA CTACGAGAAA CACAAAGTCT ACGCCTGCGA

AGTCACCCAT CAGGGCCTGA GCTCGCCCGT CACAAAGAGC TTCAACAGGG GAGAGTGT
```

FR L3 S64M (PDB) S60M (Kabat)
Seq. ID No. 43
GVPMRFSGSG SGTDFTLTIS SLQPEDFATY YC FR L3 S81R(PDB) S77R (Kabat)
Seq. ID No. 44
GVPSRFSGSG SGTDFTLTIS RLQPEDFATY YC FR L3 Q83R(PDB) Q79R (Kabat)
Seq. ID No. 45
GVPSRFSGSG SGTDFTLTIS SLRPEDFATY YC FR L3 S64M S81R(PDB) S60M S77R (Kabat)
Seq. ID No. 46
GVPMRFSGSG SGTDFTLTIS RLQPEDFATY YC FR L3 S64M Q83R(PDB) S60M Q79R (Kabat)
Seq. ID No. 47
GVPMRFSGSG SGTDFTLTIS SLRPEDFATY YC FR L3 S81R Q83R(PDB) S77R Q79R (Kabat)
Seq. ID No. 48
GVPSRFSGSG SGTDFTLTIS RLRPEDFATY YC FR L3 S64M S81R Q83R(PDB) S60M S77R Q79R (Kabat)
Seq. ID No. 49
GVPMRFSGSG SGTDFTLTIS RLRPEDFATY YC CDRL2 556D(PDB) 552D (Kabat)
Seq. ID No. 50
AADYLES CDRL2 556E(PDB) 552E (Kabat)
Seq. ID No. 51
AAEYLES FR L3 S71M(PDB) S67M (Kabat)
Seq. ID No. 52
GVPSRFSGSG SGTDFTLTIS SLQPEDFATY YC FR L3 S64M S71M (PDB) S60M S67M (Kabat)

-continued

```
                                                    Seq. ID No. 53
GVPMRFSGSG MGTDFTLTIS SLQPEDFATY YC

FR L3 S81R S71M (PDB) S77R S67M (Kabat)
                                                    Seq. ID No. 54
GVPSRFSGSG MGTDFTLTIS RLQPEDFATY YC FR L3 Q83R S71M (PDB) Q79R S67M (Kabat)
                                                    Seq. ID No. 55
GVPSRFSGSG MGTDFTLTIS SLRPEDFATY YC FR L3 S64M S81R S71M (PDB) S60M S77R S67M (Kabat)
                                                    Seq. ID No. 56
GVPMRFSGSG MGTDFTLTIS RLQPEDFATY YC FR L3 S64M Q83R S71M (PDB) S60M Q79R S67M (Kabat)
                                                    Seq. ID No. 57
GVPMRFSGSG MGTDFTLTIS SLRPEDFATY YC FR L3 S81R Q83R S71M (PDB) S77R Q79R S67M (Kabat)
                                                    Seq. ID No. 58
GVPSRFSGSG MGTDFTLTIS RLRPEDFATY YC FR L3 S64M S81R Q83R S71M (PDB) S60M S77R Q79R S67M (Kabat)
                                                    Seq. ID No. 59
GVPMRFSGSG MGTDFTLTIS RLRPEDFATY YC FR L3 S67Y (PDB) S63Y (Kabat)
                                                    Seq. ID No. 60
GVPSRFYGSG SGTDFTLTIS SLQPEDFATY YC FR L3 S64M S67Y (PDB) S60M S63Y (Kabat)
                                                    Seq. ID No. 61
GVPMRFYGSG SGTDFTLTIS SLQPEDFATY YC FR L3 S81R S67Y (PDB) S77R S63Y (Kabat)
                                                    Seq. ID No. 62
GVPSRFYGSG SGTDFTLTIS RLQPEDFATY YC FR L3 Q83R S67Y (PDB) Q79R S63Y (Kabat)
                                                    Seq. ID No. 63
GVPSRFYGSG SGTDFTLTIS SLRPEDFATY YC FR L3 S64M S81R S67Y (PDB) S60M S77R S63Y (Kabat)
                                                    Seq. ID No. 64
GVPMRFYGSG SGTDFTLTIS RLQPEDFATY YC FR L3 S64M Q83R S67Y (PDB) S60M Q79R S63Y (Kabat)
                                                    Seq. ID No. 65
GVPMRFYGSG SGTDFTLTIS SLRPEDFATY YC FR L3 S81R Q83R S67Y (PDB) S77R Q79R S63Y (Kabat)
                                                    Seq. ID No. 66
GVPSRFYGSG SGTDFTLTIS RLRPEDFATY YC FR L3 S64M S81R Q83R S67Y (PDB) S60M S77R Q79R S63Y (Kabat)
                                                    Seq. ID No. 67
GVPMRFYGSG SGTDFTLTIS RLRPEDFATY YC FR L3 S80N (PDB) S76N (Kabat)
                                                    Seq. ID No. 68
GVPSRFSGSG SGTDFTLTIN SLQPEDFATY YC FR L3 S64M S80N (PDB) S60M S76N (Kabat)
                                                    Seq. ID No. 69
GVPMRFSGSG SGTDFTLTIN SLQPEDFATY YC FR L3 S81R S80N (PDB) S77R S76N (Kabat)
                                                    Seq. ID No. 70
GVPSRFSGSG SGTDFTLTIN RLQPEDFATY YC FR L3 Q83R S80N (PDB) Q79R S76N (Kabat)
                                                    Seq. ID No. 71
GVPSRFSGSG SGTDFTLTIN SLRPEDFATY YC FR L3 S64M S81R S80N (PDB) S60M S77R S76N (Kabat)
                                                    Seq. ID No. 72
GVPMRFSGSG SGTDFTLTIN RLQPEDFATY YC FR L3 S64M Q83R S80N (PDB) S60M Q79R S76N (Kabat)
                                                    Seq. ID No. 73
```

-continued

```
GVPMRFSGSG SGTDFTLTIN SLRPEDFATY YC

FR L3 S81R Q83R S80N (PDB) S77R Q79R S76N (Kabat)
                                            Seq. ID No. 74
GVPSRFSGSG SGTDFTLTIN RLRPEDFATY YC FR L3 S64M S81R Q83R S80N (PDB) S60M S77R Q79R S76N (Kabat)
                                            Seq. ID No. 75
GVPMRFSGSG SGTDFTLTIN RLRPEDFATY YC FR L3 S80N S67Y (PDB) S76N S63Y(Kabat)
                                            Seq. ID No. 76
GVPSRFYGSG SGTDFTLTIN SLQPEDFATY YC FR L3 S64M S80N S67Y (PDB) S60M S76N S63Y (Kabat)
                                            Seq. ID No. 77
GVPMRFYGSG SGTDFTLTIN SLQPEDFATY YC FR L3 S81R S80N S67Y (PDB) S77R S76N S63Y (Kabat)
                                            Seq. ID No. 78
GVPSRFYGSG SGTDFTLTIN RLQPEDFATY YC FR L3 Q83R S80N S67Y (PDB) Q79R S76N S63Y (Kabat)
                                            Seq. ID No. 79
GVPSRFYGSG SGTDFTLTIN SLRPEDFATY YC FR L3 S64M S81R S80N S67Y (PDB) S60M S77R S76N S63Y (Kabat)
                                            Seq. ID No. 80
GVPMRFYGSG SGTDFTLTIN RLQPEDFATY YC FR L3 S64M Q83R S80N S67Y (PDB) S60M Q79R S76N S63Y (Kabat)
                                            Seq. ID No. 81
GVPMRFYGSG SGTDFTLTIN SLRPEDFATY YC FR L3 S81R Q83R S80N S67Y (PDB) S77R Q79R S76N S63Y (Kabat)
                                            Seq. ID No. 82
GVPSRFYGSG SGTDFTLTIN RLRPEDFATY YC FR L3 S64M S81R Q83R S80N S67Y (PDB) S60M S77R Q79R S76N S63Y
(Kabat)
                                            Seq. ID No. 83
GVPMRFYGSG SGTDFTLTIN RLRPEDFATY YC FR L3 S67Y S71M(PDB) S63Y S67M(Kabat)
                                            Seq. ID No. 84
GVPSRFYGSG MGTDFTLTIS SLQPEDFATY YC FR L3 S64M S67Y S71M (PDB) S60M S63Y S67M (Kabat)
                                            Seq. ID No. 85
GVPMRFYGSG MGTDFTLTIS SLQPEDFATY YC FR L3 S81R S67Y S71M (PDB) S77R S63Y S67M (Kabat)
                                            Seq. ID No. 86
GVPSRFYGSG MGTDFTLTIS RLQPEDFATY YC FR L3 Q83R S67Y S71M (PDB) Q79R S63Y S67M (Kabat)
                                            Seq. ID No. 87
GVPSRFYGSG MGTDFTLTIS SLRPEDFATY YC FR L3 S64M S81R S67Y S71M (PDB) S60M S77R S63Y S67M (Kabat)
                                            Seq. ID No. 88
GVPMRFYGSG MGTDFTLTIS RLQPEDFATY YC FR L3 S64M Q83R S67Y S71M (PDB) S60M Q79R S63Y S67M (Kabat)
                                            Seq. ID No. 89
GVPMRFYGSG MGTDFTLTIS SLRPEDFATY YC FR L3 S81R Q83R S67Y S71M (PDB) S77R Q79R S63Y S67M (Kabat)
                                            Seq. ID No. 90
GVPSRFYGSG MGTDFTLTIS RLRPEDFATY YC FR L3 S64M S81R Q83R S67Y S71M (PDB) S60M S77R Q79R S63Y S67M
(Kabat)
                                            Seq. ID No. 91
GVPMRFYGSG MGTDFTLTIS RLRPEDFATY YC FR L3 S80N S71M (PDB) S76N S67M (Kabat)
                                            Seq. ID No. 92
GVPSRFSGSG MGTDFTLTIN SLQPEDFATY YC FR L3 S64M S80N S71M (PDB) S60M S76N S67M (Kabat)
```

-continued

```
                                                    Seq. ID No. 93
GVPMRFSGSG MGTDFTLTIN SLQPEDFATY YC

FR L3 S81R S80N S71M (PDB) S77R S76N S67M (Kabat)
                                                    Seq. ID No. 94
GVPSRFSGSG MGTDFTLTIN RLQPEDFATY YC FR L3 Q83R S80N S71M (PDB) Q79R S76N S67M (Kabat)
                                                    Seq. ID No. 95
GVPSRFSGSG MGTDFTLTIN SLRPEDFATY YC FR L3 S64M S81R S80N S71M (PDB) S60M S77R S76N S67M (Kabat)
                                                    Seq. ID No. 96
GVPMRFSGSG MGTDFTLTIN RLQPEDFATY YC FR L3 S64M Q83R S80N S71M (PDB) S60M Q79R S76N S67M (Kabat)
                                                    Seq. ID No. 97
GVPMRFSGSG MGTDFTLTIN SLRPEDFATY YC FR L3 S81R Q83R S80N S71M (PDB) S77R Q79R S76N S67M (Kabat)
                                                    Seq. ID No. 98
GVPSRFSGSG MGTDFTLTIN RLRPEDFATY YC FR L3 S64M S81R Q83R S80N S71M (PDB) S60M S77R Q79R S76N S67M
(Kabat)
                                                    Seq. ID No. 99
GVPMRFSGSG MGTDFTLTIN RLRPEDFATY YC FR L3 S80N S67Y S71M (PDB) S76N S63Y S67M (Kabat)
                                                    Seq. ID No. 100
GVPSRFYGSG MGTDFTLTIN SLQPEDFATY YC FR L3 S64M S80N S67Y S71M (PDB) S60M S76N S63Y S67M (Kabat)
                                                    Seq. ID No. 101
GVPMRFYGSG MGTDFTLTIN SLQPEDFATY YC FR L3 S81R S80N S67Y S71M (PDB) S77R S76N S63Y S67M (Kabat)
                                                    Seq. ID No. 102
GVPSRFYGSG MGTDFTLTIN RLQPEDFATY YC FR L3 Q83R S80N S67Y S71M (PDB) Q79R S76N S63Y S67M (Kabat)
                                                    Seq. ID No. 103
GVPSRFYGSG MGTDFTLTIN SLRPEDFATY YC FR L3 S64M S81R S80N S67Y S71M (PDB) S60M S77R S76N S63Y S67M
(Kabat)
                                                    Seq. ID No. 104
GVPMRFYGSG MGTDFTLTIN RLQPEDFATY YC FR L3 S64M Q83R S80N S67Y S71M (PDB) S60M Q79R S76N S63Y S67M
(Kabat)
                                                    Seq. ID No. 105
GVPMRFYGSG MGTDFTLTIN SLRPEDFATY YC FR L3 S81R Q83R S80N S67Y S71M (PDB) S77R Q79R S76N S63Y S67M
(Kabat)
                                                    Seq. ID No. 106
GVPSRFYGSG MGTDFTLTIN RLRPEDFATY YC FR L3 S64M S81R Q83R S80N S67Y S71M (PDB) S60M S77R Q79R S76N
S63Y S67M (Kabat)
                                                    Seq. ID No. 107
GVPMRFYGSG MGTDFTLTIN RLRPEDFATY YC Wild-type human IgE-Fc (Ce2-Ce4 domains with numbering V224-K547
according to Dorrington & Bennich (1978) Immunol. Rev. 41:3-25)
carrying a C225A mutation; NB, in the crystallography
experiments the following mutations were also inserted into the
IgE-Fc to simplify the glycosylation pattern: N265Q & N371Q
(again according to Dorrington & Bennich numbering)
                                                    Seq. ID No. 108
VASRDFTPPT VKILQSSCDG GGHFPPTIQL LCLVSGYTPG TINITWLEDG QVMDVDLSTA

STTQEGELAS TQSELTLSQK HWLSDRTYTC QVTYQGHTFE DSTKKCADSN PRGVSAYLSR

PSPFDLFIRK SPTITCLVVD LAPSKGTVNL TWSRASGKPV NHSTRKEEKQ RNGTLTVTST

LPVGTRDWIE GETYQCRVTH PHLPRALMRS TTKTSGPRAA PEVYAFATPE WPGSRDKRTL

ACLIQNFMPE DISVQWLHNE VQLPDARHST TQPRKTKGSG FFVFSRLEVT RAEWEQKDEF
```

ICRAVHEAAS PSQTVQRAVS VNPGK

LIGHT CHAIN
Fab1
S77R_Q79R_v-region (Fab1)
Seq. ID No. 109
DIQLTQSPSS LSASVGDRVT ITCRASQSVD YDGDSYMNWY QQKPGKAPKL

LIYAASYLES GVPSRFSGSG SGTDFTLTIS RLRPEDFATY YCQQSHEDPY

TFGQGTKVEI K

S77R_Q79R_v-region (Fab1)
Seq. ID No. 110
GATATTCAGC TGACTCAGAG CCCGAGCTCA CTCTCCGCTT CCGTGGGGGA

TAGAGTGACC ATCACTTGCC GGGCATCCCA GTCGGTGGAC TACGACGGAG

ACTCCTACAT GAACTGGTAC CAGCAGAAGC CCGGAAAAGC CCCAAAGTTG

CTGATCTACG CCGCCTCCTA CCTTGAAAGC GGCGTGCCTT CACGCTTCTC

GGGAAGCGGG TCTGGCACCG ATTTCACCCT GACCATTTCG AGACTGAGGC

CGGAGGACTT CGCGACTTAC TACTGCCAAC AGTCCCACGA GGACCCCTAT

ACGTTTGGCC AGGGTACCAA GGTCGAAATC AAG

S77R_Q79R_v-region (Fab1) with signal sequence underlined and
italicised
Seq. ID No. 111
*MKWVTFISLL FLFSSAYS*DI QLTQSPSSLS ASVGDRVTIT CRASQSVDYD

GDSYMNWYQQ KPGKAPKLLI YAASYLESGV PSRFSGSGSG TDFTLTISRL

RPEDFATYYC QQSHEDPYTF GQGTKVEIK

S77R_Q79R_v-region (Fab1) with signal sequence underlined and
italicised
Seq. ID No. 112
*ATGAAGTGGG ATGAAGTGGG CTCCCTGCTG TTTCTGTTCT CCTCCGCCTA*

*CTCC*GATATT CAGCTGACTC AGAGCCCGAG CTCACTCTCC GCTTCCGTGG

GGGATAGAGT GACCATCACT TGCCGGGCAT CCCAGTCGGT GGACTACGAC

GGAGACTCCT ACATGAACTG GTACCAGCAG AAGCCCGGAA AAGCCCCAAA

GTTGCTGATC TACGCCGCCT CCTACCTTGA AAGCGGCGTG CCTTCACGCT

TCTCGGGAAG CGGGTCTGGC ACCGATTTCA CCCTGACCAT TTCGAGACTG

AGGCCGGAGG ACTTCGCGAC TTACTACTGC CAACAGTCCC ACGAGGACCC

CTATACGTTT GGCCAGGGTA CCAAGGTCGA AATCAAG

Fab2
Omalizumab v-region + kappa constant region including L154P
Fab2_v-region
Seq. ID No. 113
DIQLTQSPSS LSASVGDRVT ITCRASQSVD YDGDSYMNWY QQKPGKAPKL

LIYAASYLES GVPSRFSGSG SGTDFTLTIS SLQPEDFATY YCQQSHEDPY

TFGQGTKVEI K

Fab2_v-region
Seq. ID No. 114
GATATTCAGC TGACTCAGAG CCCGAGCTCA CTCTCCGCTT CCGTGGGGGA

TAGAGTGACC ATCACTTGCC GGGCATCCCA GTCGGTGGAC TACGACGGAG

ACTCCTACAT GAACTGGTAT CAGCAGAAGC CCGGAAAAGC CCAAAGTTG

CTGATCTACG CCGCCTCATA CCTTGAAAGC GGCGTGCCTT CGCGCTTCTC

GGGAAGCGGG TCGGGCACCG ATTTCACCCT GACCATTTCG TCGCTGCAGC

CGGAGGACTT CGCGACTTAC TACTGCCAAC AGTCCCACGA GGACCCCTAT

ACGTTTGGCC AGGGAACCAA GGTCGAAATC AAG

Fab2_v-region with signal sequence underlined and italicised
Seq. ID No. 115
*MKWVTFISLL FLFSSAYS*DI QLTQSPSSLS ASVGDRVTIT CRASQSVDYD

GDSYMNWYQQ KPGKAPKLLI YAASYLESGV PSRFSGSGSG TDFTLTISSL

QPEDFATYYC QQSHEDPYTF GQGTKVEIK

Fab2_v-region with signal
sequence underlined and italicised
Seq. ID No. 116
*ATGAAGTGGG TCACCTTCAT CTCCCTGCTG TTTCTGTTCT CCTCCGCCTA*

*CTCC*GATATT CAGCTGACTC AGAGCCCGAG CTCACTCTCC GCTTCCGTGG

GGGATAGAGT GACCATCACT TGCCGGGCAT CCCAGTCGGT GGACTACGAC

GGAGACTCCT ACATGAACTG GTATCAGCAG AAGCCCGGAA AGCCCCAAA

GTTGCTGATC TACGCCGCCT CATACCTTGA AAGCGGCGTG CCTTCGCGCT

TCTCGGGAAG CGGGTCGGGC ACCGATTTCA CCCTGACCAT TTCGTCGCTG

CAGCCGGAGG ACTTCGCGAC TTACTACTGC AACAGTCCC ACGAGGACCC

CTATACGTTT GGCCAGGGAA CCAAGGTCGA AATCAAG

Fab2_v-region + kappa constant region including L154P
Seq. ID No. 117
DIQLTQSPSS LSASVGDRVT ITCRASQSVD YDGDSYMNWY QQKPGKAPKL

LIYAASYLES GVPSRFSGSG SGTDFTLTIS SLQPEDFATY YCQQSHEDPY

TFGQGTKVEI KRTVAAPSVF IFPPSDEQLK SGTASVVCLL NNFYPREAKV

QWKVDNAPQS GNSQESVTEQ DSKDSTYSLS STLTLSKADY EKHKVYACEV

THQGLSSPVT KSFNRGEC

Fab2_v-region + kappa constant region including L154P
Seq. ID No. 118
GATATTCAGC TGACTCAGAG CCCGAGCTCA CTCTCCGCTT CCGTGGGGGA

TAGAGTGACC ATCACTTGCC GGGCATCCCA GTCGGTGGAC TACGACGGAG

ACTCCTACAT GAACTGGTAT CAGCAGAAGC CCGGAAAAGC CCCAAAGTTG

CTGATCTACG CCGCCTCATA CCTTGAAAGC GGCGTGCCTT CGCGCTTCTC

GGGAAGCGGG TCGGGCACCG ATTTCACCCT GACCATTTCG TCGCTGCAGC

CGGAGGACTT CGCGACTTAC TACTGCCAAC AGTCCCACGA GGACCCCTAT

ACGTTTGGCC AGGGAACCAA GGTCGAAATC AAGCGTACGG TAGCGGCCCC

ATCTGTCTTC ATCTTCCCGC CATCTGATGA GCAGTTGAAA TCTGGAACTG

CCTCTGTTGT GTGCCTGCTG AATAACTTCT ATCCCAGAGA GGCCAAAGTA

CAGTGGAAGG TGGATAACGC CCCGCAATCG GGTAACTCCC AGGAGAGTGT

CACAGAGCAG GACAGCAAGG ACAGCACCTA CAGCCTCAGC AGCACCCTGA

CGCTGAGCAA AGCAGACTAC GAGAAACACA AAGTCTACGC CTGCGAAGTC

ACCCATCAGG GCCTGAGCTC GCCCGTCACA AAGAGCTTCA ACAGGGGAGA

GTGT

Fab2 _v-region + kappa constant region including L154P with
signal sequence underlined and italicised
Seq. ID No. 119
*MKWVTFISLL FLFSSAYS*DI QLTQSPSSLS ASVGDRVTIT CRASQSVDYD

GDSYMNWYQQ KPGKAPKLLI YAASYLESGV PSRFSGSGSG TDFTLTISSL

QPEDFATYYC QQSHEDPYTF GQGTKVEIKR TVAAPSVFIF PPSDEQLKSG

TASVVCLLNN FYPREAKVQW KVDNAPQSGN SQESVTEQDS KDSTYSLSST

-continued

LTLSKADYEK HKVYACEVTH QGLSSPVTKS FNRGEC

Fab2 _v-region + kappa constant region including L154P with
signal sequence underlined and italicised Seq. ID No. 120

*ATGAAGTGGG TCACCTTCAT CTCCCTGCTG TTTCTGTTCT CCTCCGCCTA*

*CTCC*GATATT CAGCTGACTC AGAGCCCGAG CTCACTCTCC GCTTCCGTGG

GGGATAGAGT GACCATCACT TGCCGGGCAT CCCAGTCGGT GGACTACGAC

GGAGACTCCT ACATGAACTG GTATCAGCAG AAGCCCGGAA AGCCCCAAA

GTTGCTGATC TACGCCGCCT CATACCTTGA AAGCGGCGTG CCTTCGCGCT

TCTCGGGAAG CGGGTCGGGC ACCGATTTCA CCCTGACCAT TTCGTCGCTG

CAGCCGGAGG ACTTCGCGAC TTACTACTGC AACAGTCCC ACGAGGACCC

CTATACGTTT GGCCAGGGAA CCAAGGTCGA AATCAAGCGT ACGGTAGCGG

CCCCATCTGT CTTCATCTTC CCGCCATCTG ATGAGCAGTT GAAATCTGGA

ACTGCCTCTG TTGTGTGCCT GCTGAATAAC TTCTATCCCA GAGAGGCCAA

AGTACAGTGG AAGGTGGATA ACGCCCCGCA ATCGGGTAAC TCCCAGGAGA

GTGTCACAGA GCAGGACAGC AAGGACAGCA CCTACAGCCT CAGCAGCACC

CTGACGCTGA GCAAAGCAGA CTACGAGAAA CACAAAGTCT ACGCCTGCGA

AGTCACCCAT CAGGGCCTGA GCTCGCCCGT CACAAAGAGC TTCAACAGGG

GAGAGTGT

Fab3
S77R_Q79R_v-region (from Fab1) + kappa constant region
including L154P (from Fab2)
S77R_Q79R_v-region Seq. ID No. 121

DIQLTQSPSS LSASVGDRVT ITCRASQSVD YDGDSYMNWY QQKPGKAPKL

LIYAASYLES GVPSRFSGSG SGTDFTLTIS RLRPEDFATY YCQQSHEDPY

TFGQGTKVEI K

S77R_Q79R_v-region

Seq. ID No. 122

GATATTCAGC TGACTCAGAG CCCGAGCTCA CTCTCCGCTT CCGTGGGGGA

TAGAGTGACC ATCACTTGCC GGGCATCCCA GTCGGTGGAC TACGACGGAG

ACTCCTACAT GAACTGGTAC CAGCAGAAGC CCGGAAAAGC CCCAAAGTTG

CTGATCTACG CCGCCTCCTA CCTTGAAAGC GGCGTGCCTT CACGCTTCTC

GGGAAGCGGG TCTGGCACCG ATTTCACCCT GACCATTTCG AGACTGAGGC

CGGAGGACTT CGCGACTTAC TACTGCCAAC AGTCCCACGA GGACCCCTAT

ACGTTTGGCC AGGGTACCAA GGTCGAAATC AAG

S77R_Q79R_v-region with signal sequence underlined and
italicised

Seq. ID No. 123

*MKWVTFISLL FLFSSAYS*DI QLTQSPSSLS ASVGDRVTIT CRASQSVDYD

GDSYMNWYQQ KPGKAPKLLI YAASYLESGV PSRFSGSGSG TDFTLTISRL

RPEDFATYYC QQSHEDPYTF GQGTKVEIK

S77R_Q79R_v-region with signal sequence underlined and
italicised

Seq. ID No. 124

*ATGAAGTGGG TCACCTTCAT CTCCCTGCTG TTTCTGTTCT CCTCCGCCTA*

*CTCC*GATATT CAGCTGACTC AGAGCCCGAG CTCACTCTCC GCTTCCGTGG

GGGATAGAGT GACCATCACT TGCCGGGCAT CCCAGTCGGT GGACTACGAC

GGAGACTCCT ACATGAACTG GTACCAGCAG AAGCCCGGAA AAGCCCCAAA

```
GTTGCTGATC TACGCCGCCT CCTACCTTGA AAGCGGCGTG CCTTCACGCT

TCTCGGGAAG CGGGTCTGGC ACCGATTTCA CCCTGACCAT TTCGAGACTG

AGGCCGGAGG ACTTCGCGAC TTACTACTGC AACAGTCCC ACGAGGACCC

CTATACGTTT GGCCAGGGTA CCAAGGTCGA AATCAAG
```

S77R_Q79R_v-region + kappa constant region including
L154P
                                            Seq. ID No. 125
```
DIQLTQSPSS LSASVGDRVT ITCRASQSVD YDGDSYMNWY QQKPGKAPKL

LIYAASYLES GVPSRFSGSG SGTDFTLTIS RLRPEDFATY YCQQSHEDPY

TFGQGTKVEI KRTVAAPSVF IFPPSDEQLK SGTASVVCLL NNFYPREAKV

QWKVDNAPQS GNSQESVTEQ DSKDSTYSLS STLTLSKADY EKHKVYACEV

THQGLSSPVT KSFNRGEC
```

S77R_Q79R_v-region + kappa constant region including
L154P
                                            Seq. ID No. 126
```
GATATTCAGC TGACTCAGAG CCCGAGCTCA CTCTCCGCTT CCGTGGGGGA

TAGAGTGACC ATCACTTGCC GGGCATCCCA GTCGGTGGAC TACGACGGAG

ACTCCTACAT GAACTGGTAC CAGCAGAAGC CCGGAAAAGC CCCAAAGTTG

CTGATCTACG CCGCCTCCTA CCTTGAAAGC GGCGTGCCTT CACGCTTCTC

GGGAAGCGGG TCTGGCACCG ATTTCACCCT GACCATTTCG AGACTGAGGC

CGGAGGACTT CGCGACTTAC TACTGCCAAC AGTCCCACGA GGACCCCTAT

ACGTTTGGCC AGGGTACCAA GGTCGAAATC AAGCGTACGG TAGCGGCCCC

ATCTGTCTTC ATCTTCCCGC CATCTGATGA GCAGTTGAAA TCTGGAACTG

CCTCTGTTGT GTGCCTGCTG AATAACTTCT ATCCCAGAGA GGCCAAAGTA

CAGTGGAAGG TGGATAACGC CCCGCAATCG GGTAACTCCC AGGAGAGTGT

CACAGAGCAG GACAGCAAGG ACAGCACCTA CAGCCTCAGC AGCACCCTGA

CGCTGAGCAA AGCAGACTAC GAGAAACACA AAGTCTACGC CTGCGAAGTC

ACCCATCAGG GCCTGAGCTC GCCCGTCACA AAGAGCTTCA ACAGGGGAGA

GTGT
```

S77R_Q79R_v-region + kappa constant region including
L154P with signal sequence underlined and italicised
                                            Seq. ID No. 127
```
MKWVTFISLL FLFSSAYSDI QLTQSPSSLS ASVGDRVTIT CRASQSVDYD

GDSYMNWYQQ KPGKAPKLLI YAASYLESGV PSRFSGSGSG TDFTLTISRL

RPEDFATYYC QQSHEDPYTF GQGTKVEIKR TVAAPSVFIF PPSDEQLKSG

TASVVCLLNN FYPREAKVQW KVDNAPQSGN SQESVTEQDS KDSTYSLSST

LTLSKADYEK HKVYACEVTH QGLSSPVTKS FNRGEC
```

S77R_Q79R_v-region + kappa constant region including
L154P with signal sequence underlined and italicised
                                            Seq. ID No. 128
```
ATGAAGTGGG TCACCTTCAT CTCCCTGCTG TTTCTGTTCT CCTCCGCCTA

CTCCGATATT CAGCTGACTC AGAGCCCGAG CTCACTCTCC GCTTCCGTGG

GGGATAGAGT GACCATCACT TGCCGGGCAT CCCAGTCGGT GGACTACGAC

GGAGACTCCT ACATGAACTG GTACCAGCAG AAGCCCGGAA AAGCCCCAAA

GTTGCTGATC TACGCCGCCT CCTACCTTGA AAGCGGCGTG CCTTCACGCT

TCTCGGGAAG CGGGTCTGGC ACCGATTTCA CCCTGACCAT TTCGAGACTG
```

-continued

AGGCCGGAGG ACTTCGCGAC TTACTACTGC AACAGTCCC ACGAGGACCC

CTATACGTTT GGCCAGGGTA CCAAGGTCGA AATCAAGCGT ACGGTAGCGG

CCCCATCTGT CTTCATCTTC CCGCCATCTG ATGAGCAGTT GAAATCTGGA

ACTGCCTCTG TTGTGTGCCT GCTGAATAAC TTCTATCCCA GAGAGGCCAA

AGTACAGTGG AAGGTGGATA ACGCCCCGCA ATCGGGTAAC TCCCAGGAGA

GTGTCACAGA GCAGGACAGC AAGGACAGCA CCTACAGCCT CAGCAGCACC

CTGACGCTGA GCAAAGCAGA CTACGAGAAA CACAAAGTCT ACGCCTGCGA

AGTCACCCAT CAGGGCCTGA GCTCGCCCGT CACAAAGAGC TTCAACAGGG

GAGAGTGT

Omalizumab_v-region
                                                              Seq. ID No. 129
TQSPSSLSAS VGDRVTITCR ASQSVDYDGD SYMNWYQQKP GKAPKLLIYA

ASYLESGVPS RFSGSGSGTD FTLTISSLQP EDFATYYCQQ SHEDPYTFGQ

GTKVEIK

Omalizumab_v-region
                                                              Seq. ID No. 130
ACTCAGAGCC CGAGCTCACT CTCCGCTTCC GTGGGGGATA GAGTGACCAT

CACTTGCCGG GCATCCCAGT CGGTGGACTA CGACGGAGAC TCCTACATGA

ACTGGTATCA GCAGAAGCCC GGAAAAGCCC AAAGTTGCT GATCTACGCC

GCCTCATACC TTGAAAGCGG CGTGCCTTCG CGCTTCTCGG AAGCGGGTC

GGGCACCGAT TTCACCCTGA CCATTTCGTC GCTGCAGCCG GAGGACTTCG

CGACTTACTA CTGCCAACAG TCCCACGAGG ACCCCTATAC GTTTGGCCAG

GGAACCAAGG TCGAAATCAA G

FR3
                                                               SEQ ID NO: 131
GVPMRFSGSGMGTDFTLTISRLRPEDFATYYC

S60M_552D_667M S77R_Q79R_v-region
                                                               SEQ ID NO: 132
DIQLTQSPSS LSASVGDRVT ITCRASQSVD YDGDSYMNWY QQKPGKAPKL

LIYAADYLES GVPMRFSGSG MGTDFTLTIS RLRPEDFATY YCQQSHEDPY

TFGQGTKVEI K

S60M_552D_667M_S77R_Q79R_v-region
                                                               SEQ ID NO: 133
GATATTCAGCTGACTCAGAGCCCGAGCTCACTCTCCGCTTCCGTGGGGGATAGAGTGACCATCA

CTTGCCGGGCATCCCAGTCGGTGGACTACGACGGAGACTCCTACATGAACTGGTATCAGCAGAA

GCCCGGAAAAGCCCCAAAGTTGCTGATCTACGCCGCCGACTACCTTGAAAGCGGCGTGCCTATG

CGCTTCTCGGGAAGCGGGATGGGCACCGATTTCACCCTGACCATTTCGAGACTGAGGCCGGAGG

ACTTCGCGACTTACTACTGCCAACAGTCCCACGAGGACCCCTATACGTTTGGCCAGGGAACCAA

GGTCGAAATCAAG

S60M_S52D_S67M_S77R_Q79R_v-region with signal
sequence underlined and italicised
                                                               SEQ ID NO: 134
<u>*MKWVTFISLL FLFSSAYS*</u>DI QLTQSPSSLS ASVGDRVTIT CRASQSVDYD

GDSYMNWYQQ KPGKAPKLLI YAADYLESGV PMRFSGSGMG TDFTLTISRL

RPEDFATYYC QQSHEDPYTF GQGTKVEIK

S60M_S52D_S67M_S77R_Q79R_v-region with signal
sequence underlined and italicised
                                                               SEQ ID NO: 135
ATGAAGTGGGTCACCTTCATCTCCCTGCTGTTTCTGTTCTCCTCCGCCTACTCCGATATTCAGC -continued

```
TGACTCAGAGCCCGAGCTCACTCTCCGCTTCCGTGGGGGATAGAGTGACCATCACTTGCCGGGC

ATCCCAGTCGGTGGACTACGACGGAGACTCCTACATGAACTGGTATCAGCAGAAGCCCGGAAAA

GCCCCAAAGTTGCTGATCTACGCCGCCGACTACCTTGAAAGCGGCGTGCCTATGCGCTTCTCGG

GAAGCGGGATGGGCACCGATTTCACCCTGACCATTTCGAGACTGAGGCCGGAGGACTTCGCGAC

TTACTACTGCCAACAGTCCCACGAGGACCCCTATACGTTTGGCCAGGGAACCAAGGTCGAAATC

AAG
```

S60M_S52D_667M_S77R_Q79R_v-region + kappa constant region
SEQ ID NO: 136

DI QLTQSPSSLS ASVGDRVTIT CRASQSVDYD GDSYMNWYQQ KPGKAPKLLI

YAADYLESGV PMRFSGSGMG TDFTLTISRL RPEDFATYYC QQSHEDPYTF

GQGTKVEIKR TVAAPSVFIF PPSDEQLKSG TASVVCLLNN FYPREAKVQW

KVDNALQSGN SQESVTEQDS KDSTYSLSST LTLSKADYEK HKVYACEVTH

QGLSSPVTKS FNRGEC

S60M_S52D_667M_S77R_Q79R_v-region + kappa constant region
SEQ ID NO: 137

```
GATATTCAGCTGACTCAGAGCCCGAGCTCACTCTCCGCTTCCGTGGGGGATAGAGTGACCATCA

CTTGCCGGGCATCCCAGTCGGTGGACTACGACGGAGACTCCTACATGAACTGGTATCAGCAGAA

GCCCGGAAAAGCCCCAAAGTTGCTGATCTACGCCGCCGACTACCTTGAAAGCGGCGTGCCTATG

CGCTTCTCGGGAAGCGGGATGGGCACCGATTTCACCCTGACCATTTCGAGACTGAGGCCGGAGG

ACTTCGCGACTTACTACTGCCAACAGTCCCACGAGGACCCCTATACGTTTGGCCAGGGAACCAA

GGTCGAAATCAAGCGTACGGTAGCGGCCCCATCTGTCTTCATCTTCCCGCCATCTGATGAGCAG

TTGAAATCTGGAACTGCCTCTGTTGTGTGCCTGCTGAATAACTTCTATCCCAGAGAGGCCAAAG

TACAGTGGAAGGTGGATAACGCCCTCCAATCGGGTAACTCCCAGGAGAGTGTCACAGAGCAGGA

CAGCAAGGACAGCACCTACAGCCTCAGCAGCACCCTGACGCTGAGCAAAGCAGACTACGAGAAA

CACAAAGTCTACGCCTGCGAAGTCACCCATCAGGGCCTGAGCTCGCCCGTCACAAAGAGCTTCA

ACAGGGGAGAGTGT
```

FR3
SEQ ID NO: 138

GVPRRFSGSGMGTDFTLTISRLRPEDFATYYC

S60R_S52D_S67M_S77R_Q79R_v-region
SEQ ID NO: 139

DIQLTQSPSS LSASVGDRVT ITCRASQSVD YDGDSYMNWY QQKPGKAPKL

LIYAADYLES GVPRRFSGSG MGTDFTLTIS RLRPEDFATY YCQQSHEDPY

TFGQGTKVEI K

S60R_S52D_667M_S77R_Q79R_v-region
SEQ ID NO: 140

```
GATATTCAGCTGACTCAGAGCCCGAGCTCACTCTCCGCTTCCGTGGGGGATAGAGTGACCATCA

CTTGCCGGGCATCCCAGTCGGTGGACTACGACGGAGACTCCTACATGAACTGGTATCAGCAGAA

GCCCGGAAAAGCCCCAAAGTTGCTGATCTACGCCGCCGATTACCTTGAAAGCGGCGTGCCTCGT

CGCTTCTCGGGAAGCGGGATGGGCACCGATTTCACCCTGACCATTTCGAGACTGAGGCCGGAGG

ACTTCGCGACTTACTACTGCCAACAGTCCCACGAGGACCCCTATACGTTTGGCCAGGGAACCAA

GGTCGAAATCAAG
```

S60R_S52D_S67M_S77R_Q79R_v-region with signal
sequence underlined and italicised
SEQ ID NO: 141

*<u>MKWVTFISLL FLFSSAYS</u>*DI QLTQSPSSLS ASVGDRVTIT CRASQSVDYD

GDSYMNWYQQ KPGKAPKLLI YAADYLESGV PRRFSGSGMG TDFTLTISRL

-continued

RPEDFATYYC QQSHEDPYTF GQGTKVEIK

S60R_S52D_S67M_S77R_Q79R_v-region with signal
sequence underlined and italicised
SEQ ID NO: 142
ATGAAGTGGGTCACCTTCATCTCCCTGCTGTTTCTGTTCTCCTCCGCCTACTCCGATATTCAGC

TGACTCAGAGCCCGAGCTCACTCTCCGCTTCCGTGGGGGATAGAGTGACCATCACTTGCCGGGC

ATCCCAGTCGGTGGACTACGACGGAGACTCCTACATGAACTGGTATCAGCAGAAGCCCGGAAAA

GCCCCAAAGTTGCTGATCTACGCCGCCGATTACCTTGAAAGCGGCGTGCCTCGTCGCTTCTCGG

GAAGCGGGATGGGCACCGATTTCACCCTGACCATTTCGAGACTGAGGCCGGAGGACTTCGCGAC

TTACTACTGCCAACAGTCCCACGAGGACCCCTATACGTTTGGCCAGGGAACCAAGGTCGAAATC

AAG

S60R_552D_667M_S77R_Q79R_v-region + kappa constant region
SEQ ID NO: 143
DI QLTQSPSSLS ASVGDRVTIT CRASQSVDYD GDSYMNWYQQ KPGKAPKLLI

YAADYLESGV PRRFSGSGMG TDFTLTISRL RPEDFATYYC QQSHEDPYTF

GQGTKVEIKR TVAAPSVFIF PPSDEQLKSG TASVVCLLNN FYPREAKVQW

KVDNALQSGN SQESVTEQDS KDSTYSLSST LTLSKADYEK HKVYACEVTH

QGLSSPVTKS FNRGEC

S60R_552D_667M_S77R_Q79R_v-region + kappa constant region
SEQ ID NO: 144
GATATTCAGCTGACTCAGAGCCCGAGCTCACTCTCCGCTTCCGTGGGGGATAGAGTGACCATCA

CTTGCCGGGCATCCCAGTCGGTGGACTACGACGGAGACTCCTACATGAACTGGTATCAGCAGAA

GCCCGGAAAAGCCCCAAAGTTGCTGATCTACGCCGCCGATTACCTTGAAAGCGGCGTGCCTCGT

CGCTTCTCGGGAAGCGGGATGGGCACCGATTTCACCCTGACCATTTCGAGACTGAGGCCGGAGG

ACTTCGCGACTTACTACTGCCAACAGTCCCACGAGGACCCCTATACGTTTGGCCAGGGAACCAA

GGTCGAAATCAAGCGTACGGTAGCGGCCCCATCTGTCTTCATCTTCCCGCCATCTGATGAGCAG

TTGAAATCTGGAACTGCCTCTGTTGTGTGCCTGCTGAATAACTTCTATCCCAGAGAGGCCAAAG

TACAGTGGAAGGTGGATAACGCCCTCCAATCGGGTAACTCCCAGGAGAGTGTCACAGAGCAGGA

CAGCAAGGACAGCACCTACAGCCTCAGCAGCACCCTGACGCTGAGCAAAGCAGACTACGAGAAA

CACAAAGTCTACGCCTGCGAAGTCACCCATCAGGGCCTGAGCTCGCCCGTCACAAAGAGCTTCA

ACAGGGGAGAGTGT

S60K_552D_S67M_S77R_Q79R_v-region(Kabat)
SEQ ID NO: 145
DIQLTQSPSS LSASVGDRVT ITCRASQSVD YDGDSYMNWY QQKPGKAPKL

LIYAADYLES GVPKRFSGSG MGTDFTLTIS RLRPEDFATY YCQQSHEDPY

TFGQGTKVEI K

S60Q_552D_S67M S77R_Q79R_v-region(Kabat)
SEQ ID NO: 146
DIQLTQSPSS LSASVGDRVT ITCRASQSVD YDGDSYMNWY QQKPGKAPKL

LIYAADYLES GVPQRFSGSG MGTDFTLTIS RLRPEDFATY YCQQSHEDPY

TFGQGTKVEI K v-region + gamma 1 CH1 constant region plus linker plus CA645
gL4gH5 scFv with signal sequence underlined and italicised
SEQ ID NO: 147
*MKWVTFISLLFLFSSAYS*EVQLVESGGGLVQPGGSLRLSCAVSGYSITSGYSWNWIRQAPGKGL

EWVASITYDGSTNYNPSVKGRITISRDDSKNTFYLQMNSLRAEDTAVYYCARGSHYFGHWHFAV

WGQGTLVTVSSASTKGPSVFPLAPSSKSTSGGTAALGCLVKDYFPEPVTVSWNSGALTSGVHTF

-continued

PAVLQSSGLYSLSSVVTVPSSSLGTQTYICNVNHKPSNTKVDKKVEPKSCSGGGGTGGGGSEVQ

LLESGGGLVQPGGSLRLSCAVSGIDLSNYAINWVRQAPGKCLEWIGIIWASGTTFYATWAKGRF

TISRDNSKNTVYLQMNSLRAEDTAVYYCARTVPGYSTAPYFDLWGQGTLVTVSSGGGGSGGGGS

GGGGSGGGGSDIQMTQSPSSVSASVGDRVTITCQSSPSVWSNFLSWYQQKPGKAPKLLIYEASK

LTSGVPSRFSGSGSGTDFTLTISSLQPEDFATYYCGGGYSSISDTTFGCGTKVEIKRT v-region + gamma 1 CH1 constant region plus linker plus CA645
gL4gH5 scFv with signal sequence underlined and italicised
SEQ ID NO: 148
*ATGAAGTGGGTCACCTTCATCTCCCTGCTGTTTCTGTTCTCCAGCGCCTACTCC*GAAGTGCAGT

TGGTGGAGTCGGGTGGAGGGCTGGTGCAGCCTGGCGGTAGCCTGAGGCTGTCCTGTGCCGTGTC

CGGATACTCCATTACCTCCGGCTACTCGTGGAACTGGATCAGACAGGCTCCCGGAAAGGGACTT

GAGTGGGTGGCGTCCATCACCTACGACGGCTCAACCAACTATAACCCGTCCGTGAAGGGCCGCA

TCACCATTTCGCGCGACGACAGCAAGAATACTTTTTACCTCCAAATGAACAGCCTGCGGGCCGA

AGATACTGCCGTGTACTACTGCGCGCGGGGATCACATTACTTCGGGCACTGGCACTTCGCCGTC

TGGGGACAGGGCACCCTCGTCACTGTCTCGAGCGCTTCTACAAAGGGCCCATCGGTCTTCCCCC

TGGCACCCTCCTCCAAGAGCACCTCTGGGGGCACAGCGGCCCTGGGCTGCCTGGTCAAGGACTA

CTTCCCCGAACCAGTGACGGTGTCGTGGAACTCAGGTGCCCTGACCAGCGGCGTTCACACCTTC

CCGGCTGTCCTACAGTCTTCAGGACTCTACTCCCTGAGCAGCGTGGTGACCGTGCCCTCCAGCA

GCTTGGGCACCCAGACCTACATCTGCAACGTGAATCACAAGCCCAGCAACACCAAGGTCGATAA

GAAAGTTGAGCCCAAATCTTGTAGTGGAGGTGGGGGCACCGGTGGAGGTGGCAGCGAGGTTCAA

CTGCTTGAGTCTGGAGGAGGCCTAGTCCAGCCTGGAGGGAGCCTGCGTCTCTCTTGTGCAGTAA

GCGGCATCGACCTGAGCAATTACGCCATCAACTGGGTGAGACAAGCTCCGGGGAAGTGTTTAGA

ATGGATCGGTATAATATGGGCCAGTGGGACGACCTTTTATGCTACATGGGCGAAAGGAAGGTTT

ACAATTAGCCGGGACAATAGCAAAAACACCGTGTATCTCCAAATGAACTCCTTGCGAGCAGAGG

ACACGGCGGTGTACTATTGTGCTCGCACTGTCCCAGGTTATAGCACTGCACCCTACTTCGATCT

GTGGGGACAAGGGACCCTGGTGACTGTTTCAAGTGGCGGAGGGGGTAGTGGAGGGGGTGGCTCT

GGGGGTGGCGGAAGCGGTGGCGGGGGTTCTGACATACAAATGACTCAGTCTCCTTCATCGGTAT

CCGCGTCCGTTGGCGATAGGGTGACTATTACATGTCAAAGCTCTCCTAGCGTCTGGAGCAATTT

TCTATCCTGGTATCAACAGAAACCGGGGAAGGCTCCAAAACTTCTGATTTATGAAGCCTCGAAA

CTCACCAGTGGAGTTCCGTCAAGATTCAGTGGCTCTGGATCAGGGACAGACTTCACGTTGACAA

TCAGTTCGCTGCAACCAGAGGACTTTGCGACCTACTATTGTGGTGGAGGTTACAGTAGCATAAG

TGATACGACATTTGGGTGCGGTACTAAGGTGGAAATCAAACGTACC

Linker between CH1 and CA645 gL4gH5 scnr
SEQ ID NO: 149
SGGGGTGGGGS

CA645 gL4gH5 scnr
SEQ ID NO: 150
EVQLLESGGGLVQPGGSLRLSCAVSGIDLSNYAINWVRQAPGKCLEWIGIIWASGTTFYATWAK

GRFTISRDNSKNTVYLQMNSLRAEDTAVYYCARTVPGYSTAPYFDLWGQGTLVTVSSGGGGSGG

GGSGGGGSGGGGSDIQMTQSPSSVSASVGDRVTITCQSSPSVWSNFLSWYQQKPGKAPKLLIYE

ASKLTSGVPSRFSGSGSGTDFTLTISSLQPEDFATYYCGGGYSSISDTTFGCGTKVEIKRT

Linker between CA645 gH5 and CA645 gL4 within scnr
SEQ ID NO: 151
GGGGSGGGGSGGGGSGGGGS

CA645 CDRH1
SEQ ID NO: 152

```
GIDLSNYAIN

CA645 CDRH2                                                      SEQ ID NO: 153
IIWASGTTFYATWAKG

CA645 CDRH3                                                      SEQ ID NO: 154
TVPGYSTAPYFDL

CA645 CDRL1                                                      SEQ ID NO: 155
QSSPSVWSNFLS

CA645 CDRL2                                                      SEQ ID NO: 156
EASKLTS

CA645 CDRL3                                                      SEQ ID NO: 157
GGGYSSISDTT

S60M_S52D_667M_S77R_Q79R_S63W_S76N_v-region(Kabat)               SEQ ID NO: 158
DIQLTQSPSS LSASVGDRVT ITCRASQSVD YDGDSYMNWY QQKPGKAPKL

LIYAADYLES GVPMRFWGSG MGTDFTLTIN RLRPEDFATY YCQQSHEDPY

TFGQGTKVEI K

S60M_S52D_667M_S77R_Q79R_S63Y_676N_v-region(Kabat)               SEQ ID NO: 159
DIQLTQSPSS LSASVGDRVT ITCRASQSVD YDGDSYMNWY QQKPGKAPKL

LIYAADYLES GVPMRFYGSG MGTDFTLTIN RLRPEDFATY YCQQSHEDPY

TFGQGTKVEI K

Signal sequence                                                  SEQ ID NO: 160
MKWVTFISLL FLFSSAYS
```

---

What is claimed is:

1. A method for treating a disease in a human subject in need thereof, the method comprising administering to the subject an effective amount of an anti-IgE antibody, or antigen binding agent or a pharmaceutical composition comprising the anti-IgE antibody or antigen binding agent and one or more of a pharmaceutically acceptable excipient, diluent or carrier, wherein the anti-IgE antibody, or antigen binding agent comprises a heavy chain variable region comprising complementarity determining regions: CDR-H1 comprising SEQ ID NO:14, CDR-H2 comprising SEQ ID NO:16, CDR-H3 comprising SEQ ID NO: 18, and a light chain variable region comprising complementarity determining regions: CDR-L1 comprising SEQ ID NO:29, CDR-L2 comprising SEQ ID NO:50 or 51, and CDR-L3 comprising SEQ ID NO: 33.

2. The method of claim 1, wherein the disease is associated with a complex of human IgE and FcεRI.

3. The method of claim 2, wherein the treatment is through the disassociation of the complex of human IgE and FcεRI and the binding of human IgE by the anti-IgE antibody, or antigen binding agent.

4. The method of claim 1, wherein the disease is: allergy; allergic asthma; severe asthma; moderate asthma; chronic spontaneous urticaria; chronic idiopathic urticaria; perennial allergic rhinitis; seasonal allergic rhinitis; acute asthma exacerbations; acute bronchospasm; status asthmaticus; hyper IgE syndrome; allergic bronchopulmonary aspergillosis; food allergy; atopic dermatitis; allergic rhinitis; bee venom sensitivity; idiopathic anaphylaxis; peanut allergy; latex allergy; inflammatory skin diseases; urticaria; cutaneous mastocytosis; systemic mastocytosis; eosinophil-associated gastrointestinal disorder; bullous pemphigoid; interstitial cystitis; nasal polyps; idiopathic angioedema; or non-allergic asthma.

5. The method of claim 1, wherein the anti-IgE antibody, or antigen binding agent is selected from the group consisting of a Fab fragment, modified Fab' fragment, Fab' fragment, F(ab')₂ fragment, Fv, scFv, scAb, a diabody, bispecific antibody, triabody, FabFv, Fab-Fv-Fv, tribody, and a (Fab-Fv)²-Fc.

6. The method of claim 5, wherein the anti-IgE antibody, or antigen binding agent comprises an scFv comprising a heavy chain variable region and a light chain variable region, wherein the heavy chain variable region comprises a CDR-H1 comprising SEQ ID NO: 152, a CDR-H2 comprising SEQ ID NO: 153, and a CDR-H3 comprising SEQ ID NO: 154 and the light chain variable region comprises a CDR-L1 comprising SEQ ID NO: 155, a CDR-L2 comprising SEQ ID NO: 156, and a CDR-L3 comprising SEQ ID NO: 157.

7. The method of claim 5, wherein the anti-IgE antibody is a Fab fragment comprising a heavy chain variable region and a light chain variable region, wherein:
a) the heavy chain variable region comprises a CDR-H1 comprising SEQ ID NO: 14, a CDR-H2 comprising SEQ ID NO: 16, and a CDR-H3 comprising SEQ ID NO: 18 and the light chain variable region comprises a CDR-L1 comprising SEQ ID NO: 29, a CDR-L2 comprising SEQ ID NO: 50, a CDR-L3 comprising SEQ ID NO: 33 and a framework region FW-L3 comprising SEQ ID NO: 131 or 138; or
b) the heavy chain variable region comprises SEQ ID NO: 1 and the light chain variable region comprises SEQ ID NO: 132 or 139.

8. The method of claim 6, wherein the heavy chain variable region and the light chain variable are linked by a linker comprising SEQ ID NO:151.

9. A method for treating a disease in a human subject in need thereof, the method comprising administering to the subject an effective amount of an anti-IgE antibody, or antigen binding agent or a pharmaceutical composition comprising the anti-IgE antibody or antigen binding agent and one or more of a pharmaceutically acceptable excipient, diluent or carrier, wherein the anti-IgE antibody, or antigen binding agent comprises a heavy chain variable region and a light chain variable region, wherein:
a. the heavy chain variable region comprises a CDR-H1 comprising SEQ ID NO:14, a CDR-H2 comprising SEQ ID NO: 16 and a CDR-H3 comprising SEQ ID NO:18 and the light chain variable region comprises a CDR-L1 comprising SEQ ID NO:29, a CDR-L2 comprising SEQ ID NO:50, a CDR-L3 comprising SEQ ID NO:33 and a framework region FW-L3 comprising SEQ ID NO: 131 or 138; or
b. the heavy chain variable region comprises SEQ ID NO: 1 and the light chain variable region comprises SEQ ID NO: 132 or 139.

10. The method of claim 9, wherein the anti-IgE antibody, or antigen binding agent further comprising a light chain constant region, wherein the light chain variable region and the light chain constant region VL-CL comprise SEQ ID NO:137 or 145.

11. The method of claim 9, wherein the anti-IgE antibody, or antigen binding agent further comprises a heavy chain constant region, CH1.

12. The method of claim 9, wherein the heavy chain variable region and heavy chain constant region, VH-CH1 comprise SEQ ID NO: 5.

* * * * *

SEQUENCE LISTING

```
<160> NUMBER OF SEQ ID NOS: 160

<210> SEQ ID NO 1
<211> LENGTH: 121
<212> TYPE: PRT
<213> ORGANISM: Artificial Sequence
<220> FEATURE:
<223> OTHER INFORMATION: V-region

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
                100                 105                 110

Gln Gly Thr Leu Val Thr Val Ser Ser
            115                 120
```

<210> SEQ ID NO 2
<211> LENGTH: 363
<212> TYPE: DNA
<213> ORGANISM: Artificial Sequence
<220> FEATURE:
<223> OTHER INFORMATION: V-region

<400> SEQUENCE: 2

```
gaagtgcagt tggtggagtc gggtggaggg ctggtgcagc ctggcggtag cctgaggctg      60
tcctgtgccg tgtccggata ctccattacc tccggctact cgtggaactg gatcagacag     120
gctcccggaa agggacttga gtgggtggcg tccatcacct acgacggctc aaccaactat     180
aacccgtccg tgaagggccg catcaccatt tcgcgcgacg acagcaagaa tacttttttac     240
ctccaaatga acagcctgcg ggccgaagat actgccgtgt actactgcgc gcggggatca     300
cattacttcg gcactggca cttcgccgtc tggggacagg gcaccctcgt cactgtctcg     360
agc                                                                   363
```

<210> SEQ ID NO 3
<211> LENGTH: 139
<212> TYPE: PRT
<213> ORGANISM: Artificial Sequence
<220> FEATURE:
<223> OTHER INFORMATION: V-region with signal sequence

<400> SEQUENCE: 3

Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Gln Pro
            20                  25                  30

Gly Gly Ser Leu Arg Leu Ser Cys Ala Val Ser Gly Tyr Ser Ile Thr
        35                  40                  45

Ser Gly Tyr Ser Trp Asn Trp Ile Arg Gln Ala Pro Gly Lys Gly Leu
    50                  55                  60

Glu Trp Val Ala Ser Ile Thr Tyr Asp Gly Ser Thr Asn Tyr Asn Pro
65                  70                  75                  80

Ser Val Lys Gly Arg Ile Thr Ile Ser Arg Asp Asp Ser Lys Asn Thr
                85                  90                  95

Phe Tyr Leu Gln Met Asn Ser Leu Arg Ala Glu Asp Thr Ala Val Tyr
            100                 105                 110

Tyr Cys Ala Arg Gly Ser His Tyr Phe Gly His Trp His Phe Ala Val
        115                 120                 125

Trp Gly Gln Gly Thr Leu Val Thr Val Ser Ser
    130                 135

<210> SEQ ID NO 4
<211> LENGTH: 417
<212> TYPE: DNA
<213> ORGANISM: Artificial Sequence
<220> FEATURE:
<223> OTHER INFORMATION: V-region with signal sequence

<400> SEQUENCE: 4

```
atgaagtggg tcaccttcat ctccctgctg tttctgttct ccagcgccta ctccgaagtg      60
cagttggtgg agtcgggtgg agggctggtg cagcctggcg gtagcctgag gctgtcctgt     120
gccgtgtccg gatactccat tacctccggc tactcgtgga actggatcag acaggctccc     180
```

```
ggaaagggac ttgagtgggt ggcgtccatc acctacgacg gctcaaccaa ctataacccg      240
tccgtgaagg gccgcatcac catttcgcgc gacgacagca agaatacttt ttacctccaa      300
atgaacagcc tgcgggccga agatactgcc gtgtactact gcgcgcgggg atcacattac      360
ttcgggcact ggcacttcgc cgtctgggga cagggcaccc tcgtcactgt ctcgagc         417
```

<210> SEQ ID NO 5
<211> LENGTH: 224
<212> TYPE: PRT
<213> ORGANISM: Artificial Sequence
<220> FEATURE:
<223> OTHER INFORMATION: v-region + gamma 1 CH1 constant region

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

<210> SEQ ID NO 6
<211> LENGTH: 672
<212> TYPE: DNA
<213> ORGANISM: Artificial Sequence
<220> FEATURE:
<223> OTHER INFORMATION: v-region + gamma 1 CH1 constant region

<400> SEQUENCE: 6

```
gaagtgcagt tggtggagtc gggtggaggg ctggtgcagc ctggcggtag cctgaggctg      60
tcctgtgccg tgtccggata ctccattacc tccggctact cgtggaactg gatcagacag      120
gctcccggaa agggacttga gtgggtggcg tccatcacct acgacggctc aaccaactat      180
aacccgtccg tgaagggccg catcaccatt tcgcgcgacg acagcaagaa tactttttac      240
ctccaaatga acagcctgcg ggccgaagat actgccgtgt actactgcgc gcggggatca      300
```

```
cattacttcg ggcactggca cttcgccgtc tggggacagg gcaccctcgt cactgtctcg    360
agcgcttcta caaagggccc atcggtcttc ccctggcac cctcctccaa gagcacctct    420 ggggcacag cggccctggg ctgcctggtc aaggactact ccccgaacc ggtgacggtg    480 tcgtggaact caggcgccct gaccagcggc gtgcacacct cccggctgt cctacagtcc    540 tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gt                                                        672
```

<210> SEQ ID NO 7
<211> LENGTH: 242
<212> TYPE: PRT
<213> ORGANISM: Artificial Sequence
<220> FEATURE:
<223> OTHER INFORMATION: v-region + gamma 1 CH1 constant region with signal sequence

<400> SEQUENCE: 7

Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Gln Pro
            20                  25                  30

Gly Gly Ser Leu Arg Leu Ser Cys Ala Val Ser Gly Tyr Ser Ile Thr
        35                  40                  45

Ser Gly Tyr Ser Trp Asn Trp Ile Arg Gln Ala Pro Gly Lys Gly Leu
    50                  55                  60

Glu Trp Val Ala Ser Ile Thr Tyr Asp Gly Ser Thr Asn Tyr Asn Pro
65                  70                  75                  80

Ser Val Lys Gly Arg Ile Thr Ile Ser Arg Asp Asp Ser Lys Asn Thr
                85                  90                  95

Phe Tyr Leu Gln Met Asn Ser Leu Arg Ala Glu Asp Thr Ala Val Tyr
            100                 105                 110

Tyr Cys Ala Arg Gly Ser His Tyr Phe Gly His Trp His Phe Ala Val
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys

<210> SEQ ID NO 8
<211> LENGTH: 726
<212> TYPE: DNA
<213> ORGANISM: Artificial Sequence
<220> FEATURE:

<223> OTHER INFORMATION: v-region + gamma 1 CH1 constant region with
      signal sequence

<400> SEQUENCE: 8

```
atgaagtggg tcaccttcat ctccctgctg tttctgttct ccagcgccta ctccgaagtg    60
cagttggtgg agtcgggtgg agggctggtg cagcctggcg gtagcctgag gctgtcctgt   120
gccgtgtccg gatactccat tacctccggc tactcgtgga actggatcag acaggctccc   180
ggaaagggac ttgagtgggt ggcgtccatc acctacgacg gctcaaccaa ctataacccg   240
tccgtgaagg gccgcatcac catttcgcgc gacgacagca agaatacttt ttacctccaa   300
atgaacagcc tgcgggccga agatactgcc gtgtactact cgcgcggggg atcacattac   360
ttcgggcact ggcacttcgc cgtctgggga cagggcaccc tcgtcactgt ctcgagcgct   420
tctacaaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
tcttgt                                                              726
```

<210> SEQ ID NO 9
<211> LENGTH: 451
<212> TYPE: PRT
<213> ORGANISM: Artificial Sequence
<220> FEATURE:
<223> OTHER INFORMATION: v-region + gamma 1 full length constant region

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 10
<211> LENGTH: 1353
<212> TYPE: DNA
<213> ORGANISM: Artificial Sequence
<220> FEATURE:
<223> OTHER INFORMATION: v-region + gamma 1 full length constant region

<400> SEQUENCE: 10
gaagtgcagt tggtggagtc gggtggaggg ctggtgcagc ctggcggtag cctgaggctg    60
tcctgtgccg tgtccggata tccattacc tccggctact cgtggaactg gatcagacag   120
gctcccggaa agggacttga gtgggtggcg tccatcacct acgacggctc aaccaactat   180
aacccgtccg tgaagggccg catcaccatt tcgcgcgacg acagcaagaa tactttttac   240
ctccaaatga acagcctgcg ggccgaagat actgccgtgt actactgcgc gcggggatca   300
cattacttcg gcactggca cttcgccgtc tggggacagg gcaccctcgt cactgtctcg   360
agcgcttcta caaagggccc ctccgtgttc ccgctcgctc catcatcgaa gtctaccagc   420
ggaggcactg cggctctcgg ttgcctcgtg aaggactact cccggagcc ggtgaccgtg   480 tcgtggaaca gcggagccct gaccagcggg gtgcacacct tccggccgt cttgcagtca   540 agcggccttt actccctgtc atcagtggtg actgtcccgt ccagctcatt gggaacccaa   600

```
acctacatct gcaatgtgaa tcacaaacct agcaacacca aggttgacaa gaaagtcgag    660
cccaaatcgt gtgacaagac tcacacttgt ccgccgtgcc cggcacccga actgctggga    720
ggtcccagcg tctttctgtt ccctccaaag ccgaaagaca cgctgatgat ctcccgcacc    780
ccggaggtca cttgcgtggt cgtggacgtg tcacatgagg acccagaggt gaagttcaat    840
tggtacgtgg atggcgtcga agtccacaat gccaaaacta gcccagaga  agaacagtac    900 aattcgacct accgcgtcgt gtccgtgctc acggtgttgc atcaggattg gctgaacggg    960
aaggaataca agtgcaaagt gtccaacaag gcgctgccgg caccgatcga gaaaactatc   1020
tccaaagcga agggacagcc tagggaacct caagtctaca cgctgccacc atcacgggaa   1080
gaaatgacta agaatcaagt ctcactgact tgtctggtga aggggtttta ccctagcgac   1140
attgccgtgg agtgggaatc aacggccag  ccagagaaca actacaagac tacccctcca   1200
gtgctcgact cggatggatc gttcttcctt tactcgaagc tcaccgtgga taagtcccgg   1260
tggcagcagg gaaacgtgtt ctcctgctcg gtgatgcatg aagccctcca taaccactat   1320
acccaaaagt cgctgtccct gtcgccggga aag                                1353
```

<210> SEQ ID NO 11
<211> LENGTH: 469
<212> TYPE: PRT
<213> ORGANISM: Artificial Sequence
<220> FEATURE:
<223> OTHER INFORMATION: v-region + gamma 1 full length constant region
      with signal sequence

<400> SEQUENCE: 11

```
Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Gln Pro
            20                  25                  30

Gly Gly Ser Leu Arg Leu Ser Cys Ala Val Ser Gly Tyr Ser Ile Thr
        35                  40                  45

Ser Gly Tyr Ser Trp Asn Trp Ile Arg Gln Ala Pro Gly Lys Gly Leu
    50                  55                  60

Glu Trp Val Ala Ser Ile Thr Tyr Asp Gly Ser Thr Asn Tyr Asn Pro
65                  70                  75                  80

Ser Val Lys Gly Arg Ile Thr Ile Ser Arg Asp Asp Ser Lys Asn Thr
                85                  90                  95

Phe Tyr Leu Gln Met Asn Ser Leu Arg Ala Glu Asp Thr Ala Val Tyr
            100                 105                 110

Tyr Cys Ala Arg Gly Ser His Tyr Phe Gly His Trp His Phe Ala Val
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220
```

```
Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 12
<211> LENGTH: 1407
<212> TYPE: DNA
<213> ORGANISM: Artificial Sequence
<220> FEATURE:
<223> OTHER INFORMATION: v-region + gamma 1 full length constant region
      with signal sequence

<400> SEQUENCE: 12
atgaagtggg tcaccttcat ctccctgctg tttctgttct ccagcgccta ctccgaagtg    60
cagttggtgg agtcgggtgg agggctggtg cagcctggcg gtagcctgag gctgtcctgt   120
gccgtgtccg gatactccat tacctccggc tactcgtgga actggatcag acaggctccc   180
ggaaagggac ttgagtgggt ggcgtccatc acctacgacg gctcaaccaa ctataacccg   240
tccgtgaagg gccgcatcac catttcgcgc gacgacagca gaatactttt tacctccaa    300 atgaacagcc tgcgggccga agatactgcc gtgtactact gcgcgcgggg atcacattac   360
ttcgggcact ggcacttcgc cgtctgggga cagggcaccc tcgtcactgt ctcgagcgct   420
tctacaaagg gccctccgt gttcccgctc gctccatcat cgaagtctac cagcggaggc    480
actgcggctc tcggttgcct cgtgaaggac tacttcccgg agccggtgac cgtgtcgtgg   540
aacagcggag ccctgaccag cggggtgcac acctttccgg ccgtcttgca gtcaagcggc   600
```

```
ctttactccc tgtcatcagt ggtgactgtc ccgtccagct cattgggaac ccaaacctac    660
atctgcaatg tgaatcacaa acctagcaac accaaggttg acaagaaagt cgagcccaaa    720
tcgtgtgaca agactcacac ttgtccgccg tgcccggcac ccgaactgct gggaggtccc    780
agcgtctttc tgttccctcc aaagccgaaa gacacgctga tgatctcccg cacccccggag   840 gtcacttgcg tggtcgtgga cgtgtcacat gaggacccag aggtgaagtt caattggtac    900
gtggatggcg tcgaagtcca caatgccaaa actaagccca gagaagaaca gtacaattcg    960
acctaccgcg tcgtgtccgt gctcacggtg ttgcatcagg attggctgaa cgggaaggaa   1020
tacaagtgca aagtgtccaa caaggcgctg ccggcaccga tcgagaaaac tatctccaaa   1080
gcgaagggac agcctaggga acctcaagtc tacacgctgc caccatcacg ggaagaaatg   1140
actaagaatc aagtctcact gacttgtctg gtgaagggt tttaccctag cgacattgcc    1200
gtggagtggg aatccaacgg ccagccagag aacaactaca agactacccc tccagtgctc   1260
gactcggatg gatcgttctt cctttactcg aagctcaccg tggataagtc ccggtggcag   1320
cagggaaacg tgttctcctg ctcggtgatg catgaagccc tccataacca ctatacccaa   1380
aagtcgctgt ccctgtcgcc gggaaag                                       1407
```

<210> SEQ ID NO 13
<211> LENGTH: 25
<212> TYPE: PRT
<213> ORGANISM: Artificial Sequence
<220> FEATURE:
<223> OTHER INFORMATION: FR H1

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 14
<211> LENGTH: 11
<212> TYPE: PRT
<213> ORGANISM: Artificial Sequence
<220> FEATURE:
<223> OTHER INFORMATION: CDRH1

<400> SEQUENCE: 14

Gly Tyr Ser Ile Thr Ser Gly Tyr Ser Trp Asn
1               5                   10

<210> SEQ ID NO 15
<211> LENGTH: 14
<212> TYPE: PRT
<213> ORGANISM: Artificial Sequence
<220> FEATURE:
<223> OTHER INFORMATION: FR H2

<400> SEQUENCE: 15

Trp Ile Arg Gln Ala Pro Gly Lys Gly Leu Glu Trp Val Ala
1               5                   10

<210> SEQ ID NO 16
<211> LENGTH: 16
<212> TYPE: PRT
<213> ORGANISM: Artificial Sequence
<220> FEATURE:
<223> OTHER INFORMATION: CDRH2

<400> SEQUENCE: 16

```
Ser Ile Thr Tyr Asp Gly Ser Thr Asn Tyr Asn Pro Ser Val Lys Gly
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: FR H3

<400> SEQUENCE: 17

Arg Ile Thr Ile Ser Arg Asp Asp Ser Lys Asn Thr Phe Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 18
<211> LENGTH: 12
<212> TYPE: PRT
<213> ORGANISM: Artificial Sequence
<220> FEATURE:
<223> OTHER INFORMATION: CDRH3

<400> SEQUENCE: 18

Gly Ser His Tyr Phe Gly His Trp His Phe Ala Val
1               5                   10

<210> SEQ ID NO 19
<211> LENGTH: 11
<212> TYPE: PRT
<213> ORGANISM: Artificial Sequence
<220> FEATURE:
<223> OTHER INFORMATION: FR H4

<400> SEQUENCE: 19

Trp Gly Gln Gly Thr Leu Val Thr Val Ser Ser
1               5                   10

<210> SEQ ID NO 20
<211> LENGTH: 111
<212> TYPE: PRT
<213> ORGANISM: Artificial Sequence
<220> FEATURE:
<223> OTHER INFORMATION: V-region light

<400> SEQUENCE: 20

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys
            100                 105                 110

<210> SEQ ID NO 21
```

<211> LENGTH: 333
<212> TYPE: DNA
<213> ORGANISM: Artificial Sequence
<220> FEATURE:
<223> OTHER INFORMATION: V-region light

<400> SEQUENCE: 21

```
gatattcagc tgactcagag cccgagctca ctctccgctt ccgtggggga tagagtgacc      60
atcacttgcc gggcatccca gtcggtggac tacgacggag actcctacat gaactggtat     120
cagcagaagc ccggaaaagc cccaaagttg ctgatctacg ccgcctcata ccttgaaagc     180
ggcgtgcctt cgcgcttctc gggaagcggg tcgggcaccg atttcaccct gaccatttcg     240
tcgctgcagc cggaggactt cgcgacttac tactgccaac agtcccacga ggaccccrat     300
acgtttggcc aggaaccaa ggtcgaaatc aag                                   333
```

<210> SEQ ID NO 22
<211> LENGTH: 129
<212> TYPE: PRT
<213> ORGANISM: Artificial Sequence
<220> FEATURE:
<223> OTHER INFORMATION: V-region light with signal sequence

<400> SEQUENCE: 22

```
Met Lys Trp Val Thr Phe Ile Ser Leu Leu Phe Leu Phe Ser Ser Ala
1               5                   10                  15

Tyr Ser Asp Ile Gln Leu Thr Gln Ser Pro Ser Ser Leu Ser Ala Ser
            20                  25                  30

Val Gly Asp Arg Val Thr Ile Thr Cys Arg Ala Ser Gln Ser Val Asp
        35                  40                  45

Tyr Asp Gly Asp Ser Tyr Met Asn Trp Tyr Gln Gln Lys Pro Gly Lys
    50                  55                  60

Ala Pro Lys Leu Leu Ile Tyr Ala Ala Ser Tyr Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
        115                 120                 125

Lys
```

<210> SEQ ID NO 23
<211> LENGTH: 387
<212> TYPE: DNA
<213> ORGANISM: Artificial Sequence
<220> FEATURE:
<223> OTHER INFORMATION: V-region light with signal sequence

<400> SEQUENCE: 23

```
atgaagtggg tcaccttcat ctccctgctg tttctgttct cctccgccta ctccgatatt      60
cagctgactc agagcccgag ctcactctcc gcttccgtgg gggatagagt gaccatcact     120
tgccgggcat cccagtcggt ggactacgac ggagactcct acatgaactg gtatcagcag     180
aagcccggaa aagcccaaa gttgctgatc tacgccgcct cataccttga aagcggcgtg     240
ccttcgcgct ctcgggaag cgggtcgggc accgatttca ccctgaccat ttcgtcgctg     300
cagccggagg acttcgcgac ttactactgc caacagtccc acgaggaccc ctatacgttt     360
ggccagggaa ccaaggtcga aatcaag                                         387
```

<210> SEQ ID NO 24
<211> LENGTH: 218
<212> TYPE: PRT
<213> ORGANISM: Artificial Sequence
<220> FEATURE:
<223> OTHER INFORMATION: V-region light + kappa constant region

<400> SEQUENCE: 24

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 25
<211> LENGTH: 654
<212> TYPE: DNA
<213> ORGANISM: Artificial Sequence
<220> FEATURE:
<223> OTHER INFORMATION: V-region + kappa constant region

<400> SEQUENCE: 25
gatattcagc tgactcagag cccgagctca ctctccgctt ccgtggggga tagagtgacc     60
atcacttgcc gggcatccca gtcggtggac tacgacggag actcctacat gaactggtat    120
cagcagaagc ccggaaaagc cccaaagttg ctgatctacg ccgcctcata ccttgaaagc    180
ggcgtgcctt cgcgcttctc gggaagcggg tcgggcaccg atttcaccct gaccatttcg    240
tcgctgcagc cggaggactt cgcgacttac tactgccaac agtcccacga ggaccccfat    300 acgtttggcc agggaaccaa ggtcgaaatc aagcgtacgg tagcggcccc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480

```
ggtaactccc aggagagtgt cacagagcag gacagcaagg acagcaccta cagcctcagc      540
agcaccctga cgctgagcaa agcagactac gagaaacaca agtctacgc ctgcgaagtc       600 acccatcagg gcctgagctc gcccgtcaca aagagcttca caggggaga gtgt             654
```

<210> SEQ ID NO 26
<211> LENGTH: 236
<212> TYPE: PRT
<213> ORGANISM: Artificial Sequence
<220> FEATURE:
<223> OTHER INFORMATION: V-region + kappa constant region with signal
      sequence

<400> SEQUENCE: 26

```
Met Lys Trp Val Thr Phe Ile Ser Leu Leu Phe Leu Phe Ser Ser Ala
1               5                   10                  15

Tyr Ser Asp Ile Gln Leu Thr Gln Ser Pro Ser Ser Leu Ser Ala Ser
            20                  25                  30

Val Gly Asp Arg Val Thr Ile Thr Cys Arg Ala Ser Gln Ser Val Asp
        35                  40                  45

Tyr Asp Gly Asp Ser Tyr Met Asn Trp Tyr Gln Gln Lys Pro Gly Lys
    50                  55                  60

Ala Pro Lys Leu Leu Ile Tyr Ala Ala Ser Tyr Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 27
<211> LENGTH: 708
<212> TYPE: DNA
<213> ORGANISM: Artificial Sequence
<220> FEATURE:
<223> OTHER INFORMATION: V-region + kappa constant region with signal
      sequence

<400> SEQUENCE: 27

```
atgaagtggg tcaccttcat ctccctgctg tttctgttct cctccgccta ctccgatatt      60
cagctgactc agagcccgag ctcactctcc gcttccgtgg gggatagagt gaccatcact     120
tgccgggcat cccagtcggt ggactacgac ggagactcct acatgaactg gtatcagcag     180
```

```
aagcccggaa aagccccaaa gttgctgatc tacgccgcct cataccttga aagcggcgtg    240
ccttcgcgct tctcgggaag cgggtcgggc accgatttca ccctgaccat ttcgtcgctg    300
cagccggagg acttcgcgac ttactactgc aacagtccc acgaggaccc ctatacgttt     360
ggccagggaa ccaaggtcga aatcaagcgt acggtagcgg ccccatctgt cttcatcttc    420
ccgccatctg atgagcagtt gaaatctgga actgcctctg ttgtgtgcct gctgaataac    480
ttctatccca gagaggccaa agtacagtgg aaggtggata cgccctcca atcgggtaac     540 tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt               708
```

<210> SEQ ID NO 28
<211> LENGTH: 23
<212> TYPE: PRT
<213> ORGANISM: Artificial Sequence
<220> FEATURE:
<223> OTHER INFORMATION: FR L1

<400> SEQUENCE: 28

Asp Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 29
<211> LENGTH: 15
<212> TYPE: PRT
<213> ORGANISM: Artificial Sequence
<220> FEATURE:
<223> OTHER INFORMATION: CDRL1

<400> SEQUENCE: 29

Arg Ala Ser Gln Ser Val Asp Tyr Asp Gly Asp Ser Tyr Met Asn
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: FR L2

<400> SEQUENCE: 30

Trp Tyr Gln Gln Lys Pro Gly Lys Ala Pro Lys Leu Leu Ile Tyr
1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: CDRL2

<400> SEQUENCE: 31

Ala Ala Ser Tyr Leu Glu Ser
1               5

<210> SEQ ID NO 32
<211> LENGTH: 32
<212> TYPE: PRT
<213> ORGANISM: Artificial Sequence
<220> FEATURE:

<223> OTHER INFORMATION: FR L3

<400> SEQUENCE: 32

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 33
<211> LENGTH: 9
<212> TYPE: PRT
<213> ORGANISM: Artificial Sequence
<220> FEATURE:
<223> OTHER INFORMATION: CDRL3

<400> SEQUENCE: 33

Gln Gln Ser His Glu Asp Pro Tyr Thr
1               5

<210> SEQ ID NO 34
<211> LENGTH: 10
<212> TYPE: PRT
<213> ORGANISM: Artificial Sequence
<220> FEATURE:
<223> OTHER INFORMATION: FR L4

<400> SEQUENCE: 34

Phe Gly Gln Gly Thr Lys Val Glu Ile Lys
1               5                   10

<210> SEQ ID NO 35
<211> LENGTH: 111
<212> TYPE: PRT
<213> ORGANISM: Artificial Sequence
<220> FEATURE:
<223> OTHER INFORMATION: S60M_S77R_Q79R_v-region

<400> SEQUENCE: 35

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Met
    50                  55                  60

Arg Phe Ser Gly Ser Gly Ser Gly Thr Asp Phe Thr Leu Thr Ile Ser
65                  70                  75                  80

Arg Leu Arg Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys
            100                 105                 110

<210> SEQ ID NO 36
<211> LENGTH: 333
<212> TYPE: DNA
<213> ORGANISM: Artificial Sequence
<220> FEATURE:
<223> OTHER INFORMATION: S60M_S77R_Q79R_v-region

<400> SEQUENCE: 36
gatattcagc tgactcagag cccgagctca ctctccgctt ccgtggggga tagagtgacc    60

```
atcacttgcc gggcatccca gtcggtggac tacgacggag actcctacat gaactggtat    120
cagcagaagc ccggaaaagc ccaaagttg ctgatctacg ccgcctcata ccttgaaagc     180
ggcgtgccta tgcgcttctc gggaagcggg tcgggcaccg atttcaccct gaccatttcg    240
agactgaggc cggaggactt cgcgacttac tactgccaac agtcccacga ggaccccta    300 acgtttggcc agggaaccaa ggtcgaaatc aag                                 333
```

<210> SEQ ID NO 37
<211> LENGTH: 129
<212> TYPE: PRT
<213> ORGANISM: Artificial Sequence
<220> FEATURE:
<223> OTHER INFORMATION: S60M_S77R_Q79R_v-region with signal sequence

<400> SEQUENCE: 37

```
Met Lys Trp Val Thr Phe Ile Ser Leu Leu Phe Leu Phe Ser Ser Ala
1               5                   10                  15

Tyr Ser Asp Ile Gln Leu Thr Gln Ser Pro Ser Ser Leu Ser Ala Ser
            20                  25                  30

Val Gly Asp Arg Val Thr Ile Thr Cys Arg Ala Ser Gln Ser Val Asp
        35                  40                  45

Tyr Asp Gly Asp Ser Tyr Met Asn Trp Tyr Gln Gln Lys Pro Gly Lys
    50                  55                  60

Ala Pro Lys Leu Leu Ile Tyr Ala Ala Ser Tyr Leu Glu Ser Gly Val
65                  70                  75                  80

Pro Met Arg Phe Ser Gly Ser Gly Ser Gly Thr Asp Phe Thr Leu Thr
                85                  90                  95

Ile Ser Arg Leu Arg Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
        115                 120                 125

Lys
```

<210> SEQ ID NO 38
<211> LENGTH: 387
<212> TYPE: DNA
<213> ORGANISM: Artificial Sequence
<220> FEATURE:
<223> OTHER INFORMATION: S60M_S77R_Q79R_v-region with signal sequence

<400> SEQUENCE: 38

```
atgaagtggg tcaccttcat ctccctgctg tttctgttct cctccgccta ctccgatatt    60
cagctgactc agagcccgag ctcactctcc gcttccgtgg gggatagagt gaccatcact    120
tgccgggcat cccagtcggt ggactacgac ggagactcct acatgaactg gtatcagcag    180
aagcccggaa aagcccccaaa gttgctgatc tacgccgcct cataccttga aagcggcgtg    240
cctatgcgct ctcgggaag cgggtcgggc accgatttca ccctgaccat ttcgagactg    300
aggccggagg acttcgcgac ttactactgc aacagtccc acgaggaccc ctatacgttt    360 ggccaggaa ccaaggtcga aatcaag                                         387
```

<210> SEQ ID NO 39
<211> LENGTH: 218
<212> TYPE: PRT
<213> ORGANISM: Artificial Sequence
<220> FEATURE:
<223> OTHER INFORMATION: S60M_S77R_Q79R_v-region + kappa constant region
       including L154P

<400> SEQUENCE: 39

```
Asp Ile Gln Leu Thr Gln Ser Pro Ser Leu Ser Ala Ser Val Gly
1               5                   10                  15
Asp Arg Val Thr Ile Thr Cys Arg Ala Ser Gln Ser Val Asp Tyr Asp
            20                  25                  30
Gly Asp Ser Tyr Met Asn Trp Tyr Gln Gln Lys Pro Gly Lys Ala Pro
        35                  40                  45
Lys Leu Leu Ile Tyr Ala Ala Ser Tyr Leu Glu Ser Gly Val Pro Met
    50                  55                  60
Arg Phe Ser Gly Ser Gly Ser Gly Thr Asp Phe Thr Leu Thr Ile Ser
65                  70                  75                  80
Arg Leu Arg Pro Glu Asp Phe Ala Thr Tyr Tyr Cys Gln Gln Ser His
                85                  90                  95
Glu Asp Pro Tyr Thr Phe Gly Gln Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Pro Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 40
<211> LENGTH: 654
<212> TYPE: DNA
<213> ORGANISM: Artificial Sequence
<220> FEATURE:
<223> OTHER INFORMATION: S60M_S77R_Q79R_v-region + kappa constant region
including L154P

<400> SEQUENCE: 40

```
gatattcagc tgactcagag cccgagctca ctctccgctt ccgtggggga tagagtgacc      60
atcacttgcc gggcatccca gtcggtggac tacgacggag actcctacat gaactggtat     120
cagcagaagc ccggaaaagc cccaaagttg ctgatctacg ccgcctcata ccttgaaagc     180
ggcgtgccta tgcgcttctc gggaagcggg tcgggcaccg atttcaccct gaccatttcg     240
agactgaggc cggaggactt cgcgacttac tactgccaac agtcccacga ggacccctat     300
acgtttggcc agggaaccaa ggtcgaaatc aagcgtacgg tagcggcccc atctgtcttc     360
atcttcccgc catctgatga gcagttgaaa tctggaactg cctctgttgt gtgcctgctg     420
aataacttct atcccagaga ggccaaagta cagtggaagg tggataacgc cccgcaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600
acccatcagg gcctgagctc gcccgtcaca aagagcttca caggggaga gtgt            654
```

<210> SEQ ID NO 41

<211> LENGTH: 236
<212> TYPE: PRT
<213> ORGANISM: Artificial Sequence
<220> FEATURE:
<223> OTHER INFORMATION: S60M_S77R_Q79R_v-region + kappa constant region including L154P with signal sequence

<400> SEQUENCE: 41

Met Lys Trp Val Thr Phe Ile Ser Leu Leu Phe Leu Phe Ser Ser Ala
1               5                   10                  15

Tyr Ser Asp Ile Gln Leu Thr Gln Ser Pro Ser Ser Leu Ser Ala Ser
            20                  25                  30

Val Gly Asp Arg Val Thr Ile Thr Cys Arg Ala Ser Gln Ser Val Asp
        35                  40                  45

Tyr Asp Gly Asp Ser Tyr Met Asn Trp Tyr Gln Gln Lys Pro Gly Lys
    50                  55                  60

Ala Pro Lys Leu Leu Ile Tyr Ala Ala Ser Tyr Leu Glu Ser Gly Val
65                  70                  75                  80

Pro Met Arg Phe Ser Gly Ser Gly Ser Gly Thr Asp Phe Thr Leu Thr
                85                  90                  95

Ile Ser Arg Leu Arg Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Pro
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 42
<211> LENGTH: 708
<212> TYPE: DNA
<213> ORGANISM: Artificial Sequence
<220> FEATURE:
<223> OTHER INFORMATION: S60M_S77R_Q79R_v-region + kappa constant region including L154P with signal sequence

<400> SEQUENCE: 42
atgaagtggg tcaccttcat ctccctgctg tttctgttct cctccgccta ctccgatatt    60
cagctgactc agagcccgag ctcactctcc gcttccgtgg gggatagagt gaccatcact   120
tgccgggcat cccagtcggt ggactacgac ggagactcct acatgaactg gtatcagcag   180
aagcccggaa agcccccaaa gttgctgatc tacgccgcct cataccttga agcggcgtg    240 cctatgcgct tctcgggaag cgggtcgggc accgatttca ccctgaccat ttcgagactg   300
aggccggagg acttcgcgac ttactactgc aacagtccc acgaggaccc ctatacgttt    360
ggccagggaa ccaaggtcga aatcaagcgt acggtagcgg ccccatctgt cttcatcttc   420

```
ccgccatctg atgagcagtt gaaatctgga actgcctctg ttgtgtgcct gctgaataac    480
ttctatccca gagaggccaa agtacagtgg aaggtggata cgccccgca atcgggtaac     540 tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt                 708
```

<210> SEQ ID NO 43
<211> LENGTH: 32
<212> TYPE: PRT
<213> ORGANISM: Artificial Sequence
<220> FEATURE:
<223> OTHER INFORMATION: FR L3 S64M S60M

<400> SEQUENCE: 43

Gly Val Pro Met Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: FR L3 S81R S77R

<400> SEQUENCE: 44

Gly Val Pro Ser Arg Phe Ser Gly Ser Gly Ser Gly Thr Asp Phe Thr
1               5                   10                  15

Leu Thr Ile Ser Arg Leu Gln Pro Glu Asp Phe Ala Thr Tyr Tyr Cys
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: FR L3 Q83R Q79R

<400> SEQUENCE: 45

Gly Val Pro Ser Arg Phe Ser Gly Ser Gly Ser Gly Thr Asp Phe Thr
1               5                   10                  15

Leu Thr Ile Ser Ser Leu Arg Pro Glu Asp Phe Ala Thr Tyr Tyr Cys
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: FR L3 S64M S81R S60M S77R

<400> SEQUENCE: 46

Gly Val Pro Met Arg Phe Ser Gly Ser Gly Ser Gly Thr Asp Phe Thr
1               5                   10                  15

Leu Thr Ile Ser Arg Leu Gln Pro Glu Asp Phe Ala Thr Tyr Tyr Cys
            20                  25                  30

<210> SEQ ID NO 47
<211> LENGTH: 32
<212> TYPE: PRT
<213> ORGANISM: Artificial Sequence

```
<220> FEATURE:
<223> OTHER INFORMATION: FR L3 S64M Q83R S60M Q79R

<400> SEQUENCE: 47

Gly Val Pro Met Arg Phe Ser Gly Ser Gly Ser Gly Thr Asp Phe Thr
1               5                   10                  15

Leu Thr Ile Ser Ser Leu Arg Pro Glu Asp Phe Ala Thr Tyr Tyr Cys
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: FR L3 S81R Q83R S77R Q79R

<400> SEQUENCE: 48

Gly Val Pro Ser Arg Phe Ser Gly Ser Gly Ser Gly Thr Asp Phe Thr
1               5                   10                  15

Leu Thr Ile Ser Arg Leu Arg Pro Glu Asp Phe Ala Thr Tyr Tyr Cys
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: FR L3 S64M S81R Q83R S60M S77R Q79R

<400> SEQUENCE: 49

Gly Val Pro Met Arg Phe Ser Gly Ser Gly Ser Gly Thr Asp Phe Thr
1               5                   10                  15

Leu Thr Ile Ser Arg Leu Arg Pro Glu Asp Phe Ala Thr Tyr Tyr Cys
            20                  25                  30

<210> SEQ ID NO 50
<211> LENGTH: 7
<212> TYPE: PRT
<213> ORGANISM: Artificial Sequence
<220> FEATURE:
<223> OTHER INFORMATION: CDRL2 S56D S52D

<400> SEQUENCE: 50

Ala Ala Asp Tyr Leu Glu Ser
1               5

<210> SEQ ID NO 51
<211> LENGTH: 7
<212> TYPE: PRT
<213> ORGANISM: Artificial Sequence
<220> FEATURE:
<223> OTHER INFORMATION: CDRL2 S56E S52E

<400> SEQUENCE: 51

Ala Ala Glu Tyr Leu Glu Ser
1               5

<210> SEQ ID NO 52
<211> LENGTH: 32
<212> TYPE: PRT
<213> ORGANISM: Artificial Sequence
<220> FEATURE:
<223> OTHER INFORMATION: FR L3 S71M S67M

<400> SEQUENCE: 52
```

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 53
<211> LENGTH: 32
<212> TYPE: PRT
<213> ORGANISM: Artificial Sequence
<220> FEATURE:
<223> OTHER INFORMATION: FR L3 S64M S71M S60M S67M

<400> SEQUENCE: 53

```
Gly Val Pro Met Arg Phe Ser Gly Ser Gly Met Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 54
<211> LENGTH: 32
<212> TYPE: PRT
<213> ORGANISM: Artificial Sequence
<220> FEATURE:
<223> OTHER INFORMATION: FR L3 S81R S71M S77R S67M

<400> SEQUENCE: 54

```
Gly Val Pro Ser Arg Phe Ser Gly Ser Gly Met Gly Thr Asp Phe Thr
1               5                   10                  15

Leu Thr Ile Ser Arg Leu Gln Pro Glu Asp Phe Ala Thr Tyr Tyr Cys
            20                  25                  30
```

<210> SEQ ID NO 55
<211> LENGTH: 32
<212> TYPE: PRT
<213> ORGANISM: Artificial Sequence
<220> FEATURE:
<223> OTHER INFORMATION: FR L3 Q83R S71M Q79R S67M

<400> SEQUENCE: 55

```
Gly Val Pro Ser Arg Phe Ser Gly Ser Gly Met Gly Thr Asp Phe Thr
1               5                   10                  15

Leu Thr Ile Ser Ser Leu Arg Pro Glu Asp Phe Ala Thr Tyr Tyr Cys
            20                  25                  30
```

<210> SEQ ID NO 56
<211> LENGTH: 32
<212> TYPE: PRT
<213> ORGANISM: Artificial Sequence
<220> FEATURE:
<223> OTHER INFORMATION: FR L3 S64M S81R S71M S60M S77R S67M

<400> SEQUENCE: 56

```
Gly Val Pro Met Arg Phe Ser Gly Ser Gly Met Gly Thr Asp Phe Thr
1               5                   10                  15

Leu Thr Ile Ser Arg Leu Gln Pro Glu Asp Phe Ala Thr Tyr Tyr Cys
            20                  25                  30
```

<210> SEQ ID NO 57
<211> LENGTH: 32
<212> TYPE: PRT
<213> ORGANISM: Artificial Sequence
<220> FEATURE:
<223> OTHER INFORMATION: FR L3 S64M Q83R S71M S60M Q79R S67M

<400> SEQUENCE: 57

```
Gly Val Pro Met Arg Phe Ser Gly Ser Gly Met Gly Thr Asp Phe Thr
1               5                   10                  15

Leu Thr Ile Ser Ser Leu Arg Pro Glu Asp Phe Ala Thr Tyr Tyr Cys
                20                  25                  30
```

<210> SEQ ID NO 58
<211> LENGTH: 32
<212> TYPE: PRT
<213> ORGANISM: Artificial Sequence
<220> FEATURE:
<223> OTHER INFORMATION: FR L3 S81R Q83R S71M S77R Q79R S67M

<400> SEQUENCE: 58

```
Gly Val Pro Ser Arg Phe Ser Gly Ser Gly Met Gly Thr Asp Phe Thr
1               5                   10                  15

Leu Thr Ile Ser Arg Leu Arg Pro Glu Asp Phe Ala Thr Tyr Tyr Cys
                20                  25                  30
```

<210> SEQ ID NO 59
<211> LENGTH: 32
<212> TYPE: PRT
<213> ORGANISM: Artificial Sequence
<220> FEATURE:
<223> OTHER INFORMATION: FR L3 S64M S81R Q83R S71M S60M S77R Q79R S67M

<400> SEQUENCE: 59

```
Gly Val Pro Met Arg Phe Ser Gly Ser Gly Met Gly Thr Asp Phe Thr
1               5                   10                  15

Leu Thr Ile Ser Arg Leu Arg Pro Glu Asp Phe Ala Thr Tyr Tyr Cys
                20                  25                  30
```

<210> SEQ ID NO 60
<211> LENGTH: 32
<212> TYPE: PRT
<213> ORGANISM: Artificial Sequence
<220> FEATURE:
<223> OTHER INFORMATION: FR L3 S67Y S63Y

<400> SEQUENCE: 60

```
Gly Val Pro Ser Arg Phe Tyr Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30
```

<210> SEQ ID NO 61
<211> LENGTH: 32
<212> TYPE: PRT
<213> ORGANISM: Artificial Sequence
<220> FEATURE:
<223> OTHER INFORMATION: FR L3 S64M S67Y S60M S63Y

<400> SEQUENCE: 61

```
Gly Val Pro Met Arg Phe Tyr Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30
```

<210> SEQ ID NO 62
<211> LENGTH: 32
<212> TYPE: PRT
<213> ORGANISM: Artificial Sequence
<220> FEATURE:
<223> OTHER INFORMATION: FR L3 S81R S67Y S77R S63Y

```
<400> SEQUENCE: 62

Gly Val Pro Ser Arg Phe Tyr Gly Ser Gly Ser Gly Thr Asp Phe Thr
1               5                   10                  15

Leu Thr Ile Ser Arg Leu Gln Pro Glu Asp Phe Ala Thr Tyr Tyr Cys
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: FR L3 Q83R S67Y S79R S63Y

<400> SEQUENCE: 63

Gly Val Pro Ser Arg Phe Tyr Gly Ser Gly Ser Gly Thr Asp Phe Thr
1               5                   10                  15

Leu Thr Ile Ser Ser Leu Arg Pro Glu Asp Phe Ala Thr Tyr Tyr Cys
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: FR L3 S64M S81R S67Y S60M S77R S63Y

<400> SEQUENCE: 64

Gly Val Pro Met Arg Phe Tyr Gly Ser Gly Ser Gly Thr Asp Phe Thr
1               5                   10                  15

Leu Thr Ile Ser Arg Leu Gln Pro Glu Asp Phe Ala Thr Tyr Tyr Cys
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: FR L3 S64M Q83R S67Y S60M Q79R S63Y

<400> SEQUENCE: 65

Gly Val Pro Met Arg Phe Tyr Gly Ser Gly Ser Gly Thr Asp Phe Thr
1               5                   10                  15

Leu Thr Ile Ser Ser Leu Arg Pro Glu Asp Phe Ala Thr Tyr Tyr Cys
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: FR L3 S81R Q83R S67Y S77R Q79R S63Y

<400> SEQUENCE: 66

Gly Val Pro Ser Arg Phe Tyr Gly Ser Gly Ser Gly Thr Asp Phe Thr
1               5                   10                  15

Leu Thr Ile Ser Arg Leu Arg Pro Glu Asp Phe Ala Thr Tyr Tyr Cys
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: FR L3 S64M S81R Q83R S67Y S60M S77R Q79R S63Y
```

<400> SEQUENCE: 67

Gly Val Pro Met Arg Phe Tyr Gly Ser Gly Ser Gly Thr Asp Phe Thr
1               5                   10                  15

Leu Thr Ile Ser Arg Leu Arg Pro Glu Asp Phe Ala Thr Tyr Tyr Cys
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: FR L3 S80N S76N

<400> SEQUENCE: 68

Gly Val Pro Ser Arg Phe Ser Gly Ser Gly Ser Gly Thr Asp Phe Thr
1               5                   10                  15

Leu Thr Ile Asn Ser Leu Gln Pro Glu Asp Phe Ala Thr Tyr Tyr Cys
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: FR L3 S64M S80N S60M S76N

<400> SEQUENCE: 69

Gly Val Pro Met Arg Phe Ser Gly Ser Gly Ser Gly Thr Asp Phe Thr
1               5                   10                  15

Leu Thr Ile Asn Ser Leu Gln Pro Glu Asp Phe Ala Thr Tyr Tyr Cys
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: FR L3 S81R S80N S77R S76

<400> SEQUENCE: 70

Gly Val Pro Ser Arg Phe Ser Gly Ser Gly Ser Gly Thr Asp Phe Thr
1               5                   10                  15

Leu Thr Ile Asn Arg Leu Gln Pro Glu Asp Phe Ala Thr Tyr Tyr Cys
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: FR L3 Q83R S80N Q79R S76N

<400> SEQUENCE: 71

Gly Val Pro Ser Arg Phe Ser Gly Ser Gly Ser Gly Thr Asp Phe Thr
1               5                   10                  15

Leu Thr Ile Asn Ser Leu Arg Pro Glu Asp Phe Ala Thr Tyr Tyr Cys
            20                  25                  30

<210> SEQ ID NO 72
<211> LENGTH: 32
<212> TYPE: PRT
<213> ORGANISM: Artificial Sequence
<220> FEATURE:

<223> OTHER INFORMATION: FR L3 S64M S81R S80N S60M S77R S76N

<400> SEQUENCE: 72

Gly Val Pro Met Arg Phe Ser Gly Ser Gly Ser Gly Thr Asp Phe Thr
1               5                   10                  15

Leu Thr Ile Asn Arg Leu Gln Pro Glu Asp Phe Ala Thr Tyr Tyr Cys
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: FR L3 S64M Q83R S80N S60M Q79R S76N

<400> SEQUENCE: 73

Gly Val Pro Met Arg Phe Ser Gly Ser Gly Ser Gly Thr Asp Phe Thr
1               5                   10                  15

Leu Thr Ile Asn Ser Leu Arg Pro Glu Asp Phe Ala Thr Tyr Tyr Cys
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: FR L3 S81R Q83R S80N S77R Q79R S76N

<400> SEQUENCE: 74

Gly Val Pro Ser Arg Phe Ser Gly Ser Gly Ser Gly Thr Asp Phe Thr
1               5                   10                  15

Leu Thr Ile Asn Arg Leu Arg Pro Glu Asp Phe Ala Thr Tyr Tyr Cys
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: FR L3 S64M S81R Q83R S80N S60M S77R Q79R S76N

<400> SEQUENCE: 75

Gly Val Pro Met Arg Phe Ser Gly Ser Gly Ser Gly Thr Asp Phe Thr
1               5                   10                  15

Leu Thr Ile Asn Arg Leu Arg Pro Glu Asp Phe Ala Thr Tyr Tyr Cys
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: FR L3 S80N S67Y S76N S63Y

<400> SEQUENCE: 76

Gly Val Pro Ser Arg Phe Tyr Gly Ser Gly Ser Gly Thr Asp Phe Thr
1               5                   10                  15

Leu Thr Ile Asn Ser Leu Gln Pro Glu Asp Phe Ala Thr Tyr Tyr Cys
            20                  25                  30

<210> SEQ ID NO 77
<211> LENGTH: 32
<212> TYPE: PRT
<213> ORGANISM: Artificial Sequence

```
<220> FEATURE:
<223> OTHER INFORMATION: FR L3 S64M S80N S67Y S60M S76N S63Y

<400> SEQUENCE: 77

Gly Val Pro Met Arg Phe Tyr Gly Ser Gly Ser Gly Thr Asp Phe Thr
1               5                   10                  15

Leu Thr Ile Asn Ser Leu Gln Pro Glu Asp Phe Ala Thr Tyr Tyr Cys
            20                  25                  30

<210> SEQ ID NO 78
<211> LENGTH: 32
<212> TYPE: PRT
<213> ORGANISM: Artificial Sequence
<220> FEATURE:
<223> OTHER INFORMATION: FR L3 S81R S80N S67Y S77R S76N S63Y

<400> SEQUENCE: 78

Gly Val Pro Ser Arg Phe Tyr Gly Ser Gly Ser Gly Thr Asp Phe Thr
1               5                   10                  15

Leu Thr Ile Asn Arg Leu Gln Pro Glu Asp Phe Ala Thr Tyr Tyr Cys
            20                  25                  30

<210> SEQ ID NO 79
<211> LENGTH: 32
<212> TYPE: PRT
<213> ORGANISM: Artificial Sequence
<220> FEATURE:
<223> OTHER INFORMATION: FR L3 Q83R S80N S67Y Q79R S76N S63Y

<400> SEQUENCE: 79

Gly Val Pro Ser Arg Phe Tyr Gly Ser Gly Ser Gly Thr Asp Phe Thr
1               5                   10                  15

Leu Thr Ile Asn Ser Leu Arg Pro Glu Asp Phe Ala Thr Tyr Tyr Cys
            20                  25                  30

<210> SEQ ID NO 80
<211> LENGTH: 32
<212> TYPE: PRT
<213> ORGANISM: Artificial Sequence
<220> FEATURE:
<223> OTHER INFORMATION: FR L3 S64M S81R S80N S67Y S60M S77R S76N S63Y

<400> SEQUENCE: 80

Gly Val Pro Met Arg Phe Tyr Gly Ser Gly Ser Gly Thr Asp Phe Thr
1               5                   10                  15

Leu Thr Ile Asn Arg Leu Gln Pro Glu Asp Phe Ala Thr Tyr Tyr Cys
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: FR L3 S64M Q83R S80N S67Y S60M Q79R S76N S63Y

<400> SEQUENCE: 81

Gly Val Pro Met Arg Phe Tyr Gly Ser Gly Ser Gly Thr Asp Phe Thr
1               5                   10                  15

Leu Thr Ile Asn Ser Leu Arg Pro Glu Asp Phe Ala Thr Tyr Tyr Cys
            20                  25                  30

<210> SEQ ID NO 82
<211> LENGTH: 32
<212> TYPE: PRT
```

```
<213> ORGANISM: Artificial Sequence
<220> FEATURE:
<223> OTHER INFORMATION: FR L3 S81R Q83R S80N S67Y S77R Q79R S76N S63Y

<400> SEQUENCE: 82

Gly Val Pro Ser Arg Phe Tyr Gly Ser Gly Ser Gly Thr Asp Phe Thr
1               5                   10                  15

Leu Thr Ile Asn Arg Leu Arg Pro Glu Asp Phe Ala Thr Tyr Tyr Cys
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: FR L3 S64M S81R Q83R S80N S67Y S60M S77R Q79R
      S76N S63Y

<400> SEQUENCE: 83

Gly Val Pro Met Arg Phe Tyr Gly Ser Gly Ser Gly Thr Asp Phe Thr
1               5                   10                  15

Leu Thr Ile Asn Arg Leu Arg Pro Glu Asp Phe Ala Thr Tyr Tyr Cys
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: FR L3 S67Y S71M S63Y S67M

<400> SEQUENCE: 84

Gly Val Pro Ser Arg Phe Tyr Gly Ser Gly Met Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 85
<211> LENGTH: 32
<212> TYPE: PRT
<213> ORGANISM: Artificial Sequence
<220> FEATURE:
<223> OTHER INFORMATION: FR L3 S64M S67Y S71M S60M S63Y S67M

<400> SEQUENCE: 85

Gly Val Pro Met Arg Phe Tyr Gly Ser Gly Met Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: FR L3 S81R S67Y S71M S77R S63Y S67M

<400> SEQUENCE: 86

Gly Val Pro Ser Arg Phe Tyr Gly Ser Gly Met Gly Thr Asp Phe Thr
1               5                   10                  15

Leu Thr Ile Ser Arg Leu Gln Pro Glu Asp Phe Ala Thr Tyr Tyr Cys
            20                  25                  30

<210> SEQ ID NO 87
```

```
<211> LENGTH: 32
<212> TYPE: PRT
<213> ORGANISM: Artificial Sequence
<220> FEATURE:
<223> OTHER INFORMATION: FR L3 Q83R S67Y S71M Q79R S63Y S67M

<400> SEQUENCE: 87

Gly Val Pro Ser Arg Phe Tyr Gly Ser Gly Met Gly Thr Asp Phe Thr
1               5                   10                  15

Leu Thr Ile Ser Ser Leu Arg Pro Glu Asp Phe Ala Thr Tyr Tyr Cys
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: FR L3 S64M S81R S67Y S71M S60M S77R S63Y S67M

<400> SEQUENCE: 88

Gly Val Pro Met Arg Phe Tyr Gly Ser Gly Met Gly Thr Asp Phe Thr
1               5                   10                  15

Leu Thr Ile Ser Arg Leu Gln Pro Glu Asp Phe Ala Thr Tyr Tyr Cys
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: FR L3 S64M Q83R S67Y S71M S60M Q79R S63Y S67M

<400> SEQUENCE: 89

Gly Val Pro Met Arg Phe Tyr Gly Ser Gly Met Gly Thr Asp Phe Thr
1               5                   10                  15

Leu Thr Ile Ser Ser Leu Arg Pro Glu Asp Phe Ala Thr Tyr Tyr Cys
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: FR L3 S81R Q83R S67Y S71M S77R Q79R S63Y S67M

<400> SEQUENCE: 90

Gly Val Pro Ser Arg Phe Tyr Gly Ser Gly Met Gly Thr Asp Phe Thr
1               5                   10                  15

Leu Thr Ile Ser Arg Leu Arg Pro Glu Asp Phe Ala Thr Tyr Tyr Cys
            20                  25                  30

<210> SEQ ID NO 91
<211> LENGTH: 32
<212> TYPE: PRT
<213> ORGANISM: Artificial Sequence
<220> FEATURE:
<223> OTHER INFORMATION: FR L3 S64M S81R Q83R S67Y S71M S60M S77R Q79R
      S63Y S67M

<400> SEQUENCE: 91

Gly Val Pro Met Arg Phe Tyr Gly Ser Gly Met Gly Thr Asp Phe Thr
1               5                   10                  15

Leu Thr Ile Ser Arg Leu Arg Pro Glu Asp Phe Ala Thr Tyr Tyr Cys
            20                  25                  30
```

<210> SEQ ID NO 92
<211> LENGTH: 32
<212> TYPE: PRT
<213> ORGANISM: Artificial Sequence
<220> FEATURE:
<223> OTHER INFORMATION: FR L3 S80N S71M S76N S67M

<400> SEQUENCE: 92

Gly Val Pro Ser Arg Phe Ser Gly Ser Gly Met Gly Thr Asp Phe Thr
1               5                   10                  15

Leu Thr Ile Asn Ser Leu Gln Pro Glu Asp Phe Ala Thr Tyr Tyr Cys
            20                  25                  30

<210> SEQ ID NO 93
<211> LENGTH: 32
<212> TYPE: PRT
<213> ORGANISM: Artificial Sequence
<220> FEATURE:
<223> OTHER INFORMATION: FR L3 S64M S80N S71M S60M S76N S67M (

<400> SEQUENCE: 93

Gly Val Pro Met Arg Phe Ser Gly Ser Gly Met Gly Thr Asp Phe Thr
1               5                   10                  15

Leu Thr Ile Asn Ser Leu Gln Pro Glu Asp Phe Ala Thr Tyr Tyr Cys
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: FR L3 S81R S80N S71M S77R S76N S67M

<400> SEQUENCE: 94

Gly Val Pro Ser Arg Phe Ser Gly Ser Gly Met Gly Thr Asp Phe Thr
1               5                   10                  15

Leu Thr Ile Asn Arg Leu Gln Pro Glu Asp Phe Ala Thr Tyr Tyr Cys
            20                  25                  30

<210> SEQ ID NO 95
<211> LENGTH: 32
<212> TYPE: PRT
<213> ORGANISM: Artificial Sequence
<220> FEATURE:
<223> OTHER INFORMATION: FR L3 Q83R S80N S71M Q79R S76N S67M

<400> SEQUENCE: 95

Gly Val Pro Ser Arg Phe Ser Gly Ser Gly Met Gly Thr Asp Phe Thr
1               5                   10                  15

Leu Thr Ile Asn Ser Leu Arg Pro Glu Asp Phe Ala Thr Tyr Tyr Cys
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: FR L3 S64M S81R S80N S71M S60M S77R S76N S67M

<400> SEQUENCE: 96

Gly Val Pro Met Arg Phe Ser Gly Ser Gly Met Gly Thr Asp Phe Thr
1               5                   10                  15

Leu Thr Ile Asn Arg Leu Gln Pro Glu Asp Phe Ala Thr Tyr Tyr Cys
            20                  25                  30

<210> SEQ ID NO 97
<211> LENGTH: 32
<212> TYPE: PRT
<213> ORGANISM: Artificial Sequence
<220> FEATURE:
<223> OTHER INFORMATION: FR L3 S64M Q83R S80N S71M S60M Q79R S76N S67M

<400> SEQUENCE: 97

Gly Val Pro Met Arg Phe Ser Gly Ser Gly Met Gly Thr Asp Phe Thr
1               5                   10                  15

Leu Thr Ile Asn Ser Leu Arg Pro Glu Asp Phe Ala Thr Tyr Tyr Cys
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: FR L3 S81R Q83R S80N S71M S77R Q79R S76N S67M

<400> SEQUENCE: 98

Gly Val Pro Ser Arg Phe Ser Gly Ser Gly Met Gly Thr Asp Phe Thr
1               5                   10                  15

Leu Thr Ile Asn Arg Leu Arg Pro Glu Asp Phe Ala Thr Tyr Tyr Cys
            20                  25                  30

<210> SEQ ID NO 99
<211> LENGTH: 32
<212> TYPE: PRT
<213> ORGANISM: Artificial Sequence
<220> FEATURE:
<223> OTHER INFORMATION: FR L3 S64M S81R Q83R S80N S71M S60M S77R Q79R
      S76N S67M

<400> SEQUENCE: 99

Gly Val Pro Met Arg Phe Ser Gly Ser Gly Met Gly Thr Asp Phe Thr
1               5                   10                  15

Leu Thr Ile Asn Arg Leu Arg Pro Glu Asp Phe Ala Thr Tyr Tyr Cys
            20                  25                  30

<210> SEQ ID NO 100
<211> LENGTH: 32
<212> TYPE: PRT
<213> ORGANISM: Artificial Sequence
<220> FEATURE:
<223> OTHER INFORMATION: FR L3 S80N S67Y S71M S76N S63Y S67M

<400> SEQUENCE: 100

Gly Val Pro Ser Arg Phe Tyr Gly Ser Gly Met Gly Thr Asp Phe Thr
1               5                   10                  15

Leu Thr Ile Asn Ser Leu Gln Pro Glu Asp Phe Ala Thr Tyr Tyr Cys
            20                  25                  30

<210> SEQ ID NO 101
<211> LENGTH: 32
<212> TYPE: PRT
<213> ORGANISM: Artificial Sequence
<220> FEATURE:
<223> OTHER INFORMATION: FR L3 S64M S80N S67Y S71M S60M S76N S63Y S67M

<400> SEQUENCE: 101

Gly Val Pro Met Arg Phe Tyr Gly Ser Gly Met Gly Thr Asp Phe Thr
1               5                   10                  15

Leu Thr Ile Asn Ser Leu Gln Pro Glu Asp Phe Ala Thr Tyr Tyr Cys
            20                  25                  30

<210> SEQ ID NO 102
<211> LENGTH: 32
<212> TYPE: PRT
<213> ORGANISM: Artificial Sequence
<220> FEATURE:
<223> OTHER INFORMATION: FR L3 S81R S80N S67Y S71M S77R S76N S63Y S67M

<400> SEQUENCE: 102

Gly Val Pro Ser Arg Phe Tyr Gly Ser Gly Met Gly Thr Asp Phe Thr
1               5                   10                  15

Leu Thr Ile Asn Arg Leu Gln Pro Glu Asp Phe Ala Thr Tyr Tyr Cys
            20                  25                  30

<210> SEQ ID NO 103
<211> LENGTH: 32
<212> TYPE: PRT
<213> ORGANISM: Artificial Sequence
<220> FEATURE:
<223> OTHER INFORMATION: FR L3 Q83R S80N S67Y S71M Q79R S76N S63Y S67M

<400> SEQUENCE: 103

Gly Val Pro Ser Arg Phe Tyr Gly Ser Gly Met Gly Thr Asp Phe Thr
1               5                   10                  15

Leu Thr Ile Asn Ser Leu Arg Pro Glu Asp Phe Ala Thr Tyr Tyr Cys
            20                  25                  30

<210> SEQ ID NO 104
<211> LENGTH: 32
<212> TYPE: PRT
<213> ORGANISM: Artificial Sequence
<220> FEATURE:
<223> OTHER INFORMATION: FR L3 S64M S81R S80N S67Y S71M S60M S77R S76N
     S63Y S67M

<400> SEQUENCE: 104

Gly Val Pro Met Arg Phe Tyr Gly Ser Gly Met Gly Thr Asp Phe Thr
1               5                   10                  15

Leu Thr Ile Asn Arg Leu Gln Pro Glu Asp Phe Ala Thr Tyr Tyr Cys
            20                  25                  30

<210> SEQ ID NO 105
<211> LENGTH: 32
<212> TYPE: PRT
<213> ORGANISM: Artificial Sequence
<220> FEATURE:
<223> OTHER INFORMATION: FR L3 S64M Q83R S80N S67Y S71M S60M Q79R S76N
     S63Y S67M

<400> SEQUENCE: 105

Gly Val Pro Met Arg Phe Tyr Gly Ser Gly Met Gly Thr Asp Phe Thr
1               5                   10                  15

Leu Thr Ile Asn Ser Leu Arg Pro Glu Asp Phe Ala Thr Tyr Tyr Cys
            20                  25                  30

<210> SEQ ID NO 106
<211> LENGTH: 32
<212> TYPE: PRT
<213> ORGANISM: Artificial Sequence
<220> FEATURE:
<223> OTHER INFORMATION: FR L3 S81R Q83R S80N S67Y S71M S77R Q79R S76N
     S63Y S67M

<400> SEQUENCE: 106

```
Gly Val Pro Ser Arg Phe Tyr Gly Ser Gly Met Gly Thr Asp Phe Thr
1               5                   10                  15

Leu Thr Ile Asn Arg Leu Arg Pro Glu Asp Phe Ala Thr Tyr Tyr Cys
            20                  25                  30
```

<210> SEQ ID NO 107
<211> LENGTH: 30
<212> TYPE: PRT
<213> ORGANISM: Artificial Sequence
<220> FEATURE:
<223> OTHER INFORMATION: FR L3 S64M S81R Q83R S80N S67Y S71M S60M S77R
      Q79R S76N S63Y S67M

<400> SEQUENCE: 107

```
Pro Met Arg Phe Tyr Gly Ser Gly Met Gly Thr Asp Phe Thr Leu Thr
1               5                   10                  15

Ile Asn Arg Leu Arg Pro Glu Asp Phe Ala Thr Tyr Tyr Cys
            20                  25                  30
```

<210> SEQ ID NO 108
<211> LENGTH: 325
<212> TYPE: PRT
<213> ORGANISM: Artificial Sequence
<220> FEATURE:
<223> OTHER INFORMATION: Wild-type human IgE-Fc (CE2-CE4 domains with
      numbering V224-K547 according to Dorrington & Bennich (1978)

<400> SEQUENCE: 108

```
Val Ala Ser Arg Asp Phe Thr Pro Pro Thr Val Lys Ile Leu Gln Ser
1               5                   10                  15

Ser Cys Asp Gly Gly Gly His Phe Pro Pro Thr Ile Gln Leu Leu Cys
                20                  25                  30

Leu Val Ser Gly Tyr Thr Pro Gly Thr Ile Asn Ile Thr Trp Leu Glu
            35                  40                  45

Asp Gly Gln Val Met Asp Val Asp Leu Ser Thr Ala Ser Thr Thr Gln
        50                  55                  60

Glu Gly Glu Leu Ala Ser Thr Gln Ser Glu Leu Thr Leu Ser Gln Lys
65                  70                  75                  80

His Trp Leu Ser Asp Arg Thr Tyr Thr Cys Gln Val Thr Tyr Gln Gly
                85                  90                  95

His Thr Phe Glu Asp Ser Thr Lys Lys Cys Ala Asp Ser Asn Pro Arg
            100                 105                 110

Gly Val Ser Ala Tyr Leu Ser Arg Pro Ser Pro Phe Asp Leu Phe Ile
        115                 120                 125

Arg Lys Ser Pro Thr Ile Thr Cys Leu Val Val Asp Leu Ala Pro Ser
130                 135                 140

Lys Gly Thr Val Asn Leu Thr Trp Ser Arg Ala Ser Gly Lys Pro Val
145                 150                 155                 160

Asn His Ser Thr Arg Lys Glu Glu Lys Gln Arg Asn Gly Thr Leu Thr
                165                 170                 175

Val Thr Ser Thr Leu Pro Val Gly Thr Arg Asp Trp Ile Glu Gly Glu
            180                 185                 190

Thr Tyr Gln Cys Arg Val Thr His Pro His Leu Pro Arg Ala Leu Met
        195                 200                 205

Arg Ser Thr Thr Lys Thr Ser Gly Pro Arg Ala Ala Pro Glu Val Tyr
    210                 215                 220

Ala Phe Ala Thr Pro Glu Trp Pro Gly Ser Arg Asp Lys Arg Thr Leu
225                 230                 235                 240
```

```
Ala Cys Leu Ile Gln Asn Phe Met Pro Glu Asp Ile Ser Val Gln Trp
            245                 250                 255

Leu His Asn Glu Val Gln Leu Pro Asp Ala Arg His Ser Thr Thr Gln
            260                 265                 270

Pro Arg Lys Thr Lys Gly Ser Gly Phe Phe Val Phe Ser Arg Leu Glu
            275                 280                 285

Val Thr Arg Ala Glu Trp Glu Gln Lys Asp Glu Phe Ile Cys Arg Ala
            290                 295                 300

Val His Glu Ala Ala Ser Pro Ser Gln Thr Val Gln Arg Ala Val Ser
305                 310                 315                 320

Val Asn Pro Gly Lys
            325

<210> SEQ ID NO 109
<211> LENGTH: 111
<212> TYPE: PRT
<213> ORGANISM: Artificial Sequence
<220> FEATURE:
<223> OTHER INFORMATION: S77R_Q79R_v-region (Fab1)

<400> SEQUENCE: 109

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Tyr Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Arg Leu Arg Pro Glu Asp Phe Ala Thr Tyr Tyr Cys Gln Gln Ser His
            85                  90                  95

Glu Asp Pro Tyr Thr Phe Gly Gln Gly Thr Lys Val Glu Ile Lys
            100                 105                 110

<210> SEQ ID NO 110
<211> LENGTH: 333
<212> TYPE: DNA
<213> ORGANISM: Artificial Sequence
<220> FEATURE:
<223> OTHER INFORMATION: 77R_Q79R_v-region (Fab1)

<400> SEQUENCE: 110
gatattcagc tgactcagag cccgagctca ctctccgctt ccgtggggga tagagtgacc      60
atcacttgcc gggcatccca gtcggtggac tacgacggag actcctacat gaactggtac     120
cagcagaagc ccggaaaagc cccaaagttg ctgatctacg ccgcctccta ccttgaaagc     180
ggcgtgcctt cacgcttctc gggaagcggg tctggcaccg atttcaccct gaccatttcg     240
agactgaggc cggaggactt cgcgacttac tactgccaac agtcccacga ggacccctat     300
acgtttggcc agggtaccaa ggtcgaaatc aag                                  333

<210> SEQ ID NO 111
<211> LENGTH: 129
<212> TYPE: PRT
<213> ORGANISM: Artificial Sequence
<220> FEATURE:
<223> OTHER INFORMATION: S77R_Q79R_v-region (Fab1) with signal sequence
```

<400> SEQUENCE: 111

Met Lys Trp Val Thr Phe Ile Ser Leu Leu Phe Leu Phe Ser Ser Ala
1               5                   10                  15

Tyr Ser Asp Ile Gln Leu Thr Gln Ser Pro Ser Ser Leu Ser Ala Ser
            20                  25                  30

Val Gly Asp Arg Val Thr Ile Thr Cys Arg Ala Ser Gln Ser Val Asp
        35                  40                  45

Tyr Asp Gly Asp Ser Tyr Met Asn Trp Tyr Gln Gln Lys Pro Gly Lys
    50                  55                  60

Ala Pro Lys Leu Leu Ile Tyr Ala Ala Ser Tyr Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Arg Leu Arg Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
        115                 120                 125

Lys

<210> SEQ ID NO 112
<211> LENGTH: 387
<212> TYPE: DNA
<213> ORGANISM: Artificial Sequence
<220> FEATURE:
<223> OTHER INFORMATION: S77R_Q79R_v-region (Fab1) with signal sequence

<400> SEQUENCE: 112
atgaagtggg tcaccttcat ctccctgctg tttctgttct cctccgccta ctccgatatt      60
cagctgactc agagcccgag ctcactctcc gcttccgtgg gggatagagt gaccatcact     120
tgccgggcat cccagtcggt ggactacgac ggagactcct acatgaactg gtaccagcag     180
aagcccggaa agcccccaaa gttgctgatc tacgccgcct cctaccttga agcggcgtg      240 ccttcacgct ctcgggaag cgggtctggc accgatttca ccctgaccat ttcgagactg      300
aggccggagg acttcgcgac ttactactgc aacagtccc acgaggaccc ctatacgttt      360
ggccagggta ccaaggtcga aatcaag                                          387

<210> SEQ ID NO 113
<211> LENGTH: 111
<212> TYPE: PRT
<213> ORGANISM: Artificial Sequence
<220> FEATURE:
<223> OTHER INFORMATION: Fab2_v-region

<400> SEQUENCE: 113

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His

```
                     85                  90                  95
Glu Asp Pro Tyr Thr Phe Gly Gln Gly Thr Lys Val Glu Ile Lys
            100                 105                 110

<210> SEQ ID NO 114
<211> LENGTH: 333
<212> TYPE: DNA
<213> ORGANISM: Artificial Sequence
<220> FEATURE:
<223> OTHER INFORMATION: Fab2_v-region

<400> SEQUENCE: 114
gatattcagc tgactcagag cccgagctca ctctccgctt ccgtggggga tagagtgacc    60
atcacttgcc gggcatccca gtcggtggac tacgacggag actcctacat gaactggtat   120
cagcagaagc ccggaaaagc cccaaagttg ctgatctacg ccgcctcata ccttgaaagc   180
ggcgtgcctt cgcgcttctc gggaagcggg tcgggcaccg atttcaccct gaccatttcg   240
tcgctgcagc cggaggactt cgcgacttac tactgccaac agtcccacga ggaccccttat  300 acgtttggcc agggaaccaa ggtcgaaatc aag                                333

<210> SEQ ID NO 115
<211> LENGTH: 129
<212> TYPE: PRT
<213> ORGANISM: Artificial Sequence
<220> FEATURE:
<223> OTHER INFORMATION: Fab2_v-region with signal sequence

<400> SEQUENCE: 115

Met Lys Trp Val Thr Phe Ile Ser Leu Leu Phe Leu Phe Ser Ser Ala
1               5                   10                  15

Tyr Ser Asp Ile Gln Leu Thr Gln Ser Pro Ser Ser Leu Ser Ala Ser
            20                  25                  30

Val Gly Asp Arg Val Thr Ile Thr Cys Arg Ala Ser Gln Ser Val Asp
        35                  40                  45

Tyr Asp Gly Asp Ser Tyr Met Asn Trp Tyr Gln Gln Lys Pro Gly Lys
    50                  55                  60

Ala Pro Lys Leu Leu Ile Tyr Ala Ala Ser Tyr Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
        115                 120                 125

Lys

<210> SEQ ID NO 116
<211> LENGTH: 387
<212> TYPE: DNA
<213> ORGANISM: Artificial Sequence
<220> FEATURE:
<223> OTHER INFORMATION: Fab2_v-region with signal sequence

<400> SEQUENCE: 116
atgaagtggg tcaccttcat ctccctgctg tttctgttct cctccgccta ctccgatatt    60
cagctgactc agagcccgag ctcactctcc gcttccgtgg gggatagagt gaccatcact   120
tgccgggcat cccagtcggt ggactacgac ggagactcct acatgaactg gtatcagcag   180
```

```
aagcccggaa aagccccaaa gttgctgatc tacgccgcct cataccttga aagcggcgtg    240
ccttcgcgct tctcgggaag cgggtcgggc accgatttca ccctgaccat ttcgtcgctg    300
cagccggagg acttcgcgac ttactactgc aacagtccc acgaggaccc ctatacgttt    360
ggccagggaa ccaaggtcga aatcaag                                        387
```

```
<210> SEQ ID NO 117
<211> LENGTH: 218
<212> TYPE: PRT
<213> ORGANISM: Artificial Sequence
<220> FEATURE:
<223> OTHER INFORMATION: Fab2_v-region + kappa constant region including
      L154P

<400> SEQUENCE: 117
```

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Pro Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

```
<210> SEQ ID NO 118
<211> LENGTH: 654
<212> TYPE: DNA
<213> ORGANISM: Artificial Sequence
<220> FEATURE:
<223> OTHER INFORMATION: Fab2_v-region + kappa constant region including
      L154P

<400> SEQUENCE: 118
```

```
gatattcagc tgactcagag cccgagctca ctctccgctt ccgtggggga tagagtgacc    60
atcacttgcc gggcatccca gtcggtggac tacgacggag actcctacat gaactggtat    120
cagcagaagc ccggaaaagc cccaaagttg ctgatctacg ccgcctcata ccttgaaagc    180
ggcgtgcctt cgcgcttctc gggaagcggg tcgggcaccg atttcaccct gaccatttcg    240
```

```
tcgctgcagc cggaggactt cgcgacttac tactgccaac agtcccacga ggacccctat    300
acgtttggcc agggaaccaa ggtcgaaatc aagcgtacgg tagcggcccc atctgtcttc    360
atcttcccgc atctgatga gcagttgaaa tctggaactg cctctgttgt gtgcctgctg    420
aataacttct atcccagaga ggccaaagta cagtggaagg tggataacgc cccgcaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttca caggggaga gtgt    654
```

<210> SEQ ID NO 119
<211> LENGTH: 236
<212> TYPE: PRT
<213> ORGANISM: Artificial Sequence
<220> FEATURE:
<223> OTHER INFORMATION: Fab2_v-region + kappa constant region including
      L154P with signal sequence

<400> SEQUENCE: 119

```
Met Lys Trp Val Thr Phe Ile Ser Leu Leu Phe Leu Phe Ser Ser Ala
1               5                   10                  15

Tyr Ser Asp Ile Gln Leu Thr Gln Ser Pro Ser Ser Leu Ser Ala Ser
            20                  25                  30

Val Gly Asp Arg Val Thr Ile Thr Cys Arg Ala Ser Gln Ser Val Asp
        35                  40                  45

Tyr Asp Gly Asp Ser Tyr Met Asn Trp Tyr Gln Gln Lys Pro Gly Lys
    50                  55                  60

Ala Pro Lys Leu Leu Ile Tyr Ala Ala Ser Tyr Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Pro
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 120
<211> LENGTH: 708
<212> TYPE: DNA
<213> ORGANISM: Artificial Sequence
<220> FEATURE:
<223> OTHER INFORMATION: Fab2_v-region + kappa constant region including
      L154P with signal sequence

<400> SEQUENCE: 120

```
atgaagtggg tcaccttcat ctccctgctg tttctgttct cctccgccta ctccgatatt    60
cagctgactc agagcccgag ctcactctcc gcttccgtgg gggatagagt gaccatcact   120
tgccgggcat cccagtcggt ggactacgac ggagactcct acatgaactg gtatcagcag   180
aagcccggaa aagccccaaa gttgctgatc tacgccgcct cataccttga aagcggcgtg   240
ccttcgcgct ctcgggaag cgggtcgggc accgatttca ccctgaccat ttcgtcgctg   300
cagccggagg acttcgcgac ttactactgc aacagtccc acgaggaccc ctatacgttt   360
ggccagggaa ccaaggtcga aatcaagcgt acggtagcgg ccccatctgt cttcatcttc   420
ccgccatctg atgagcagtt gaaatctgga actgcctctg ttgtgtgcct gctgaataac   480
ttctatccca gagaggccaa agtacagtgg aaggtggata cgccccgca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt              708
```

<210> SEQ ID NO 121
<211> LENGTH: 111
<212> TYPE: PRT
<213> ORGANISM: Artificial Sequence
<220> FEATURE:
<223> OTHER INFORMATION: Fab3_S77R_Q79R_v-region

<400> SEQUENCE: 121

```
Asp Ile Gln Leu Thr Gln Ser Pro Ser Ser Leu Ser Ala Ser Val Gly
1               5                   10                  15
Asp Arg Val Thr Ile Thr Cys Arg Ala Ser Gln Ser Val Asp Tyr Asp
            20                  25                  30
Gly Asp Ser Tyr Met Asn Trp Tyr Gln Gln Lys Pro Gly Lys Ala Pro
        35                  40                  45
Lys Leu Leu Ile Tyr Ala Ala Ser Tyr Leu Glu Ser Gly Val Pro Ser
    50                  55                  60
Arg Phe Ser Gly Ser Gly Ser Gly Thr Asp Phe Thr Leu Thr Ile Ser
65                  70                  75                  80
Arg Leu Arg Pro Glu Asp Phe Ala Thr Tyr Tyr Cys Gln Gln Ser His
                85                  90                  95
Glu Asp Pro Tyr Thr Phe Gly Gln Gly Thr Lys Val Glu Ile Lys
            100                 105                 110
```

<210> SEQ ID NO 122
<211> LENGTH: 333
<212> TYPE: DNA
<213> ORGANISM: Artificial Sequence
<220> FEATURE:
<223> OTHER INFORMATION: Fab3_S77R_Q79R_v-region

<400> SEQUENCE: 122

```
gatattcagc tgactcagag cccgagctca ctctccgctt ccgtggggga tagagtgacc    60
atcacttgcc gggcatccca gtcggtggac tacgacggag actcctacat gaactggtac   120
cagcagaagc ccggaaaagc cccaaagttg ctgatctacg ccgcctccta ccttgaaagc   180
ggcgtgcctt cacgcttctc gggaagcggg tctggcaccg atttcaccct gaccatttcg   240
agactgaggc cggaggactt cgcgacttac tactgccaac agtcccacga ggacccctat   300
acgtttggcc agggtaccaa ggtcgaaatc aag                                333
```

<210> SEQ ID NO 123
<211> LENGTH: 129
<212> TYPE: PRT
<213> ORGANISM: Artificial Sequence
<220> FEATURE:
<223> OTHER INFORMATION: Fab3_S77R_Q79R_v-region with signal sequence

<400> SEQUENCE: 123

```
Met Lys Trp Val Thr Phe Ile Ser Leu Leu Phe Leu Phe Ser Ser Ala
1               5                   10                  15

Tyr Ser Asp Ile Gln Leu Thr Gln Ser Pro Ser Ser Leu Ser Ala Ser
            20                  25                  30

Val Gly Asp Arg Val Thr Ile Thr Cys Arg Ala Ser Gln Ser Val Asp
        35                  40                  45

Tyr Asp Gly Asp Ser Tyr Met Asn Trp Tyr Gln Gln Lys Pro Gly Lys
    50                  55                  60

Ala Pro Lys Leu Leu Ile Tyr Ala Ala Ser Tyr Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Arg Leu Arg Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
        115                 120                 125

Lys
```

<210> SEQ ID NO 124
<211> LENGTH: 387
<212> TYPE: DNA
<213> ORGANISM: Artificial Sequence
<220> FEATURE:
<223> OTHER INFORMATION: Fab3_S77R_Q79R_v-region with signal sequence

<400> SEQUENCE: 124

```
atgaagtggg tcaccttcat ctccctgctg tttctgttct cctccgccta ctccgatatt      60
cagctgactc agagcccgag ctcactctcc gcttccgtgg gggatagagt gaccatcact     120
tgccgggcat cccagtcggt ggactacgac ggagactcct acatgaactg gtaccagcag     180
aagcccggaa agcccccaaa gttgctgatc tacgccgcct cctaccttga aagcggcgtg     240
ccttcacgct ctcgggaag cgggtctggc accgatttca ccctgaccat ttcgagactg     300
aggccggagg acttcgcgac ttactactgc aacagtccc acgaggaccc ctatacgttt     360
ggccagggta ccaaggtcga aatcaag                                         387
```

<210> SEQ ID NO 125
<211> LENGTH: 218
<212> TYPE: PRT
<213> ORGANISM: Artificial Sequence
<220> FEATURE:
<223> OTHER INFORMATION: Fab3_S77R_Q79R_v-region + kappa constant region
      including L154P

<400> SEQUENCE: 125

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
```

```
              35                  40                  45
Lys Leu Leu Ile Tyr Ala Ala Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Arg Leu Arg Pro Glu Asp Phe Ala Thr Tyr Tyr Cys Gln Gln Ser His
                 85                  90                  95

Glu Asp Pro Tyr Thr Phe Gly Gln Gly Thr Lys Val Glu Ile Lys Arg
             100                 105                 110

Thr Val Ala Ala Pro Ser Val Phe Ile Phe Pro Pro Ser Asp Glu Gln
         115                 120                 125

Leu Lys Ser Gly Thr Ala Ser Val Val Cys Leu Leu Asn Asn Phe Tyr
     130                 135                 140

Pro Arg Glu Ala Lys Val Gln Trp Lys Val Asp Asn Ala Pro Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 126
<211> LENGTH: 654
<212> TYPE: DNA
<213> ORGANISM: Artificial Sequence
<220> FEATURE:
<223> OTHER INFORMATION: Fab3_S77R_Q79R_v-region + kappa constant region
      including L154P

<400> SEQUENCE: 126

```
gatattcagc tgactcagag cccgagctca ctctccgctt ccgtggggga tagagtgacc      60
atcacttgcc gggcatccca gtcggtggac tacgacggag actcctacat gaactggtac    120
cagcagaaag ccggaaaagc cccaaagttg ctgatctacg ccgcctccta ccttgaaagc    180
ggcgtgcctt cacgcttctc gggaagcggg tctggcaccg atttcaccct gaccatttcg    240
agactgaggc cggaggactt cgcgacttac tactgccaac agtcccacga ggacccctat    300
acgtttggcc agggtaccaa ggtcgaaatc aagcgtacgg tagcggcccc atctgtcttc    360
atcttcccgc catctgatga gcagttgaaa tctggaactg cctctgttgt gtgcctgctg    420
aataacttct atcccagaga ggccaaagta cagtggaagg tggataacgc cccgcaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600
acccatcagg gcctgagctc gcccgtcaca aagagcttca cagggagag tgt            654
```

<210> SEQ ID NO 127
<211> LENGTH: 236
<212> TYPE: PRT
<213> ORGANISM: Artificial Sequence
<220> FEATURE:
<223> OTHER INFORMATION: Fab3_S77R_Q79R_v-region + kappa constant region
      including L154P with signal sequence

<400> SEQUENCE: 127

Met Lys Trp Val Thr Phe Ile Ser Leu Leu Phe Leu Phe Ser Ser Ala
1               5                   10                  15

Tyr Ser Asp Ile Gln Leu Thr Gln Ser Pro Ser Ser Leu Ser Ala Ser
            20                  25                  30

Val Gly Asp Arg Val Thr Ile Thr Cys Arg Ala Ser Gln Ser Val Asp
        35                  40                  45

Tyr Asp Gly Asp Ser Tyr Met Asn Trp Tyr Gln Gln Lys Pro Gly Lys
    50                  55                  60

Ala Pro Lys Leu Leu Ile Tyr Ala Ala Ser Tyr Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Arg Leu Arg Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Pro
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 128
<211> LENGTH: 708
<212> TYPE: DNA
<213> ORGANISM: Artificial Sequence
<220> FEATURE:
<223> OTHER INFORMATION: Fab3_S77R_Q79R_v-region + kappa constant region
      including L154P with signal sequence

<400> SEQUENCE: 128
atgaagtggg tcaccttcat ctccctgctg tttctgttct cctccgccta ctccgatatt    60
cagctgactc agagcccgag ctcactctcc gcttccgtgg gggatagagt gaccatcact   120
tgccgggcat cccagtcggt ggactacgac ggagactcct acatgaactg gtaccagcag   180
aagcccggaa agcccccaaa gttgctgatc tacgccgcct cctaccttga aagcggcgtg   240
ccttcacgct ctctcgggaa gcgggtctgg accgatttca ccctgaccat ttcgagactg   300
aggccggagg acttcgcgac ttactactgc caacagtccc acgaggaccc ctatacgttt   360
ggccagggta ccaaggtcga aatcaagcgt acggtagcgg ccccatctgt cttcatcttc   420
ccgccatctg atgagcagtt gaaatctgga actgcctctg ttgtgtgcct gctgaataac   480
ttctatccca gagaggccaa agtacagtgg aaggtggata acgcccgcca atcgggtaac   540
tcccaggaga gtgtcacaga gcaggacagc aaggacagca cctacagcct cagcagcacc   600
ctgacgctgt caaagcagac tacgagaaaa cacaaagtct acgcctgcga agtcaccat   660 cagggcctga gctcgcccgt cacaaagagc ttcaacaggg gagagtgt                708

<210> SEQ ID NO 129
<211> LENGTH: 107
<212> TYPE: PRT
<213> ORGANISM: Artificial Sequence
<220> FEATURE:
<223> OTHER INFORMATION: Omalizumab_v-region

<400> SEQUENCE: 129

```
Thr Gln Ser Pro Ser Ser Leu Ser Ala Ser Val Gly Asp Arg Val Thr
1               5                   10                  15

Ile Thr Cys Arg Ala Ser Gln Ser Val Asp Tyr Asp Gly Asp Ser Tyr
            20                  25                  30

Met Asn Trp Tyr Gln Gln Lys Pro Gly Lys Ala Pro Lys Leu Leu Ile
        35                  40                  45

Tyr Ala Ala Ser Tyr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Glu Asp Pro Tyr
                85                  90                  95

Thr Phe Gly Gln Gly Thr Lys Val Glu Ile Lys
            100                 105
```

<210> SEQ ID NO 130
<211> LENGTH: 321
<212> TYPE: DNA
<213> ORGANISM: Artificial Sequence
<220> FEATURE:
<223> OTHER INFORMATION: Omalizumab_v-region

<400> SEQUENCE: 130

```
actcagagcc cgagctcact ctccgcttcc gtgggggata gagtgaccat cacttgccgg    60
gcatcccagt cggtggacta cgacggagac tcctacatga actggtatca gcagaagccc   120
ggaaaagccc caaagttgct gatctacgcc gcctcatacc ttgaaagcgg cgtgccttcg   180
cgcttctcgg gaagcgggtc gggcaccgat ttcaccctga ccatttcgtc gctgcagccg   240
gaggacttcg cgacttacta ctgccaacag tcccacgagg accccctatac gtttggccag   300 ggaaccaagg tcgaaatcaa g                                              321
```

<210> SEQ ID NO 131
<211> LENGTH: 32
<212> TYPE: PRT
<213> ORGANISM: Artificial Sequence
<220> FEATURE:
<223> OTHER INFORMATION: FR3

<400> SEQUENCE: 131

```
Gly Val Pro Met Arg Phe Ser Gly Ser Gly Met Gly Thr Asp Phe Thr
1               5                   10                  15

Leu Thr Ile Ser Arg Leu Arg Pro Glu Asp Phe Ala Thr Tyr Tyr Cys
            20                  25                  30
```

<210> SEQ ID NO 132
<211> LENGTH: 111
<212> TYPE: PRT
<213> ORGANISM: Artificial Sequence
<220> FEATURE:
<223> OTHER INFORMATION: S60M_S52D_S67M_S77R_Q79R_v-region

<400> SEQUENCE: 132

```
Asp Ile Gln Leu Thr Gln Ser Pro Ser Ser Leu Ser Ala Ser Val Gly
 1               5                   10                  15

Asp Arg Val Thr Ile Thr Cys Arg Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Asp Tyr Leu Glu Ser Gly Val Pro Met
 50                  55                  60

Arg Phe Ser Gly Ser Gly Met Gly Thr Asp Phe Thr Leu Thr Ile Ser
 65                  70                  75                  80

Arg Leu Arg Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys
            100                 105                 110
```

<210> SEQ ID NO 133
<211> LENGTH: 333
<212> TYPE: DNA
<213> ORGANISM: Artificial Sequence
<220> FEATURE:
<223> OTHER INFORMATION: S60M_S52D_S67M_S77R_Q79R_v-region

<400> SEQUENCE: 133

```
gatattcagc tgactcagag cccgagctca ctctccgctt ccgtggggga tagagtgacc    60
atcacttgcc gggcatccca gtcggtggac tacgacggag actcctacat gaactggtat   120
cagcagaagc ccgaaaaagc cccaaagttg ctgatctacg ccgccgacta ccttgaaagc   180
ggcgtgccta tgcgcttctc gggaagcggg atgggcaccg atttcaccct gaccatttcg   240
agactgaggc cggaggactt cgcgacttac tactgccaac agtcccacga ggaccccttat  300
acgtttggcc agggaaccaa ggtcgaaatc aag                                333
```

<210> SEQ ID NO 134
<211> LENGTH: 129
<212> TYPE: PRT
<213> ORGANISM: Artificial Sequence
<220> FEATURE:
<223> OTHER INFORMATION: S60M_S52D_S67M_S77R_Q79R_v-region with signal
      sequence

<400> SEQUENCE: 134

```
Met Lys Trp Val Thr Phe Ile Ser Leu Leu Phe Leu Phe Ser Ser Ala
 1               5                   10                  15

Tyr Ser Asp Ile Gln Leu Thr Gln Ser Pro Ser Ser Leu Ser Ala Ser
                20                  25                  30

Val Gly Asp Arg Val Thr Ile Thr Cys Arg Ala Ser Gln Ser Val Asp
            35                  40                  45

Tyr Asp Gly Asp Ser Tyr Met Asn Trp Tyr Gln Gln Lys Pro Gly Lys
 50                  55                  60

Ala Pro Lys Leu Leu Ile Tyr Ala Ala Asp Tyr Leu Glu Ser Gly Val
 65                  70                  75                  80

Pro Met Arg Phe Ser Gly Ser Gly Met Gly Thr Asp Phe Thr Leu Thr
                85                  90                  95

Ile Ser Arg Leu Arg Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
            115                 120                 125
```

Lys

<210> SEQ ID NO 135
<211> LENGTH: 387
<212> TYPE: DNA
<213> ORGANISM: Artificial Sequence
<220> FEATURE:
<223> OTHER INFORMATION: S60M_S52D_S67M_S77R_Q79R_v-region with signal
      sequence

<400> SEQUENCE: 135

```
atgaagtggg tcaccttcat ctccctgctg tttctgttct cctccgccta ctccgatatt    60
cagctgactc agagcccgag ctcactctcc gcttccgtgg gggatagagt gaccatcact   120
tgccgggcat cccagtcggt ggactacgac ggagactcct acatgaactg gtatcagcag   180
aagcccggaa agcccccaaa gttgctgatc tacgccgccg actaccttga aagcggcgtg   240
cctatgcgct ctcgggaag cgggatgggc accgatttca ccctgaccat ttcgagactg   300
aggccggagg acttcgcgac ttactactgc caacagtccc acgaggaccc ctatacgttt   360
ggccagggaa ccaaggtcga aatcaag                                       387
```

<210> SEQ ID NO 136
<211> LENGTH: 218
<212> TYPE: PRT
<213> ORGANISM: Artificial Sequence
<220> FEATURE:
<223> OTHER INFORMATION: S60M_S52D_S67M_S77R_Q79R_v-region + kappa
      constant region

<400> SEQUENCE: 136

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Asp Tyr Leu Glu Ser Gly Val Pro Met
    50                  55                  60

Arg Phe Ser Gly Ser Gly Met Gly Thr Asp Phe Thr Leu Thr Ile Ser
65                  70                  75                  80

Arg Leu Arg Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 137
<211> LENGTH: 654
<212> TYPE: DNA
<213> ORGANISM: Artificial Sequence
<220> FEATURE:
<223> OTHER INFORMATION: S60M_S52D_S67M_S77R_Q79R_v-region + kappa constant region

<400> SEQUENCE: 137

```
gatattcagc tgactcagag cccgagctca ctctccgctt ccgtgggga tagagtgacc      60
atcacttgcc gggcatccca gtcggtggac tacgacggag actcctacat gaactggtat   120
cagcagaagc ccggaaaagc cccaaagttg ctgatctacg ccgccgacta ccttgaaagc   180
ggcgtgccta tgcgcttctc gggaagcggg atgggcaccg atttcaccct gaccatttcg   240
agactgaggc cggaggactt cgcgacttac tactgccaac agtcccacga ggaccctat    300
acgtttggcc agggaaccaa ggtcgaaatc aagcgtacgg tagcggcccc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600
acccatcagg gcctgagctc gcccgtcaca aagagcttca caggggaga gtgt           654
```

<210> SEQ ID NO 138
<211> LENGTH: 32
<212> TYPE: PRT
<213> ORGANISM: Artificial Sequence
<220> FEATURE:
<223> OTHER INFORMATION: FR3

<400> SEQUENCE: 138

```
Gly Val Pro Arg Arg Phe Ser Gly Ser Gly Met Gly Thr Asp Phe Thr
1               5                   10                  15
Leu Thr Ile Ser Arg Leu Arg Pro Glu Asp Phe Ala Thr Tyr Tyr Cys
            20                  25                  30
```

<210> SEQ ID NO 139
<211> LENGTH: 111
<212> TYPE: PRT
<213> ORGANISM: Artificial Sequence
<220> FEATURE:
<223> OTHER INFORMATION: S60R_S52D_S67M_S77R_Q79R_v-region

<400> SEQUENCE: 139

```
Asp Ile Gln Leu Thr Gln Ser Pro Ser Ser Leu Ser Ala Ser Val Gly
1               5                   10                  15
Asp Arg Val Thr Ile Thr Cys Arg Ala Ser Gln Ser Val Asp Tyr Asp
            20                  25                  30
Gly Asp Ser Tyr Met Asn Trp Tyr Gln Gln Lys Pro Gly Lys Ala Pro
        35                  40                  45
Lys Leu Leu Ile Tyr Ala Ala Asp Tyr Leu Glu Ser Gly Val Pro Arg
    50                  55                  60
Arg Phe Ser Gly Ser Gly Met Gly Thr Asp Phe Thr Leu Thr Ile Ser
65                  70                  75                  80
Arg Leu Arg Pro Glu Asp Phe Ala Thr Tyr Tyr Cys Gln Gln Ser His
            85                  90                  95
Glu Asp Pro Tyr Thr Phe Gly Gln Gly Thr Lys Val Glu Ile Lys
```

-continued

```
                 100              105              110
```

<210> SEQ ID NO 140
<211> LENGTH: 333
<212> TYPE: DNA
<213> ORGANISM: Artificial Sequence
<220> FEATURE:
<223> OTHER INFORMATION: S60R_S52D_S67M_S77R_Q79R_v-region

<400> SEQUENCE: 140

```
gatattcagc tgactcagag cccgagctca ctctccgctt ccgtggggga tagagtgacc      60
atcacttgcc gggcatccca gtcggtggac tacgacggag actcctacat gaactggtat    120
cagcagaagc ccggaaaagc cccaaagttg ctgatctacg ccgccgatta ccttgaaagc    180
ggcgtgcctc gtcgcttctc gggaagcggg atgggcaccg atttcaccct gaccatttcg    240
agactgaggc cggaggactt cgcgacttac tactgccaac agtcccacga ggaccctat     300 acgtttggcc agggaaccaa ggtcgaaatc aag                                 333
```

<210> SEQ ID NO 141
<211> LENGTH: 129
<212> TYPE: PRT
<213> ORGANISM: Artificial Sequence
<220> FEATURE:
<223> OTHER INFORMATION: S60R_S52D_S67M_S77R_Q79R_v-region with signal
      sequence

<400> SEQUENCE: 141

```
Met Lys Trp Val Thr Phe Ile Ser Leu Leu Phe Leu Phe Ser Ser Ala
1               5                   10                  15

Tyr Ser Asp Ile Gln Leu Thr Gln Ser Pro Ser Ser Leu Ser Ala Ser
            20                  25                  30

Val Gly Asp Arg Val Thr Ile Thr Cys Arg Ala Ser Gln Ser Val Asp
        35                  40                  45

Tyr Asp Gly Asp Ser Tyr Met Asn Trp Tyr Gln Gln Lys Pro Gly Lys
    50                  55                  60

Ala Pro Lys Leu Leu Ile Tyr Ala Ala Asp Tyr Leu Glu Ser Gly Val
65                  70                  75                  80

Pro Arg Arg Phe Ser Gly Ser Gly Met Gly Thr Asp Phe Thr Leu Thr
                85                  90                  95

Ile Ser Arg Leu Arg Pro Glu Asp Phe Ala Thr Tyr Tyr Cys Gln Gln
            100                 105                 110

Ser His Glu Asp Pro Tyr Thr Phe Gly Gln Gly Thr Lys Val Glu Ile
        115                 120                 125

Lys
```

<210> SEQ ID NO 142
<211> LENGTH: 387
<212> TYPE: DNA
<213> ORGANISM: Artificial Sequence
<220> FEATURE:
<223> OTHER INFORMATION: S60R_S52D_S67M_S77R_Q79R_v-region with signal
      sequence

<400> SEQUENCE: 142

```
atgaagtggg tcaccttcat ctccctgctg tttctgttct cctccgccta ctccgatatt      60
cagctgactc agagcccgag ctcactctcc gcttccgtgg gggatagagt gaccatcact    120
tgccgggcat cccagtcggt ggactacgac ggagactcct acatgaactg gtatcagcag    180
aagcccggaa aagcccccaaa gttgctgatc tacgccgccg attaccttga aagcggcgtg   240
```

```
cctcgtcgct tctcgggaag cgggatgggc accgatttca ccctgaccat ttcgagactg    300
aggccggagg acttcgcgac ttactactgc caacagtccc acgaggaccc ctatacgttt    360
ggccagggaa ccaaggtcga aatcaag                                        387
```

<210> SEQ ID NO 143
<211> LENGTH: 218
<212> TYPE: PRT
<213> ORGANISM: Artificial Sequence
<220> FEATURE:
<223> OTHER INFORMATION: S60R_S52D_S67M_S77R_Q79R_v-region + kappa
    constant region

<400> SEQUENCE: 143

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Asp Tyr Leu Glu Ser Gly Val Pro Arg
    50                  55                  60

Arg Phe Ser Gly Ser Gly Met Gly Thr Asp Phe Thr Leu Thr Ile Ser
65                  70                  75                  80

Arg Leu Arg Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 144
<211> LENGTH: 654
<212> TYPE: DNA
<213> ORGANISM: Artificial Sequence
<220> FEATURE:
<223> OTHER INFORMATION: S60R_S52D_S67M_S77R_Q79R_v-region + kappa
    constant region

<400> SEQUENCE: 144

```
gatattcagc tgactcagag cccgagctca ctctccgctt ccgtggggga tagagtgacc     60
atcacttgcc gggcatccca gtcggtggac tacgacggag actcctacat gaactggtat    120
cagcagaagc ccgaaaaagc cccaaagttg ctgatctacg ccgccgatta ccttgaaagc    180
ggcgtgcctc gtcgcttctc gggaagcggg atgggcaccg atttcaccct gaccattcg     240
```

-continued

```
agactgaggc cggaggactt cgcgacttac tactgccaac agtcccacga ggacccctat    300
acgtttggcc agggaaccaa ggtcgaaatc aagcgtacgg tagcggcccc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttca cagggagag tgt            654
```

```
<210> SEQ ID NO 145
<211> LENGTH: 111
<212> TYPE: PRT
<213> ORGANISM: Artificial Sequence
<220> FEATURE:
<223> OTHER INFORMATION: S60K_S52D_S67M_S77R_Q79R_v-region

<400> SEQUENCE: 145

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Asp Tyr Leu Glu Ser Gly Val Pro Lys
    50                  55                  60

Arg Phe Ser Gly Ser Gly Met Gly Thr Asp Phe Thr Leu Thr Ile Ser
65                  70                  75                  80

Arg Leu Arg Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys
            100                 105                 110
```

```
<210> SEQ ID NO 146
<211> LENGTH: 111
<212> TYPE: PRT
<213> ORGANISM: Artificial Sequence
<220> FEATURE:
<223> OTHER INFORMATION: S60Q_S52D_S67M_S77R_Q79R_v-region

<400> SEQUENCE: 146

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Asp Tyr Leu Glu Ser Gly Val Pro Gln
    50                  55                  60

Arg Phe Ser Gly Ser Gly Met Gly Thr Asp Phe Thr Leu Thr Ile Ser
65                  70                  75                  80

Arg Leu Arg Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys
            100                 105                 110
```

```
<210> SEQ ID NO 147
<211> LENGTH: 506
```

```
<212> TYPE: PRT
<213> ORGANISM: Artificial Sequence
<220> FEATURE:
<223> OTHER INFORMATION: v-region + gamma 1 CH1 constant region plus
      linker plus CA645 gL4gH5 scFv with signal sequence

<400> SEQUENCE: 147
```

Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Gln Pro
            20                  25                  30

Gly Gly Ser Leu Arg Leu Ser Cys Ala Val Ser Gly Tyr Ser Ile Thr
        35                  40                  45

Ser Gly Tyr Ser Trp Asn Trp Ile Arg Gln Ala Pro Gly Lys Gly Leu
    50                  55                  60

Glu Trp Val Ala Ser Ile Thr Tyr Asp Gly Ser Thr Asn Tyr Asn Pro
65                  70                  75                  80

Ser Val Lys Gly Arg Ile Thr Ile Ser Arg Asp Asp Ser Lys Asn Thr
                85                  90                  95

Phe Tyr Leu Gln Met Asn Ser Leu Arg Ala Glu Asp Thr Ala Val Tyr
            100                 105                 110

Tyr Cys Ala Arg Gly Ser His Tyr Phe Gly His Trp His Phe Ala Val
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Ser Gly Gly Gly Gly Thr Gly Gly Gly Ser Glu Val Gln
                245                 250                 255

Leu Leu Glu Ser Gly Gly Gly Leu Val Gln Pro Gly Gly Ser Leu Arg
            260                 265                 270

Leu Ser Cys Ala Val Ser Gly Ile Asp Leu Ser Asn Tyr Ala Ile Asn
        275                 280                 285

Trp Val Arg Gln Ala Pro Gly Lys Cys Leu Glu Trp Ile Gly Ile Ile
    290                 295                 300

Trp Ala Ser Gly Thr Thr Phe Tyr Ala Thr Trp Ala Lys Gly Arg Phe
305                 310                 315                 320

Thr Ile Ser Arg Asp Asn Ser Lys Asn Thr Val Tyr Leu Gln Met Asn
                325                 330                 335

Ser Leu Arg Ala Glu Asp Thr Ala Val Tyr Tyr Cys Ala Arg Thr Val
            340                 345                 350

Pro Gly Tyr Ser Thr Ala Pro Tyr Phe Asp Leu Trp Gly Gln Gly Thr
        355                 360                 365

Leu Val Thr Val Ser Ser Gly Gly Gly Gly Ser Gly Gly Gly Gly Ser
    370                 375                 380

Gly Gly Gly Gly Ser Gly Gly Gly Ser Asp Ile Gln Met Thr Gln
385                 390                 395                 400

Ser Pro Ser Ser Val Ser Ala Ser Val Gly Asp Arg Val Thr Ile Thr
                405                 410                 415

Cys Gln Ser Ser Pro Ser Val Trp Ser Asn Phe Leu Ser Trp Tyr Gln
            420                 425                 430

Gln Lys Pro Gly Lys Ala Pro Lys Leu Leu Ile Tyr Glu Ala Ser Lys
        435                 440                 445

Leu Thr Ser Gly Val Pro Ser Arg Phe Ser Gly Ser Gly Ser Gly Thr
    450                 455                 460

Asp Phe Thr Leu Thr Ile Ser Ser Leu Gln Pro Glu Asp Phe Ala Thr
465                 470                 475                 480

Tyr Tyr Cys Gly Gly Gly Tyr Ser Ser Ile Ser Asp Thr Thr Phe Gly
                485                 490                 495

Cys Gly Thr Lys Val Glu Ile Lys Arg Thr
            500                 505

<210> SEQ ID NO 148
<211> LENGTH: 1518
<212> TYPE: DNA
<213> ORGANISM: Artificial Sequence
<220> FEATURE:
<223> OTHER INFORMATION: v-region + gamma 1 CH1 constant region plus
      linker plus CA645 gL4gH5 scFv with signal sequence

<400> SEQUENCE: 148
atgaagtggg tcaccttcat ctccctgctg tttctgttct ccagcgccta ctccgaagtg      60
cagttggtgg agtcgggtgg agggctggtg cagcctggcg gtagcctgag gctgtcctgt     120
gccgtgtccg gatactccat tacctccggc tactcgtgga actggatcag acaggctccc     180
ggaaagggac ttgagtgggt ggcgtccatc acctacgacg gctcaaccaa ctataacccg     240
tccgtgaagg gccgcatcac catttcgcgc gacgacagca gaatactttt tacctccaa     300 atgaacagcc tgcgggccga agatactgcc gtgtactact gcgcgcgggg atcacattac     360
ttcgggcact ggcacttcgc cgtctgggga caggcacccc tcgtcactgt ctcgagcgct     420
tctacaaagg gcccatcggt cttccccctg gcaccctcct ccaagagcac ctctgggggc     480
acagcggccc tgggctgcct ggtcaaggac tacttccccg aaccagtgac ggtgtcgtgg     540
aactcaggtg ccctgaccag cggcgttcac accttcccgg ctgtcctaca gtcttcagga     600
ctctactccc tgagcagcgt ggtgaccgtg ccctccagca gcttgggcac ccagacctac     660
atctgcaacg tgaatcacaa gcccagcaac accaaggtcg ataagaaagt tgagcccaaa     720
tcttgtagtg gaggtggggg caccggtgga ggtggcagcg aggttcaact gcttgagtct     780
ggaggaggcc tagtccagcc tggagggagc ctgcgtctct cttgtgcagt aagcggcatc     840
gacctgagca attacgccat caactgggtg agacaagctc cggggaagtg tttagaatgg     900
atcggtataa tatgggccag tggacgacc ttttatgcta catgggcgaa aggaaggttt     960
acaattagcc gggacaatag caaaaacacc gtgtatctcc aaatgaactc cttgcgagca    1020
gaggacacgg cggtgtacta ttgtgctcgc actgtcccag ttatagcac tgcaccctac    1080 ttcgatctgt ggggacaagg gaccctggtg actgtttcaa gtggcggagg gggtagtgga    1140
gggggtggct ctgggggtgg cggaagcggt ggcgggggtt ctgacataca aatgactcag    1200
tctccttcat cggtatccgc gtccgttggc gataggtgta ctattacatg tcaaagctct    1260
cctagcgtct ggagcaattt tctatcctgg tatcaacaga aaccggggaa ggctccaaaa    1320

```
cttctgattt atgaagcctc gaaactcacc agtggagttc cgtcaagatt cagtggctct   1380
ggatcaggga cagacttcac gttgacaatc agttcgctgc aaccagagga ctttgcgacc   1440
tactattgtg gtggaggtta cagtagcata agtgatacga catttgggtg cggtactaag   1500
gtggaaatca aacgtacc                                                  1518
```

<210> SEQ ID NO 149
<211> LENGTH: 11
<212> TYPE: PRT
<213> ORGANISM: Artificial Sequence
<220> FEATURE:
<223> OTHER INFORMATION: Linker between CH1 and CA645 gL4gH5 scFv

<400> SEQUENCE: 149

Ser Gly Gly Gly Gly Thr Gly Gly Gly Gly Ser
1               5                   10

<210> SEQ ID NO 150
<211> LENGTH: 253
<212> TYPE: PRT
<213> ORGANISM: Artificial Sequence
<220> FEATURE:
<223> OTHER INFORMATION: CA645 gL4gH5 scFv

<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gly Gly Gly Tyr Ser Ser Ile Ser Asp Thr
225                 230                 235                 240

Thr Phe Gly Cys Gly Thr Lys Val Glu Ile Lys Arg Thr
                245                 250

<210> SEQ ID NO 151
<211> LENGTH: 20
<212> TYPE: PRT
<213> ORGANISM: Artificial Sequence
<220> FEATURE:
<223> OTHER INFORMATION: Linker between CA645 gH5 and CA645 gL4 within scFv

<400> SEQUENCE: 151

Gly Gly Gly Gly Ser Gly Gly Gly Gly Ser Gly Gly Gly Gly Ser Gly
1               5                   10                  15

Gly Gly Gly Ser
            20

<210> SEQ ID NO 152
<211> LENGTH: 10
<212> TYPE: PRT
<213> ORGANISM: Artificial Sequence
<220> FEATURE:
<223> OTHER INFORMATION: CA645 CDRH1

<400> SEQUENCE: 152

Gly Ile Asp Leu Ser Asn Tyr Ala Ile Asn
1               5                   10

<210> SEQ ID NO 153
<211> LENGTH: 16
<212> TYPE: PRT
<213> ORGANISM: Artificial Sequence
<220> FEATURE:
<223> OTHER INFORMATION: CA645 CDRH2

<400> SEQUENCE: 153

Ile Ile Trp Ala Ser Gly Thr Thr Phe Tyr Ala Thr Trp Ala Lys Gly
1               5                   10                  15

<210> SEQ ID NO 154
<211> LENGTH: 13
<212> TYPE: PRT
<213> ORGANISM: Artificial Sequence
<220> FEATURE:
<223> OTHER INFORMATION: CA645 CDRH3

<400> SEQUENCE: 154

Thr Val Pro Gly Tyr Ser Thr Ala Pro Tyr Phe Asp Leu
1               5                   10

<210> SEQ ID NO 155
<211> LENGTH: 12
<212> TYPE: PRT
<213> ORGANISM: Artificial Sequence
<220> FEATURE:
<223> OTHER INFORMATION: CA645 CDRL1

<400> SEQUENCE: 155

Gln Ser Ser Pro Ser Val Trp Ser Asn Phe Leu Ser
1               5                   10

<210> SEQ ID NO 156
<211> LENGTH: 7
<212> TYPE: PRT
<213> ORGANISM: Artificial Sequence
<220> FEATURE:
<223> OTHER INFORMATION: CA645 CDRL2

<400> SEQUENCE: 156

Glu Ala Ser Lys Leu Thr Ser
1               5

<210> SEQ ID NO 157
<211> LENGTH: 10
<212> TYPE: PRT
<213> ORGANISM: Artificial Sequence
<220> FEATURE:
<223> OTHER INFORMATION: CA645 CDRL3

<400> SEQUENCE: 157

Gly Gly Tyr Ser Ser Ile Ser Asp Thr Thr
1               5                   10

<210> SEQ ID NO 158
<211> LENGTH: 111
<212> TYPE: PRT
<213> ORGANISM: Artificial Sequence
<220> FEATURE:
<223> OTHER INFORMATION: S60M_S52D_S67M_S77R_Q79R_S63W_S76N_v-region

<400> SEQUENCE: 158

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Asp Tyr Leu Glu Ser Gly Val Pro Met
        50                  55                  60

Arg Phe Trp Gly Ser Gly Met Gly Thr Asp Phe Thr Leu Thr Ile Asn
65                  70                  75                  80

Arg Leu Arg Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys
            100                 105                 110

<210> SEQ ID NO 159
<211> LENGTH: 111
<212> TYPE: PRT
<213> ORGANISM: Artificial Sequence
<220> FEATURE:
<223> OTHER INFORMATION: S60M_S52D_S67M_S77R_Q79R_S63Y_S76N_v-region

<400> SEQUENCE: 159

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Asp Tyr Leu Glu Ser Gly Val Pro Met
        50                  55                  60

Arg Phe Tyr Gly Ser Gly Met Gly Thr Asp Phe Thr Leu Thr Ile Asn
65                  70                  75                  80

Arg Leu Arg Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys
            100                 105                 110

```
<210> SEQ ID NO 160
<211> LENGTH: 18
<212> TYPE: PRT
<213> ORGANISM: Artificial Sequence
<220> FEATURE:
<223> OTHER INFORMATION: Signal sequence

<400> SEQUENCE: 160

Met Lys Trp Val Thr Phe Ile Ser Leu Leu Phe Leu Phe Ser Ser Ala
1               5                   10                  15

Tyr Ser
```